US012606520B2

(12) United States Patent
Baudry

(10) Patent No.: US 12,606,520 B2
(45) Date of Patent: Apr. 21, 2026

(54) CALPAIN-2 INHIBITOR COMPOUNDS AND METHODS OF TREATMENT

(71) Applicant: WESTERN UNIVERSITY OF HEALTH SCIENCES, Pomona, CA (US)

(72) Inventor: Michel Baudry, Corona, CA (US)

(73) Assignee: Western University of Health Sciences, Pomona, CA (US)

( * ) Notice: Subject to any disclaimer, the term of this patent is extended or adjusted under 35 U.S.C. 154(b) by 565 days.

(21) Appl. No.: 17/904,208

(22) PCT Filed: Feb. 12, 2021

(86) PCT No.: PCT/US2021/018042

§ 371 (c)(1), (2) Date: Aug. 12, 2022

(87) PCT Pub. No.: WO2021/163631

PCT Pub. Date: Aug. 19, 2021

(65) Prior Publication Data

US 2023/0091121 A1 Mar. 23, 2023

Related U.S. Application Data

(60) Provisional application No. 62/975,644, filed on Feb. 12, 2020.

(51) Int. Cl.

| | |
|---|---|
| ***C07C 275/24*** | (2006.01) |
| ***A61K 9/00*** | (2006.01) |
| ***A61K 9/08*** | (2006.01) |
| ***A61K 9/127*** | (2006.01) |
| ***C07C 307/06*** | (2006.01) |

(52) U.S. Cl.

CPC .......... *C07C 275/24* (2013.01); *A61K 9/0019* (2013.01); *A61K 9/08* (2013.01); *A61K 9/127* (2013.01); *C07C 307/06* (2013.01); *C07C 2601/08* (2017.05); *C07C 2601/14* (2017.05); *C07C 2601/18* (2017.05)

(58) Field of Classification Search

CPC ... C07C 275/24; C07C 307/06; A61K 9/0019; A61K 9/08

See application file for complete search history.

(56) References Cited

U.S. PATENT DOCUMENTS

| | | | | |
|---|---|---|---|---|
| 2011/0053858 A1 | 3/2011 | Powers et al. | | |
| 2019/0030114 A1* | 1/2019 | Baudry | .................. | A61P 25/00 |

FOREIGN PATENT DOCUMENTS

| | | | | |
|---|---|---|---|---|
| WO | WO-2016077461 A2 * | 5/2016 | ............. | A61K 38/06 |
| WO | 2020037012 A1 | 2/2020 | | |

OTHER PUBLICATIONS

International Search Report mailed Apr. 28, 2021 in PCT/US2021/018042.

Office Action mailed in corresponding JP Application No. 2022-548842 on Jan. 27, 2025.

* cited by examiner

*Primary Examiner* — Sikarl A Witherspoon

(74) *Attorney, Agent, or Firm* — Fox Rothschild LLP; Peter F. Corless

(57) ABSTRACT

Compounds of Formula (I) or (X) are provided including for treatment of disorders such as a disorder or symptom associated with neuronal cell death. In one aspect, compounds which are selective inhibitors of calpain-2 are provided. Preferred compounds can be useful to treat acute neurodegeneration.

31 Claims, 12 Drawing Sheets

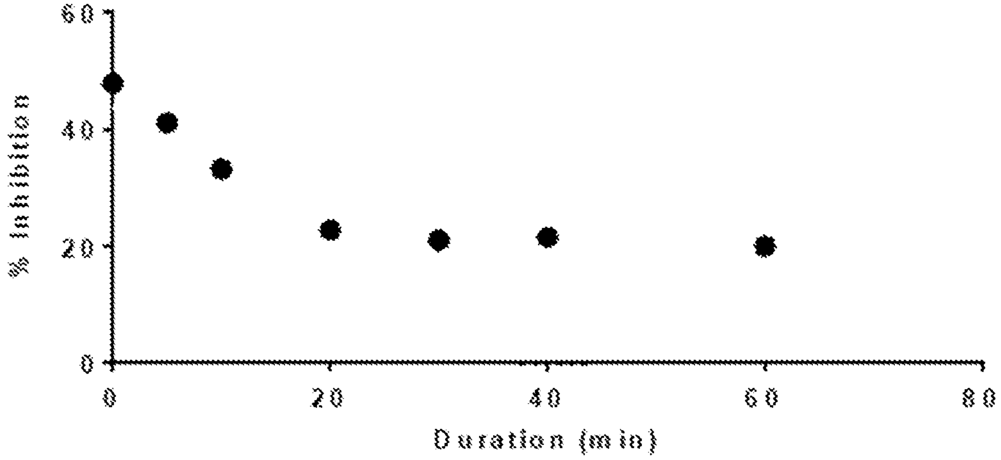
FIG. 9
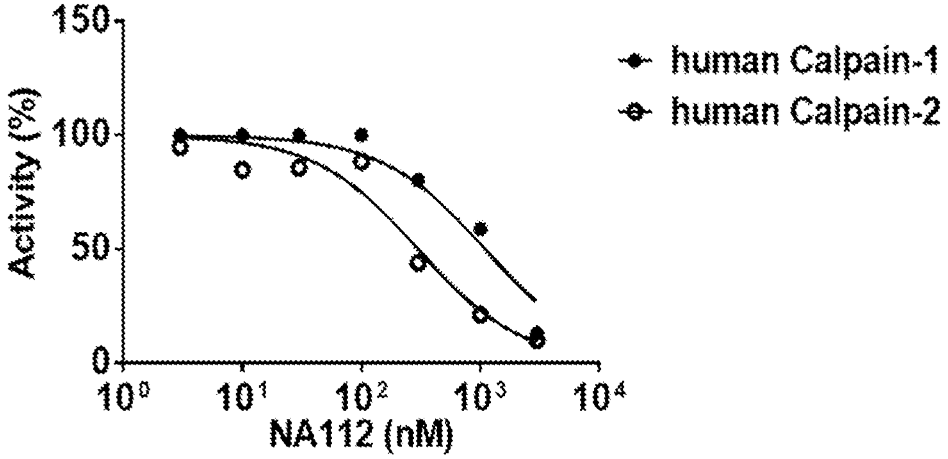
FIG. 10A
| NA112 in liposome | eCalpain-1 | hCalpain-2 |
|---|---|---|
| IC50 | 1092 nM | 298 nM |
| Ki | 622 nM | 189 nM |
Ratio: 3.3
| NA112 in DMSO | eCalpain-1 | hCalpain-2 |
|---|---|---|
| Ki | 208 nM | 72 nM |
Ratio: 2.9
FIG. 10B Half-life in plasma: 7.8 h

CALPAIN-2 INHIBITOR COMPOUNDS AND METHODS OF TREATMENT

CROSS-REFERENCES TO RELATED APPLICATIONS

This application is a U.S. national phase application, pursuant to 35 U.S.C. § 371, of International Patent Application No. PCT/US2021/018042, filed Feb. 12, 2021, which claims the benefit of U.S. Provisional Patent Application No. 62/975,644, filed Feb. 12, 2020, each of which are incorporated herein in their entirety and for all purposes.

STATEMENT OF GOVERNMENT SUPPORT

This invention was made with government support under W81XWH-19-1-0329 awarded by the Defense Health Agency, Medical Research and Development Branch. The government has certain rights in the invention.

FIELD OF THE INVENTION

The invention relates to products that inhibit calpain-2 function, and methods for specifically inhibiting calpain-2 activation or activity, and to methods of treating and preventing neurodegenerative diseases that are susceptible to treatment with molecules that interfere with calpain-2 function.

BACKGROUND

Many studies have shown that the calcium-dependent protease, calpain, is involved in neurodegeneration in both acute and chronic animal models of neurodegeneration. In particular, calpain has been shown to play an important role in the neuronal degeneration and axonal damage that follow Traumatic Brain Injury (TBI). Although much has been learned over the last decades regarding the mechanisms responsible for the neuropathology resulting from TBI, most treatments for TBI target the symptoms that follow TBI, and in particular, the neurobehavioral disorders, with very few treatments attempting to provide neuroprotection.

The two major calpain isoforms in the brain, calpain-1 and calpain-2, play opposite functions in both synaptic plasticity and neurodegeneration. While calpain-1 is required for the induction of synaptic plasticity, calpain-2 limits the extent of synaptic plasticity during the minutes following the induction event (Wang et al., 2014); likewise, calpain-1 is neuroprotective and calpain-2 is neurodegenerative (Wang et al., 2013). These dual and opposite functions of calpain-1/2, as well as the lack of selective inhibitors for these two calpain isoforms account for the previous difficulties in developing calpain inhibitors for translational applications, and in particular for preventing neurodegeneration. Calpain-1 activation is linked to synaptic NMDA receptor stimulation, which accounts for its necessary role in long term potentiation (LTP) induction. It is also involved in neuroprotection elicited by synaptic NMDA receptor stimulation. On the other hand, calpain-2 is linked to extrasynaptic NMDA receptor stimulation and is involved in neurodegeneration. Calpain-2 is also activated by BDNF→ERK-mediated phosphorylation and limits the extent of LTP following theta-burst stimulation (TBS). Thus, a selective calpain-2 inhibitor can be both neuroprotective and a cognitive enhancer. Selective calpain-2 inhibitors could be used not only for TBI, but also for a number of acute indications associated with neuronal death, including stroke, concussion, intracerebral hemorrhage, acute glaucoma, and spinal cord injury. They could also be used to prevent neurodegeneration elicited by seizure activity and could therefore be useful to prevent epileptogenesis.

SUMMARY OF THE INVENTION

In one aspect, compounds which are selective inhibitors of calpain-2 are provided.

Preferred compounds can be useful to treat acute neurodegeneration.

In a particular aspect, compounds of the following Formula (I) are provided:

(I)

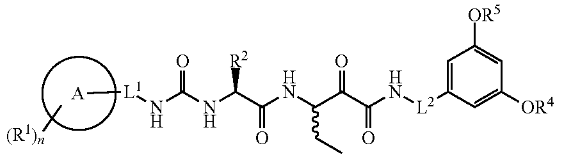

wherein A is carbocyclic aryl or heteroaryl;

$R^1$ is a non-hydrogen substituent such as $C_1$-$C_6$ alkyl, halogen, cyano, nitro, $C_1$-$C_6$ alkoxy, —$CO(CH_2)_mN(R^a)(R^b)$, —$O(CH_2)_mN(R^a)(R^b)$, —$CONH(CH_2)_mN(R^a)(R^b)$, —CONH—$CH(R^c)(R^d)$, —$(CH_2)_mN(R^a)(R^b)$, or —$O(CH_2)_mOH$;

$R^a$, $R^b$, $R^c$, and $R^d$ are independently hydrogen or unsubstituted $C_1$-$C_6$ alkyl, which may be linear or branched alkyl;

n is independently an integer from 0 (where the ring A is unsubstituted) to the value permitted by the valence of the ring such as 5 where A is phenyl;

m is independently an integer from 0 to 6;

$L^1$ and $L^2$ are each the same or different optionally substituted alkylene having one to 6 carbons (e.g. —$(CH_2)_p$ where p is 1 to 6 and each carbon may have zero, one or two non-hydrogen substituents), $R^2$ is non-hydrogen substituent such as optionally substituted $C_1$-$C_6$ alkyl, $R^4$ and $R^5$ are independently hydrogen, or unsubstituted $C_1$-$C_6$ alkyl such as methyl; and pharmaceutically acceptable salts thereof.

In certain preferred aspect, $R^a$ and $R^b$ are independently hydrogen or unsubstituted $C_1$-$C_6$ alkyl. In a particular aspect, $R^a$ and $R^b$ are independently hydrogen, methyl, ethyl, or propyl (e.g., isopropyl). In a particular aspect, $R^a$ and $R^b$ are independently hydrogen or methyl. In a particular aspect, $R^a$ and $R^b$ are hydrogen. In a particular aspect, $R^a$ and $R^b$ are methyl. In a particular aspect, $R^a$ is hydrogen and $R^b$ is methyl. In a particular aspect, $R^a$ and $R^b$ are independently hydrogen or isopropyl. In a particular aspect, $R^a$ is hydrogen and $R^b$ is isopropyl.

In certain preferred aspect, $R^c$ and $R^d$ are independently hydrogen or unsubstituted $C_1$-$C_6$ alkyl. In a particular aspect, $R^c$ and $R^d$ are independently hydrogen, methyl, ethyl, or propyl (e.g., isopropyl). In a particular aspect, $R^c$ and $R^d$ are independently hydrogen or methyl. In a particular aspect, $R^c$ and $R^d$ are hydrogen. In a particular aspect, $R^c$ and $R^d$ are methyl. In a particular aspect, $R^c$ is hydrogen and $R^d$ is methyl.

In certain preferred aspects, $R^4$ and $R^5$ are independently hydrogen, methyl or ethyl. In a particular aspect, $R^4$ and $R^5$ are methyl.

In preferred aspects, one or both of $L^1$ and $L^2$ are unsubstituted alkylene such as methylene (—$CH_2$—) and ethylene (—$CH_2$—$CH_2$—).

In additional preferred aspects, the group A is carbocyclic aryl such as phenyl or a heteroaryl with one of more nitrogen ring members such as optionally substituted pyridinyl or optionally substituted pyrazinyl.

In certain aspects, n may be 0, 1, 2, or 3, such as 0 or 1, or 1.

In certain preferred aspects, provided is the compound having the structure of formula (II).

(II)

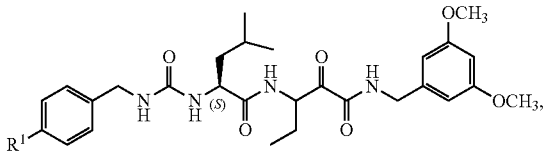

The compound may be a racemate including:

(IIA)

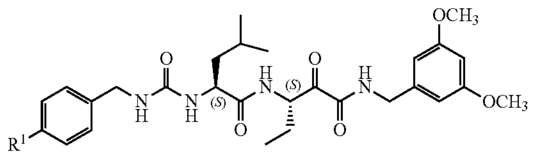

or.

(IIB)

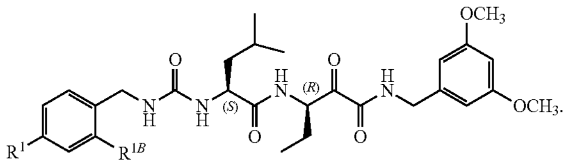

The compound has preferably the formula (IIA):

(IIA)

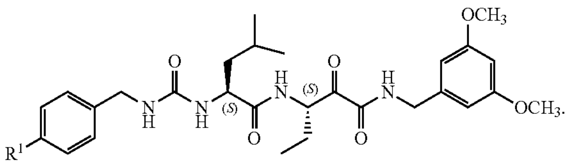

In a particular aspect, $R^1$ is —$CO(CH_2)_mN(R^a)(R^b)$ wherein m is 0 or 1, preferably m is 0, and $R^a$ and $R^b$ are hydrogen or methyl. For example, $R^1$ is —$CONH_2$, or —$CONHCH_3$.

In a particular aspect, $R^1$ is —$O(CH_2)_mN(R^a)(R^b)$, wherein m is 1, 2, or 3, preferably m is 2, and $R^a$ and $R^b$ are hydrogen or methyl. For example, $R^1$ is —$OCH_2CH_2N(CH_3)_2$ or —$OCH_2CH_2NHCH_3$.

In a particular aspect, $R^1$ is —$CONH(CH_2)_mN(R^a)(R^b)$, wherein m is 1, 2, or 3, preferably m is 2, and $R^a$ and $R^b$ are hydrogen, methyl or isopropyl. For example, $R^1$ is —$CONHCH_2CH_2NHCH(CH_3)_2$, —$CONHCH_2CH_2N(CH_3)_2$, or —$CONHCH_2CH_2NH(CH_3)$.

In a particular aspect, $R^1$ is —CONH—$CH(R^c)(R^d)$ wherein $R^c$ and $R^d$ are independently hydrogen or methyl. For example, $R^1$ is —$CONHCH(CH_3)_2$, or —$CONHCH_2CH_3$.

In a particular aspect, $R^1$ is —$(CH_2)_mN(R^a)(R^b)$, wherein m is 1, 2, or 3, preferably m is 1, and $R^a$ and $R^b$ are hydrogen or methyl. For example, $R^1$ is —$CH_2NH_2$, —$CH_2NH(CH_3)$, or. —$CH_2N(CH_3)_2$.

In a particular aspect, $R^1$ is —$O(CH_2)_mOH$, wherein m is 1, 2, or 3, preferably m is 2. For example, $R^1$ is —$OCH_2CH_2OH$.

In certain preferred aspects, provided is the compound having the structure of formula (III):

(III)

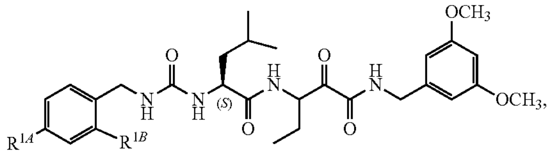

wherein $R^{1A}$ is cyano, or unsubstituted $C_1$-$C_6$ alkyl, and $R^{1B}$ is $C_1$-$C_6$ alkoxy.

The compound may be a racemate including:

(IIIA)

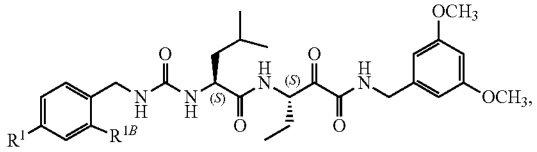

or (IIIB)

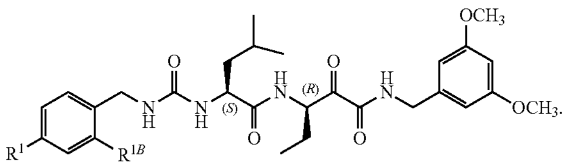

The compound has preferably the formula (IIIA):

(IIIA)

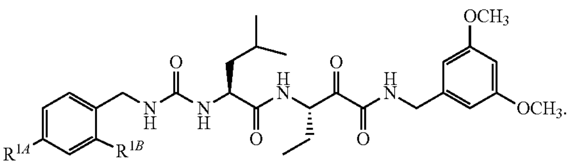

In a particular aspect, $R^{1A}$ is cyano (—CN) or unsubstituted alkyl such as methyl and $R^{1B}$ is $C_1$-$C_6$ alkoxy, preferably —$OCH_3$.

In particularly preferred aspects, provided is the compound having the following structure:

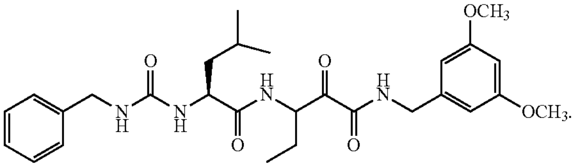 [SMILES: CCC(NC(=O)[C@H](CC(C)C)NC(=O)NCc1ccccc1)C(=O)C(=O)NCc1cc(OC)cc(OC)c1]

The compound may be a racemate including:

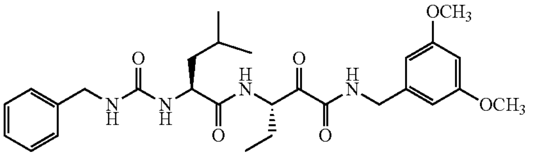

and

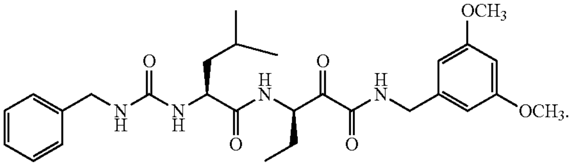

The compound has preferably the structure of

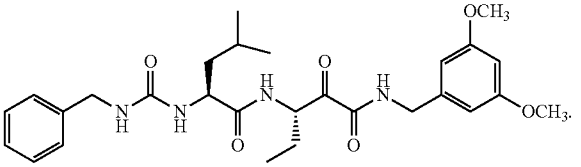 [SMILES: CC[C@H](NC(=O)[C@H](CC(C)C)NC(=O)NCc1ccccc1)C(=O)C(=O)NCc1cc(OC)cc(OC)c1]

In a particular aspect, compounds of the following Formula (X) are provided:

(X)

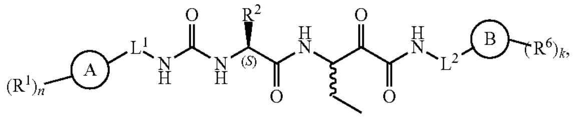

wherein:

A is $C_1$-$C_6$ alkyl, carboxyl (—C(O)O—), aryl, heteroaryl, cycloalkyl, or heterocycloalkyl;

B is carbocyclic aryl, heteroaryl, cycloalkyl, or heterocycloalkyl;

$L^1$ is a bond, or substituted or unsubstituted $C_1$-$C_6$ alkylene, $L^2$ is a bond, substituted or unsubstituted $C_1$-$C_6$ alkylene, or —$S(O)_2$—, Each $R^1$ is independently $C_1$-$C_6$ alkyl, halogen, cyano, nitro, $C_1$-$C_6$ alkoxy, aryl, heterocycloaryl, heterocycloalkyl, —$C(O)(CH_2)_mN(R^a)(R^b)$, —$O(CH_2)_mN(R^a)(R^b)$, —$CONH(CH_2)_mN(R^a)(R^b)$, —C(O)NH—$CH(R^c)(R^d)$, —$C(O)OCH(R^c)(R^d)$, —$(CH_2)_mN(R^a)(R^b)$, —$(CH_2)_mN(R^a)C(O)R^b$, —$(CH_2)_mN(R^a)C(O)OR^b$, —$O(CH_2)_mR^c$, —$O(CH_2)_mOH$, —$S(O)_2R^b$, or —O(Ph)X;

$R^2$ is unsubstituted $C_1$-$C_6$ alkyl;

Each $R^6$ is independently $C_1$-$C_6$ alkyl, halogen, cyano, nitro, $C_1$-$C_6$ alkoxy, aryl, heterocycloaryl, heterocycloalkyl —$C(O)(CH_2)_mN(R^a)(R^b)$, —$O(CH_2)_mN(R^a)(R^b)$, —$CONH(CH_2)_mN(R^a)(R^b)$, —C(O)NH—$CH(R^c)(R^d)$, —$C(O)OCH(R^c)(R^d)$, —$(CH_2)_mN(R^a)(R^b)$, —$(CH_2)_mN(R^a)C(O)R^b$, —$(CH_2)_mN(R^a)C(O)OR^b$, —$O(CH_2)_mR^c$, —$O(CH_2)_mOH$, or —O(Ph)X;

Two $R^6$ together with atoms attached thereto are optionally joined to form a cycloalkyl, or heterocycloalkyl;

$R^a$, $R^b$, $R^c$, and $R^d$ are independently hydrogen, $C_1$-$C_6$ alkyl that may be optionally substituted with halogen, —OH, amine, or unsubstituted $C_{3-6}$ cycloalkyl;

X is halogen;

n is independently an integer from 0 to 12;

m is independently an integer from 0 to 6;

k is independently an integer from 0 to 12;

and pharmaceutically acceptable salts thereof.

In certain preferred aspect, A is phenyl and $L^1$ is —$(CH_2)_p$— wherein p is 1 to 4.

The compound has the following Formula (XI).

(XI)

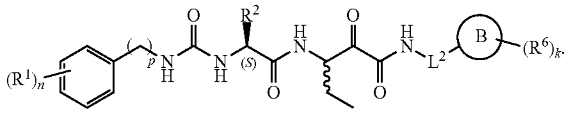

B, $R^1$, n, p, $R^2$, $L^2$, $R^6$ and k are as defined above, n is an integer of 0 to 5.

In certain preferred aspect, -$L^2$-B- is

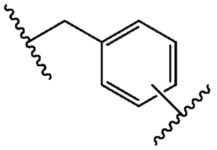

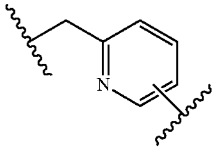

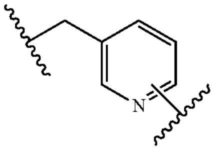

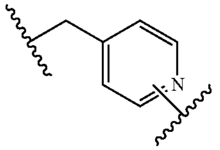

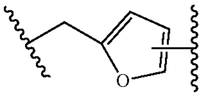

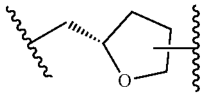

or

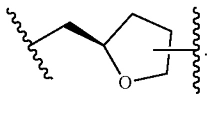

The compound has the following Formula (XI-a),

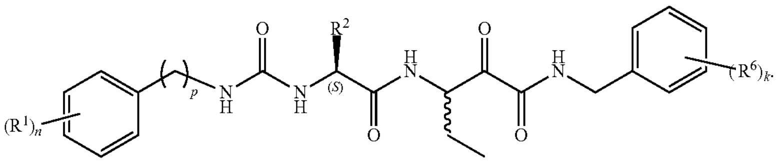

(XI-a)

$R^1$, n, p, $R^2$, $L^2$, and $R^6$ are as defined above. k is an integer of 0 to 5.

The compound has the following Formula (XI-b),

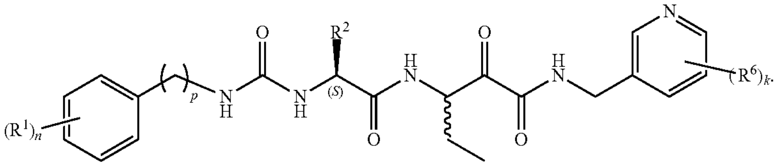

(XI-b)

$R^1$, n, p, $R^2$, $L^2$, and $R^6$ are as defined above. k is an integer of 0 to 4.

The compound has the following Formula (XI-c),

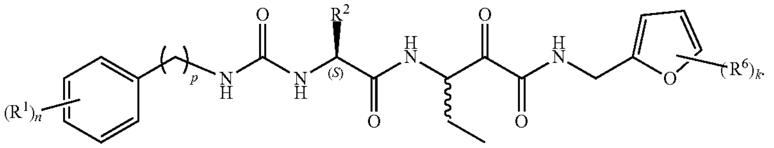

(XI-c)

$R^1$, n, p, $R^2$, $L^2$ and $R^6$ are as defined above. k is an integer of 0 to 3.

The compound has the following Formula (XI-d),

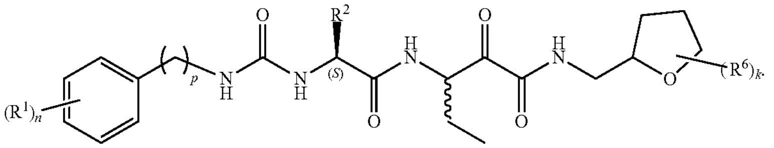

(XI-d)

$R^1$, n, p, $R^2$, $L^2$, and $R^6$ are as defined above. k is an integer of 0 to 6.

In certain preferred aspects, $L^1$ is a bond, methylene, or ethylene and A is $C_{1-4}$ alkyl, cycloalkyl, or heterocycloalkyl.

In particularly certain preferred aspects, $-L^1-A-R^1$ is

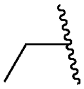 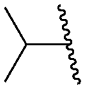 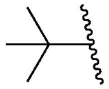 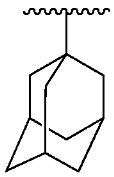 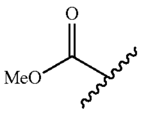

-continued

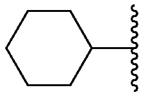 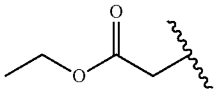

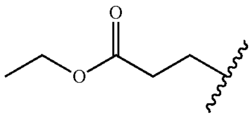 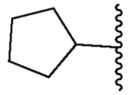 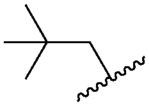

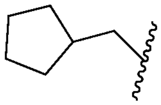 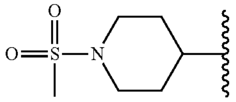 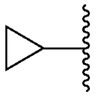

-continued

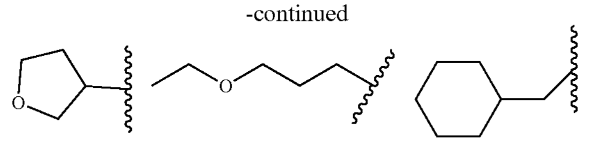

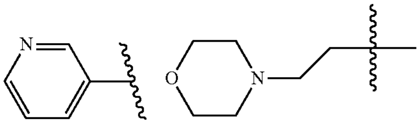

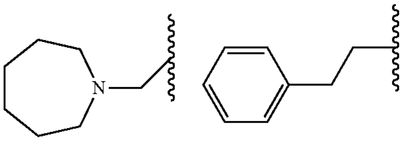

or

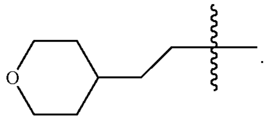

In certain preferred aspect, the compound has the following Formula (XII), (XII)

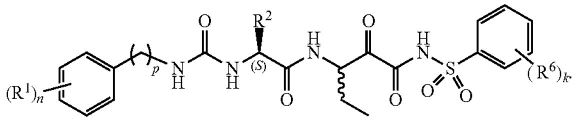

$R^1$, p, $R^2$, $L^2$, and $R^6$ are as defined above. k is an integer of 0 to 5 and n is an integer of 0 to 5.

In a particular aspect, compounds of the following Formula (XIII) are provided:

(XIII)

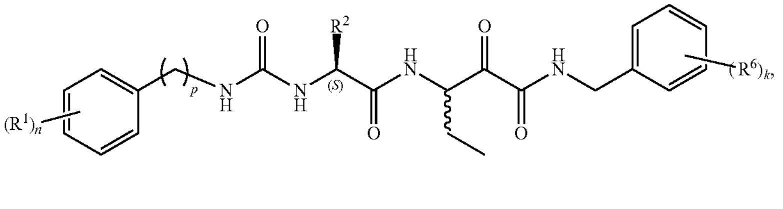

wherein:

Each $R^1$ is independently $C_1$-$C_6$ alkyl, halogen, cyano, nitro, $C_1$-$C_6$ alkoxy, aryl, heterocycloaryl, heterocycloalkyl, —$C(O)(CH_2)_mN(R^a)(R^b)$, —$O(CH_2)_mN(R^a)(R^b)$, —$CONH(CH_2)_mN(R^a)(R^b)$, —C(O)NH—$CH(R^c)(R^d)$, —$C(O)OCH(R^c)(R^d)$, —$(CH_2)_mN(R^a)(R^b)$, —$(CH_2)_mN(R^a)C(O)R^b$, —$(CH_2)_mN(R^a)C(O)OR^b$, —$O(CH_2)_mR^c$, —$O(CH_2)_mOH$, —$S(O)_2R^b$, or —O(Ph)X;

$R^2$ is unsubstituted $C_1$-$C_6$ alkyl;

Each $R^6$ is independently $C_1$-$C_6$ alkyl, halogen, cyano, nitro, $C_1$-$C_6$ alkoxy, aryl, heterocycloaryl, heterocycloalkyl —$C(O)(CH_2)_mN(R^a)(R^b)$, —$O(CH_2)_mN(R^a)(R^b)$, —$CONH(CH_2)_mN(R^a)(R^b)$, —C(O)NH—$CH(R^c)(R^d)$, —$C(O)OCH(R^c)(R^d)$, —$(CH_2)_mN(R^a)(R^b)$, —$(CH_2)_mN(R^a)C(O)R^b$, —$(CH_2)_mN(R^a)C(O)OR^b$, —$O(CH_2)_mR^c$, —$O(CH_2)_mOH$, or —O(Ph)X;

Two $R^6$ together with atoms attached thereto are optionally joined to form a cycloalkyl, or heterocycloalkyl;

$R^a$, $R^b$, $R^c$, and $R^d$ are independently hydrogen, $C_1$-$C_6$ alkyl that may be optionally substituted with halogen, —OH, amine, or unsubstituted $C_{3-6}$ cycloalkyl;

X is halogen;

n is independently an integer from 0 to 5;

m is independently an integer from 0 to 6;

k is independently an integer from 0 to 5;

p is independently an integer from 0 to 6;

and pharmaceutically acceptable salts thereof.

In a particular aspect, compounds of the following Formula (XIV) are provided:

(XIV)

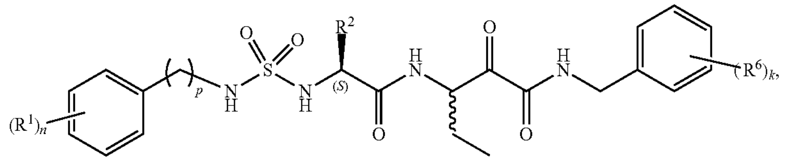

wherein:

Each $R^1$ is independently $C_1$-$C_6$ alkyl, halogen, cyano, nitro, $C_1$-$C_6$ alkoxy, aryl, heterocycloaryl, heterocycloalkyl, $—C(O)(CH_2)_mN(R^a)(R^b)$, $—O(CH_2)_mN(R^a)(R^b)$, $—CONH(CH_2)_mN(R^a)(R^b)$, $—C(O)NH—CH(R^c)(R^d)$, $—C(O)OCH(R^c)(R^d)$, $—(CH_2)_mN(R^a)(R^b)$, $—(CH_2)_mN(R^a)C(O)R^b$, $—(CH_2)_mN(R^a)C(O)OR^b$, $—O(CH_2)_mR^c$, $—O(CH_2)_mOH$, $—S(O)_2R^b$, or —O(Ph)X;

$R^2$ is unsubstituted $C_1$-$C_6$ alkyl;

Each $R^6$ is independently $C_1$-$C_6$ alkyl, halogen, cyano, nitro, $C_1$-$C_6$ alkoxy, aryl, heterocycloaryl, heterocycloalkyl $—C(O)(CH_2)_mN(R^a)(R^b)$, $—O(CH_2)_mN(R^a)(R^b)$, $—CONH(CH_2)_mN(R^a)(R^b)$, $—C(O)NH—CH(R^c)(R^d)$, $—C(O)OCH(R^c)(R^d)$, $—(CH_2)_mN(R^a)(R^b)$, $—(CH_2)_mN(R^a)C(O)R^b$, $—(CH_2)_mN(R^a)C(O)OR^b$, $—O(CH_2)_mR^c$, $—O(CH_2)_mOH$, or —O(Ph)X; Two $R^6$ together with atoms attached thereto are optionally joined to form a cycloalkyl, or heterocycloalkyl;

$R^a$, $R^b$, $R^c$, and $R^d$ are independently hydrogen, $C_1$-$C_6$ alkyl that may be optionally substituted with halogen, —OH, amine, or unsubstituted $C_{3-6}$ cycloalkyl;

X is halogen;

n is independently an integer from 0 to 5;

m is independently an integer from 0 to 6;

k is independently an integer from 0 to 5;

p is independently an integer from 0 to 6;

and pharmaceutically acceptable salts thereof.

In preferred aspects, each $R^a$, $R^b$, $R^c$, and $R^d$ is independently hydrogen, methyl, ethyl, propyl or isopropyl.

In particularly preferred aspects, provided is the compound having the following structure:

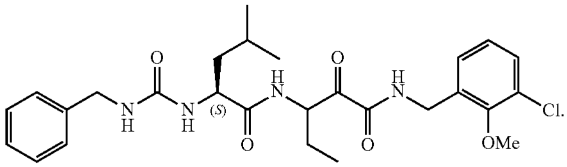

The compound may be a racemate including:

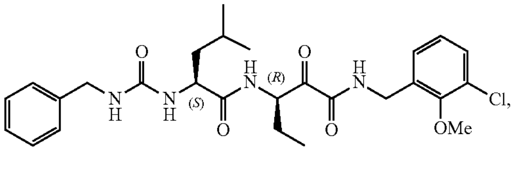

or

-continued

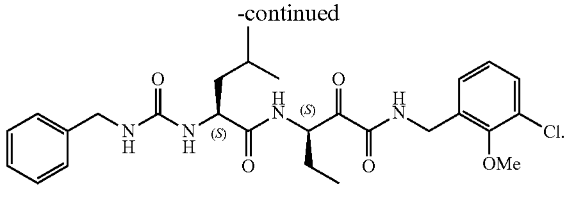

The compound has preferably the structure of,

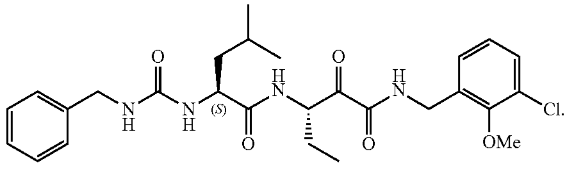

Pharmaceutical compositions comprising said compounds, and methods of treating neurodegenerative disorders with said compounds are also provided. In particular aspects, methods are provided for treating traumatic brain injury (TBI) in a patient and the methods include administering to a patient in need thereof an effective amount of a compound or composition described herein. In particular aspect, methods are provided for treating a subject suffering from a disorder or symptom associated with neuronal cell death by administering to the subject an effective amount of a compound or composition as described herein. For instance, the subject may be identified as suffering from a particular disease or disorder such as stroke, concussion, intracerebral hemorrhage, epilepsy, acute glaucoma, and spinal cord injury. The compound or composition is administered via a method selected from the group consisting of oral administration, intravenous injection, subcutaneous injection, intranasal delivery, or intracisternal injection.

Methods of treatment is general comprise administering to a subject such as a mammal, particularly a primate including a human, an effective amount of one or more compounds as disclosed herein. A suitable subject may be identified and selected for treatment. The one or more compounds disclosed herein then may be administered to the identified subject.

Other aspects of the invention are disclosed infra.

BRIEF DESCRIPTION OF THE DRAWINGS

FIG. 9 shows that NA112A (S-S isomer) became inactive in mouse plasma.

FIG. 10A shows assay results showing selectivity in vitro of NA112 in liposomal formation for calpain-2 vs calpain-1.

FIG. 10B shows values obtained with NA112 dissolved in DMSO are shown for comparison to FIG. 10A.

DETAILED DESCRIPTION

Compounds

Figure 1:
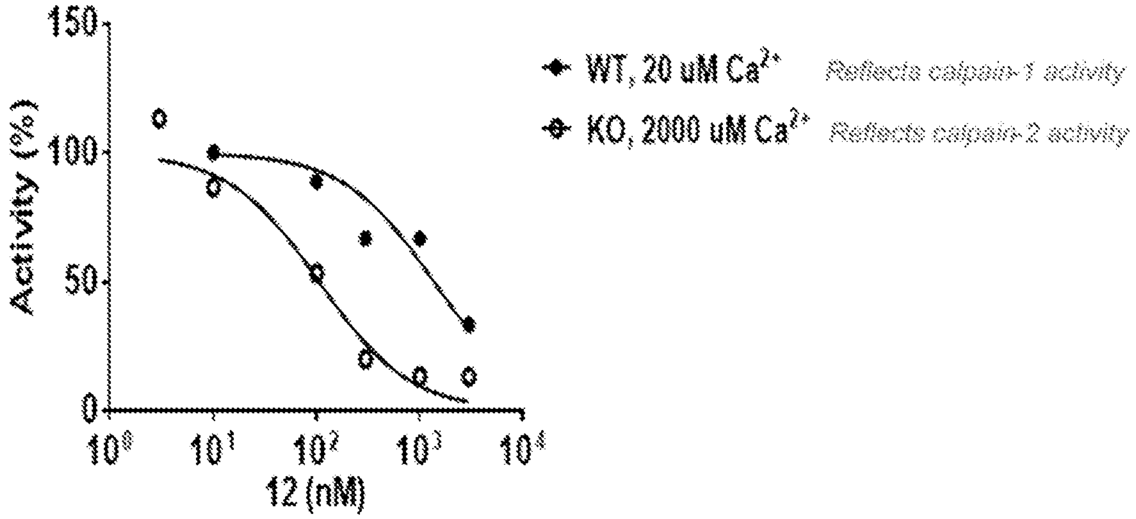
FIG. 1 shows assay results showing selectivity in vitro of NA112 for calpain-2 vs calpain-1.

As discussed, in one aspect, compounds of the following Formula (I) are provided:

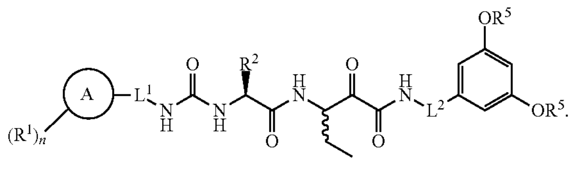

wherein A, $R^1$, n, $L^1$, $R^2$, $L^2$, $R^4$ and $R^5$ are as defined above. In certain aspects, preferably, $R^1$ is absent (n is 0 and the A ring does not contain any non-hydrogen substituents), alkyl, alkoxy or halogen, A is carbocyclic aryl such as phenyl or heteroaryl, $L^1$ and $L^2$ are each unsubstituted alkylene, particularly methylene ($-CH_2-$), $R^4$ and $R^5$ are independently hydrogen, or unsubstituted $C_1$-$C_6$ alkyl such as methyl.

In certain preferred aspects, $R^4$ and $R^5$ are independently hydrogen, methyl or ethyl. In a particular aspect, $R^4$ and $R^5$ are methyl.

Exemplary preferred A-$L^1$- groups include the following:

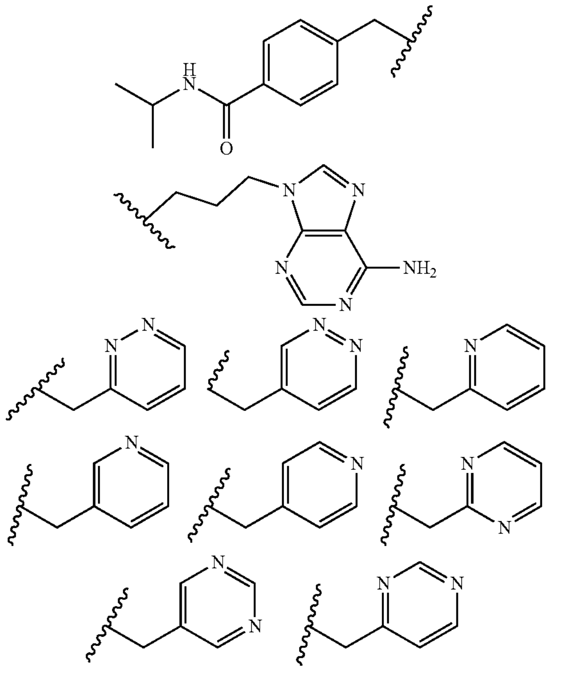

The above are also preferred A groups with other $L^1$ linkers.

In certain preferred aspects, the chiral carbon most adjacent $L^1$ has an (S) configuration.

For certain aspects, the chiral carbon most adjacent to $L^1$ has an (R) configuration.

In certain preferred aspects, the chiral carbon most adjacent to $L^2$ has an (S) configuration. For certain aspects, the chiral carbon most adjacent to $L^2$ has an (R) configuration Compounds of the invention may be utilized as racemic or optically enriched mixtures.

Particularly preferred compounds of the invention are compounds analog of NA112, which may have the following formula (II) or (III).

(II)

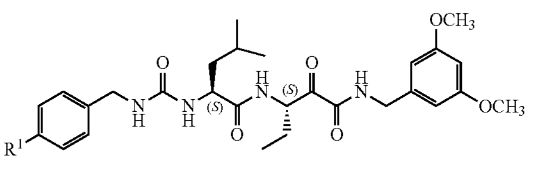

or

-continued (III)

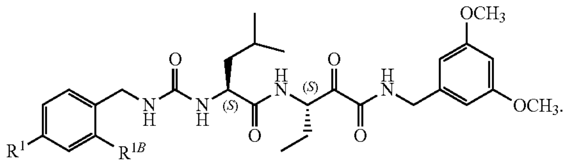

In a certain aspect, $R^{1A}$ is cyano, or unsubstituted $C_1$-$C_6$ alkyl, and $R^{1B}$ is $C_1$-$C_6$ alkoxy. In a particular aspect, $R^{1A}$ is cyano (—CN) or unsubstituted alkyl such as methyl and $R^{1B}$ is $C_1$-$C_6$ alkoxy, preferably $—OCH_3$.

Particularly preferred compound, NA112, has the following structure.

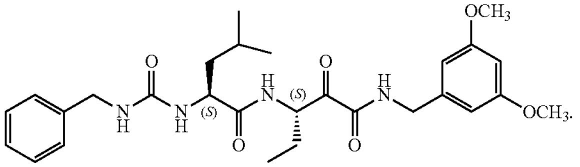

In another aspect, provided is a compound of Formula (X), (X)

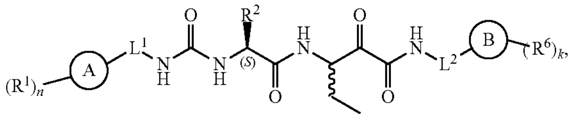

wherein:

A is $C_1$-$C_6$ alkyl, carboxyl (—C(O)O—), aryl, heteroaryl, cycloalkyl, or heterocycloalkyl;

B is carbocyclic aryl, heteroaryl, cycloalkyl, or heterocycloalkyl;

$L^1$ is a bond, or substituted or unsubstituted $C_1$-$C_6$ alkylene, $L^2$ is a bond, substituted or unsubstituted $C_1$-$C_6$ alkylene, or $—S(O)_2—$, Each $R^1$ is a non-hydrogen substituent such as $C_1$-$C_6$ alkyl, halogen, cyano, nitro, $C_1$-$C_6$ alkoxy, aryl, heterocycloaryl, heterocycloalkyl $—C(O)(CH_2)_mN(R^a)(R^b)$, $—O(CH_2)_mN(R^a)(R^b)$, $—CONH(CH_2)_mN(R^a)(R^b)$, $—C(O)NH—CH(R^c)(R^d)$, $—C(O)OCH(R^c)(R^d)$, $—(CH_2)_mN(R^a)(R^b)$, $—(CH_2)_mN(R^a)C(O)R^b$, $—(CH_2)_mN(R^a)C(O)OR^b$, $—O(CH_2)_mR^c$, $—O(CH_2)_mOH$, $—S(O)_2R^b$, or —O(Ph)X;

$R^2$ is non-hydrogen substituent such as optionally substituted $C_1$-$C_6$ alkyl;

Each $R^6$ is independently a non-hydrogen substituent such as $C_1$-$C_6$ alkyl, halogen, cyano, nitro, $C_1$-$C_6$ alkoxy, aryl, heterocycloaryl, heterocycloalkyl $—C(O)(CH_2)_mN(R^a)(R^b)$, $—O(CH_2)_mN(R^a)(R^b)$, $—CONH(CH_2)_mN(R^a)(R^b)$, $—C(O)NH—CH(R^c)(R^d)$, $—C(O)OCH(R)(R^d)$, $—(CH_2)_mN(R^a)(R^b)$, $—(CH_2)_mN(R^a)C(O)R^b$, $—(CH_2)_mN(R^a)C(O)OR^b$, $—O(CH_2)_mR^c$, $—O(CH_2)_mOH$, or —O(Ph)X;

Two $R^6$ together with atoms attached thereto are optionally joined to form a cycloalkyl, or heterocycloalkyl;

$R^a$, $R^b$, $R^c$, and $R^d$ are independently hydrogen, $C_1$-$C_6$ alkyl that may be optionally substituted with halogen, —OH, amine, or unsubstituted $C_{3-6}$ cycloalkyl;

X is halogen;

n is independently an integer from 0 (where the ring A is unsubstituted) to the value permitted by the valence of the ring such as 5 where A is phenyl;

m is independently an integer from 0 to 6;

k is independently an integer from 0 (where the ring B is unsubstituted) to the value permitted by the valence of the ring such as 5 where B is phenyl;

and pharmaceutically acceptable salts thereof.

In a certain embodiment, the compound of Formula (X) may be a racemate including

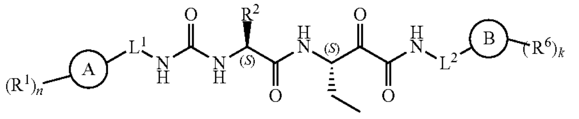

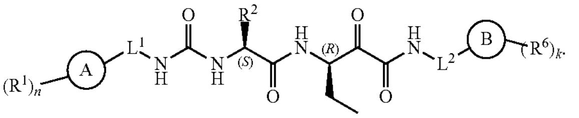

A, B, $R^1$, $R^2$, $L^1$, $L^2$, $R^6$, n and k are as defined above.

In a certain embodiment, $L^1$ is optionally substituted $C_1$-$C_6$ alkylene having (e.g. $—(CH_2)_p$ where p is 1 to 6 and each carbon may have zero, one or two non-hydrogen substituents), In a certain embodiment, $L^2$ is optionally substituted alkylene having one to 6 carbons (e.g. $—(CH_2)_p$ where p is 1 to 6 and each carbon may have zero, one or two non-hydrogen substituents), or $—S(O)_2—$.

In a certain embodiment, $R^2$ is unsubstituted $C_1$-$C_6$ alkyl. For example, $R^2$ is a linear unsubstituted $C_1$-$C_6$ alkyl, or branched $C_3$-$C_6$ alkyl e.g., isopropyl, isobutyl or t-butyl.

In a certain embodiment, $R^a$ and $R^b$ are independently hydrogen, methyl, ethyl, propyl or isopropyl.

In a certain embodiment, $R^c$ and $R^d$ are independently hydrogen or methyl.

In certain preferred aspect, $R^a$ and $R^b$ are independently hydrogen or unsubstituted $C_1$-$C_6$ alkyl. In a particular aspect, $R^a$ and $R^b$ are independently hydrogen, methyl, ethyl, or propyl (e.g., isopropyl). In a particular aspect, $R^a$ and $R^b$ are independently hydrogen or methyl. In a particular aspect, $R^a$ and $R^b$ are hydrogen. In a particular aspect, $R^a$ and $R^b$ are methyl. In a particular aspect, $R^a$ is hydrogen and $R^b$ is methyl. In a particular aspect, $R^a$ and $R^b$ are independently hydrogen or isopropyl. In a particular aspect, $R^a$ is hydrogen and $R^b$ is isopropyl.

In certain preferred aspect, $R^c$ and $R^d$ are independently hydrogen or unsubstituted $C_1$-$C_6$ alkyl. In a particular aspect, $R^c$ and $R^d$ are independently hydrogen, methyl, ethyl, or propyl (e.g., isopropyl). In a particular aspect, $R^c$ and $R^d$ are independently hydrogen or methyl. In a particular aspect, $R^c$ and $R^d$ are hydrogen. In a particular aspect, $R^c$ and $R^d$ are methyl. In a particular aspect, $R^c$ is hydrogen and $R^d$ is methyl.

In a certain embodiment, A is phenyl and $L^1$ is $—(CH_2)_p—$ and p is 0 to 6 (when p is 0, $L^1$ is a bond). Preferably, p is 1 to 6.

The compound may have a Formula (XI).

(XI)

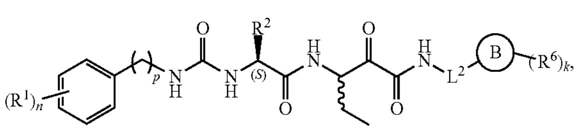

wherein B, $R^1$, p, $R^2$, $L^2$, $R^6$ and k are as defined above.

n is an integer of 0 to 5.

In a certain embodiment, the compound of Formula (XI) may be a racemate including

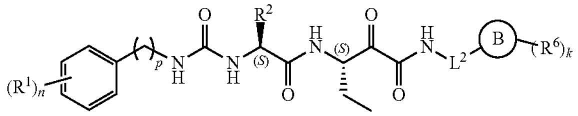

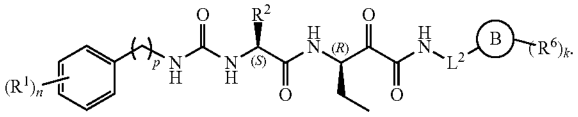

B, $R^1$, $R^2$, $L^1$, $L^2$, $R^6$, p, and k are as defined above.

In a certain embodiment, $-L^2-B-$ is

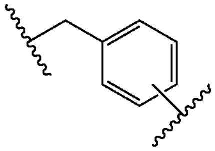

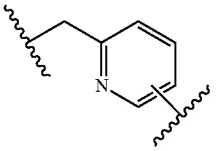

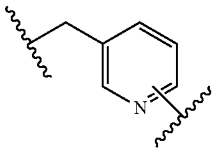

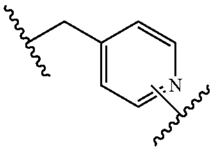

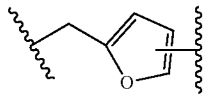

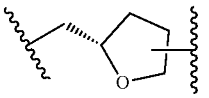

or

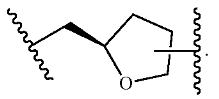

The compound may have a Formula (XI-a).

(XI-a)

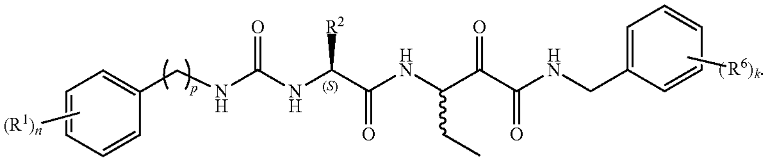

$R^1$, n, p, $R^2$, and $R^6$ are as defined above. k is an integer of 0 to 5.

In a certain embodiment, the compound of Formula (XI-a) may be a racemate including

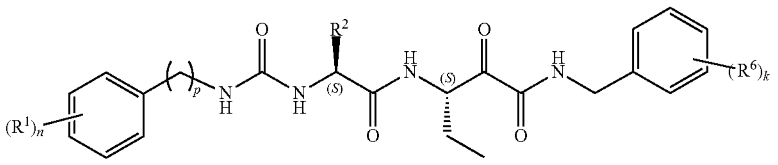

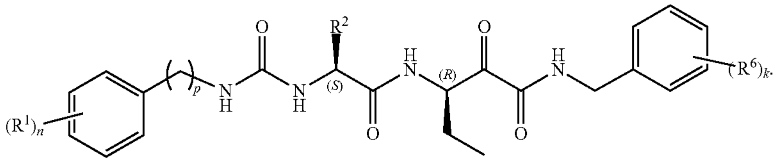

$R^1$, n, p, $R^2$, k, and $R^6$ are as defined above.

In a certain embodiment, in Formula (XI-a), n is 0. For example, the compound is
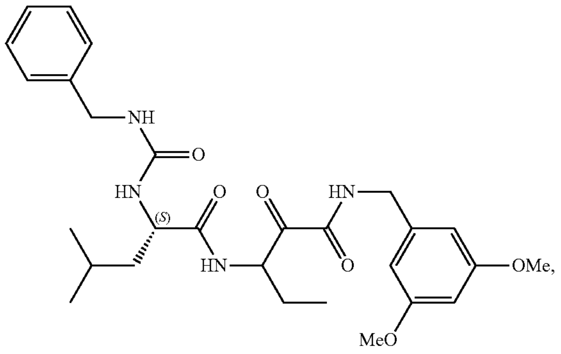
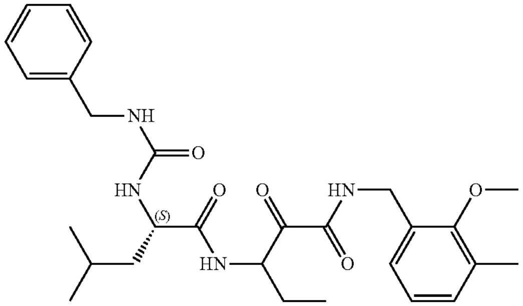
,
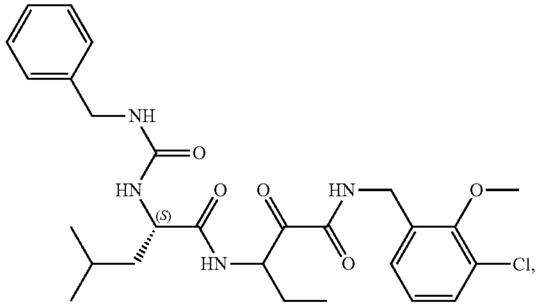
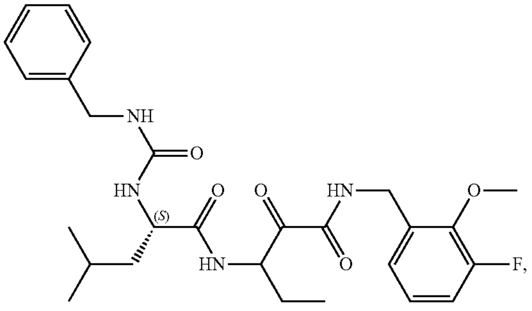
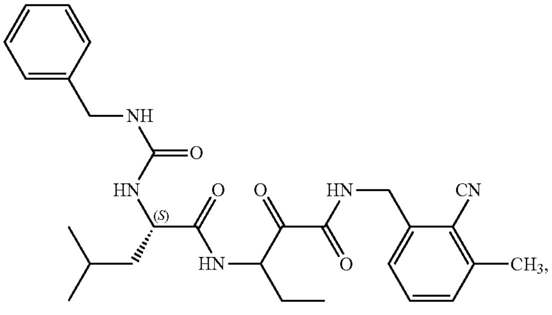
-continued
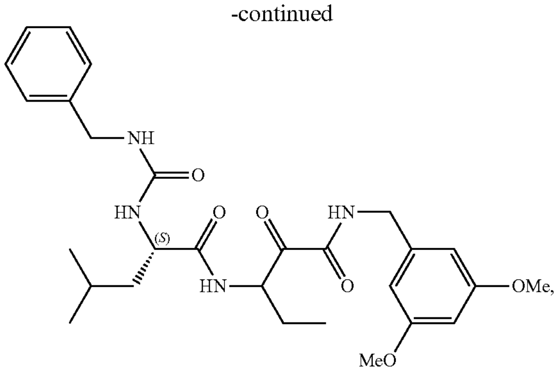
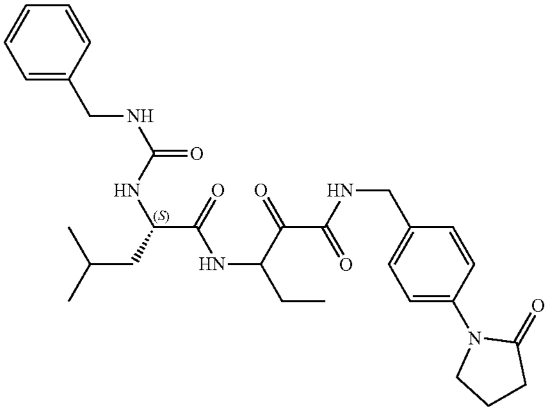
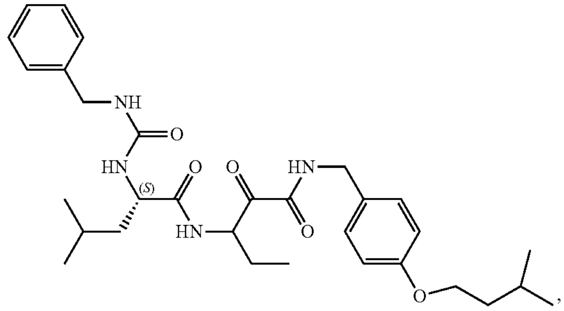
,
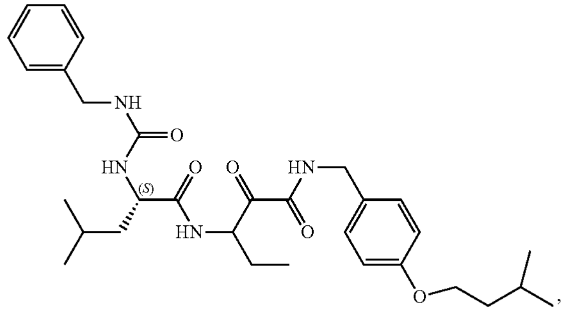
,
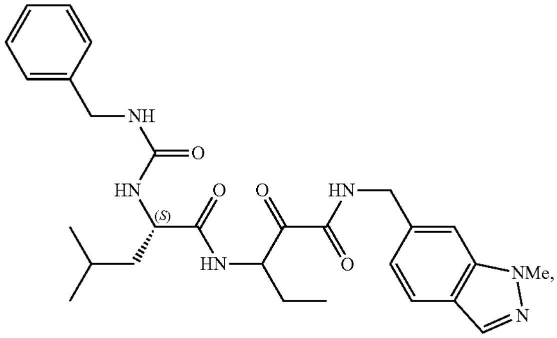

-continued
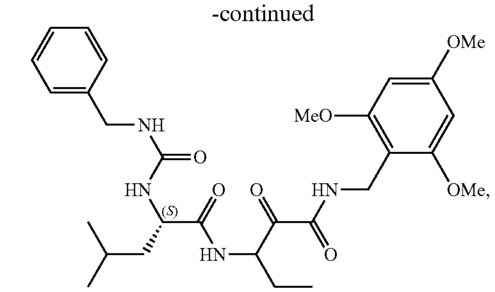
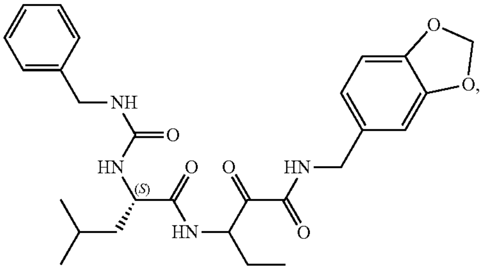
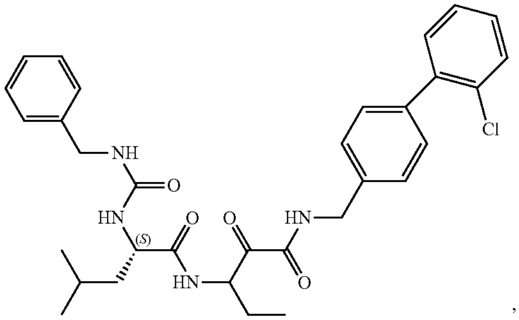
,
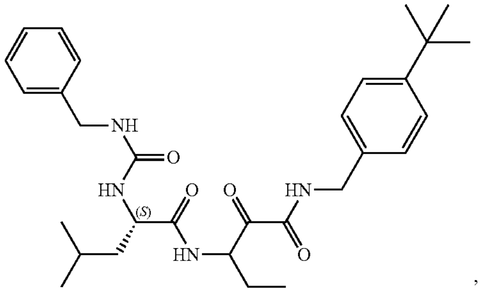
,
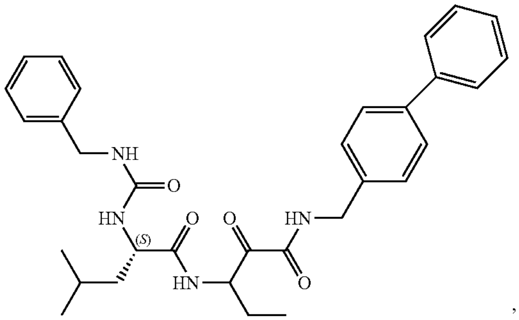
,
-continued
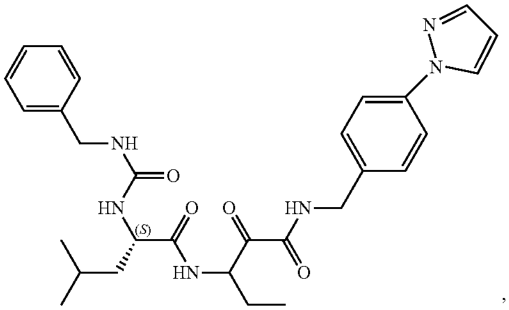
,
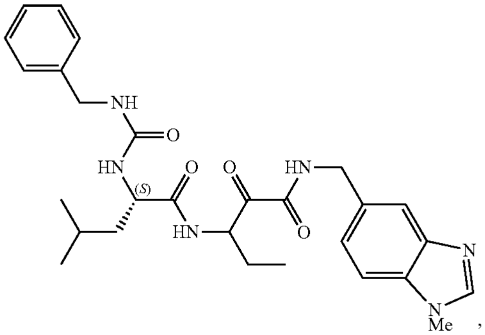
,
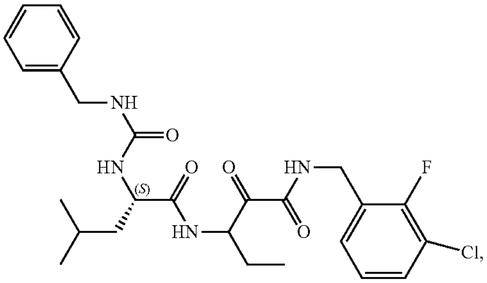
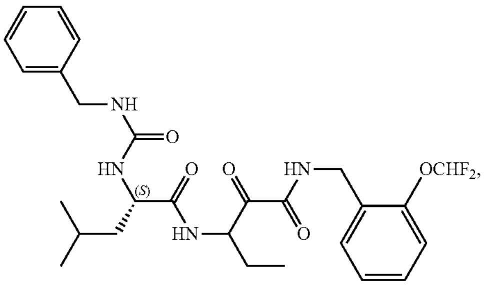
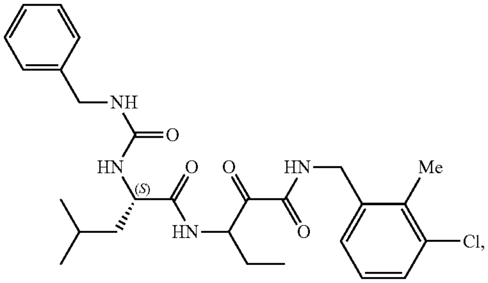

-continued
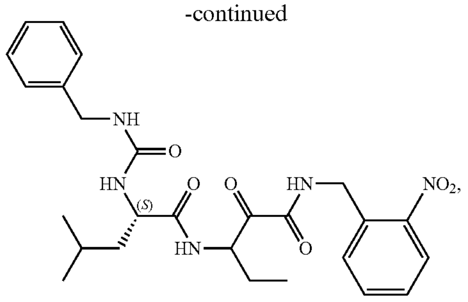
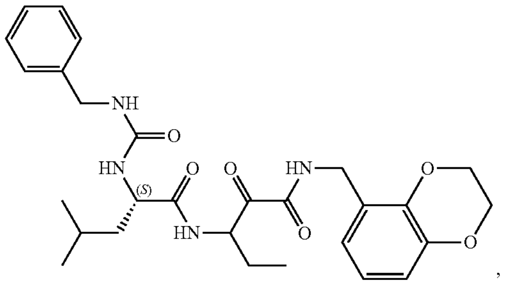
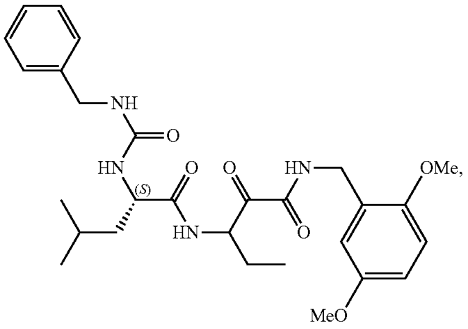
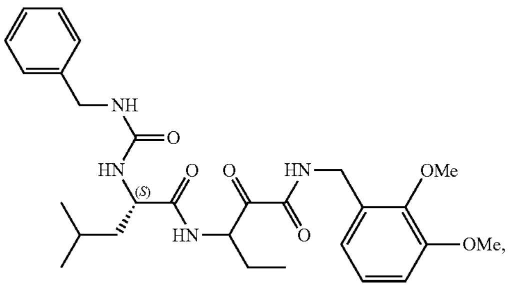
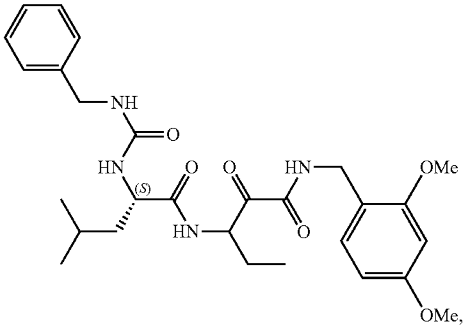
-continued
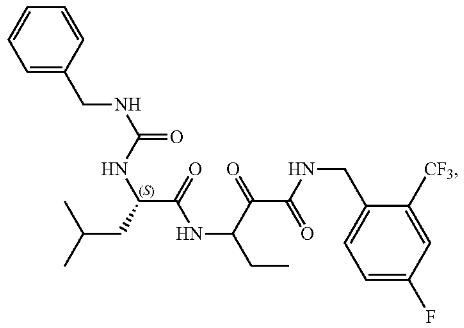
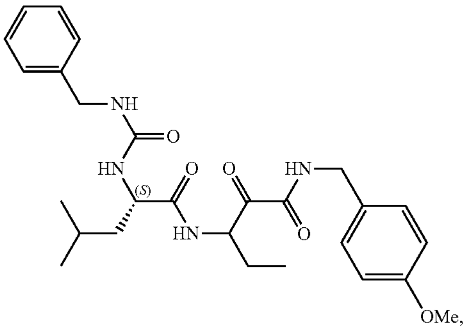
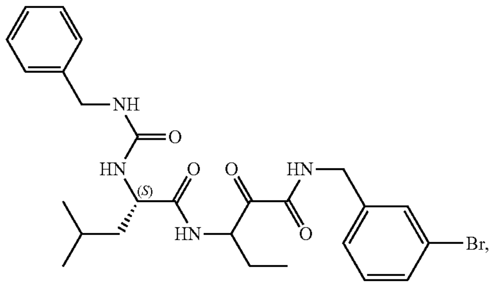
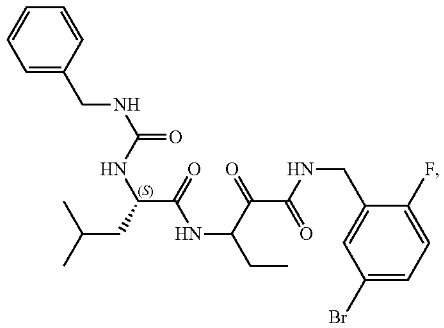
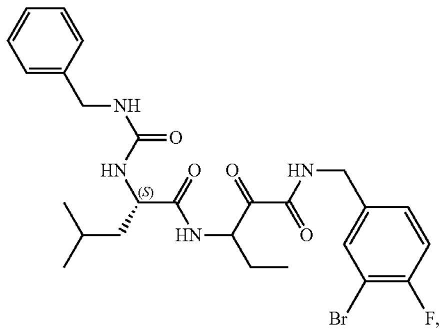

-continued
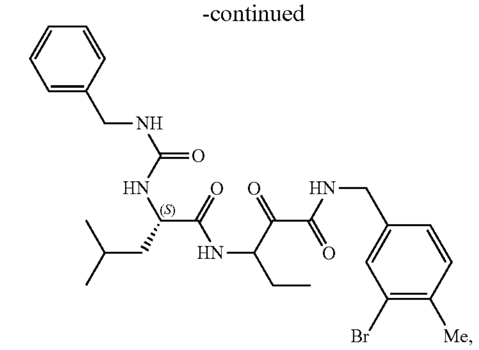
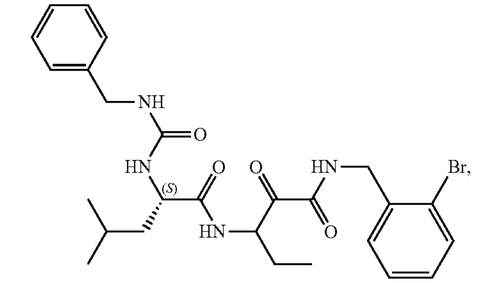
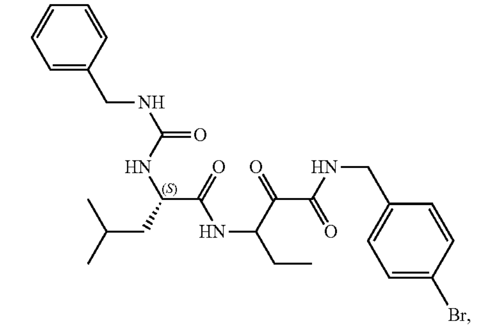
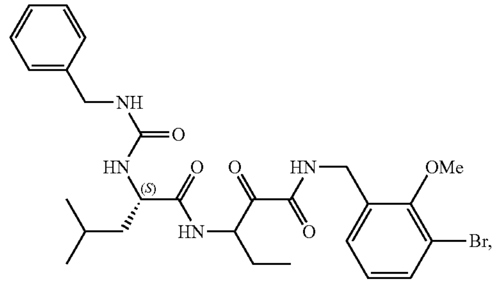
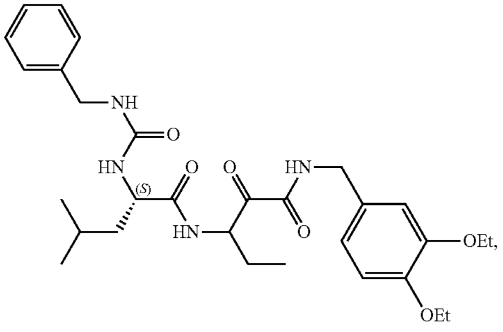
-continued
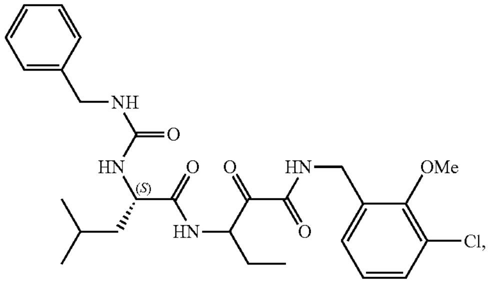
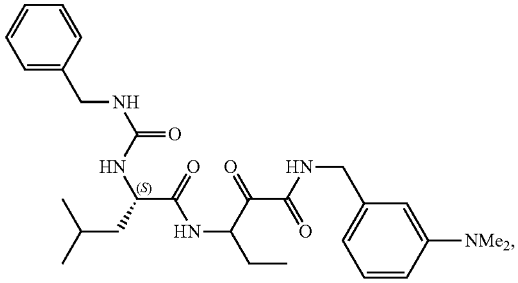
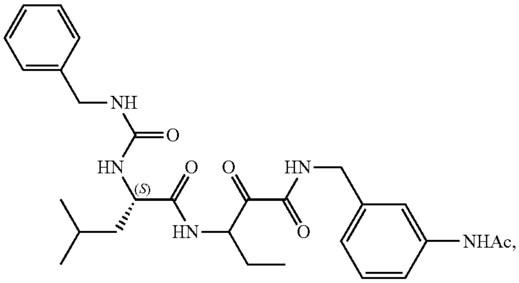
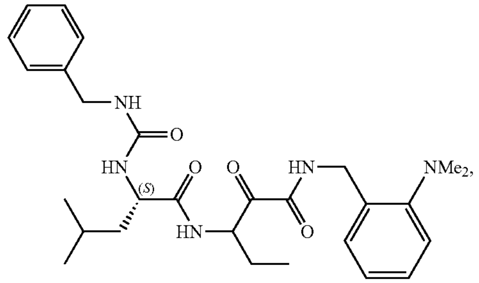
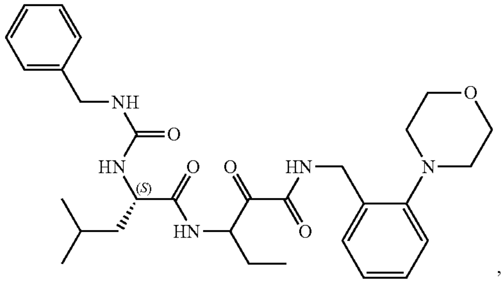
, or
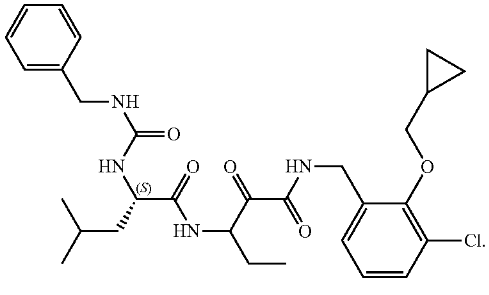

In a certain embodiment, in Formula (XI-a), n is 1 to 2. For example, the compound is
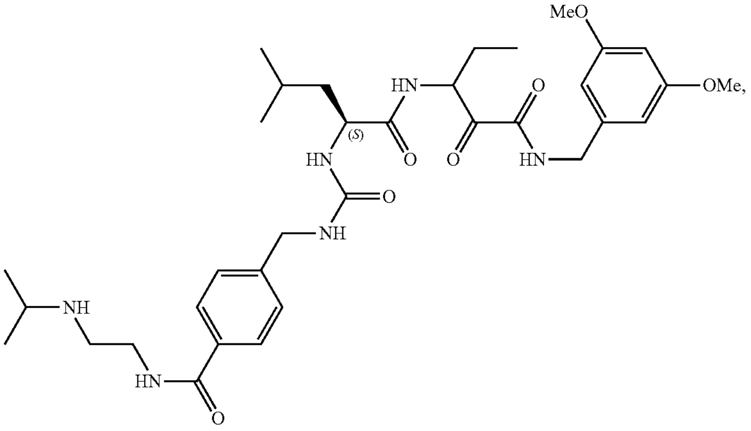
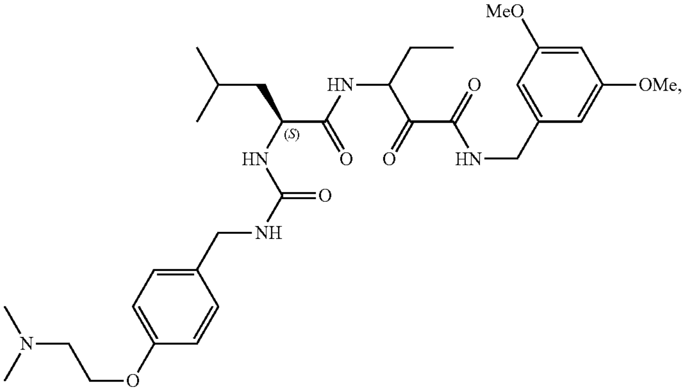
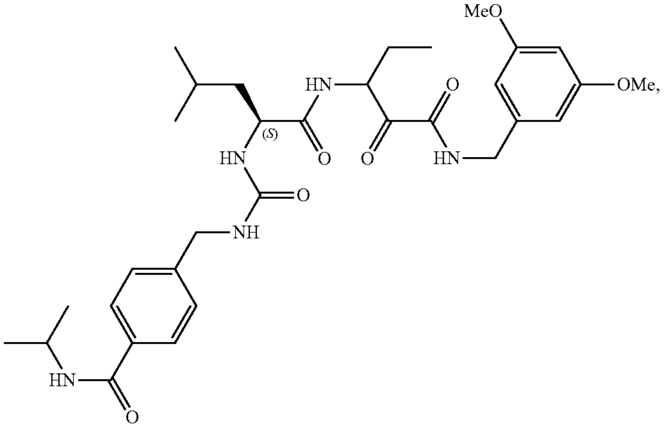
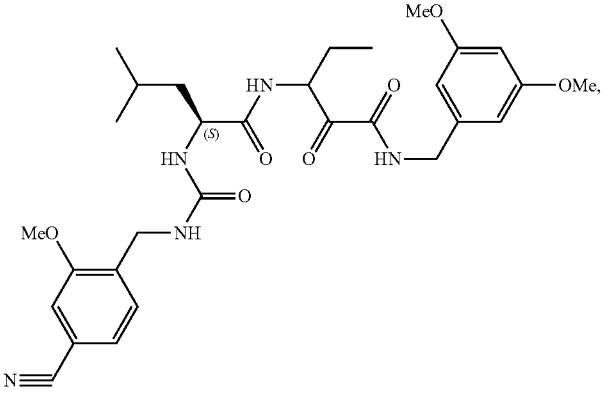

-continued
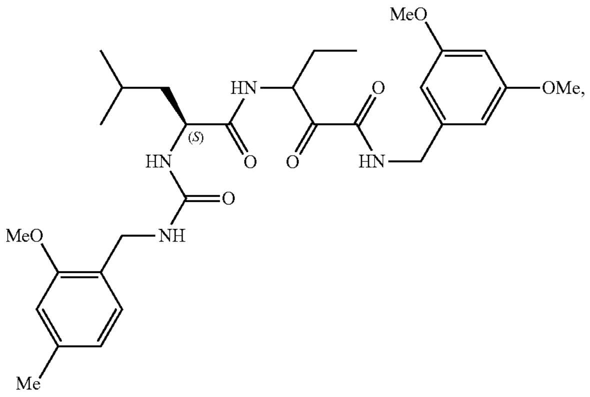
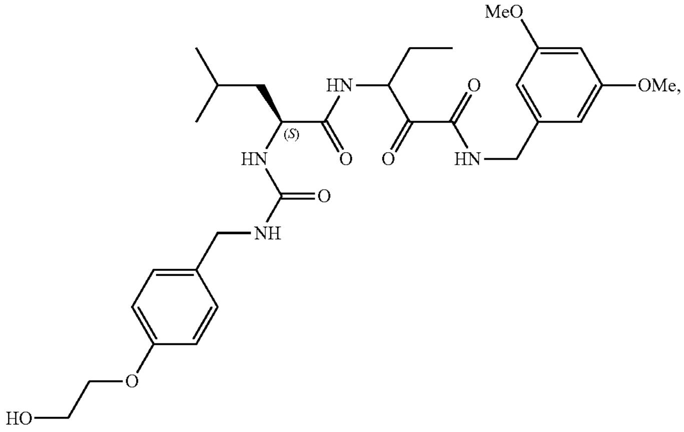
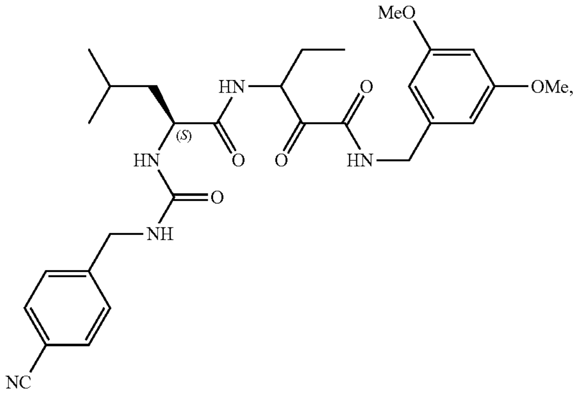
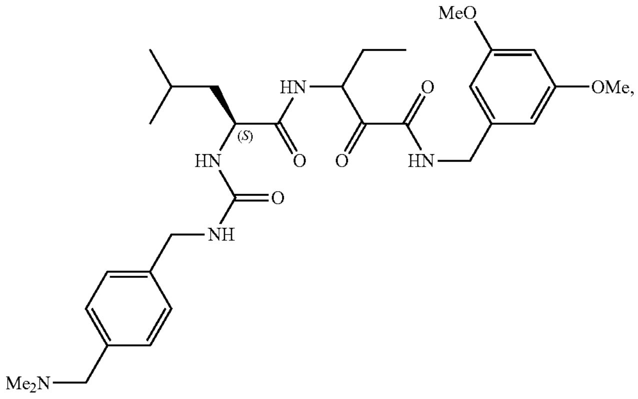

-continued
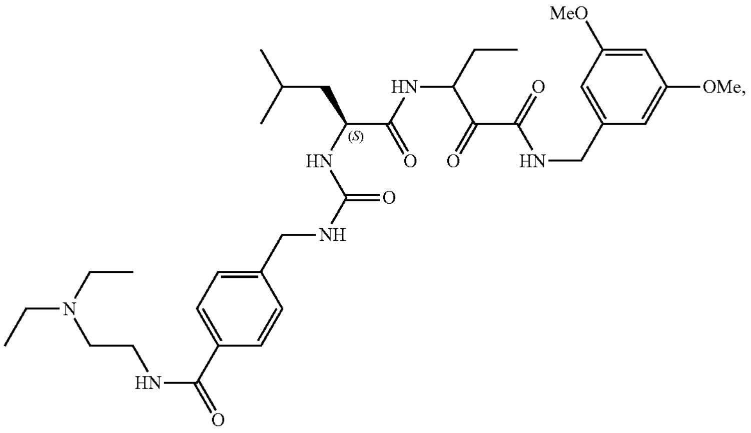
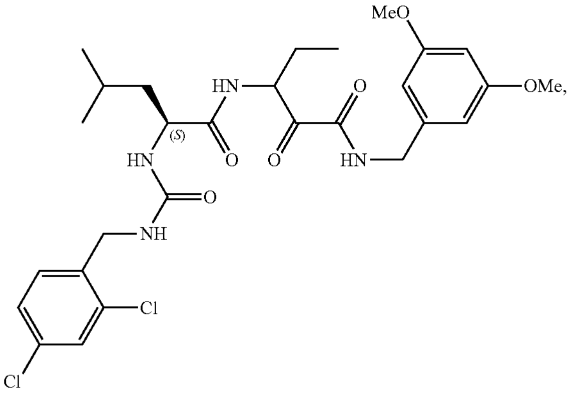
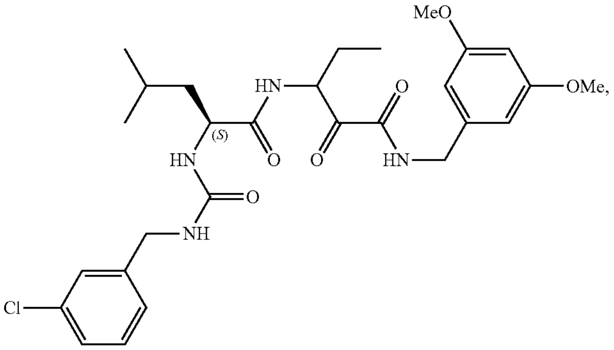
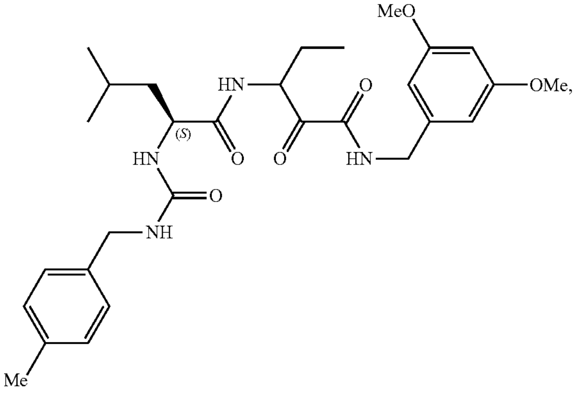

-continued
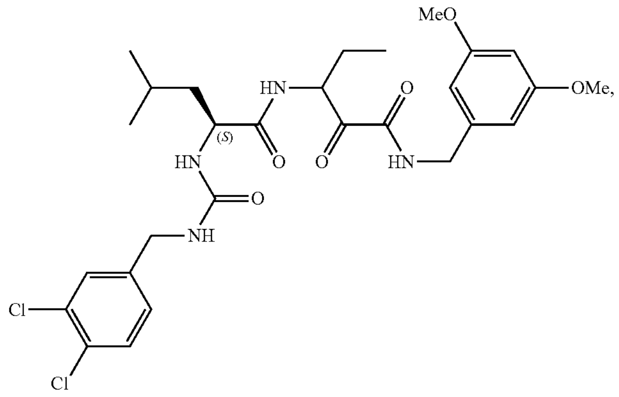
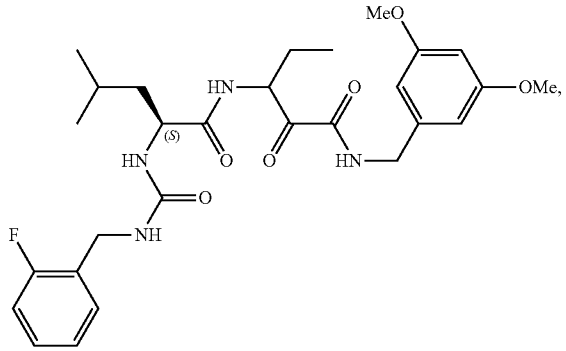
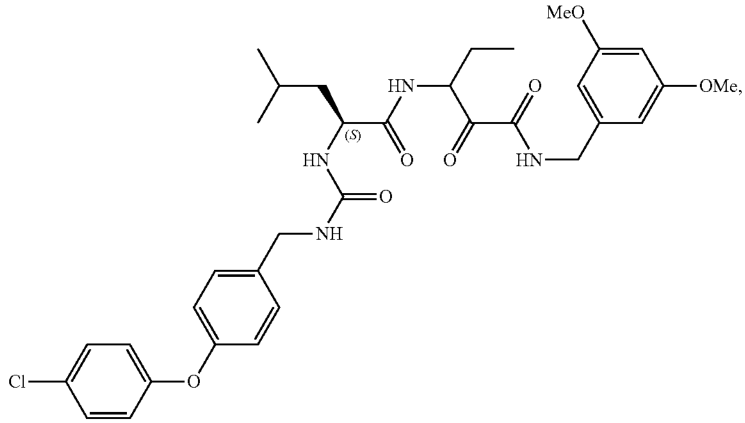
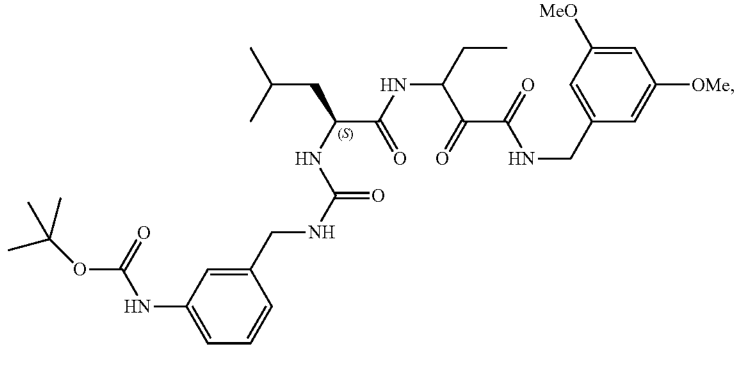

-continued
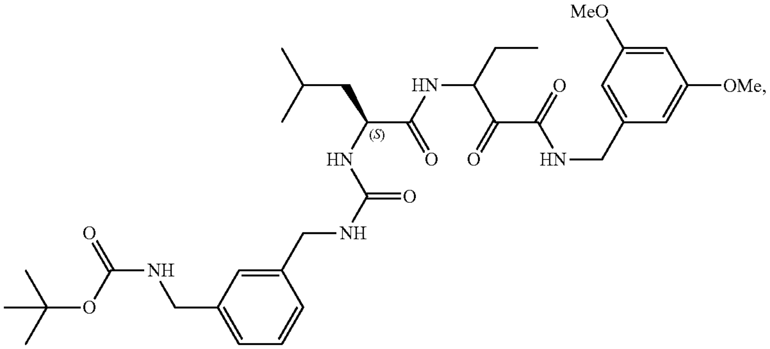
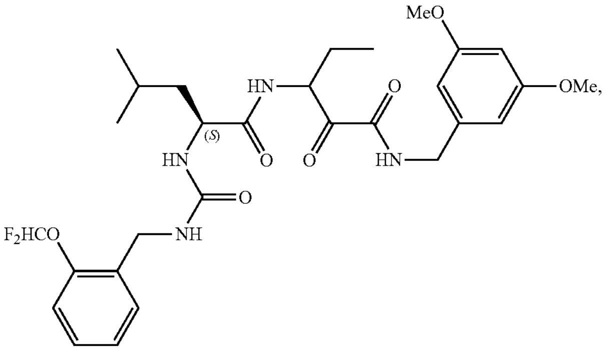
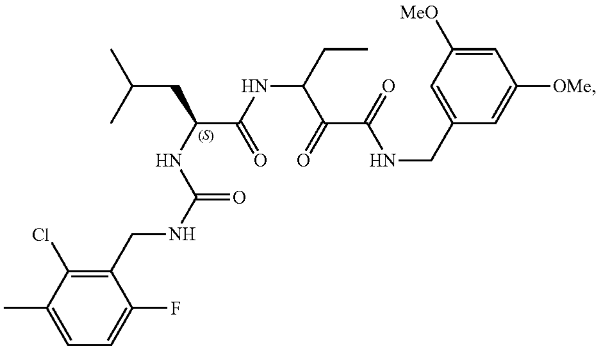
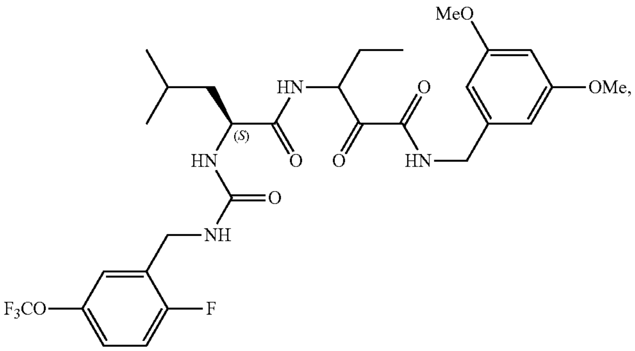

-continued
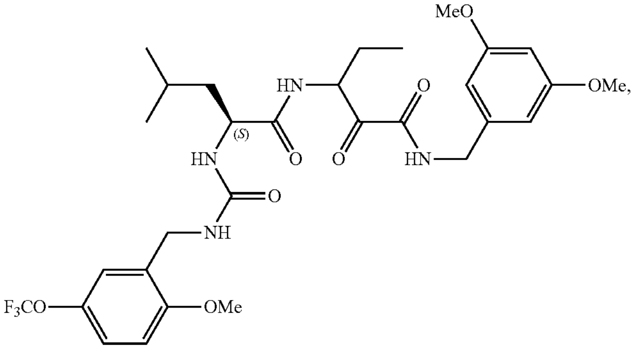
,
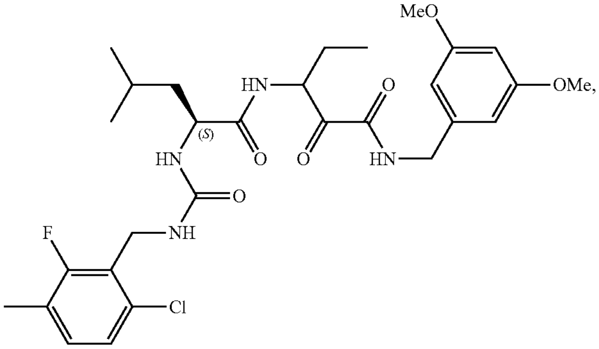
,
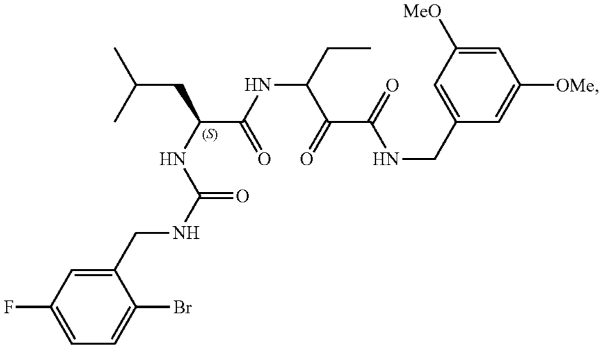
,
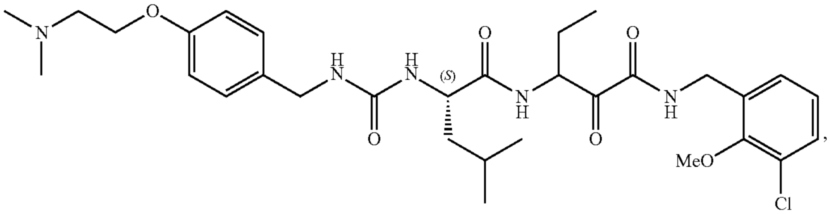
,
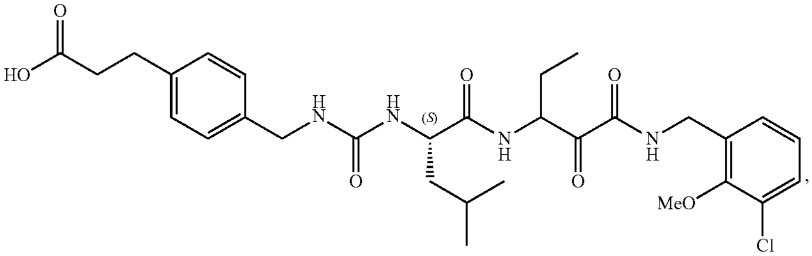
,
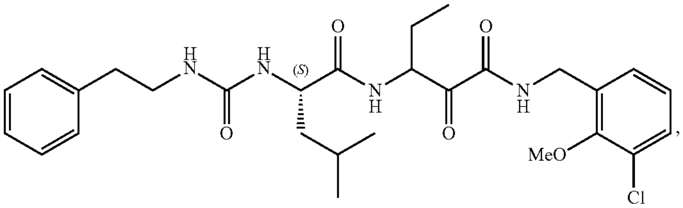
, or -continued
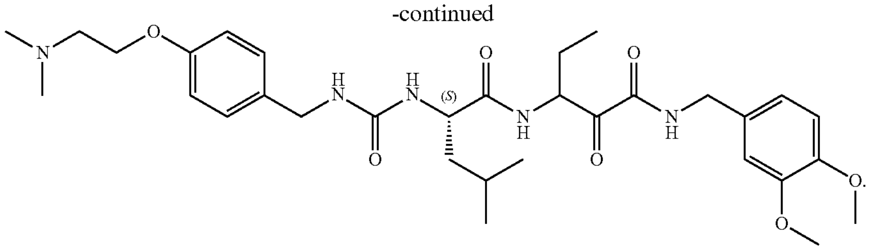
The compound may have a Formula (XI-b).
(XI-b)
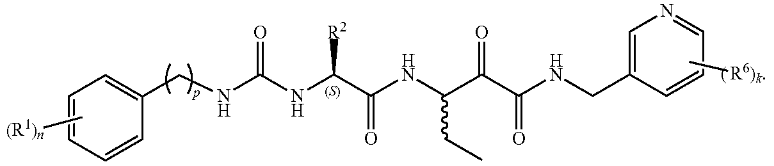
$R^1$, p, $R^2$, and $R^6$ are as defined above. n is an integer of 0 to 5 and k is an integer of 0 to 4.
In a certain embodiment, the compound of Formula (XI-b) may be a racemate including
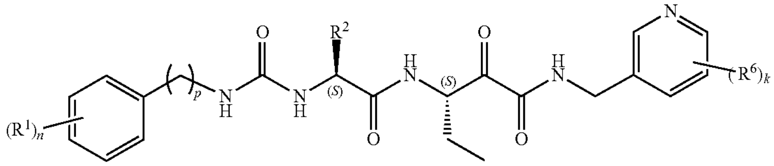
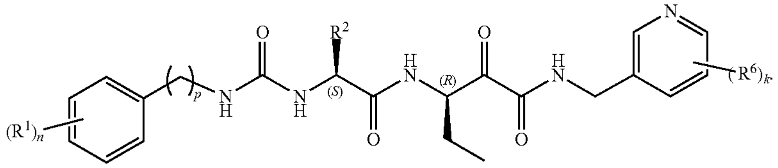
$R^1$, n, k, p, $R^2$, and $R^6$ are as defined above.
For example, the compound is
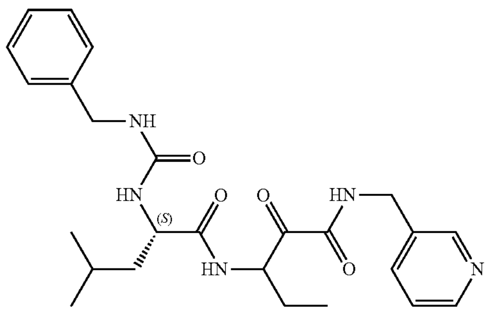
or
-continued
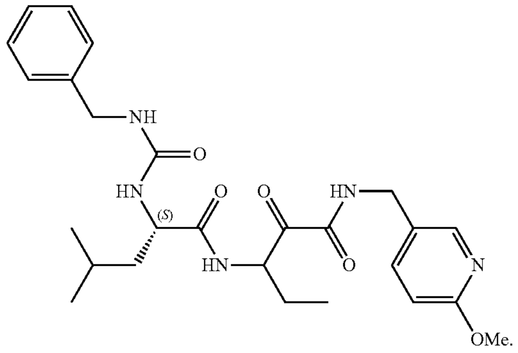
The compound may have a Formula (XI-c).

(XI-c)

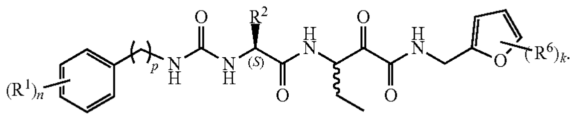

$R^1$, n, p, $R^2$, and $R^6$ are as defined above. k is an integer of 0 to 3.

In a certain embodiment, the compound of Formula (XI-c) may be a racemate including

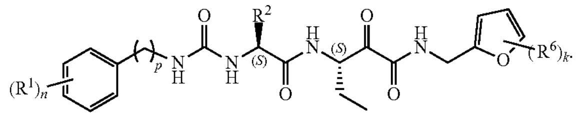

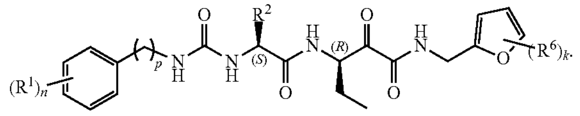

$R^1$, n, k, p, $R^2$, and $R^6$ are as defined above.

For example, the compound is

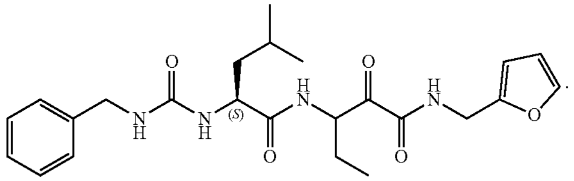

The compound may have a Formula (XI-d), (XI-d)

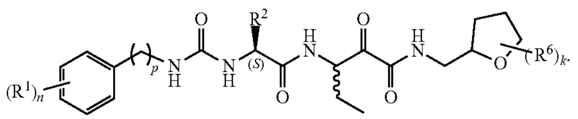

$R^1$, n, p, $R^2$, and $R^6$ are as defined above. k is an integer of 0 to 6.

In a certain embodiment, the compound of Formula (XI-d) may be a racemate including

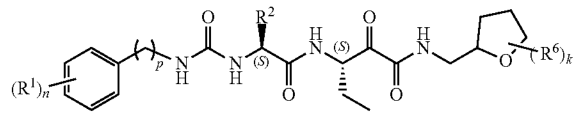

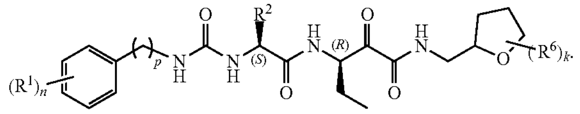

$R^1$, n, k, p, $R^2$, and $R^6$ are as defined above.

For example, the compound is

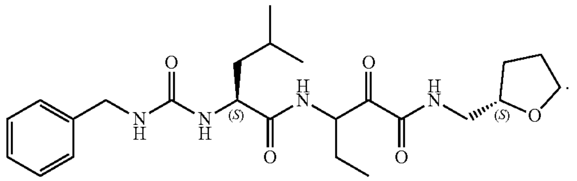

In a certain embodiment, $L^1$ is a bond, methylene, or ethylene and A is $C_{1-4}$ alkyl, cycloalkyl (e.g., adamantyl, cyclopropyl, cyclobutyl, cyclopentyl, or cyclohexyl), or heterocycloalkyl (e.g., 5 to 12 membered heterocycloalkylene).

In a certain embodiment, the $-L^1-A-R^1$ is

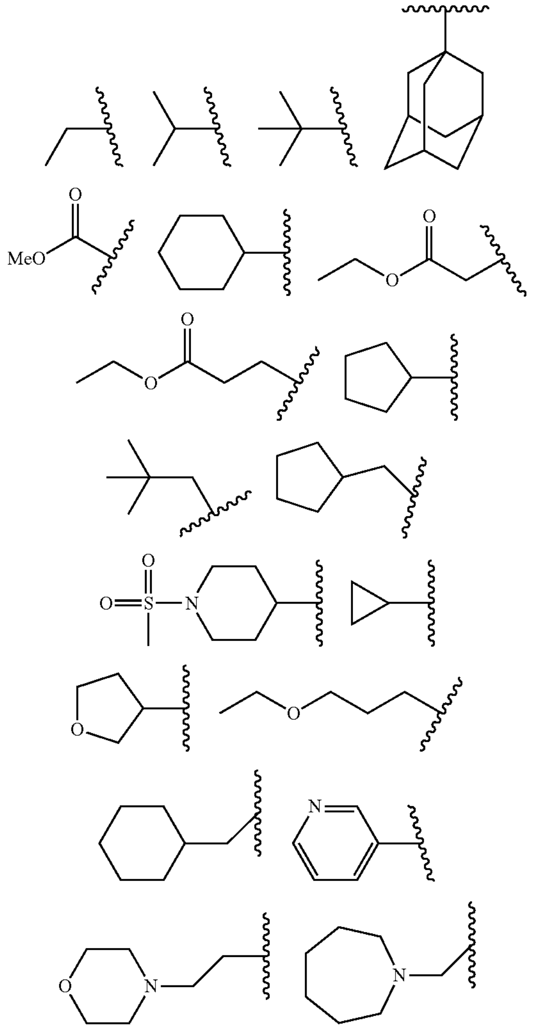

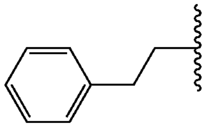

or

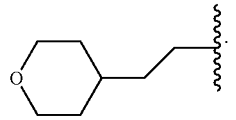

.

For example, the compound is
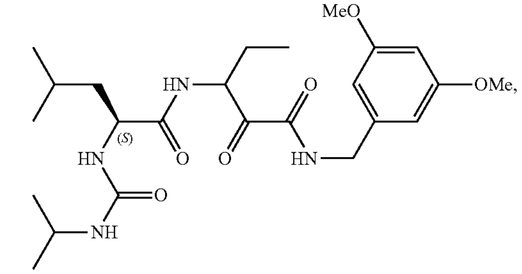
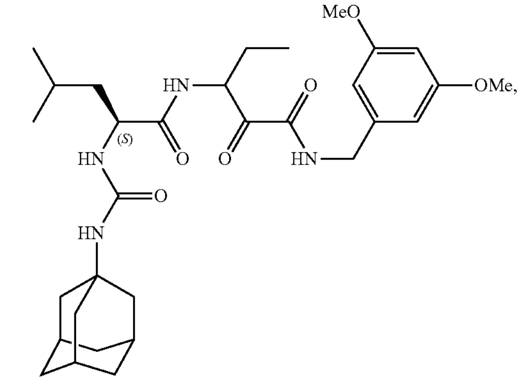
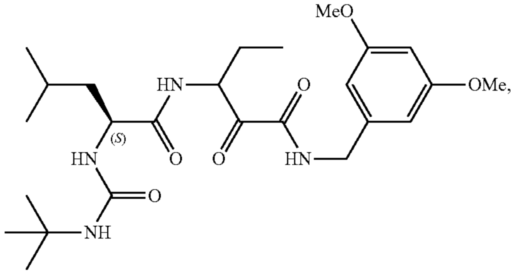
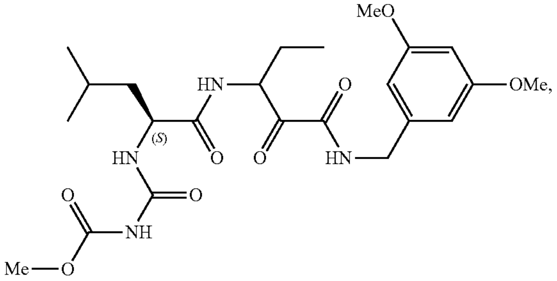
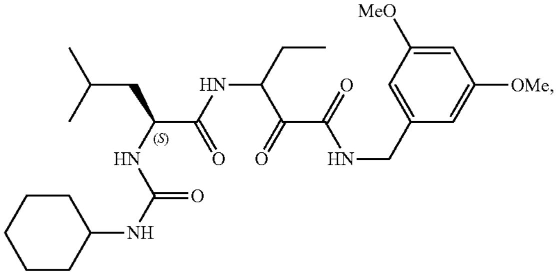
-continued
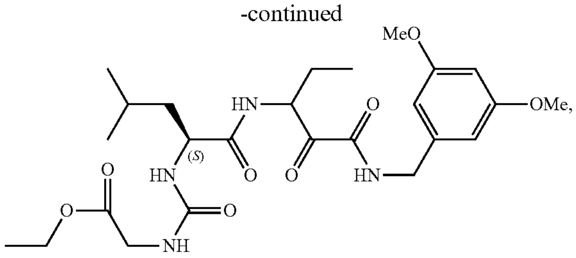
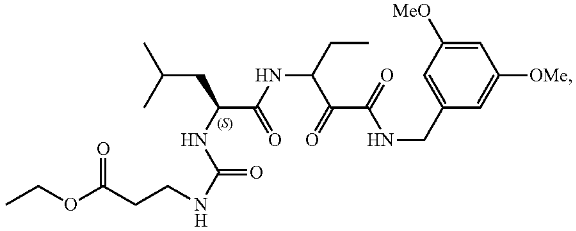
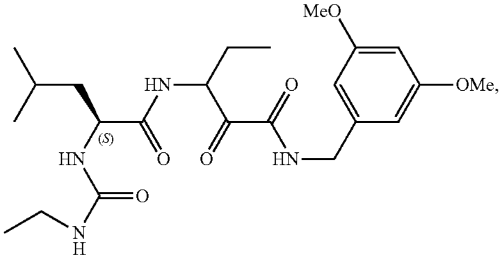
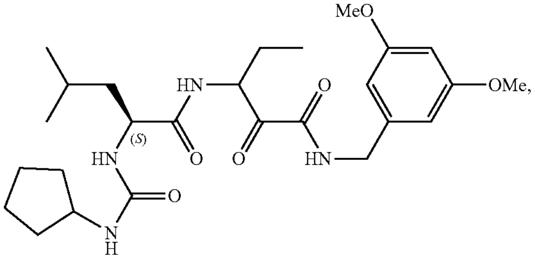
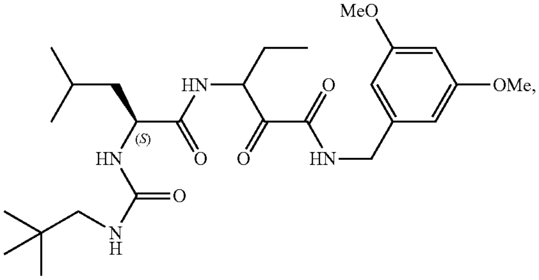
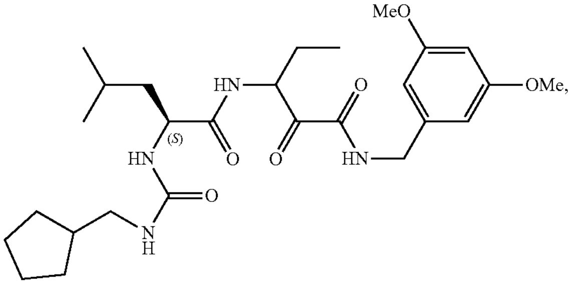

-continued
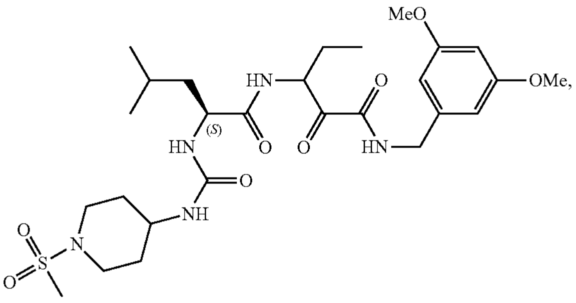
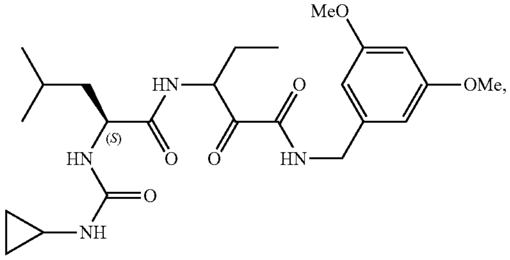
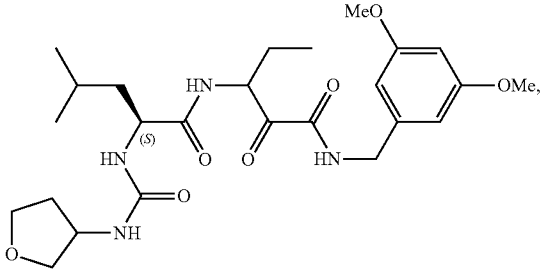
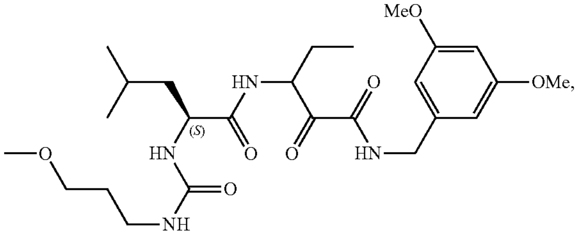
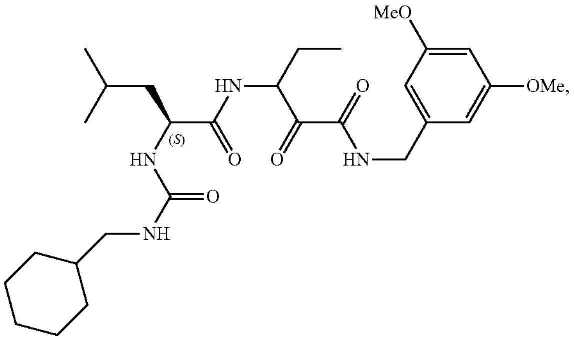
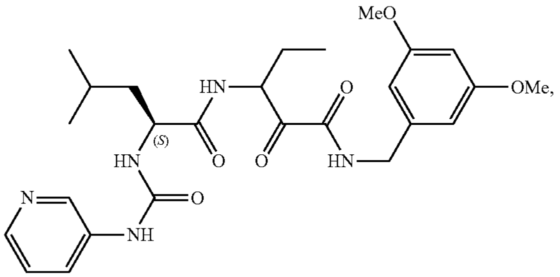
-continued
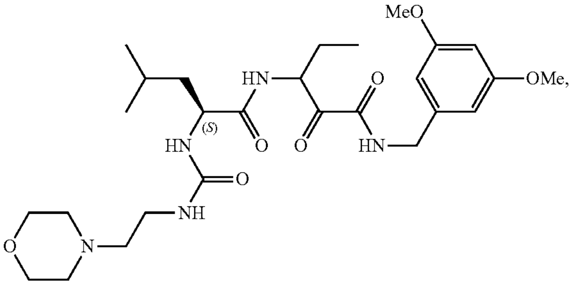
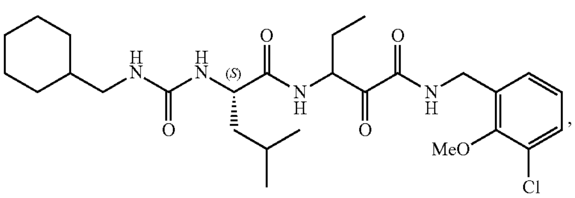
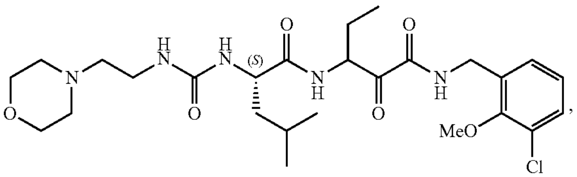
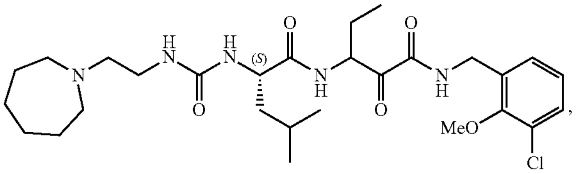
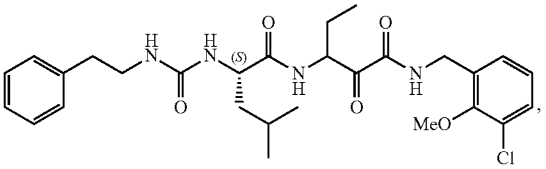
or
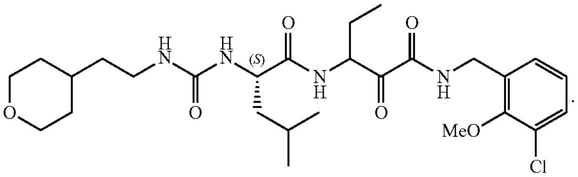
In a certain embodiment, $-L^2-B$ is
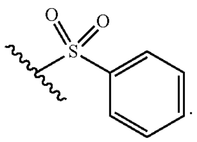 [SMILES: *S(=O)(=O)c1ccccc1]
In a certain embodiment, the compound has a Formula (XII).

(XII)

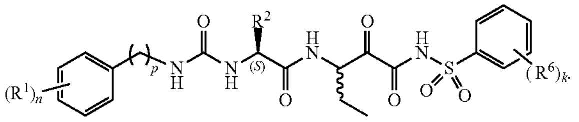

$R^1$, p, $R^2$, and $R^6$ are as defined above. n is an integer of 0 to 5 and k is an integer of 0 to 5.

In a certain embodiment, the compound of Formula (XII) may be a racemate including

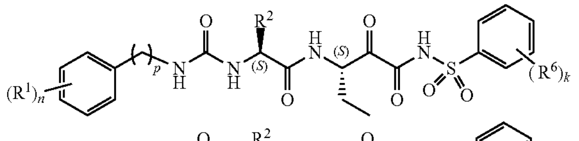

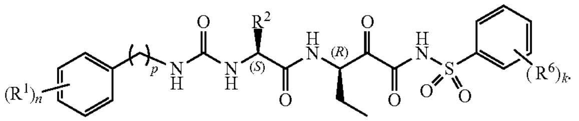

$R^1$, n, p, k, $R^2$, and $R^6$ are as defined above.

In a certain embodiment, two $R^6$ together with atoms attached thereto are joined to form a cycloalkyl, or heterocycloalkyl.

The compound of Formula (XII) may have the structure of

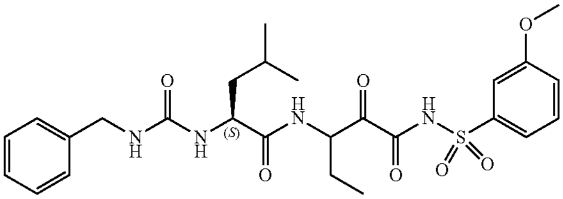

,

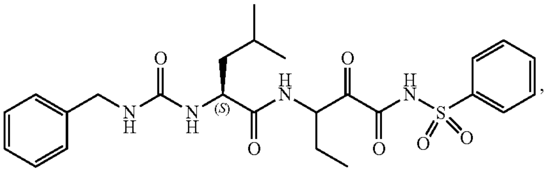

, or

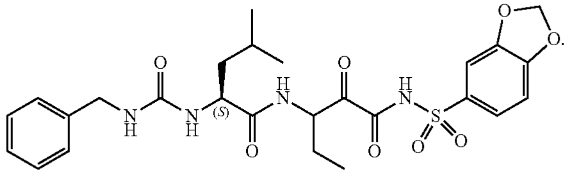

In an aspect, the compound has a Formula (XIII), (XIII)

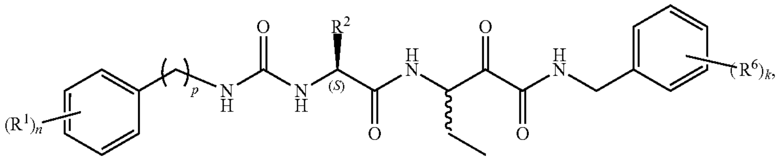

wherein:

Each $R^1$ is independently $C_1$-$C_6$ alkyl, halogen, cyano, nitro, $C_1$-$C_6$ alkoxy, aryl, heterocycloaryl, heterocycloalkyl, —$C(O)(CH_2)_mN(R^a)(R^b)$, —$O(CH_2)_mN(R^a)(R^b)$, —$CONH(CH_2)_mN(R^a)(R^b)$, —$C(O)NH$—$CH(R^c)(R^d)$, —$C(O)OCH(R^c)(R^d)$, —$(CH_2)_mN(R^a)(R^b)$, —$(CH_2)_mN(R^a)C(O)R^b$, —$(CH_2)_mN(R^a)C(O)OR^b$, —$O(CH_2)_mR^c$, —$O(CH_2)_mOH$, —$S(O)_2R^b$, or —O(Ph)X;

$R^2$ is unsubstituted $C_1$-$C_6$ alkyl;

Each $R^6$ is independently $C_1$-$C_6$ alkyl, halogen, cyano, nitro, $C_1$-$C_6$ alkoxy, aryl, heterocycloaryl, heterocycloalkyl —$C(O)(CH_2)_mN(R^a)(R^b)$, —$O(CH_2)_mN(R^a)(R^b)$, —$CONH(CH_2)_mN(R^a)(R^b)$, —$C(O)NH$—$CH(R^c)(R^d)$, —$C(O)OCH(R^c)(R^d)$, —$(CH_2)_mN(R^a)(R^b)$, —$(CH_2)_mN(R^a)C(O)R^b$, —$(CH_2)_mN(R^a)C(O)OR^b$, —$O(CH_2)_mR^c$, —$O(CH_2)_mOH$, or —O(Ph)X;

Two $R^6$ together with atoms attached thereto are optionally joined to form a cycloalkyl, or heterocycloalkyl;

$R^a$, $R^b$, $R^c$, and $R^d$ are independently hydrogen, $C_1$-$C_6$ alkyl that may be optionally substituted with halogen, —OH, amine, or unsubstituted $C_{3-6}$ cycloalkyl;

X is halogen;

n is independently an integer from 0 to 5;

m is independently an integer from 0 to 6;

k is independently an integer from 0 to 5;

p is independently an integer from 0 to 6;

and pharmaceutically acceptable salts thereof.

In a certain embodiment, the compound of Formula (XIII) may be a racemate including

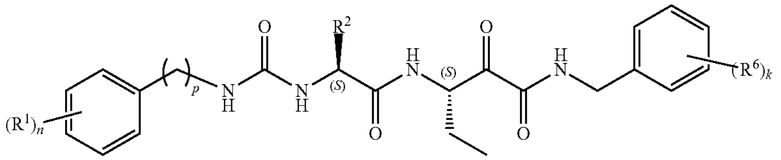

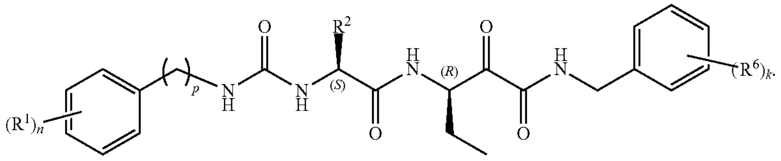

$R^1$, n, k, p, $R^2$, and $R^6$ are as defined above.

For example, the compound is

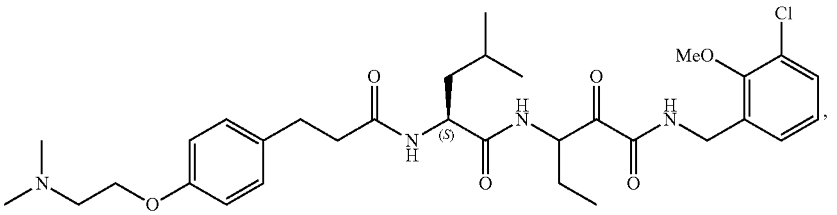

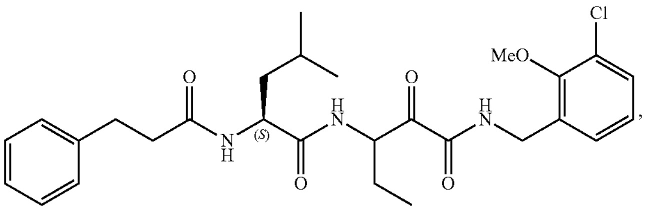

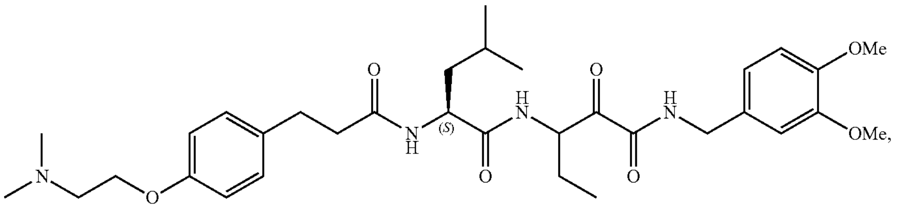

or

-continued

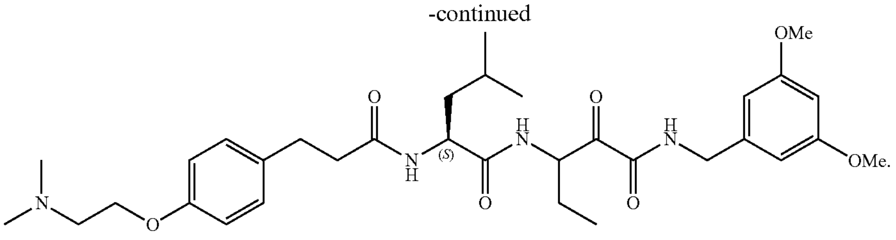

In an aspect, the compound may have a Formula (XIV), (XIV)

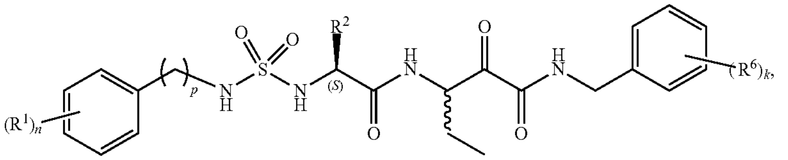

wherein:

Each $R^1$ is independently $C_1$-$C_6$ alkyl, halogen, cyano, nitro, $C_1$-$C_6$ alkoxy, aryl, heterocycloaryl, heterocycloalkyl, —$C(O)(CH_2)_mN(R^a)(R^b)$, —$O(CH_2)_mN(R^a)(R^b)$, —$CONH(CH_2)_mN(R^a)(R^b)$, —$C(O)NH$—$CH(R^c)(R^d)$, —$C(O)OCH(R^c)(R^d)$, —$(CH_2)_mN(R^a)(R^b)$, —$(CH_2)_mN(R^a)C(O)R^b$, —$(CH_2)_mN(R^a)C(O)OR^b$, —$O(CH_2)_mR^c$, —$O(CH_2)_mOH$, —$S(O)_2R^b$, or —O(Ph)X;

$R^2$ is unsubstituted $C_1$-$C_6$ alkyl;

Each $R^6$ is independently $C_1$-$C_6$ alkyl, halogen, cyano, nitro, $C_1$-$C_6$ alkoxy, aryl, heterocycloaryl, heterocycloalkyl —$C(O)(CH_2)_mN(R^a)(R^b)$, —$O(CH_2)_mN(R^a)(R^b)$, —$CONH(CH_2)_mN(R^a)(R^b)$, —$C(O)NH$—$CH(R^c)(R^d)$, —$C(O)OCH(R^c)(R^d)$, —$(CH_2)_mN(R^a)(R^b)$, —$(CH_2)_mN(R^a)C(O)R^b$, —$(CH_2)_mN(R^a)C(O)OR^b$, —$O(CH_2)_mR^c$, —$O(CH_2)_mOH$, or —O(Ph)X;

Two $R^6$ together with atoms attached thereto are optionally joined to form a cycloalkyl, or heterocycloalkyl;

$R^a$, $R^b$, $R^c$, and $R^d$ are independently hydrogen, $C_1$-$C_6$ alkyl that may be optionally substituted with halogen, —OH, amine, or unsubstituted $C_{3-6}$ cycloalkyl;

X is halogen;

n is independently an integer from 0 to 5;

m is independently an integer from 0 to 6;

k is independently an integer from 0 to 5;

p is independently an integer from 0 to 6;

and pharmaceutically acceptable salts thereof.

In a certain embodiment, the compound of Formula (XIV) may be a racemate including

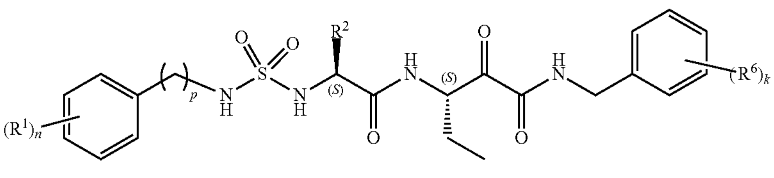

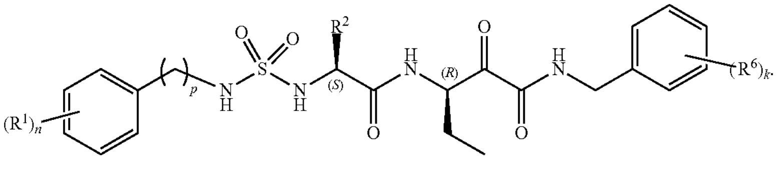

For example, the compound is

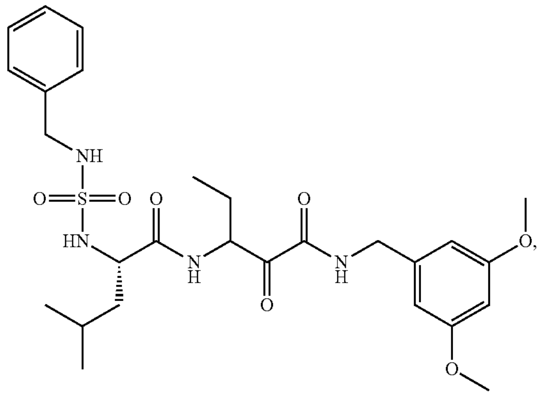

or

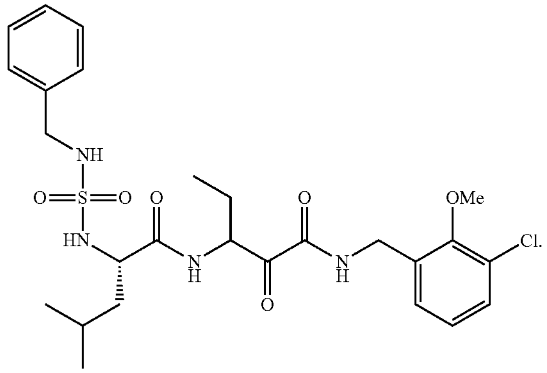

Preferred compound, NA184, has the following structure.

(NA184)

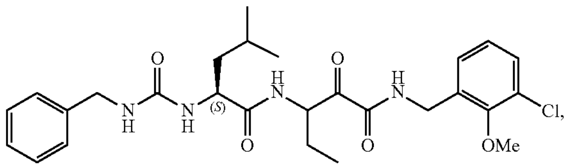

(NA184B)

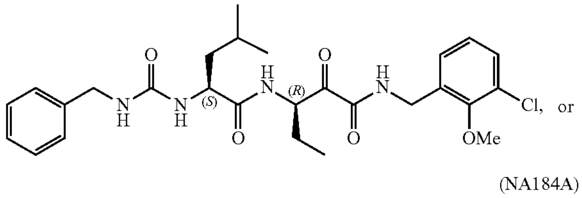

or (NA184A)

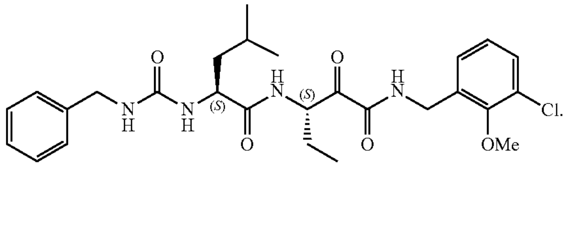

The compound may be a racemate including:

(NA184B)

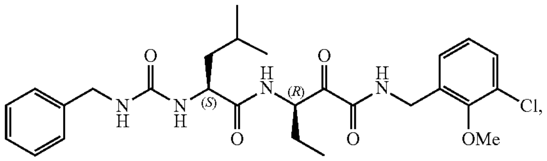

or (NA184A)

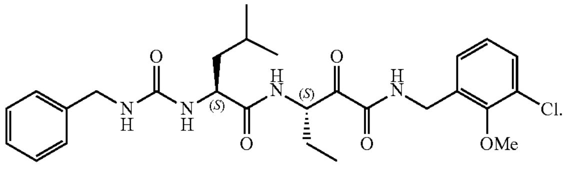

Particularly preferred compound, NA184, is S—S isomer having the following structure (NA184)

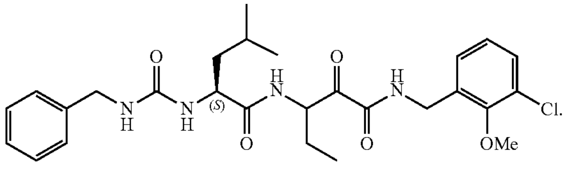

These compounds can be calpain-2 selective inhibitors. A "calpain-2 selective inhibitor" or a "selective calpain-2 inhibitor" as referred to herein is a compound with a calpain-2 inhibition constant (Ki) lower than its Ki for calpain-1. For example, a calpain-2 selective inhibitor is a compound with a Ki for calpain-2 that is 2-fold to 10-fold lower than its Ki for calpain-1. Preferably, a calpain-2 selective inhibitor is a compound with an $IC_{50}$ value for calpain-2 that is 10-50-fold lower than its $IC_{50}$ for calpain-1 in an in situ assay. For example, $IC_{50}$ values for NA112 on the activity of in situ calpain-1 and calpain-2 activities were measured (Wang et al., 2014). The selectivity of NA112 for calpain-2, measured as a ratio of $IC_{50}$ calpain-1/$IC_{50}$ calpain-2 was about 13.

Compounds of the invention possess asymmetric carbon atoms (optical or chiral centers); the enantiomers, racemates, stereoisometric forms that may be defined, in terms of absolute stereochemistry, as (R)- or (S)-isomers, and individual isomers are encompassed within the scope of the present invention. The present invention is meant to include compounds in racemic and optically pure forms as discussed above. Optically active (R)- and (S)-isomers maybe prepared using chiral synthons or chiral reagents or resolved using conventional techniques.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

"Alkyl" refers to a saturated, straight or branched hydrocarbon chain radical consisting solely of carbon and hydrogen atoms, having from one to twelve carbon atoms ($C_1$-$C_{12}$ alkyl), from one to eight carbon atoms ($C_1$-$C_8$ alkyl) or from one to six carbon atoms ($C_1$-$C_6$ alkyl), and which is attached to the rest of the molecule by a single bond. Exemplary alkyl groups include methyl, ethyl, n-propyl, 1-methylethyl (iso-propyl), n-butyl, n-pentyl, 1,1-dimethylethyl (t-butyl), 3-methylhexyl, 2-methylhexyl, and the like.

"Alkylene" or "alkylene chain" refers to a straight or branched divalent hydrocarbon (alkyl) chain linking the rest of the molecule to a radical group, consisting solely of carbon and hydrogen, respectively. Alkylenes can have from one to twelve carbon atoms, e.g., methylene, ethylene, propylene, n-butylene, and the like. The alkylene chain is attached to the rest of the molecule through a single or double bond. The points of attachment of the alkylene chain to the rest of the molecule can be through one carbon or any two carbons within the chain. "Optionally substituted alkylene" refers to alkylene or substituted alkylene.

"Alkoxy" refers to a radical of the formula —$OR^a$ where $R^a$ is an alkyl having the indicated number of carbon atoms as defined above. Examples of alkoxy groups include without limitation —O-methyl (methoxy), —O-ethyl (ethoxy), —O-propyl (propoxy), —O-isopropyl (iso propoxy) and the like.

"Cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

"Carbocyclic aryl" or "cycloalkyl" refers to a hydrocarbon ring system radical comprising hydrogen, 6 to 18 carbon atoms and at least one aromatic ring, but without any hetero (N, O or S) ring members in the aromatic ring. Exemplary carbocyclic aryls are hydrocarbon ring system radical comprising hydrogen and 6 to 9 carbon atoms and at least one aromatic ring; hydrocarbon ring system radical comprising hydrogen and 9 to 12 carbon atoms and at least one aromatic ring; hydrocarbon ring system radical comprising hydrogen and 12 to 15 carbon atoms and at least one aromatic ring; or hydrocarbon ring system radical comprising hydrogen and 15 to 18 carbon atoms and at least one aromatic ring. For purposes of this invention, the carbocyclic aryl radical may be a monocyclic, bicyclic, tricyclic or tetracyclic ring system, which may include fused or bridged ring systems. Carbocyclic aryl radicals include, but are not limited to, carbocyclic aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. "Optionally substituted carbocyclic aryl" refers to an unsubstituted carbocyclic aryl group or a substituted carbocylic aryl group.

A cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo [2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

A heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring.

The term "heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a stable 5-12 membered ring, a stable 5-10 membered ring, a stable 5-9 membered ring, a stable 5-8 membered ring, a stable 5-7 membered ring, or a stable 6 membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl).

The symbol "〰" denotes the point of attachment of a chemical moiety to the remainder of a molecule or chemical formula.

Various compounds and substituents that are "optionally substituted" or "substituted" may be suitably substituted at one or more available positions by, but not limited to, halogen (F, Cl, Br, I); nitro; hydroxy; amino; alkyl such as $C_1$-$C_4$ alkyl; alkenyl such as $C_2$-$C_8$ alkenyl; alkoxy e.g. $C_1$-$C_6$ alkxoy, alkylamino such as $C_1$-$C_8$ alkylamino; carbocyclic aryl such as phenyl, naphthyl, anthracenyl, etc; heteroaryl; and the like.

Composition, Pharmaceutical Composition and Formulation

Pharmaceutical compositions of the invention comprise NA112 or NA184, and a pharmaceutically acceptable excipient. Excipients used in pharmaceutical composition of the invention are safe and provide the appropriate delivery for the desired route of administration, of an effective amount of NA112, or NA184.

A compound of the invention, as described above, can be formulated as a pharmaceutical dosage form and administered to a subject in need of treatment, for example, a mammal, such as a human patient, in a variety of forms adapted to the chosen route of administration. The compositions of the present invention may be administered in a variety of different ways, including oral administration, intravenous injection, intramuscular injection, subcutaneous injection or by intranasal delivery. For example, the compounds may be included in solutions, suspensions and other dosage forms adapted for intravenous or subcutaneous injection.

Solutions of the compounds of the invention can be prepared in water or a physiologically acceptable buffer, optionally mixed with a nontoxic surfactant, including cyclodextrins. Dispersions can also be prepared in glycerol, liquid polyethylene glycols, triacetin, liposomes, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds of the invention which are adapted for the extemporaneous preparation of sterile injectable or infusible solutions or dispersions. In all cases, the ultimate dosage form should be sterile, fluid and stable under the conditions of manufacture and storage. The liquid carrier can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compounds of the invention in the required amount in the appropriate solvent with various of the other ingredients enumerated above, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Useful dosages of compounds of the invention can be determined by comparing their in vitro activity, and in vivo activity in animal models. Methods for the extrapolation of effective dosages in mice, and other animals, to humans are known to the art; for example, see U.S. Pat. No. 4,938,949. The amount of the compounds of the invention required for use in treatment will vary depending on the particular therapeutic agent, the composition, if there is one, that comprises the therapeutic agent, the route of administration, the nature of the condition being treated and the age and condition of the patient, and will be ultimately at the discretion of the attendant physician or clinician.

A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, considering the particulars of the case (e.g., the subject, the disease, the disease state involved, and whether the treatment is prophylactic). Treatment may involve daily or multi-daily doses of compound(s) over a period of a few days to months, or even years.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

Methods

Methods provided herein are methods for treating traumatic brain injury (TBI) in a patient. Preferred method includes administering to a patient in need thereof an effective amount of a compound or composition as described herein.

In an aspect, provided is a method of treating a subject suffering from a disorder or symptom associated with neuronal cell death, and the method includes administering to the subject an effective amount of a compound or composition as described herein.

In a certain embodiment, the subject is suffering from stroke, concussion, intracerebral hemorrhage, acute glaucoma, seizure activity and/or spinal cord injury.

In a certain embodiment, the patient has been identified as suffering or susceptible to a disorder or symptom associated with neuronal cell death and the compound is administered to the identified subject.

In a certain embodiment, the compound or composition is administered via a method selected from the group consisting of oral administration, intravitreal injection, intraocular injection, intraocular perfusion, periocular injection and sub-Tenon injection.

In a certain embodiment, the subject is a human.

EXAMPLES

Example 1: Synthesis of Compounds NA112

Compound NA112

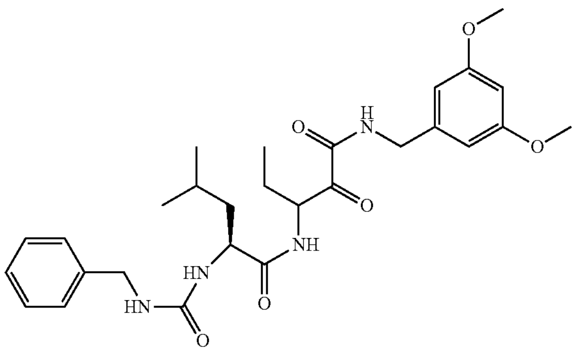

(S)-2-(3-benzylureido)-N-((S)-1-((3,5-dimethoxybenzyl)amino)-1,2-dioxopentan-3-yl)-4-methylpentanamide The compound NA110 can be synthesized according to Scheme 1.

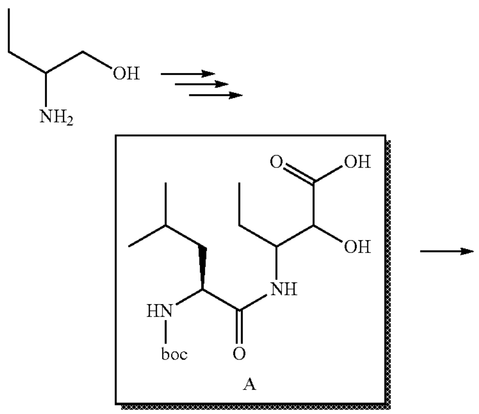

-continued

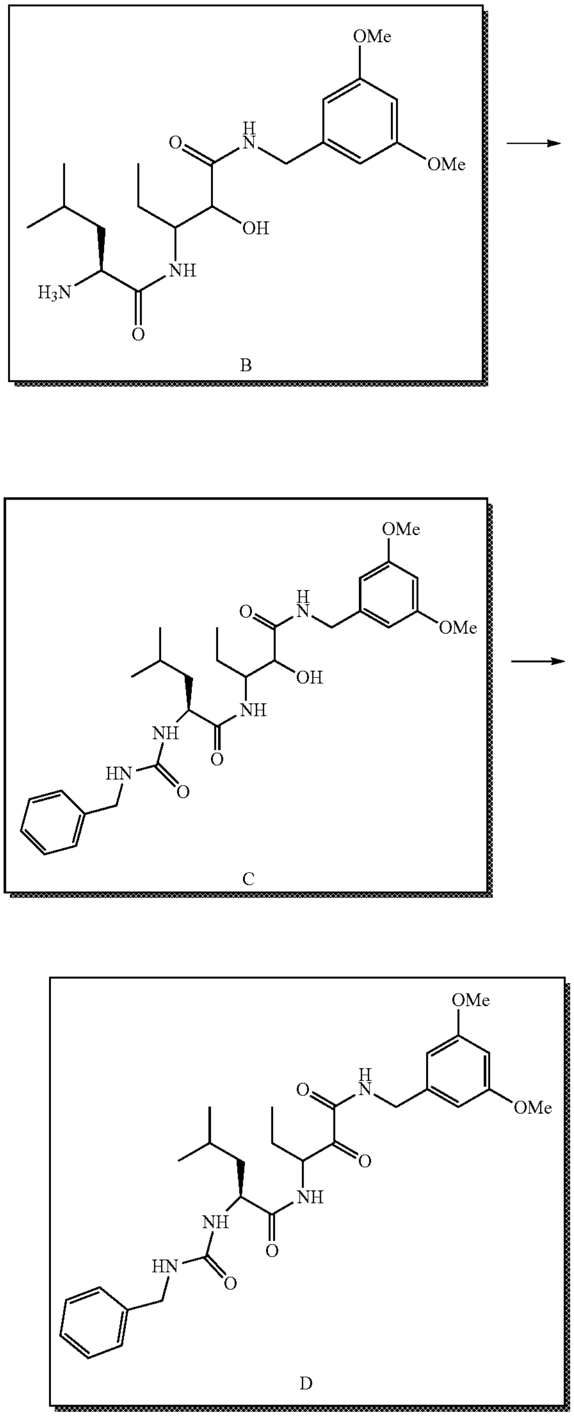

Preparation of Intermediate A

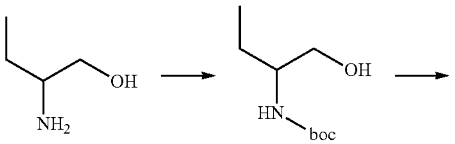

89 189

-continued

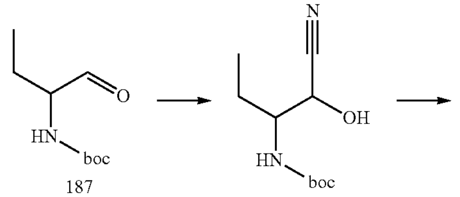

187 214

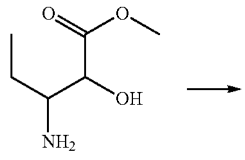

147

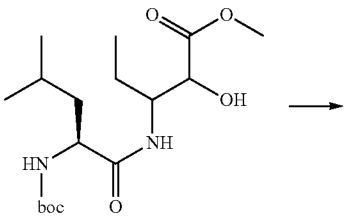

360

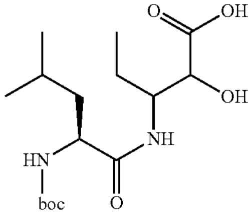

346

Intermediate A

Preparation of 3-((S)-2-((tert-butoxycarbonyl) amino)-4-methylpentanamido)-2-hydroxypentanoic acid (Intermediate A)

Intermediate A

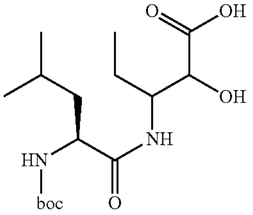

346

Step 1: Preparation of tert-butyl (1-hydroxybutan-2-yl)carbamate

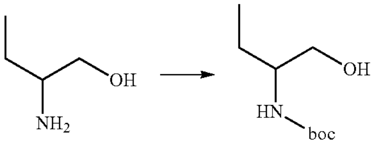

89 189

2-aminobutan-1-ol (10 g) was dissolved in chloroform (300 mL) and treated with di-tert-butyl dicarbonate (25 g) and sodium hydroxide solution (200 mL, 2M). After stirring overnight at room temperature, the solvents were removed and the residue purified by flash chromatography (hexane/ethyl acetate 0-50%) to afford tert-butyl (1-hydroxybutan-2-yl)carbamate (18 g, 86% yield).

Step 2: Preparation of tert-butyl (1-oxobutan-2-yl)carbamate

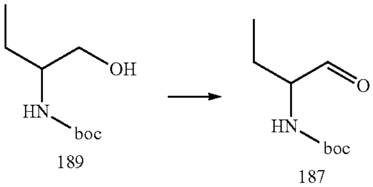

189 187

DMSO (25 ml) was added to a stirred solution of oxalyl chloride (13 ml) in $CH_2Cl_2$ (200 mL) at −78° C. After stirring for 10 min, tert-butyl (1-hydroxybutan-2-yl)carbamate (18 g) in $CH_2Cl_2$ (100 mL) was added dropwise and the resulting mixture was allowed to stir for 30 min. Then $Et_3N$ (50 ml) was added and the reaction mixture was allowed to warm to room temperature and stirred for a further 30 min. Water (200 mL) was then added, the reaction mixture was extracted with $CH_2Cl_2$ (3×100 mL), and the combined organic extracts were dried and concentrated in vacuo to give a residue which was purified by column silica gel chromatography (hexane/ethyl acetate 0-20%) to afford tert-butyl (1-oxobutan-2-yl)carbamate (10.6 g, 58%)

Step 3: Preparation of tert-butyl (1-cyano-1-hydroxybutan-2-yl)carbamate

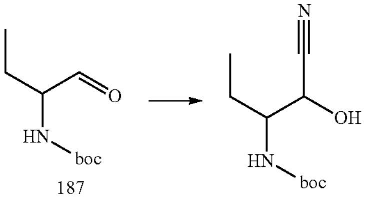

187 214

Tert-butyl (1-oxobutan-2-yl)carbamate (10.6 g) was dissolved in dioxane (200 mL) and chilled to 0° C. for 10 min, at which time $NaHSO_3$ (24 g) in water (100 ml) was added.

The reaction mixture was allowed to stir at 0° C. for 10 min and KCN (13 g) in water (100 ml) was added and the solution was stirred overnight. The reaction mixture was worked up by diluting with ethyl acetate (1 L) and washing the organic layer with three portions of saturated sodium bicarbonate (3*100 ml). The organic layer was dried over sodium sulfate, filtered and concentrated to dryness to give tert-butyl (1-cyano-1-hydroxybutan-2-yl)carbamate (9.7 g, 80%).

Step 4: Preparation of methyl 3-amino-2-hydroxypentanoate

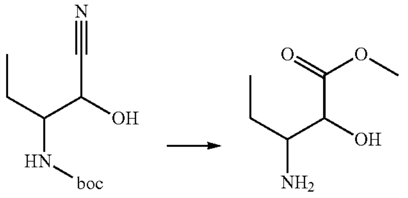

214 147

Tert-butyl (1-cyano-1-hydroxybutan-2-yl)carbamate (9.7 g) was dissolved in dry MeOH (200 ml) and HCl gas (prepared by substituting reaction H2SO4 with NaCl) was bubbled through the solution until the apparent absorption/dissolution of the gas (4-5 hours, LCMS control). Then the solution was refluxed for ~16 hours, evaporated to dryness and dried in high vacuum for overnight. The crude product (8.5 g) was used in next step without additional purification.

Step 5: Preparation of methyl 3-((S)-2-((tert-butoxycarbonyl)amino)-4-methylpentanamido)-2-hydroxypentanoate

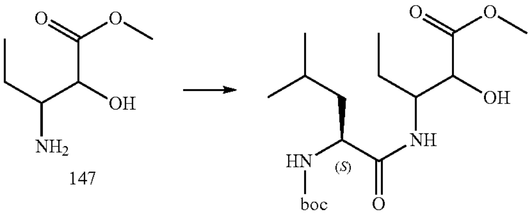

360

The crude methyl 3-amino-2-hydroxypentanoate HCl salt (8.5 g) was suspended in acetonitrile (300 mL) and treated with triethylamine (20 mL), HATU (19 g) followed by BOC-leusine hydrate (11.5 g) and the mixture stirred overnight at room temperature (LCMS control). Then the mixture was evaporated, diluted with ethyl acetate (300 ml) and washed with 0.1M aqueous HCl (2*100 ml). The organics was evaporated and crude was purified by column silica gel chromatography (hexane/EtOAc, 0 to 30%) giving a mixture of 4 diastereomers. Yield 8.6 g (52%).

Step 6: Preparation of 3-((S)-2-((tert-butoxycarbonyl)amino)-4-methylpentanamido)-2-hydroxypentanoic acid (Intermediate A)

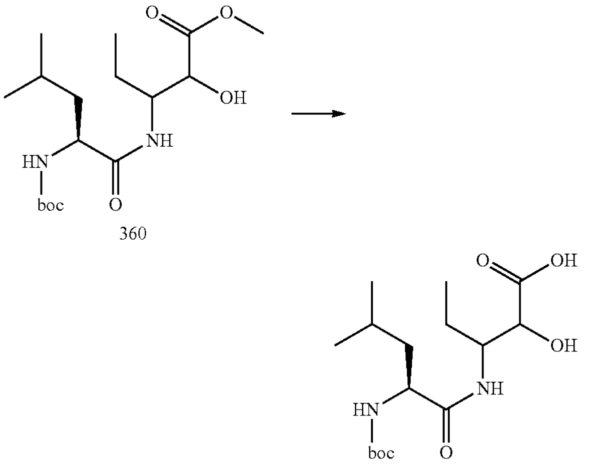

346
Intermediate A

Methyl 3-((S)-2-((tert-butoxycarbonyl)amino)-4-methylpentanamido)-2-hydroxypentanoate (8.6 g) was dissolved in a mixture of 1M NaOH (30 ml) and THE (30 ml) and stirred overnight (LCMS control). Then the solution was diluted with ethyl acetate (200 ml) and 0.5M aqueous HCL (200 ml). Organic layer was separated and aqueous was extracted with ethyl acetate (2×50 ml). The combined extracts were dried (MgSO4), filtered and evaporated to dryness to afford 3-((S)-2-((tert-butoxycarbonyl)amino)-4-methylpentanamido)-2-hydroxypentanoic acid (6.62 g, 80% yield).

Preparation of (2S)-2-amino-N-(1-((2,5-dimethoxybenzyl)amino)-2-hydroxy-1-oxopentan-3-yl)-4-methylpentanamide

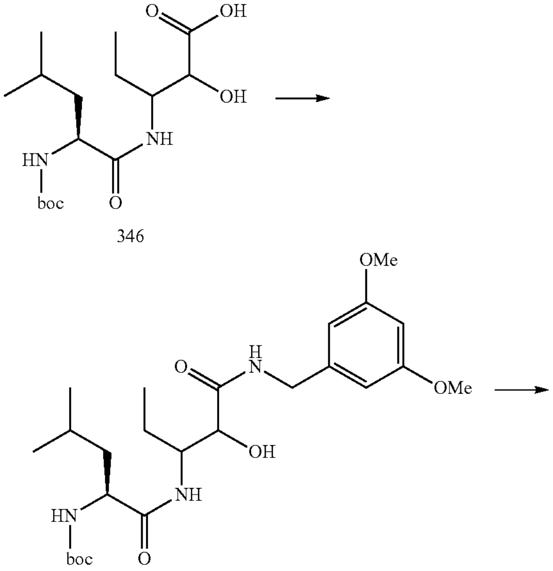

-continued

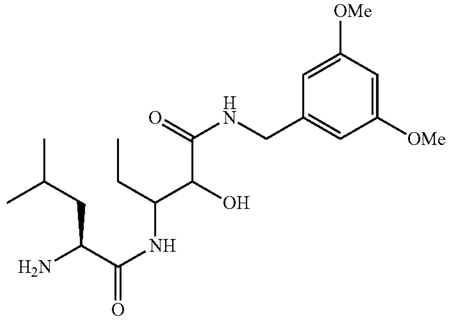

Intermediate B

Step 1: Preparation of tert-butyl ((2S)-1-((1-(3,5-dimethoxybenzylamino)-2-hydroxy-1-oxopentan-3-yl)amino)-4-methyl-1-oxopentan-2-yl)carbamate

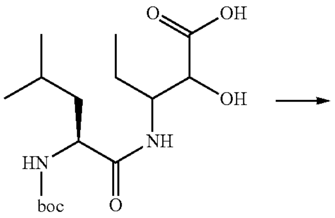

346

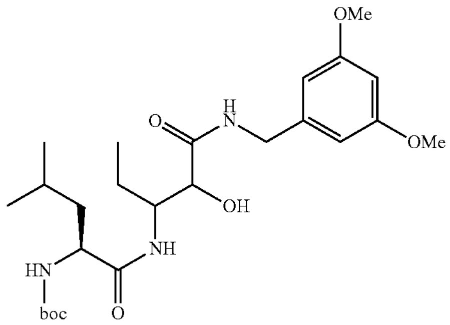

3-((S)-2-((tert-butoxycarbonyl)amino)-4-methylpentanamido)-2-hydroxypentanoic acid (6.62 g) was dissolved in acetonitrile (100 mL) and treated with (3,5-dimethoxyphenyl)methanamine (3.5 g), HATU (8.7 g), and DIPEA (4.6 ml) and stirred overnight at room temperature. The solution was evaporated to dryness and crude was purified by column silica gel chromatography (hexane-ethyl acetate, 0-100%) to afford tert-butyl ((2S)-1-((1-((3,5-dimethoxybenzyl)amino)-2-hydroxy-1-oxopentan-3-yl)amino)-4-methyl-1-oxopentan-2-yl)carbamate (5.4 g, 57%).

Step 2: Preparation of (2S)-2-amino-N-(1-(3,5-dimethoxybenzylamino)-2-hydroxy-1-oxopentan-3-yl)-4-methylpentanamide (Intermediate B)

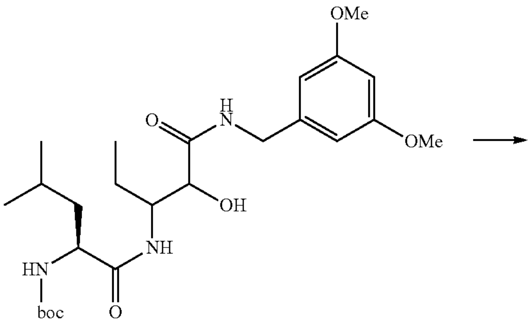

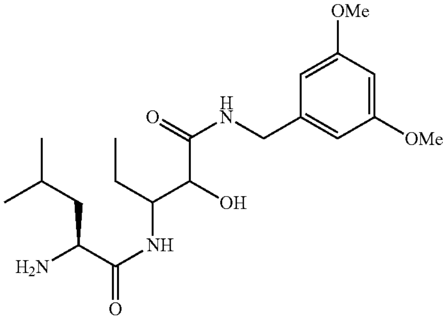

Intermediate B

Tert-butyl ((2S)-1-((1-((3,5-dimethoxybenzyl)amino)-2-hydroxy-1-oxopentan-3-yl)amino)-4-methyl-1-oxopentan-2-yl)carbamate (5.4 g) was dissolved in dioxane/HCl (50 mL, 4M) and stirred at room temperature for 30 min. Removal of the solvent followed by drying in vacuo affords pure (2S)-2-amino-N-(1-((3,5-dimethoxybenzyl)amino)-2-hydroxy-1-oxopentan-3-yl)-4-methylpentanamide hydrochloride salt (5.2 g, 100%)

Preparation of (2S)-2-(3-benzylureido)-N-(1-((3,5-dimethoxybenzyl)amino)-1,2-dioxopentan-3-yl)-4-methylpentanamide (Compound NA112)

Compound NA112

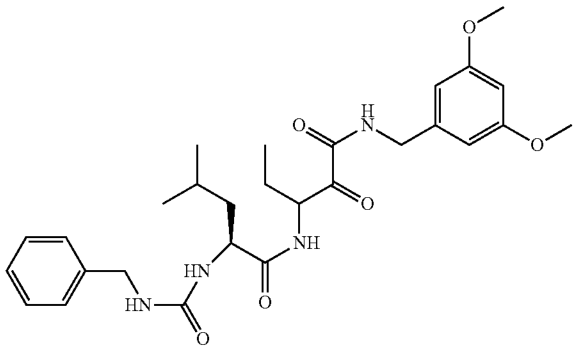

Step 1: Acylation of (2S)-2-amino-N-(1-(3,5-dimethoxybenzylamino)-2-hydroxy-1-oxopentan-3-yl)-4-methylpentanamide

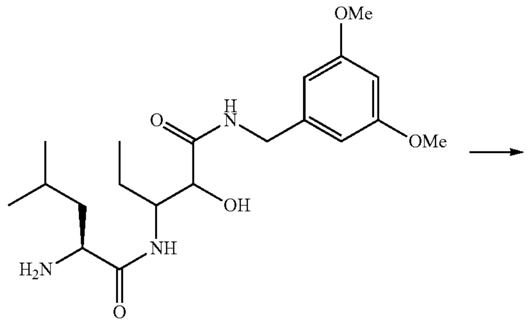

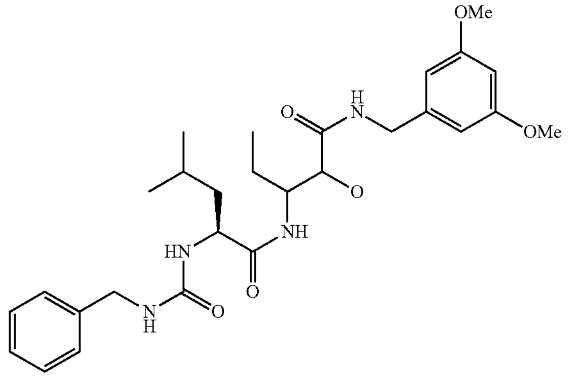

(2S)-2-amino-N-(1-(3,5-dimethoxybenzylbenzylamino)-2-hydroxy-1-oxopentan-3-yl)-4-methylpentanamide hydrochloride salt (5.2 g) was suspended in acetonitrile (50 mL), and treated with benzyl isocyanate (2.5 g, 1.75 equiv), and triethylamine (6 ml, 4 equiv) and stirred at room temperature until LCMS analysis indicates completion of reaction. Evaporation of the solvents gives a residue which was purified by column silica gel chromatography to afford the corresponding urea (4.2 g, 65% yield).

Step 2: Oxidation to (2S)-2-(3-benzylureido)-N-(1-((3,5-dimethoxybenzyl)amino)-1,2-dioxopentan-3-yl)-4-methylpentanamide (Compound NA112)

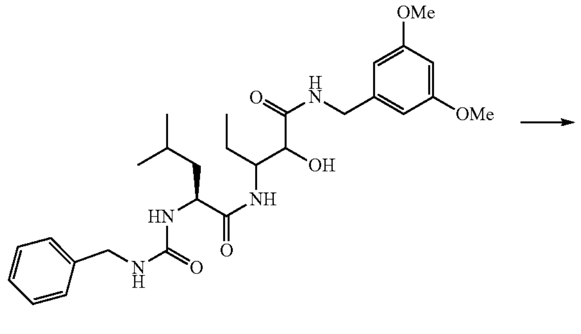

-continued

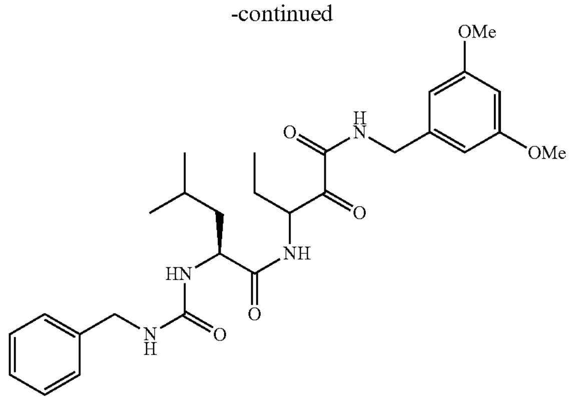

The hydroxy compound (4.2 g) was dissolved/suspended in dichloromethane (150 mL) and treated with Dess-Martin periodinane (6.7 g) stirring at room temperature for 2 h (absence of starting material on LC). Then the reaction mixture was partitioned between saturated bicarbonate solution (300 ml) and ethyl acetate (300 ml). The aqueous layer was extracted twice more with ethyl acetate (2*100 ml) and the combined organic layers are washed with water (100 ml), dried, filtered, and concentrated to dryness. The residue was then purified by column chromatography to afford 1.8 g (~70% LCMS purity) of target compound. This material was recrystallized from DCM (~20 ml) to give 0.835 g (20% yield, purity ~97.4% by LCMS) of target (2S)-2-(3-benzylureido)-N-(1-((3,5-dimethoxybenzyl)amino)-1,2-dioxopentan-3-yl)-4-methylpentanamide (Compound NA112).

Example 2: Calpain Assay Selectivity—In vitro Selectivity

Cerebellar homogenates from wild-type (WT) or calpain-1 Knock-out (KO) mice were incubated with 20 μM calcium to activate calpain-1 or with 2 mM calcium to activate calpain-2, respectively, and increasing concentrations of NA112 (12). Calpain activity was measured by the cleavage of Succinyl-Leu-Tyr-7-amino-4-methylcoumarin (Suc-Leu-Tyr-AMC), resulting in increased fluorescence. Activity is normalized to the value measured in the presence of vehicle (DMSO). The graph in FIG. 1 shows the assay results of selectivity of NA112 for calpain-2 vs calpain-1 and the data from FIG. 1 were used to calculate the $IC_{50}$ of NA112 for calpain-1 and calpain-2.

TABLE 1

| | 20 μM $Ca^{2+}$ (Calpain-1) | 2000 μM $Ca^{2+}$ (Calpain-1) |
|---|---|---|
| $IC_{50}$ | 1376 nM | 106 nM |
| Ratio | | 13 |

Example 3: Calpain Assay Selectivity—In Vivo Selectivity

Figure 2:
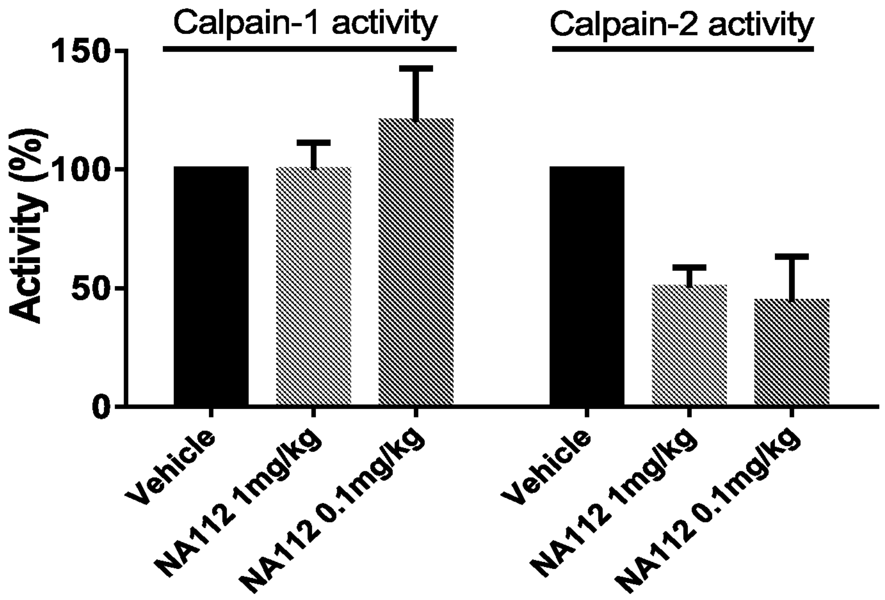
FIG. 2 shows assay results showing selectivity in vivo of NA112 for calpain-2 vs calpain-1.
Figure 3:
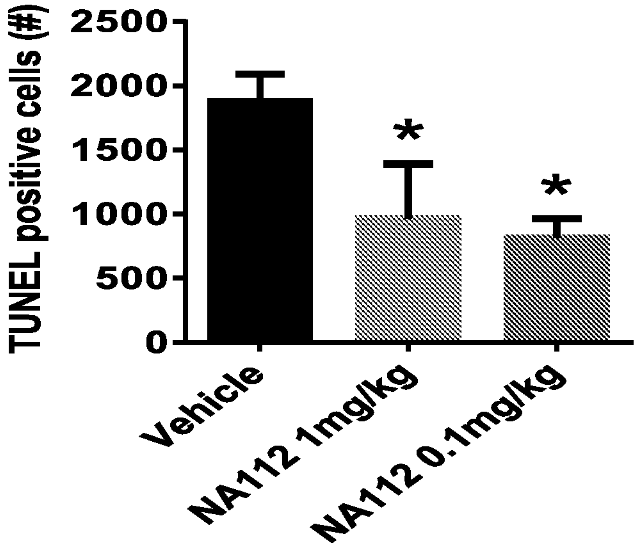
FIG. 3 shows in vivo efficacy of NA112 in DMSO solution administered 24 h after TBI plus i.p. injection of NA112 at 0.1 or 1.0 mg/kg

Calpain activity in cerebellar P2 fractions was measured 24 h after traumatic brain injury (TBI) in adult wild-type mice and the assay results for calpain-1 and calpain-2 are shown in FIG. 2. 0.1 or 1 mg/kg of NA112 was injected intraperitoneally 1 h after TBI. Each measurement of in vivo selectivity was obtained as follows:

Calpain-1 activity: Calpain activity with 20 μM $Ca^{2+}$. Normalized to Vehicle.

Calpain-2 activity: Calpain activity with 5 mM $Ca^{2+}$ minus Calpain activity with 20 μM $Ca^{2+}$. Results are means S.E.M. of 3 experiments.

Example 4: In Vivo Efficacy (DMSO Solution)

Quantification of TUNEL staining 24 h after TBI plus i.p. injection of NA112 at 0.1 or 1.0 mg/kg. Total numbers of TUNEL-positive cells in 3 coronal sections (Bregma 0.50, −0.58, −1.58 mm) of each brain were counted and averaged. Results are means S.E.M. of 3 animals. * p<0.05 vs Vehicle. One-way ANOVA followed by Bonferroni test.

Example 5: Comparison Between NA101 and NA112

Figure 4:
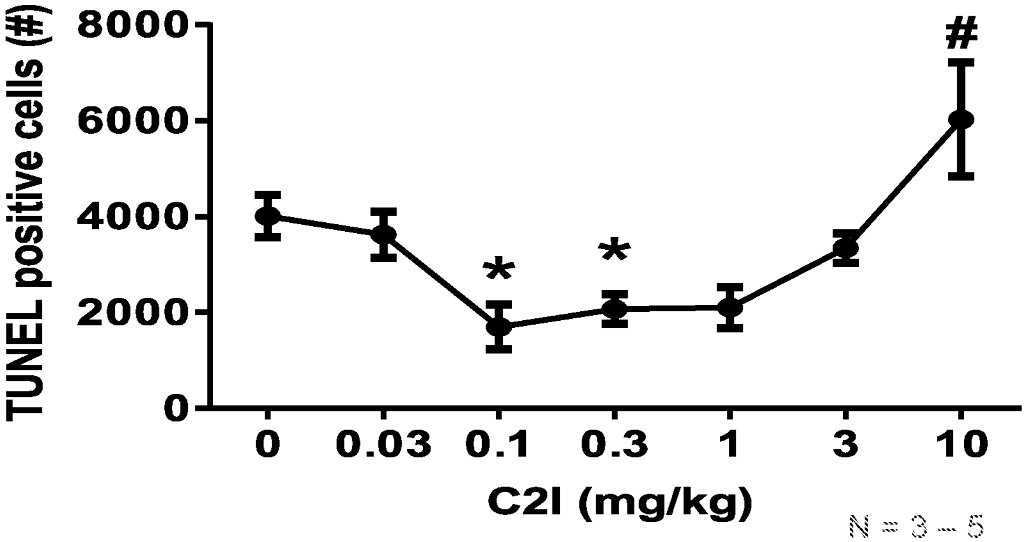
FIG. 4 shows the number of TUNEL-labelled degenerating cells in the ipsilateral side of the brain where indicated doses of NA101 (C2I) were injected intraperitoneally to WT mice at 1 h after TBI and the cells were analyzed 24 h after TBI.
Figure 5:
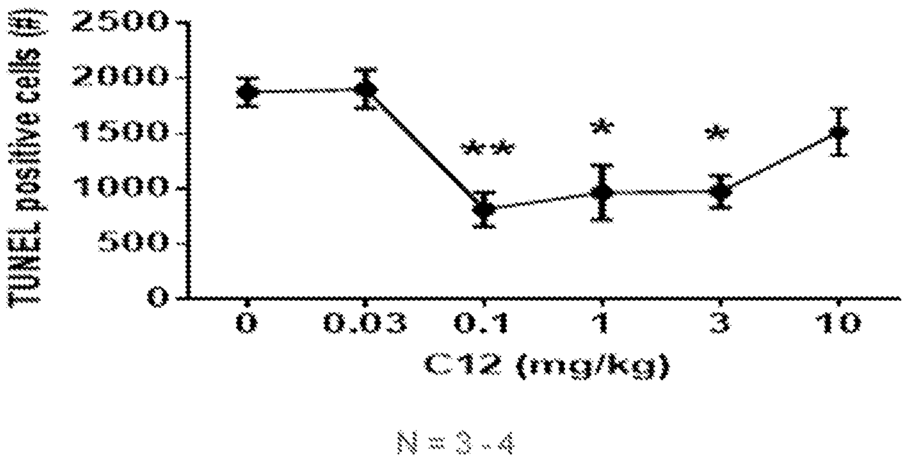
FIG. 5 shows the number of TUNEL-labelled degenerating cells in the ipsilateral side of the brain where indicated doses of NA112 (C12) were injected intraperitoneally to WT mice at 1 h after TBI and the cells were analyzed 24 h after TBI.

Indicated doses of NA101 (C2I, FIG. 4) or NA112 (C12; FIG. 5) were injected intraperitoneally to WT mice at 1 h after TBI. The number of TUNEL-labelled degenerating cells in the ipsilateral side of the brain was analyzed 24 h after TBI.

The following structures shows the compound NA101.

(NA101)

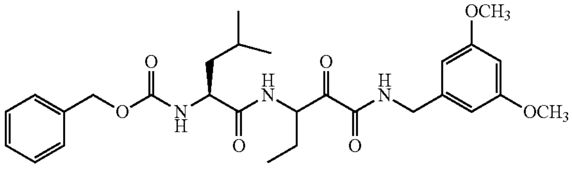

Example 6: NA112 Stability in Mouse Plasma

Figure 6:
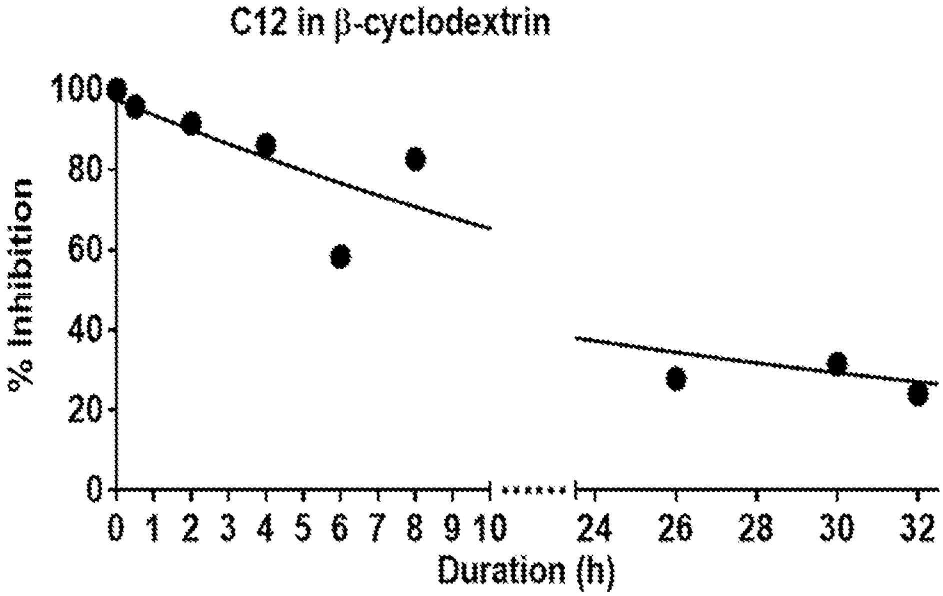
FIG. 6 shows stability of NA112 in mouse plasma.

NA112 in B-cyclodextrin formulation demonstrated good plasma stability with an estimated half-life of 17 hours (FIG. 6). NA112 (C12, 0.2 mM) was incubated with mouse plasma at 37° C. for the indicated periods of time. Aliquots were taken and the degree of inhibition of purified human calpain-2 was measured. Results were normalized to the maximum degree of inhibition (100%) measured at to.

Example 7: NA112 Stability in Mouse Liver Homogenates

Figure 7:
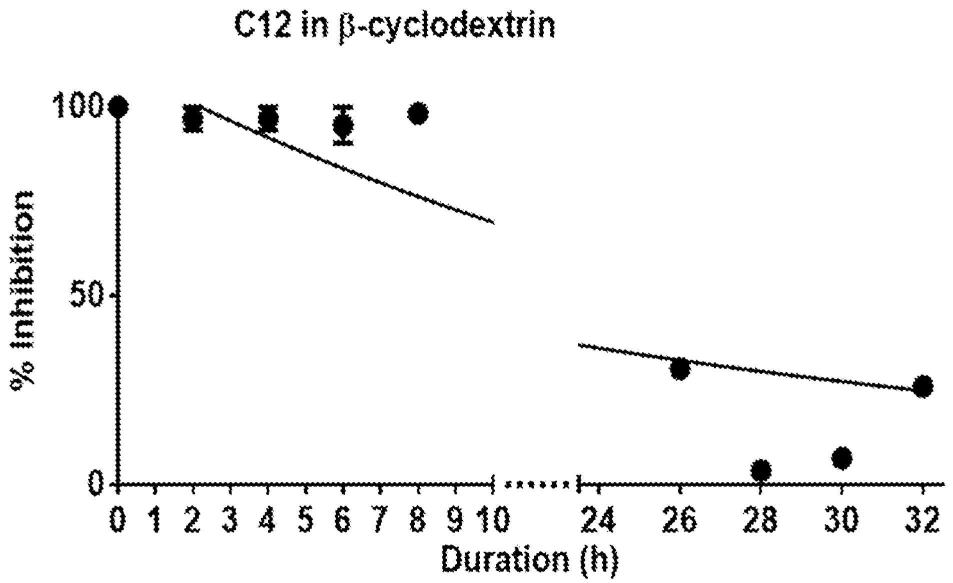
FIG. 7 shows stability of NA112 in mouse liver homogenate with an estimated half-life.

NA112 in B-cyclodextrin formulation demonstrated good stability in mouse liver homogenate with an estimated half-life of NA112 was 15 hours (FIG. 7). Aliquots were taken and the degree of inhibition of purified human calpain-2 was measured. Results were normalized to the maximum degree of inhibition (100%) measured at t0.

Example 8: Separation of Isomers and Activities Thereof

Like in NA101, there are 2 chiral centers for NA112. NA112A, where chiral center 1 is the S-form and chiral center 2 is the S-form was separated from the S-R- form (NA112B) using methods that are well-known methods for separating diastereoisomers.

NA112A

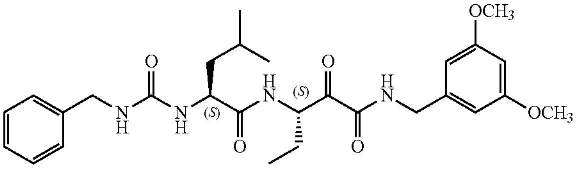

NA112B

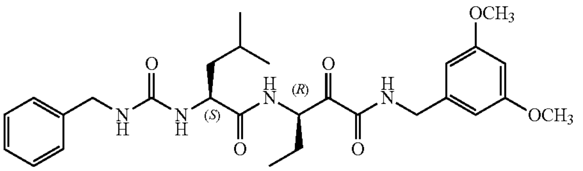

Figure 8:
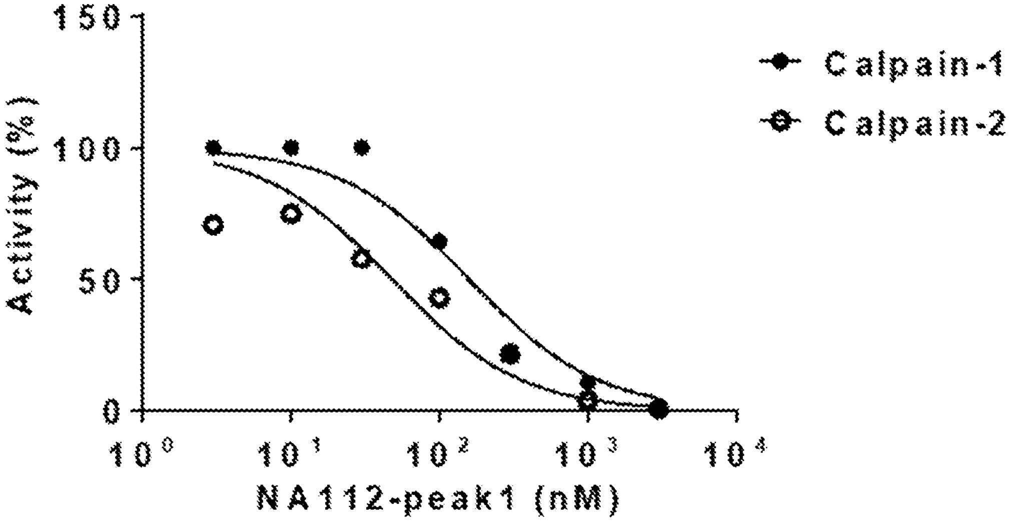
FIG. 8 shows activity of NA112A (S-S isomer) against calpain-2 and calpain-1.

The inhibitory activity of the compounds NA112A (S-S isomer) and NA112B (S-R stereoisomer) against calpain-1 and calpain-2 were determined. The NA112B compound (S-R stereoisomer) had no inhibitory activity at the highest concentration tested, 3 μM. As shown in FIG. 8, NA112A (S-S isomer) showed the expected inhibitory activity against calpain-2 and calpain-1.

NA112A (S-S stereoisomer) was incubated in mouse plasma at 37° C. to determine whether it undergoes epimerization and therefore becomes inactive. As shown in FIG. 9, NA112A rapidly inactivated in mouse plasma. NA112A in β-cyclodextrin formulation (10 μM) was incubated in mouse plasma at 37° C. for the indicated periods of time. Aliquots were taken and the degree of inhibition of purified human calpain-2 was measured. Results were normalized to the maximum degree of inhibition (50%) measured at t0.

Example 9: NA112 Liposomal Formulation

Liposomes were prepared as follows:

Composition (Each for 1 ml of Liposomal Formulation)

NA112—1 mg

Dimyristoyl phosphatidylcholine (DMPC)—15 mg 1,2-Dimyristoyl-sn-glycero-3-phosphoglycerol, sodium salt (DMPG-Na)—5 mg Aqueous medium: Phosphate Buffered Saline pH 6.8-1 ml Procedure 1) Dissolved 2 mg NA112, 30 mg DMPC and 10 mg DMPG-Na in Chloroform (700 μL) and Methanol (200 μL), evaporated the organic solvent (time taken 1.5 hours), placed in vacuum overnight (16 hours).

2) To the lipid film, 2 ml of PBS (pH 6.8) was added, vortexed to hydrate the phospholipids.

3) Sonicated using probe sonicator (30% amplitude, 40 s pulse) for 7 cycles using cooling pads. (1 cycle: 30% amplitude, 40 second pulse).

4) Measured particle size, PDI and zeta potential.

5) Control was prepared as described without NA 112

Results

Characteristics of the liposome particles are indicated below (Table 2).

TABLE 2

| | Particle Size nm | Poly Dispersity Index | Zeta Potential mV |
|---|---|---|---|
| Control | 95.23 | 0.296 | −73.9 |
| NA 112 | 91.47 | 0.338 | −44.2 |

Various parameters reflecting the size of the liposomal particles were determined.

Example 10: NA112 In Vitro Selectivity in Liposomal Formulation

Various concentrations of NA112 in the liposomal formulation were incubated with human calpain-1 (purified from erythrocytes, ecalpain-1) or a recombinant human calpain-2 (hcalpain-2) and calpain activity assayed as in FIG. 1. $IC_{50}$ were determined and transformed into Ki values (FIG. 10A, 10B). Values previously obtained with NA112 dissolved in DMSO are shown for comparison (FIG. 10B).

Example 11: NA112 In Vivo Efficacy in Liposome Formulation

Calpain activity in cerebellar P2 fractions was measured 24 h after TBI in adult WT mice, and vehicle or 0.1 or 1 mg/kg of NA112 (12) dissolved in DMSO or liposomal formulation (lipo) was injected intraperitoneally 1 h after TBI. Each measurement of in vivo selectivity was obtained as follows:

Calpain-1 activity: Calpain activity with 20 μM $Ca^{2+}$, normalized to Vehicle.

Calpain-2 activity: Calpain activity with 5 mM $Ca^{2+}$ minus Calpain activity with 20 μM $Ca^{2+}$, then normalized to vehicle.

Figure 11:
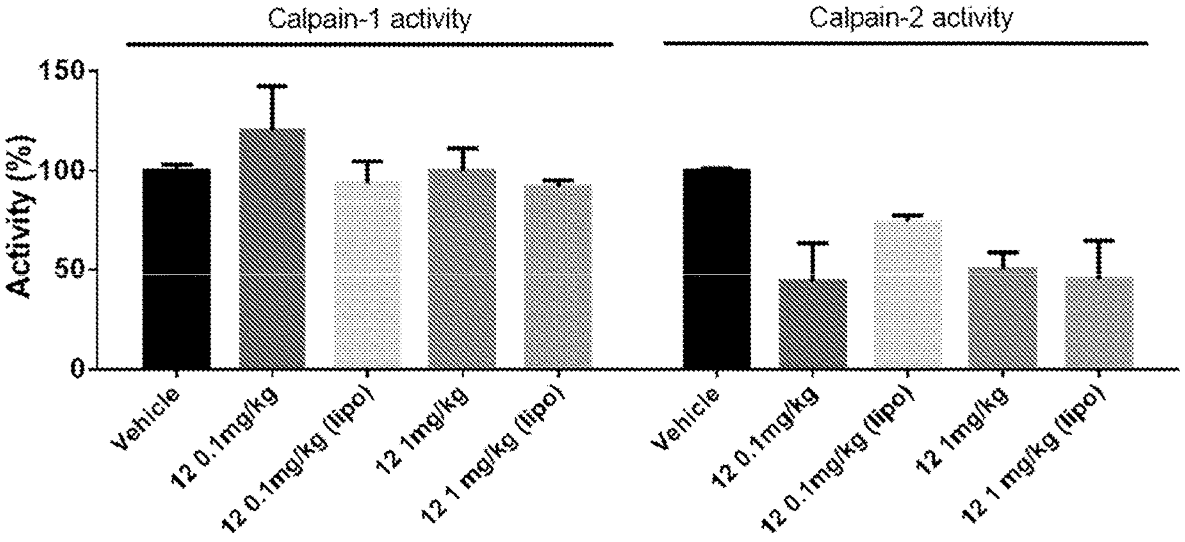
FIG. 11 shows in vivo efficacy of NA112 in liposomes vs DMSO.

Vehicle (DMSO or liposomes) or 0.1 or 1 mg/kg of NA112 (12) dissolved in DMSO or liposomal formulation (lipo) was injected intraperitoneally 1 h after TBI in WT mice. Calpain activity was measured 24 h later in cerebellar P2 fractions. Calpain-1 activity was measured in the presence of 20 μM calcium and calpain-2 activity was measured as the difference between calpain activity measured in the presence of 5 mM calcium and that measured in the presence of 20 μM calcium (FIG. 11). In both cases, calpain activity was normalized to the values measured in vehicle-treated mice. Results are means±S.E.M. of 3 animals. Note that NA112 produced the same degree of calpain-2 inhibition whether it is dissolved in DMSO or liposomes.

Vehicle (control liposomes) or 0.1 or 1 mg/kg of NA112 dissolved in liposomal formulation was injected 1 h after TBI in WT mice. Animals were sacrificed 24 h later and brains were stained with TUNEL staining to analyze the extent of cell death. Images from 2 different animals are shown in FIG. 12 to illustrate the decrease in TUNEL staining in NA112-treated mice.

Figure 12:
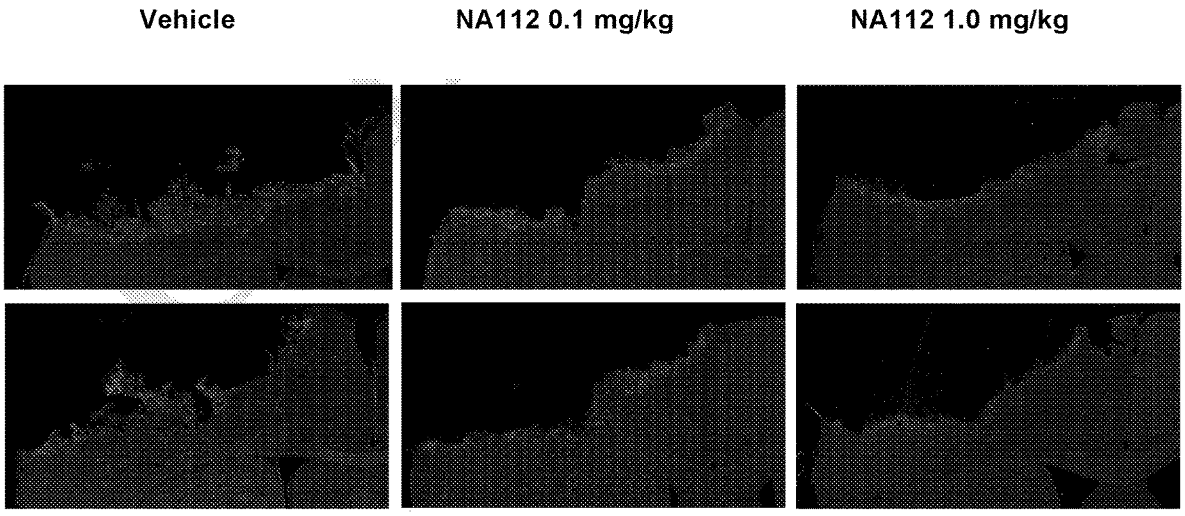
FIG. 12 shows in vivo efficacy of NA112 in liposomes and images from two different animals are shown to illustrate the decrease in TUNEL staining in NA112-treated mice.
Figure 13:
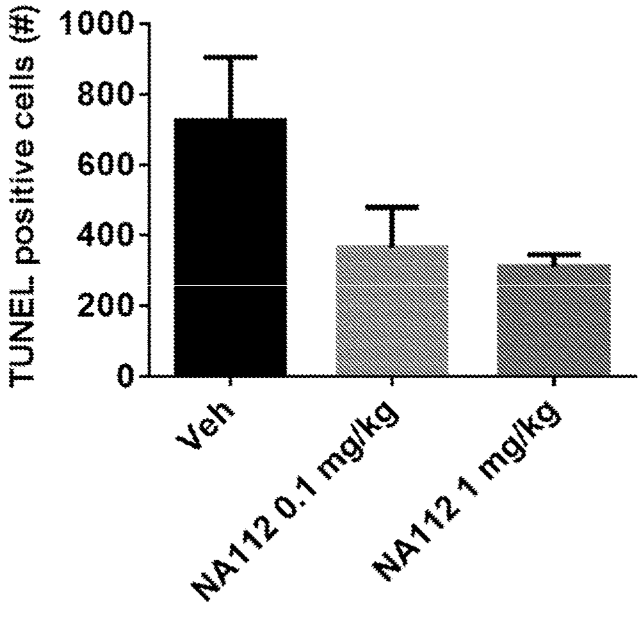
FIG. 13 shows a graph with the numbers of TUNEL-positive cells in images similar to those shown in FIG. 12.

The number of TUNEL-positive cells in images similar to those shown in FIG. 12 was quantified (FIG. 13). Results in FIG. 13 are Means±S.E.M. of 3 different animals.

Example 12: PK Studies in Liposomal Formulation

NA112 was prepared in liposomes at a concentration of 1.5 mg/ml. Mice were injected in the tail vein with 200 μl of NA112 in liposomes (corresponding to a dose of 10 mg/kg) and were sacrificed at the following time-points: 1, 5, 15, 30 min, 1, 2, 4, 8, 16 and 24 h. Blood was collected and plasma rapidly prepared by centrifugation. Brains were also collected. NA112 in plasma and in brain homogenates was assayed with LC/Ms and the sensitivity of the assay was 1 ng/ml. Experiments were performed in duplicate (A1 and A2 in Table 3). Results were averaged for preparing the figure and calculating the half-life of NA112 in plasma and in brain.

TABLE 3

Plasma concentration of NA112 at various times after iv injection.

| Time | Concentration (ng/ml) | | |
|---|---|---|---|
| (hr) | A1 | A2 | Mean (ng/ml) |
| 0.0167 | 45294.48 | 63500.33 | 54397.41 |
| 0.0833 | 115611.68 | 69072.87 | 92342.27 |
| 0.25 | 2116.14 | 939.49 | 1527.82 |
| 0.5 | 6756.57 | 432.29 | 3594.43 |
| 1 | 5553.83 | 389.53 | 2971.68 |
| 2 | 106.89 | 84.04 | 95.46 |
| 4 | 34.63 | 29.98 | 32.31 |
| 8 | 17.45 | 20.59 | 19.02 |
| 16 | 10.85 | 9.79 | 10.32 |
| 24 | 5.63 | 4.67 | 5.15 |

Figure 14:
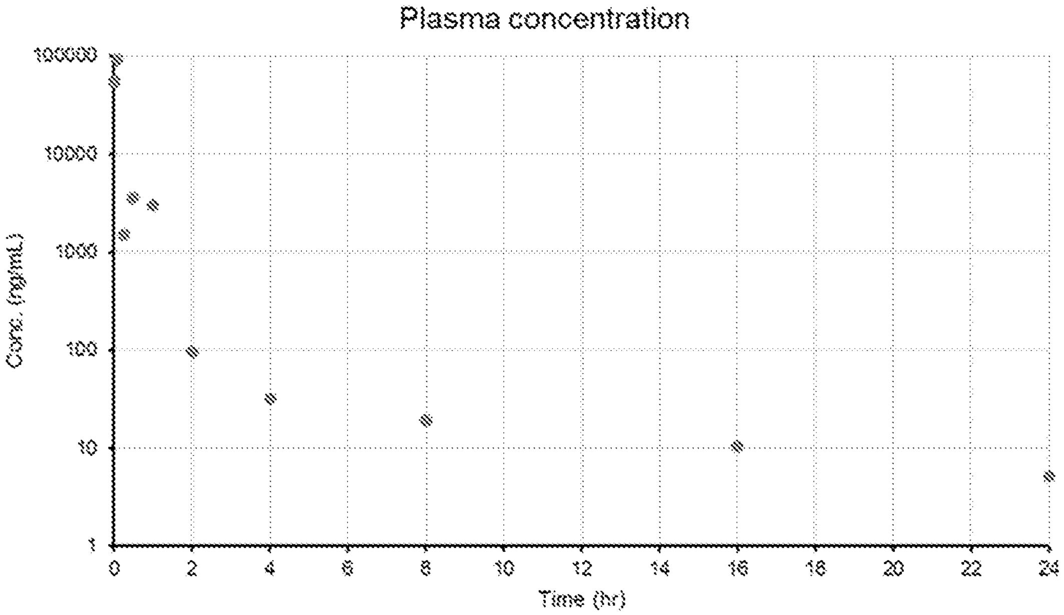
FIG. 14 shows changes in NA112 plasma concentration at various times after intravenous injection.

FIG. 14 shows changes in NA112 plasma concentration at various times after iv injection and the data in table 3 are plotted as a function of time.

TABLE 4

Brain concentration of NA112 at various times after iv injection (assay sensitivity: 2 ng/ml) (BLQ: below the limit of quantification)

| | Concentration (ng/ml) | | |
|---|---|---|---|
| Time (hr) | A1 | A2 | Mean (ng/ml) |
| 0.0167 | 519.69 | 305.17 | 412.43 |
| 0.0833 | 167.99 | 129.33 | 148.66 |
| 0.25 | 106.42 | 62.29 | 84.36 |
| 0.5 | 60.58 | 63.37 | 61.98 |
| 1 | 45.60 | 48.44 | 47.02 |
| 2 | 25.91 | 30.87 | 28.39 |
| 4 | 13.97 | 21.30 | 17.63 |
| 8 | 19.47 | 15.43 | 17.45 |
| 16 | 6.65 | 9.41 | 8.03 |
| 24 | BLQ | BLQ | BLQ |

(BLQ: below the limit of quantification)

Figure 15:
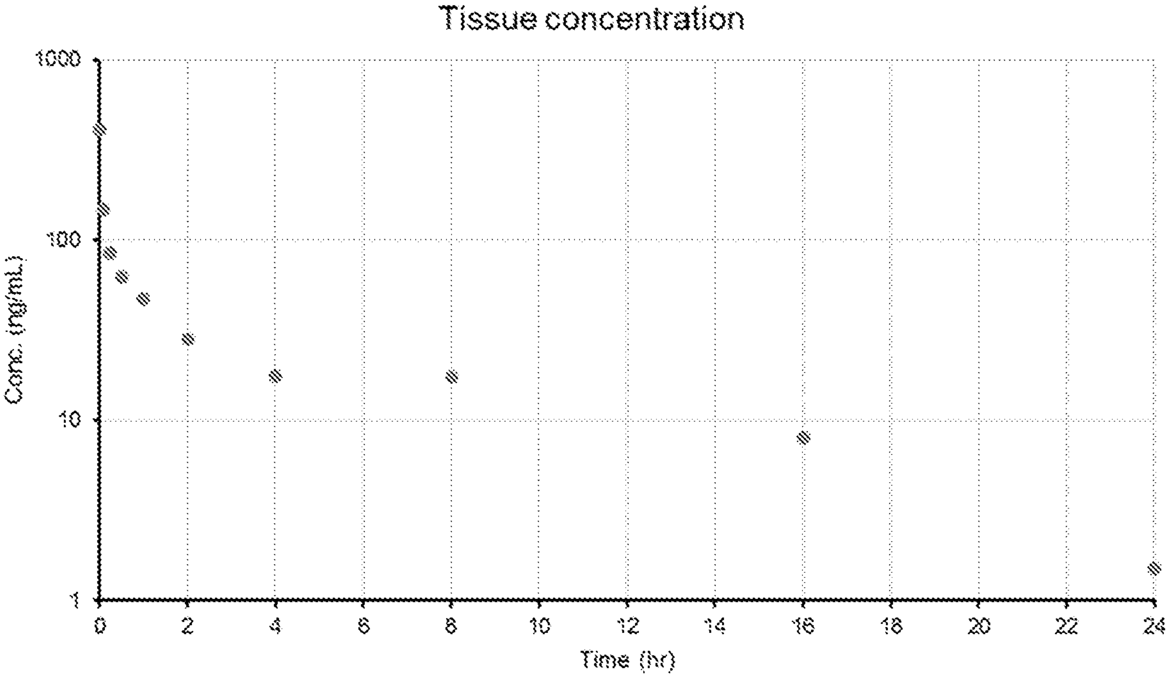
FIG. 15 shows changes in NA112 brain concentration at various times after intravenous injection.

FIG. 15 shows changes in NA112 brain concentration at various times after intravenous injection. Data from table 4 are plotted as a function of time. While the curve is not easily fitted with a 2-compartment model, the slower component appears to have a half-life of about 3 h.

TABLE 5

PK calculation for NA112 in plasma based on a 2-compartmental model

| Parameter | Value | Unit |
|---|---|---|
| $T½β$ | 7.80 | hr |
| $T½α$ | 0.23 | hr |
| α | 3.01 | 1/hr |
| β | 0.09 | 1/hr |
| A | 28944.68 | ng/ml |
| B | 42.70 | ng/ml |
| AUC0-00 | 16993.88 | ng/ml · h |

Figure 16:
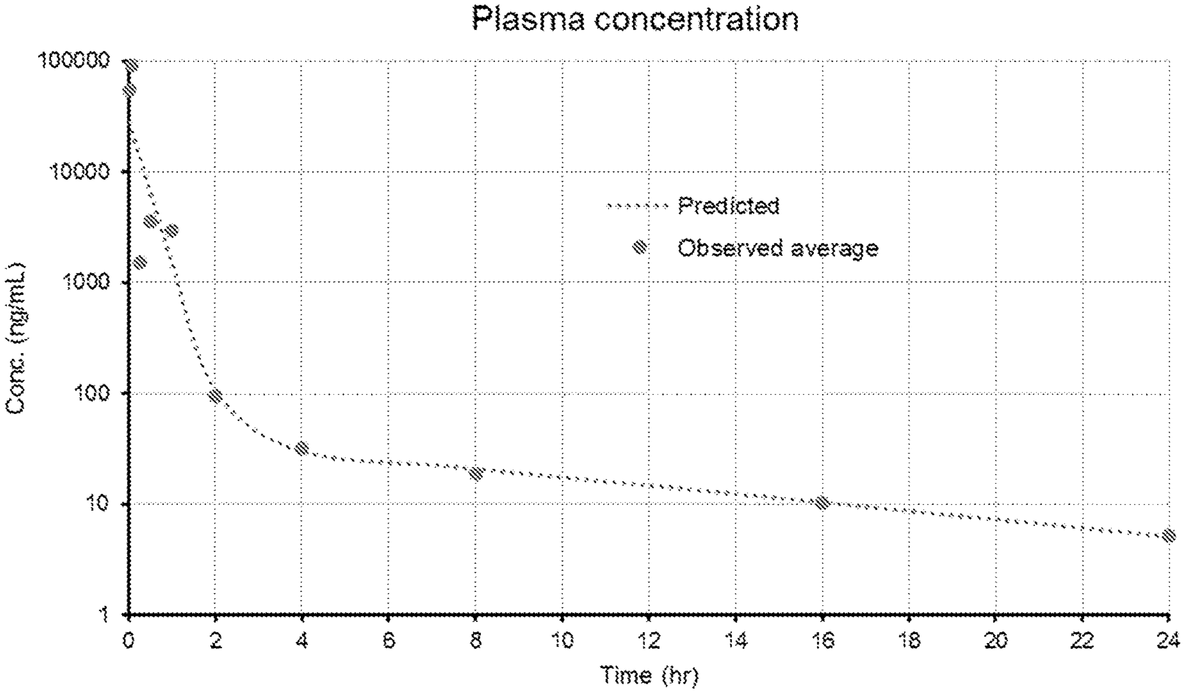
FIG. 16 shows changes in NA112 plasma concentrations fitted with the 2-compartment model.

A two-compartment model was used to analyze the data from FIG. 14. This assumes that there is a rapid distribution of the drug from the plasma to various organs, followed by a slower elimination of the drug form the plasma. In this case, the curve is well-fitted with the 2-compartment model (FIG. 16), indicating a half-life in the plasma of 7.8 h. In FIG. 16, changes in NA112 plasma concentrations fitted with the 2-compartment model. The data from FIG. 14 are fitted with the 2-compartment model equation, showing the very good fit between the predicted values and the observed values.

Example 13: Preparation of Analogs with Diversity in the Benzylamide (Right-Hand Side)

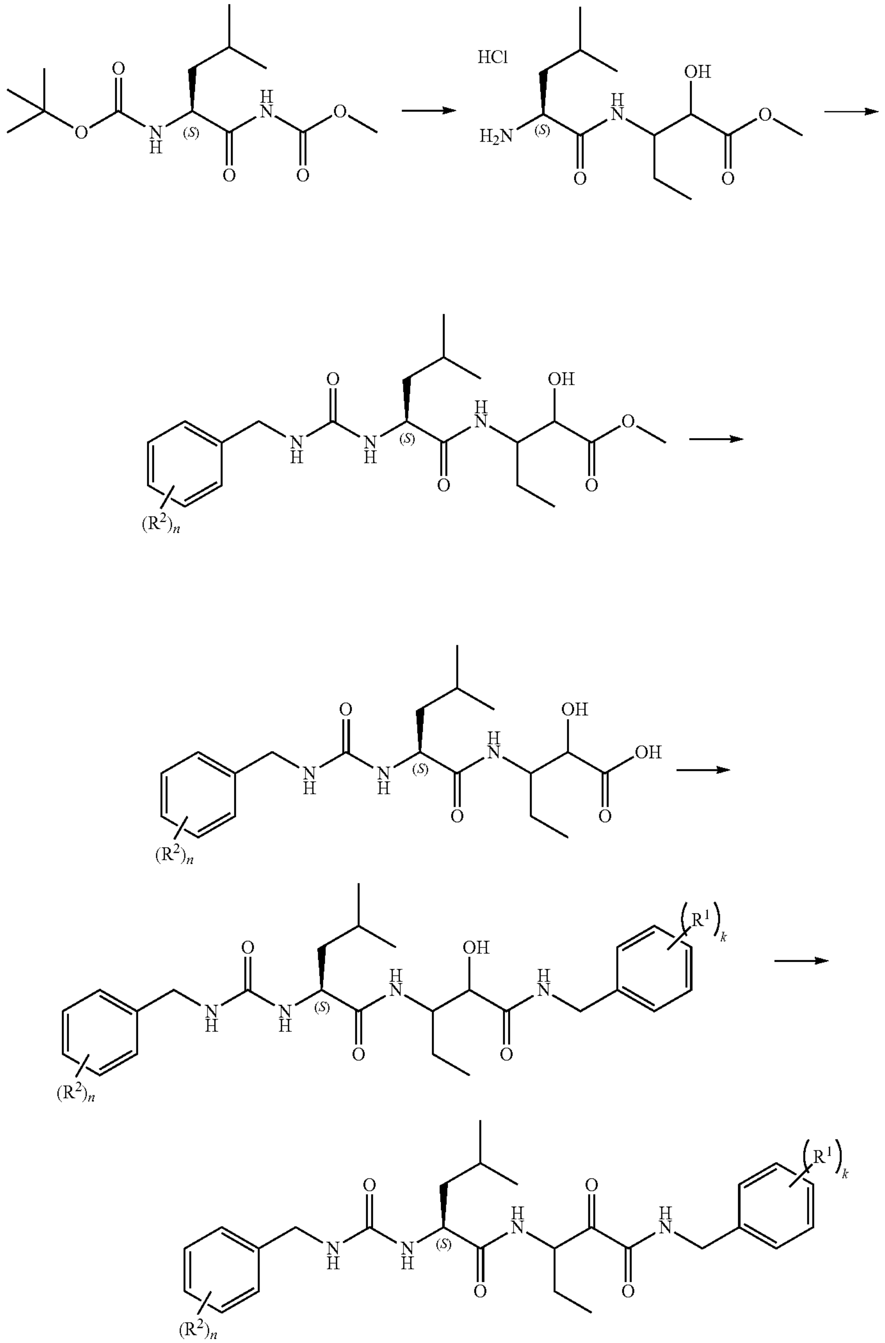

$R^1$ is —$OR^4$ or —$OR^5$ in Formula (I)
$R^2$ is same as $R^2$ in Formula (I)
n is an integer of 0 to 5
k is an integer of 1 to 5

Methyl 3-((S)-2-((tert-butoxycarbonyl)amino)-4-methylpentanamido)-2-hydroxypentanoate (previously described in WO2020/037012) is Boc-deprotected to afford methyl 3-((S)-2-(amino)-4-methylpentanamido)-2-hydroxypentanoate hydrochloride salt. The free base of the amino group is then reacted with an ($R_2$-substituted) benzylisocyanate or equivalent reagent to construct the desired methyl 3-((S)-2-(3-($R_2$-substituted)benzylureido)-4-methylpentanamido)-2-hydroxypentanoate. The methyl ester of this intermediate is hydrolyzed to the corresponding acid, 3-((S)-2-(3-($R_2$-substituted)benzylureido)-4-methylpentanamido)-2-hydroxypentanoic acid. The acid is then functionalized with a series of ($R_1$-substituted)benzylamines to afford the desired N-($R_1$-substituted)benzyl-3-((S)-2-(3-($R_2$-substituted)benzylureido)-4-methylpentan-amido)-2-hydroxypentanamide which is oxidized at the secondary alcohol position to afford the final products, the N-($R_1$-substituted)benzyl-3-((S)-2-(3-($R_2$-substituted)benzylureido)-4-methylpentanamido)-2-oxopentanamides.

Example 13-1

Step 1: Preparation of methyl 3-((S)-2-amino-4-methylpentanamido)-2-hydroxy-pentanoate

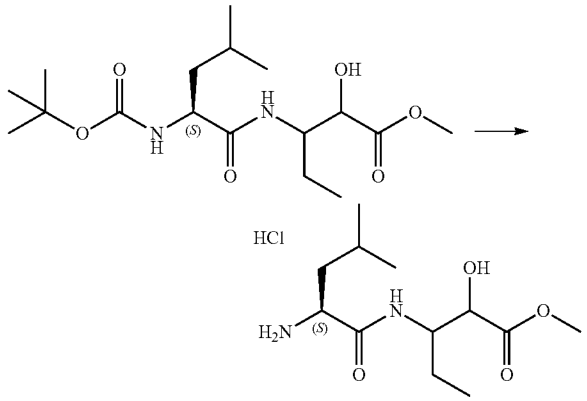

Methyl 3-((S)-2-((tert-butoxycarbonyl)amino)-4-methylpentanamido)-2-hydroxypentanoate (3.6 g) was dissolved in dioxane/HCl (50 mL, 4M) and stirred at room temperature for 1 h. Removal of the solvent followed by drying in vacuo affords pure methyl 3-((S)-2-amino-4-methylpentanamido)-2-hydroxypentanoate hydrochloride salt (3.2 g) Without further purification, this material was used in next step. LCMS [M+H]+=261.3

Step 2: Preparation of methyl 3-((S)-2-(3-benzylureido)-4-methylpentanamido)-2-hydroxypentanoate

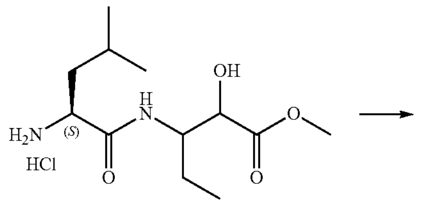

-continued

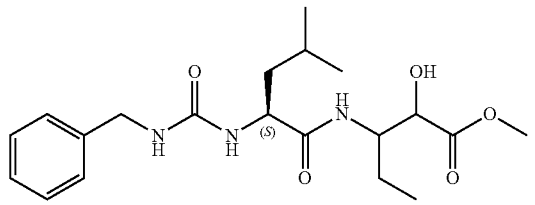

Methyl 3-((S)-2-(amino)-4-methylpentanamido)-2-hydroxypentanoate hydrochloride salt (3.2 g) with some dioxane from previous step was dissolved in $CH_3CN$/THE (1/1) mixture (80 ml) and $Et_3N$ (2 ml) was added in one portion. Benzylisocyanate (1.33 g, 1.2 equiv) was added in one portion, and the reaction mixture was stirred for 4 h at room temperature (LCMS control). The mixture was evaporated to dryness and the residue was dissolved in ethyl acetate (100 ml). The solution was washed with 0.5 M HCl (20 ml) and saturated $NaHCO_3$ solution (20 ml). The organics were evaporated and the crude material was purified by silica gel flash chromatography to afford pure methyl 3-((S)-2-(3-benzylureido)-4-methylpentanamido)-2-hydroxypentanoate (0.61 g 39% yield) after evaporation. The material was used in next step without further purification. LCMS $[M+H]^+$=394.6.

Step 3: Preparation of 3-((S)-2-(3-benzylureido)-4-methylpentanamido)-2-hydroxy-pentanoic acid

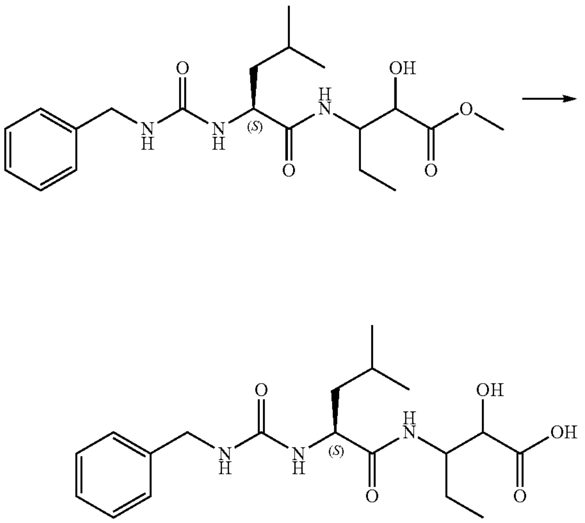

Methyl 3-((S)-2-(3-benzylureido)-4-methylpentanamido)-2-hydroxypentanoate from the previous step was dissolved in THE/H2O/MeOH (1/1/0.5, 20 mL) and lithium hydroxide monohydrate (130 mg) was added. The mixture was stirred at room temperature for 6 h and quenched with 1M HCl to pH~3, then extracted with EtOAc (3x10 ml). The organic layer was dried over $Na_2SO_4$ and concentrated to dryness to give 3-((S)-2-(3-benzylureido)-4-methyl-pentanamido)-2-hydroxypentanoic acid (0.51 g, ~90%) as a colorless glass. LCMS [M+H]+=380.4. This material was used in next step without further purification.

Step 4: Preparation of (2S)-2-(3-benzylureido)-N-(1-((3-fluoro-2-methoxybenzyl)amino)-2-hydroxy-1-oxopentan-3-yl)-4-methylpentanamide

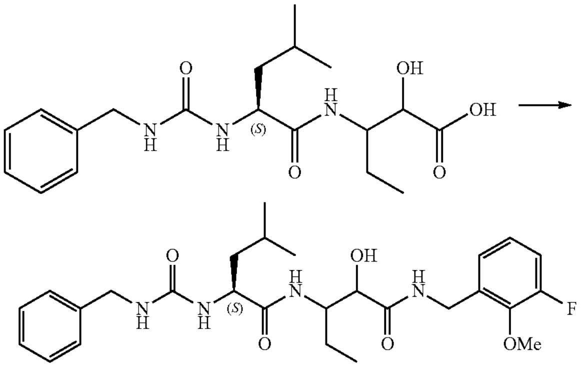

3-((S)-2-(3-benzylureido)-4-methylpentanamido)-2-hydroxypentanoic acid (113 mg, 1 equiv) was dissolved in acetonitrile (5 mL) then (3-fluoro-2-methoxyphenyl)methanamine (1.2 equiv) was added followed by HATU (170 mg, 1.5 equiv) and DIPEA (100 μL). After 24 h the reaction was complete (LCMS) and then was quenched by the addition of saturated $NaHCO_3$ solution (20 ml). The solution was extracted with ethyl acetate (3×10 mL). The combined organics were washed with 0.5 M aqueous HCl solution (2×5 ml), dried over $Na_2SO_4$ and concentrated to dryness. The crude residue (150 mg), (2S)-2-(3-benzylureido)-N-(1-((3-fluoro-2-methoxybenzyl)amino)-2-hydroxy-1-oxopentan-3-yl)-4-methylpentanamide was used in next step without additional purification. LCMS $[M+H]^+$=517.4.

Step 5: Preparation of (2S)-2-(3-benzylureido)-N-(1-((3-fluoro-2-methoxybenzyl)amino)-1,2-dioxopentan-3-yl)-4-methylpentanamide (NSN23482)

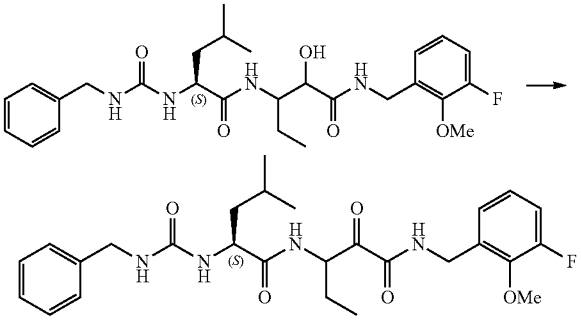

Crude (2S)-2-(3-benzylureido)-N-(1-((3-fluoro-2-methoxybenzyl)amino)-2-hydroxy-1-oxopentan-3-yl)-4-methylpentanamide (150 mg) was dissolved in $CH_3CN$ (10 mL) and 1 drop of water, pyridine (150 μL), and DMSO (100 μL) were added, then Dess-Martin periodinane (150 mg) was added and the reaction was stirred at room temperature for 2 h. The mixture was quenched by the addition of saturated aqueous $NaHCO_3$ (20 mL) and extracted with ethyl acetate (3×10 ml). The organic layer was dried over $Na_2SO_4$ and concentrated to dryness. The crude residue was submitted for reverse phase HPLC purification to afford pure (2S)-2-(3-benzylureido)-N-(1-((3-fluoro-2-methoxybenzyl)amino)-1,2-dioxopentan-3-yl)-4-methylpentanamide (NSN23482). Yield after HPLC purification—11.2 mg (14%) NSN23482. LCMS [M+H]+=515.3.

Example 13-2

Step 1: Preparation of (2S)-2-(3-benzylureido)-N-(2-hydroxy-1-((2-methoxy-3-methyl-benzyl)amino)-1-oxopentan-3-yl)-4-methylpentanamide

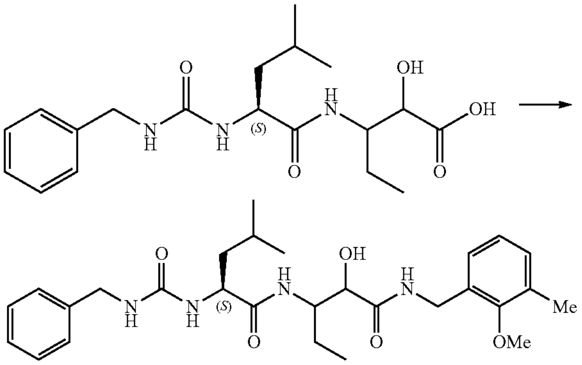

3-((S)-2-(3-benzylureido)-4-methylpentanamido)-2-hydroxypentanoic acid (113 mg, 1 equiv) was dissolved in acetonitrile (5 mL), then (2-methoxy-3-methylphenyl)methanamine (1.2 equiv) was added followed by HATU (170 mg, 1.5 equiv) and DIPEA (100 μL). After 24 h the reaction was complete (LCMS). The mixture was quenched by the addition of saturated $NaHCO_3$ solution (20 ml) and extracted with ethyl acetate (3×10 mL). The combined organics were washed with 0.5M aqueous HCl solution (2×5 mL), dried over $Na_2SO_4$ and concentrated to dryness to afford (2S)-2-(3-benzylureido)-N-(2-hydroxy-1-((2-methoxy-3-methyl, benzyl)amino)-1-oxopentan-3-yl)-4-methylpentanamide. The crude material (150 mg) was used in next step without additional purification. LCMS $[M+H]^+$=513.1

Step 2: Preparation of (2S)-2-(3-benzylureido)-N-(1-((2-methoxy-3-methylbenzyl)-amino)-1,2-dioxopentan-3-yl)-4-methylpentanamide (NSN23482)

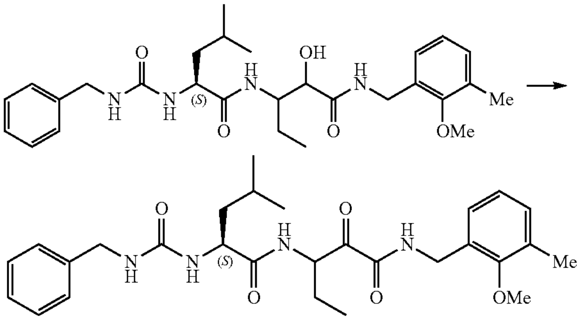

The crude (2S)-2-(3-benzylureido)-N-(2-hydroxy-1-((2-methoxy-3-methyl,benzyl)amino)-1-oxopentan-3-yl)-4-methylpentanamide from the previous step (150 mg) was dissolved in $CH_3CN$ (10 mL) and 1 drop of water, pyridine (150 μL), and DMSO (100 μL) were added, then Dess-Martin Periodinane (150 mg) was added and the reaction stirred at room temperature for 2 h. The mixture was quenched by the addition of saturated aqueous $NaHCO_3$ (20 ml) and extracted with ethyl acetate (3×10 mL). The organic layer was dried over $Na_2SO_4$ and concentrated to dryness. The crude residue was submitted for reverse phase HPLC purification to afford pure (2S)-2-(3-benzylureido)-N-(1-((2-methoxy-3-methylbenzyl),amino)-1,2-dioxopentan-3-yl)-4-methylpentanamide (NSN23482). Yield after HPLC purification—31 mg (40%) NSN23482. LCMS [M+H]+=511.2.

Example 13-3

Step 1: Preparation of (2S)-2-(3-benzylureido)-N-(1-((3-chloro-2-methoxy-benzyl)amino)-2-hydroxy-1-oxopentan-3-yl)-4-methylpentanamide

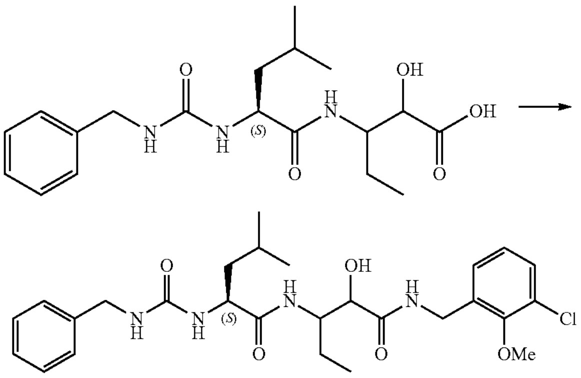

3-((S)-2-(3-benzylureido)-4-methylpentanamido)-2-hydroxypentanoic acid (113 mg, 1 equiv) was dissolved in acetonitrile (5 mL), then (3-chloro-2-methoxyphenyl)methanamine (1.2 equiv) was added followed by HATU (170 mg, 1.5 equiv) and DIPEA (100μ). After 24 h the reaction was complete (LCMS). The mixture was quenched with saturated $NaHCO_3$ solution (20 ml) and extracted with ethyl acetate (3×10 mL). The combined organics were washed with 0.5M aqueous HCl solution (2×5 ml), dried over $Na_2SO_4$ and concentrated to dryness to afford crude (2S)-2-(3-benzylureido)-N-(1-((3-chloro-2-methoxybenzyl) amino)-2-hydroxy-1-oxopentan-3-yl)-4-methylpentanamide (150 mg) which was used in next step without additional purification. LCMS [M+H]+=533.5

Step 2: Preparation of (2S)-2-(3-benzylureido)-N-(1-((3-chloro-2-methoxy-benzyl)amino)-1,2-dioxo-pentan-3-yl)-4-methylpentanamide (NA184)

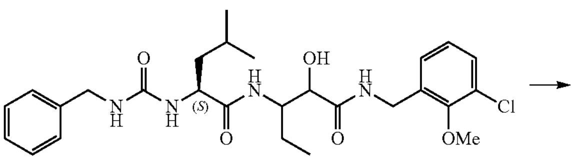

-continued

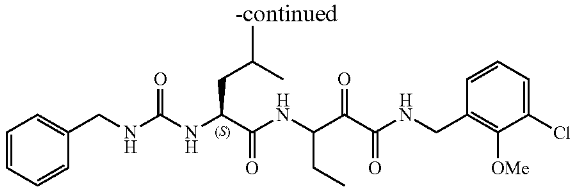

The crude alcohol (2S)-2-(3-benzylureido)-N-(1-((3-chloro-2-methoxybenzyl)amino)-2-hydroxy-1-oxopentan-3-yl)-4-methylpentanamide from the previous step (150 mg) was dissolved in $CH_3CN$ (10 mL) and 1 drop of water, pyridine (150 μL), and DMSO (100 μL) were added, then Dess-Martin Periodinane (150 mg) was added and the reaction stirred at room temperature for 2 h. The mixture was quenched by the addition of saturated aqueous $NaHCO_3$ (20 ml) and extracted with ethyl acetate (3×10 mL). The organic layer was dried over $Na_2SO_4$ and concentrated to dryness. The crude residue was submitted for reverse phase HPLC purification to afford pure (2S)-2-(3-benzylureido)-N-(1-((3-chloro-2-methoxybenzyl)amino)-1,2-dioxopentan-3-yl)-4-methylpentanamide (NA184). Yield after HPLC purification—-51 mg (64%) NA184. LCMS $[M+H]^+$=531.1.

Example 13-4

Step 1: Preparation of 2-(bromomethyl)-6-methylbenzonitrile

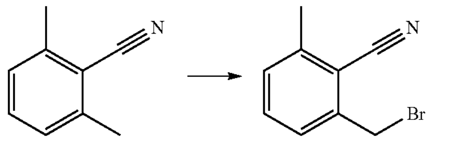

2,6-Dimethyl-bensonitrile (1.3 g) was dissolved in $CCl_4$ (50 mL) and NBS (1.8 g) was added to the solution. The mixture was stirred overnight at room temperature (LC control). The mixture was diluted with dichloromethane (100 mL) and washed with saturated $NaHCO_3$ solution (2×50 mL). The organic solution was evaporated and the crude was purified by flash (silica column) to give pure 2-(bromomethyl)-6-methylbenzonitrile (1.26 g, 60%).

Step 2: Preparation of 2-(azidomethyl)-6-methylbenzonitrile

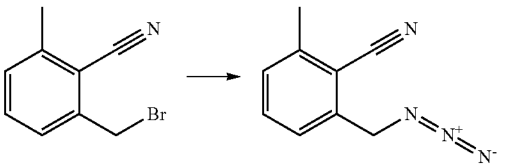

2-(bromomethyl)-6-methylbenzonitrile (1.26 g) was dissolved in dry acetonitrile (30 mL) and sodium azide (1.2 g) was added. The reaction mixture was heated at reflux for 4 h (TLC control), diluted with cold water (200 mL) and extracted with ethyl acetate (2×30 mL). The combined extracts were evaporated to dryness to afford 2-(azidomethyl)-6-methylbenzonitrile (1.05 g, 100%).

Step 3: Preparation of 2-(aminomethyl)-6-methylbenzonitrile

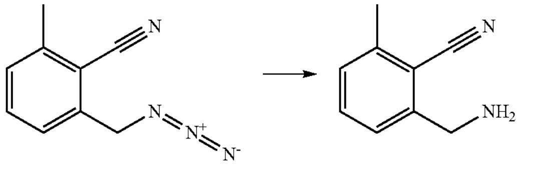

2-(azidomethyl)-6-methylbenzonitrile (1.05 g) was dissolved in methanol (50 mL) and 1 g of 10% Pd/C (wet) was added. The suspension was stirred in an atmosphere of hydrogen (1.3 atm) for 1.5 h at room temperature (LC and TLC control). After all the azide was consumed, the mixture was filtered through Celite and evaporated to dryness. The crude material was purified by flash silica column to give pure 2-(aminomethyl)-6-methylbenzonitrile (0.26 g, 30%).

Step 4: Preparation of (2S)-2-(3-benzylureido)-N-(1-((2-cyano-3-methylbenzyl)amino)-2-hydroxy-1-oxopentan-3-yl)-4-methylpentanamide

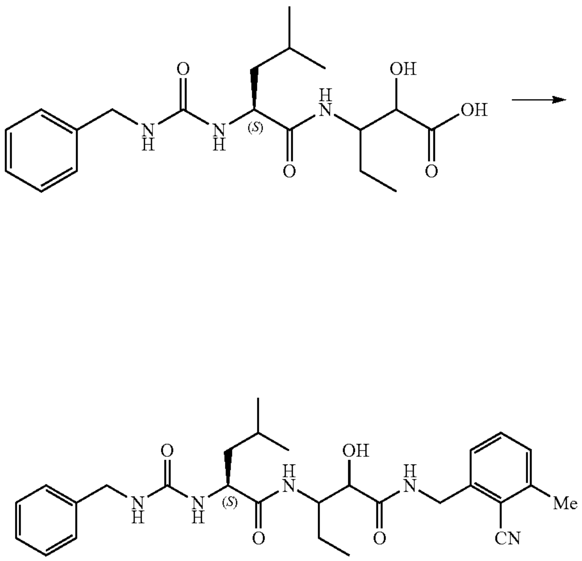

3-((S)-2-(3-benzylureido)-4-methylpentanamido)-2-hydroxypentanoic acid (113 mg, 1 equiv) was dissolved in acetonitrile (5 mL) then 2-(aminomethyl)-6-methylbenzonitrile (1.2 equiv) was added followed by HATU (170 mg, 1.5 equiv) and DIPEA (100 μL). After 24 h the reaction was complete (LCMS). The mixture was quenched with saturated $NaHCO_3$ solution (20 ml) and extracted with ethyl acetate (3×10 ml). The combined organics were washed with 0.5M aqueous HCl solution (2×5 ml), dried over $Na_2SO_4$ and concentrated to dryness to afford crude (2S)-2-(3-benzylureido)-N-(1-((2-cyano-3-methylbenzyl)amino)-2-hydroxy-1-oxopentan-3-yl)-4-methylpentanamide (150 mg) which was used in next step without additional purification. LCMS [M+H]+=508.3.

Step 5: Preparation of (2S)-2-(3-benzylureido)-N-(1-((2-cyano-3-methylbenzyl)amino)-1,2-dioxopentan-3-yl)-4-methylpentanamide (NSN23500)

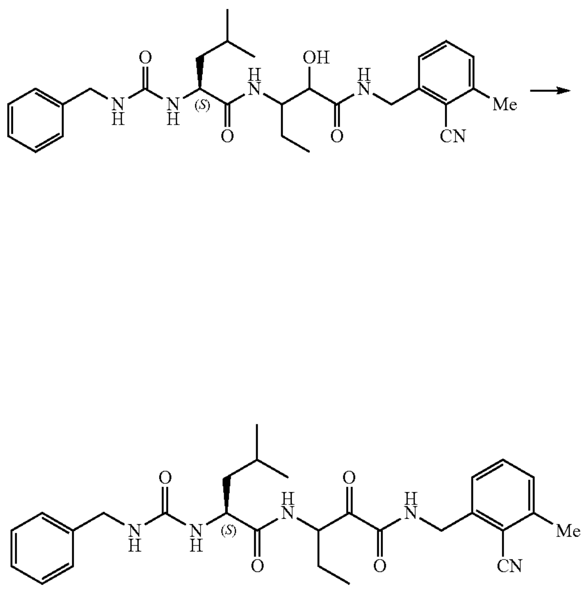

The crude alcohol (2S)-2-(3-benzylureido)-N-(1-((2-cyano-3-methylbenzyl)amino)-2-hydroxy-1-oxopentan-3-yl)-4-methylpentanamide from the previous step (150 mg) was dissolved in $CH_3CN$ (10 mL) and 1 drop of water, pyridine (150 μL), and DMSO (100 μL) were added, then Dess-Martin Periodinane (150 mg) was added and the reaction stirred at room temperature for 2 h. The mixture was quenched by the addition of saturated aqueous $NaHCO_3$ (20 ml) and extracted with ethyl acetate (3×10 mL). The organic layer was dried over $Na_2SO_4$ and concentrated to dryness. The crude residue was submitted for reverse phase HPLC purification to afford pure (2S)-2-(3-benzylureido)-N-(1-((2-cyano-3-methylbenzyl)amino)-1,2-dioxopentan-3-yl)-4-methylpentanamide (NSN23500) Yield after HPLC purification—28 mg (37%) NSN23500 LCMS $[M+H]^+$=506.5.

Example 13-5

Using General Method #1 were prepared the following analogs:

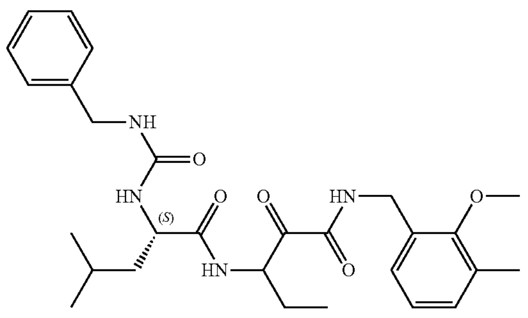

(2S)-2-(3-benzylureido)-N-(1-((2-methoxy-3-methylbenzyl)amino)-1,2-dioxopentan-3-yl)-4-methylpentanamide

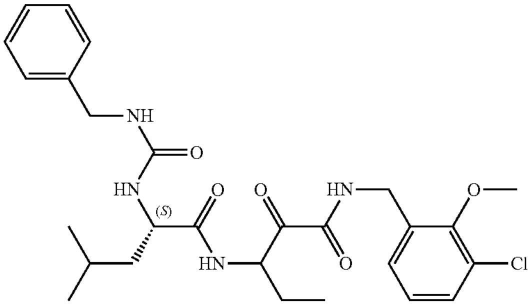

(2S)-2-(3-benzylureido)-N-(1-((3-chloro-2-methoxybenzyl)amino)-1,2-dioxopentan-3-yl)-4-methylpentanamide

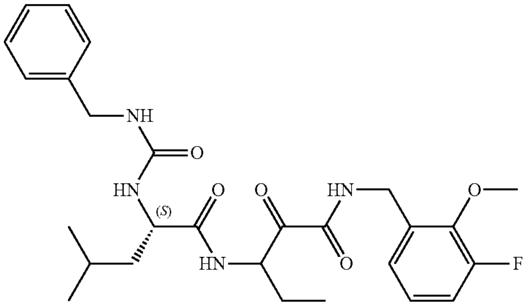

(2S)-2-(3-benzylureido)-N-(1-((3-fluoro-2-methoxybenzyl)amino)-1,2-dioxopentan-3-yl)-4-methylpentanamide

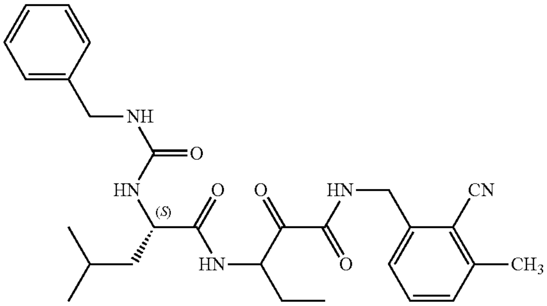

(2S)-2-(3-benzylureido)-N-(1-((2-cyano-3-methylbenzyl)amino)-1,2-dioxopentan-3-yl)-4-methylpentanamide

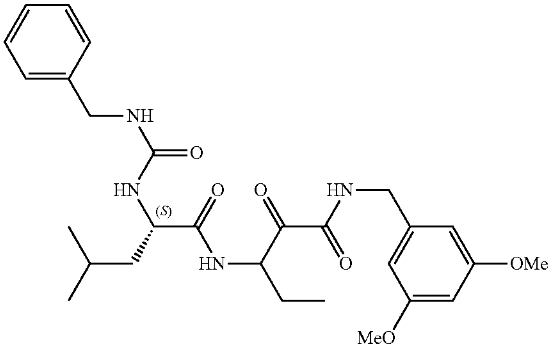

(2S)-2-(3-benzylureido)-N-(1-((3,5-dimethoxybenzyl)amino)-1,2-dioxopentan-3-yl)-4-methylpentanamide

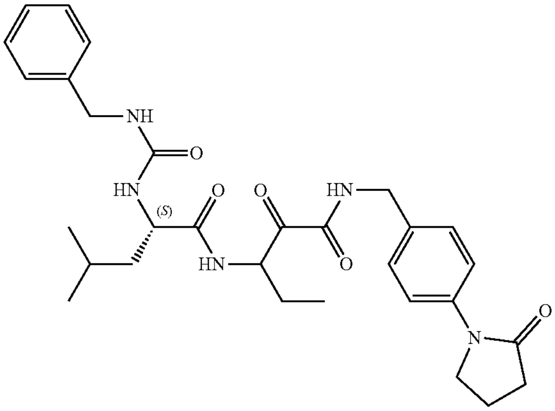

(2S)-2-(3-benzylureido)-N-(1,2-dioxo-1-((4-(2-oxopyrrolidin-1-yl)benzyl)amino)pentan-3-yl)-4-methylpentanamide

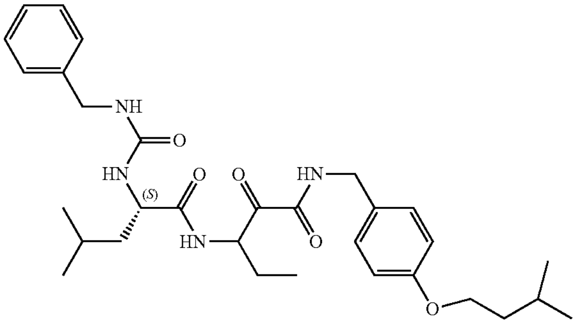

(2S)-2-(3-benzylureido)-N-(1-((4-(isopentyloxy)benzyl)amino)-1,2-dioxopentan-3-yl)-4-methylpentanamide

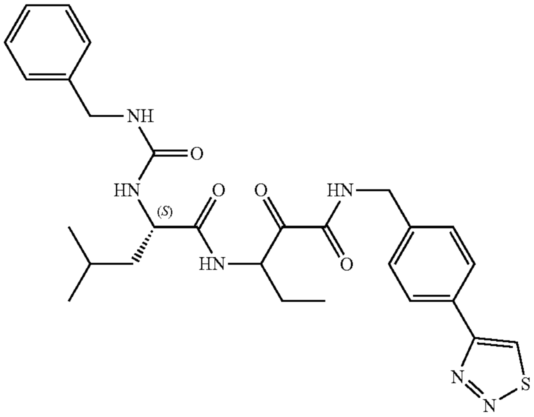

N-(4-(1,2,3-thiadiazol-4-yl)benzyl)-3-((S)-2-(3-benzylureido)-4-methylpentanamido)-2-oxopentanamide

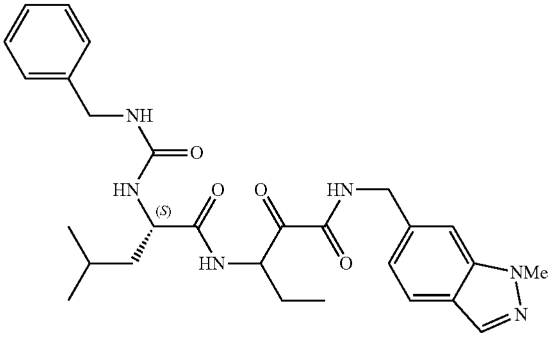

(2S)-2-(3-benzylureido)-4-methyl-N-(1-(((1-methyl-1H-indazol-6-yl)methyl)amino)-1,2-dioxopentan-3-yl)pentanamide

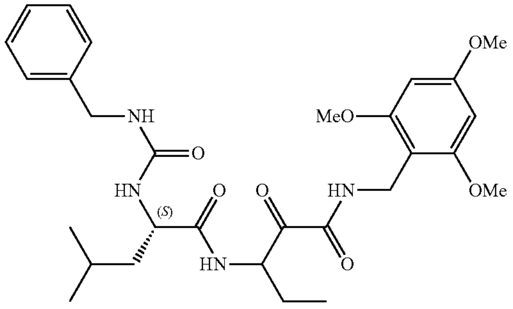

(2S)-2-(3-benzylureido)-N-(1,2-dioxo-1-((2,4,6-trimethoxybenzyl)amino)pentan-3-yl)-4-methylpentanamide

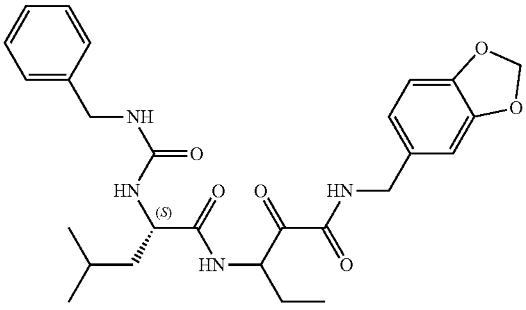

N-(benzo[d][1,3]dioxol-5-ylmethyl)-3-((S)-2-(3-benzylureido)-4-methylpentanamido)-2-oxopentanamide

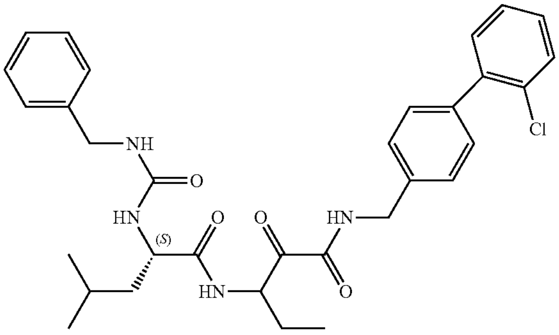

(2S)-2-(3-benzylureido)-N-(1-(((2'-chloro-[1,1'-biphenyl]-4-yl)methyl)amino)-1,2-dioxopentan-3-yl)-4-methylpentanamide

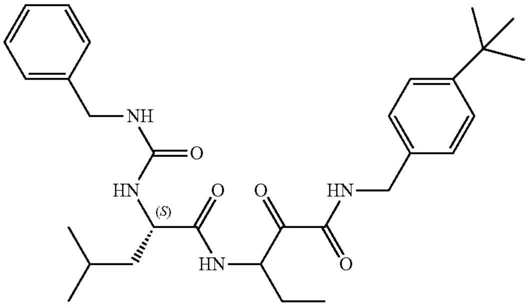

(2S)-2-(3-benzylureido)-N-(1-((4-(tert-butyl)benzyl)amino)-1,2-dioxopentan-3-yl)-4-methylpentanamide

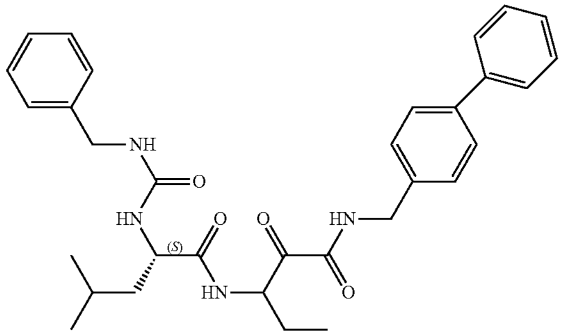

N-([1,1'-biphenyl]-4-ylmethyl)-3-((S)-2-(3-benzylureido)-4-methylpentanamido)-2-oxopentanamide

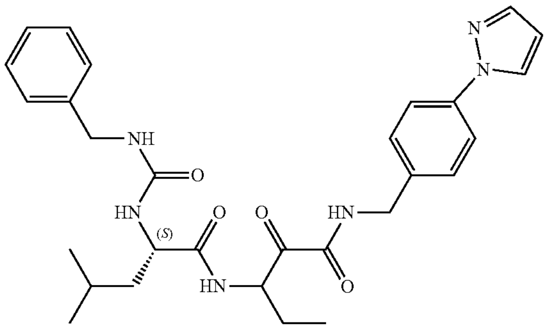

N-(4-(1H-pyrazol-1-yl)benzyl)-3-((S)-2-(3-benzylureido)-4-methylpentanamido)-2-oxopentanamide

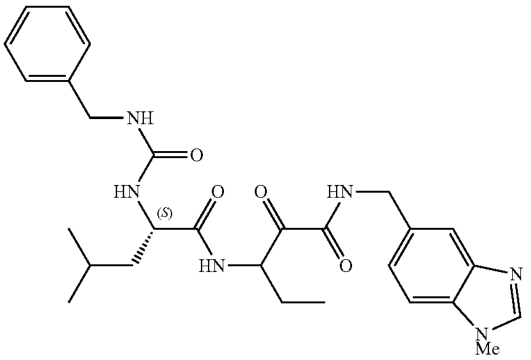

(2S)-2-(3-benzylureido)-4-methyl-N-(1-(((1-methyl-1H-benzo[d]imidazol-5-yl)methyl)amino)-1,2-dioxopentan-3-yl)pentanamide

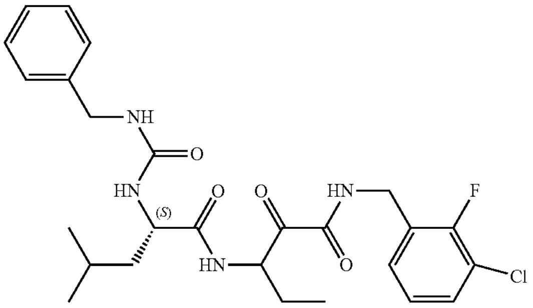

(2S)-2-(3-benzylureido)-N-(1-((3-chloro-2-fluorobenzyl)amino)-1,2-dioxopentan-3-yl)-4-methylpentanamide

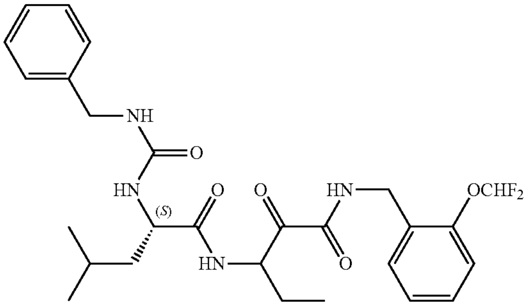

(2S)-2-(3-benzylureido)-N-(1-((2-(difluoromethoxy)benzyl)amino)-1,2-dioxopentan-3-yl)-4-methylpentanamide

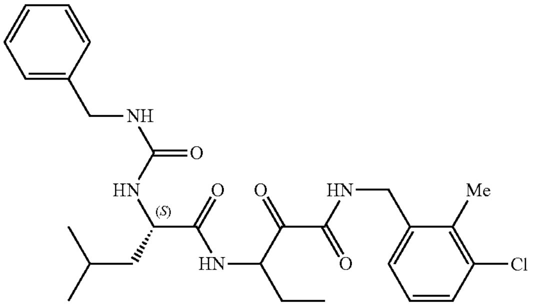

(2S)-2-(3-benzylureido)-N-(1-((3-chloro-2-methylbenzyl)amino)-1,2-dioxopentan-3-yl)-4-methylpentanamide

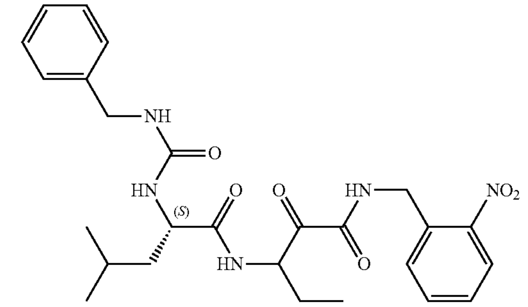

(2S)-2-(3-benzylureido)-4-methyl-N-(1-((2-nitrobenzyl)amino)-1,2-dioxopentan-3-yl)pentanamide

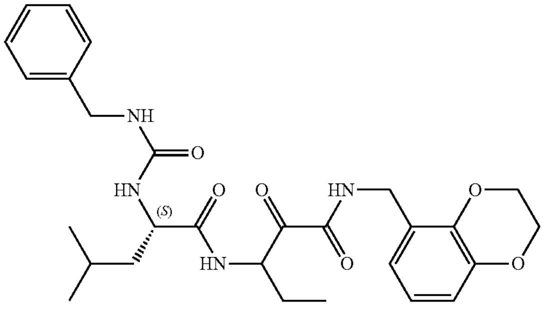

(2S)-2-(3-benzylureido)-N-(1-(((2,3-dihydrobenzo[b][1,4]dioxin-5-yl)methyl)amino)-1,2-dioxopentan-3-yl)-4-methylpentanamide

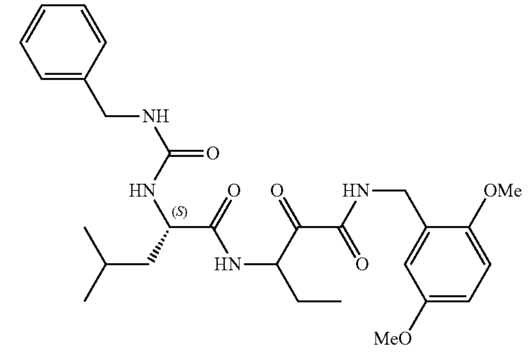

(2S)-2-(3-benzylureido)-N-(1-((2,5-dimethoxybenzyl)amino)-1,2-dioxopentan-3-yl)-4-methylpentanamide

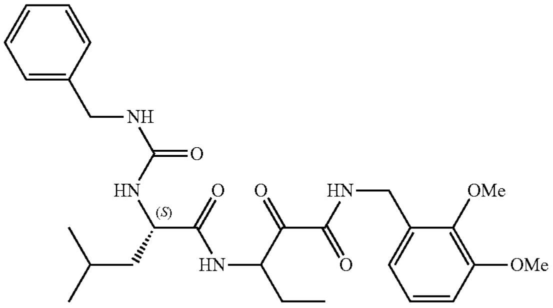

(2S)-2-(3-benzylureido)-N-(1-((2,3-dimethoxybenzyl)amino)-1,2-dioxopentan-3-yl)-4-methylpentanamide

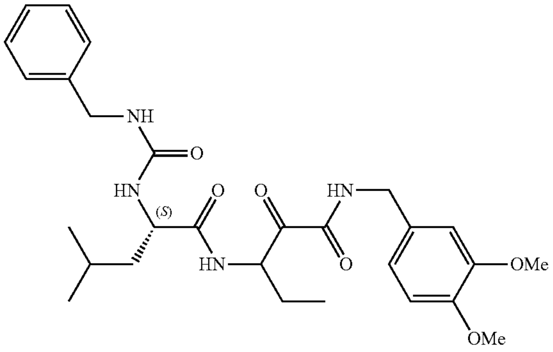

(2S)-2-(3-benzylureido)-N-(1-((3,4-dimethoxybenzyl)amino)-1,2-dioxopentan-3-yl)-4-methylpentanamide

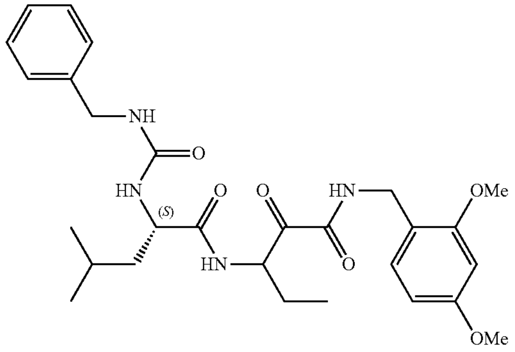

(2S)-2-(3-benzylureido)-N-(1-((2,4-dimethoxybenzyl)amino)-1,2-dioxopentan-3-yl)-4-methylpentanamide

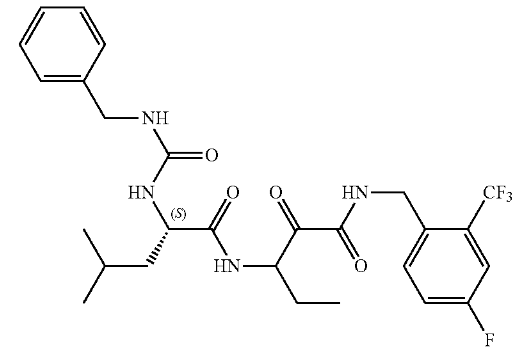

(2S)-2-(3-benzylureido)-N-(1-((4-fluoro-2-(trifluoromethyl)benzyl)amino)-1,2-dioxopentan-3-yl)-4-methylpentanamide

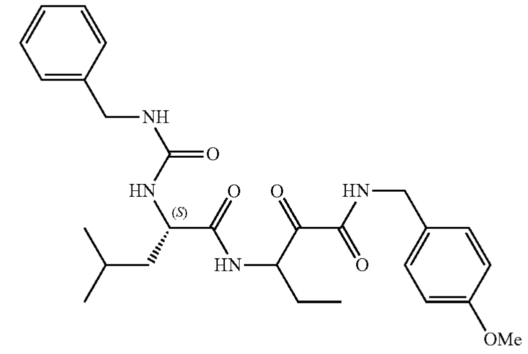

(2S)-2-(3-benzylureido)-N-(1-((4-methoxybenzyl)amino)-1,2-dioxopentan-3-yl)-4-methylpentanamide

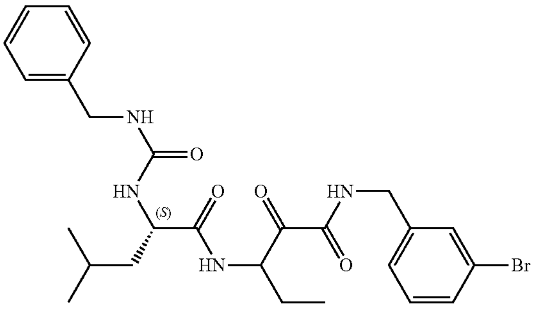

(2S)-2-(3-benzylureido)-N-(1-((3-bromobenzyl)amino)-1,2-dioxopentan-3-yl)-4-methylpentanamide

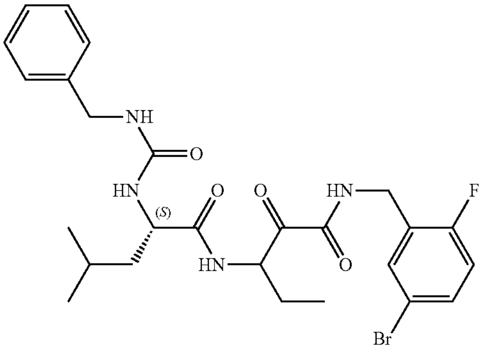

(2S)-2-(3-benzylureido)-N-(1-((5-bromo-2-fluorobenzyl)amino)-1,2-dioxopentan-3-yl)-4-methylpentanamide

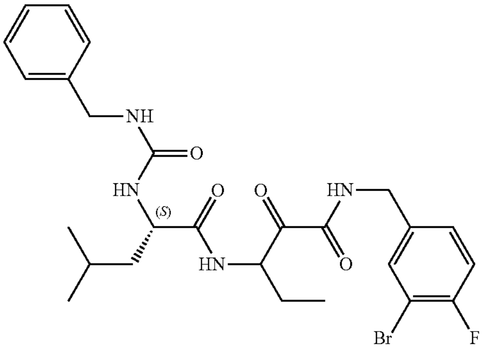

(2S)-2-(3-benzylureido)-N-(1-((3-bromo-4-fluorobenzyl)amino)-1,2-dioxopentan-3-yl)-4-methylpentanamide

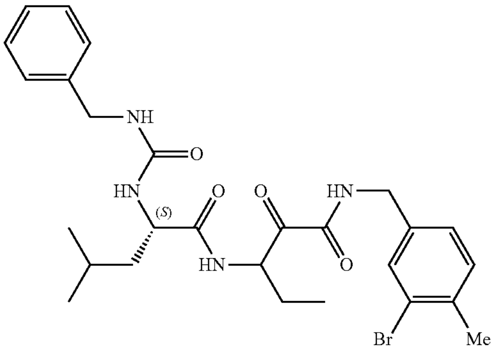

(2S)-2-(3-benzylureido)-N-(1-((3-bromo-4-methylbenzyl)amino)-1,2-dioxopentan-3-yl)-4-methylpentanamide

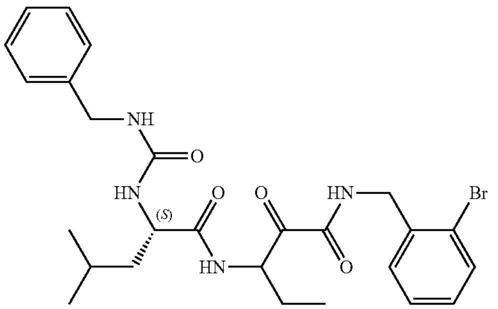

(2S)-2-(3-benzylureido)-N-(1-((2-bromobenzyl)amino)-1,2-dioxopentan-3-yl)-4-methylpentanamide

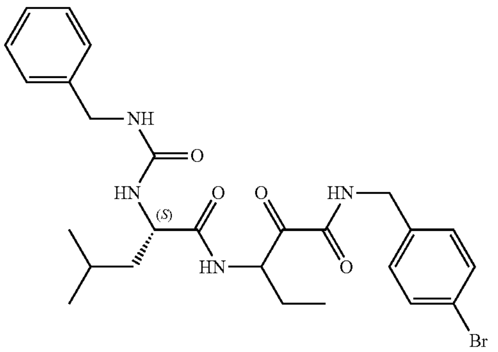

(2S)-2-(3-benzylureido)-N-(1-((4-bromobenzyl)amino)-1,2-dioxopentan-3-yl)-4-methylpentanamide

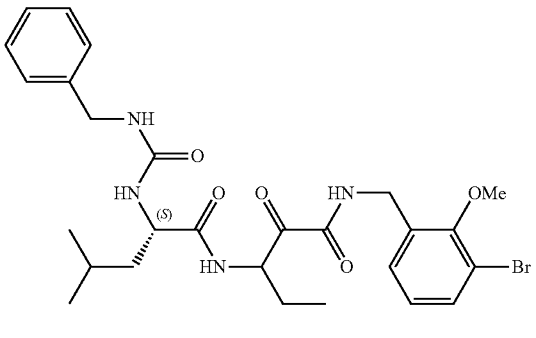

(2S)-2-(3-benzylureido)-N-(1-((3-bromo-2-methoxybenzyl)amino)-1,2-dioxopentan-3-yl)-4-methylpentanamide

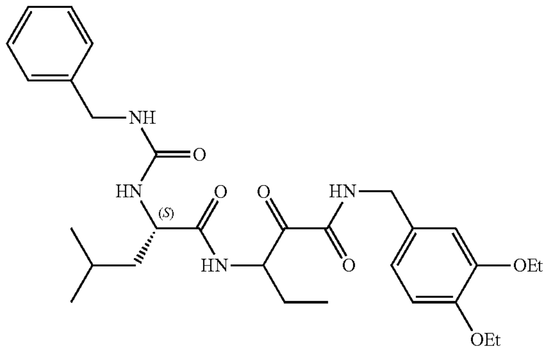

(2S)-2-(3-benzylureido)-N-(1-((3,4-diethoxybenzyl)amino)-1,2-dioxopentan-3-yl)-4-methylpentanamide

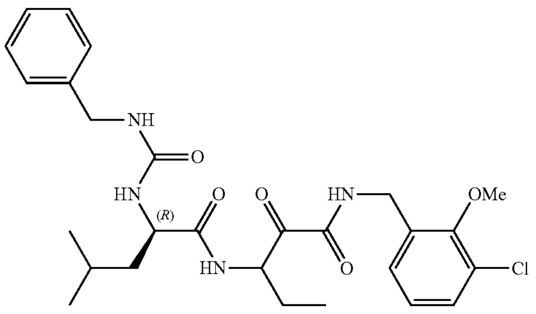

(2R)-2-(3-benzylureido)-N-(1-((3-chloro-2-methoxybenzyl)amino)-1,2-dioxopentan-3-yl)-4-methylpentanamide

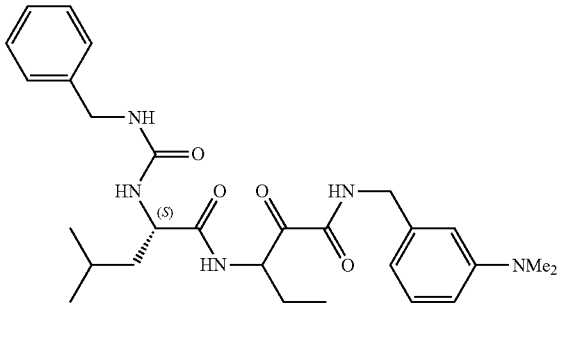

(2S)-2-(3-benzylureido)-N-(1-((3-(dimethylamino)benzyl)amino)-1,2-dioxopentan-3-yl)-4-methylpentanamide

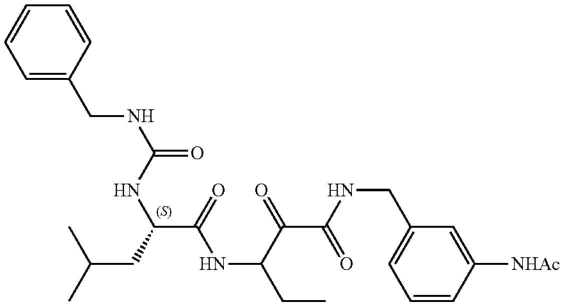

N-(3-acetamidobenzyl)-3-((S)-2-(3-benzylureido)-4-methylpentanamido)-2-oxopentanamide

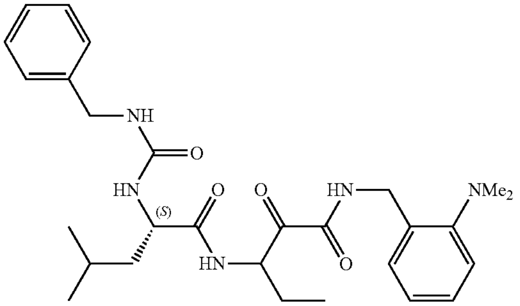

(2S)-2-(3-benzylureido)-N-(1-((2-(dimethylamino)benzyl)amino)-1,2-dioxopentan-3-yl)-4-methylpentanamide

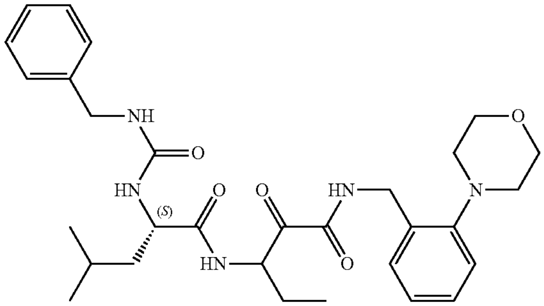

(2S)-2-(3-benzylureido)-4-methyl-N-(1-((2-morpholinobenzyl)amino)-1,2-dioxopentan-3-yl)pentanamide

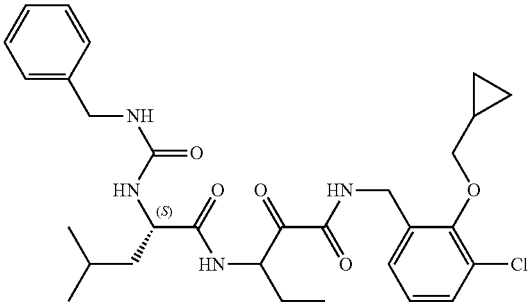

(2S)-2-(3-benzylureido)-N-(1-((3-chloro-2-(cyclopropylmethoxy)benzyl)amino)-1,2-dioxopentan-3-yl)-4-methylpentanamide

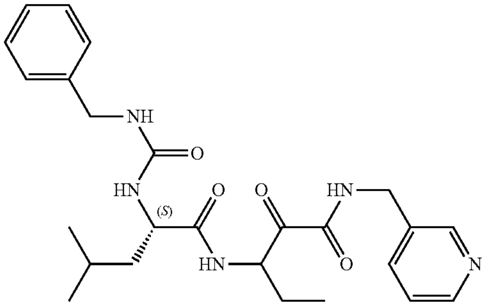

(2S)-2-(3-benzylureido)-N-(1,2-dioxo-1-((pyridin-3-ylmethyl)amino)pentan-3-yl)-4-methylpentanamide

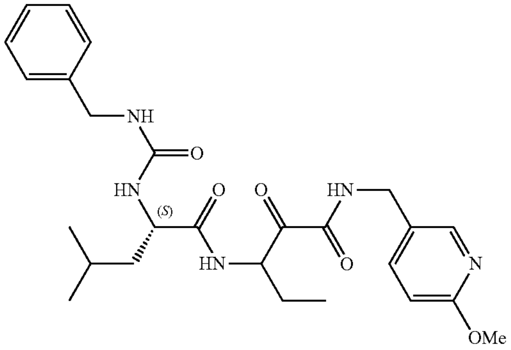

(2S)-2-(3-benzylureido)-N-(1-(((6-methoxypyridin-3-yl)methyl)amino)-1,2-dioxopentan-3-yl)-4-methylpentanamide

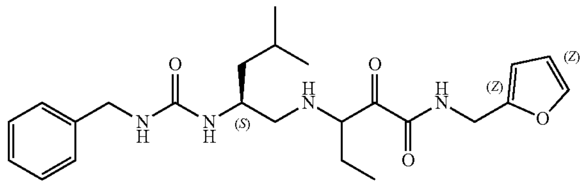

(2S)-2-(3-benzylureido)-N-(1-((furan-2-ylmethyl)amino)-1,2-dioxopentan-3-yl)-4-methylpentanamide

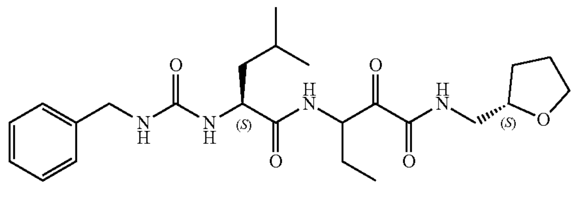

(2S)-2-(3-benzylureido)-N-(1,2-dioxo-1-((((S)-tetrahydrofuran-2-yl)methyl)amino)pentan-3-yl)-4-methylpentanamide Benzylurea—Arylsulfonamide Analogs

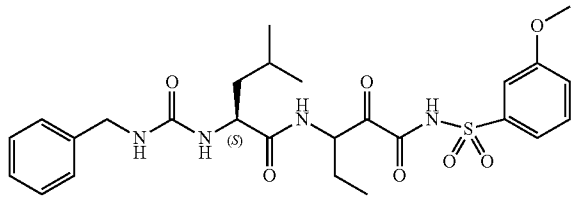

(2S)-2-(3-benzylureido)-N-(1-((3-methoxyphenyl)sulfonamido)-1,2-dioxopentan-3-yl)-4-methylpentanamide

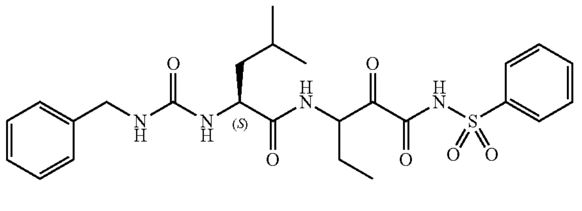

(2S)-2-(3-benzylureido)-N-(1,2-dioxo-1-(phenylsulfonamido)pentan-3-yl)-4-methylpentanamide

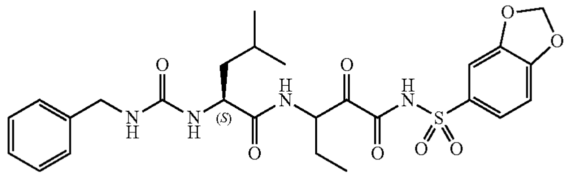

N-(benzo[d][1,3]dioxol-5-ylsulfonyl)-3-((S)-2-(3-benzylureido)-4-methylpentanamido)-2-oxopentanamide Example 14: Preparation of Analogs with Diversity in the Urea (Left Hand Side)

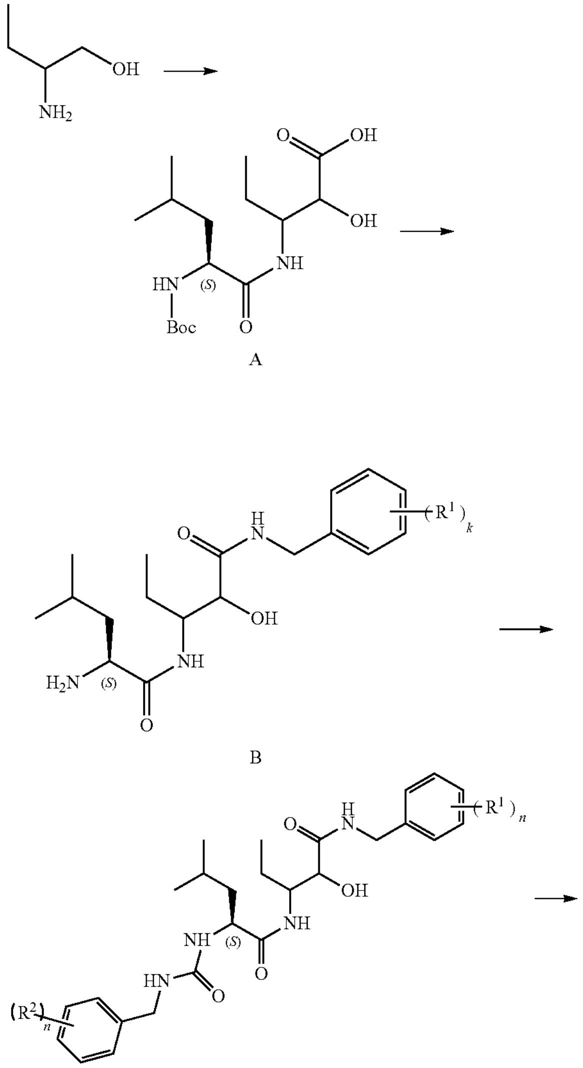

A

B

C

-continued

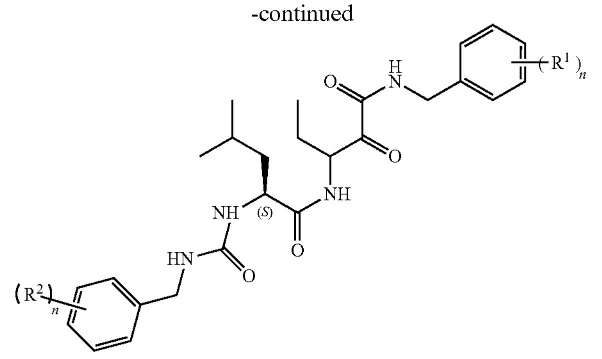

D $R^1$ is $^-OR^4$ or $^-OR^5$ in Formula (I)
$R^2$ is same as $R^2$ in Formula (I)
n is an inteter of 0 to 5
k is an integer of 1 to 5

Using previously reported methodology (WO2020/037012), commercially available 2-aminobutan-1-ol is transformed into the key Intermediate A, 3-((S)-2-((tert-butoxycarbonyl)amino)-4-methylpentanamido)-2-hydroxy-pentanoic acid. Intermediate A is functionalized on the acid terminus with the desired ($R_1$-substituted)benzyl amine and then after deprotection of the Boc-protected amine, affords Intermediate B, (2S)-2-amino-N-(1-(($R_1$-substituted)benzylamino)-2-hydroxy-1-oxopentan-3-yl)-4-methylpentanamide. Intermediate B is then transformed into a series of ureas by reacting the desired ($R_2$-substituted) benzylamine-derived isocyanate or equivalent reagent. Each member of the series of N-($R_1$-substituted)-benzyl-3-((S)-2-(3-($R_2$-substituted)benzylureido)-4-methylpentanamido)-2-hydroxy-pentanamides thus formed (Intermediate C) is oxidized at the secondary hydroxyl group to afford each final product, an N-($R_1$-substituted) benzyl-3-((S)-2-(3-($R_2$-substituted) benzylureido)-4-methylpentanamido)-2-oxopentanamide, Product D.

Example 14-1

Step 1: Preparation of 3-((S)-2-((tert-butoxycarbonyl)amino)-4-methylpentanamido)-2-hydroxypentanoic acid

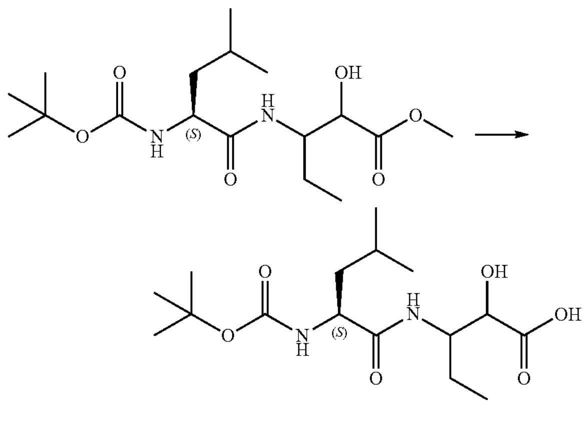

Methyl 3-((S)-2-((tert-butoxycarbonyl)amino)-4-methyl-pentanamido)-2-hydroxypentanoate (7.2 g) was dissolved in a mixture of 1M NaOH (30 ml) and THF (60 ml) and stirred overnight (LCMS control). The solution was diluted with ethyl acetate (300 ml) and 0.5 M HCL (300 ml). The organic layer was separated and the aqueous phase was extracted with ethyl acetate (3x50 mL). The combined extracts was dried over sodium sulfate, filtered and evaporated to dryness to afford 3-((S)-2-((tert-butoxycarbonyl)amino)-4-methyl-pentanamido)-2-hydroxypentanoic acid (intermediate A) (6.5 g, 94% yield). LCMS $[M+H]^+$=347.3.

Step 2: Preparation of tert-butyl ((2S)-1-((1-((3,5-dimethoxybenzyl)amino)-2-hydroxy-1-oxopentan-3-yl)amino)-4-methyl-1-oxopentan-2-yl)carbamate

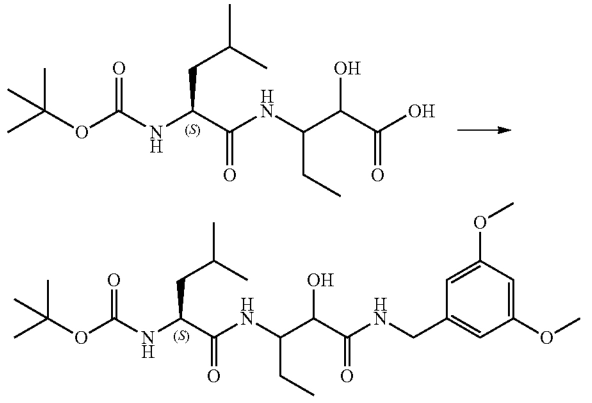

3-((S)-2-((tert-butoxycarbonyl)amino)-4-methylpentanamido)-2-hydroxypentanoic acid (6.5 g) was dissolved in acetonitrile (150 mL) and treated with (3,5-dimethoxyphenyl) methanamine (3.5 g), HATU (8.9 g), and DIPEA (11 mL) and stirred for 1 h at room temperature (LCMS control). The mixture was evaporated, extracted with ethyl acetate (200 mL) and washed with 0.5M HCl (2x50 mL). The crude product was purified by flash chromatography (hexane-ethyl acetate, 0-100% to afford tert-butyl ((2S)-1-((1-((3,5-dimethoxybenzyl)amino)-2-hydroxy-1-oxopentan-3-yl) amino)-4-methyl-1-oxopentan-2-yl)carbamate as a colorless oil (4.7 g, 50%). LCMS $[M+H]^+$=496.4.

Step 3: Preparation of (2S)-2-amino-N-(1-((3,5-dimethoxybenzyl)amino)-2-hydroxy-1-oxopentan-3-yl)-4-methylpentanamide

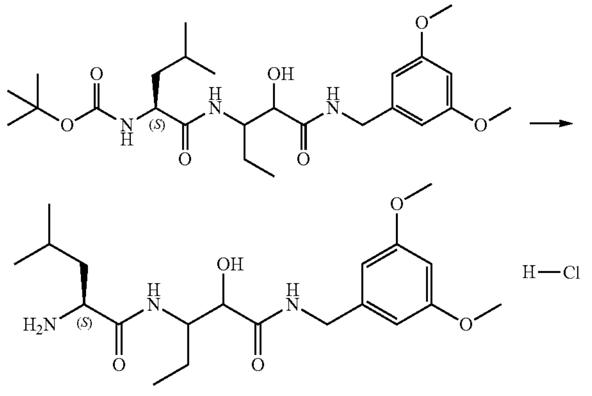

Tert-butyl ((2S)-1-((1-((3,5-dimethoxybenzyl)amino)-2-hydroxy-1-oxopentan-3-yl)amino)-4-methyl-1-oxopentan-2-yl)carbamate (3.5 g) was dissolved in dioxane/HCl (30 mL, 4M) and stirred at room temperature for 1 h. Removal of the solvent followed by drying in vacuo afforded pure (2S)-2-amino-N-(1-((3,5-dimethoxybenzyl)amino)-2-hydroxy-1-oxopentan-3-yl)-4-methylpentanamide hydrochloride salt (2.9 g, 100%) LCMS [M+H]+=396.2.

Step 4: Preparation of methyl 4-((5S)-12-(3,5-dimethoxyphenyl)-8-ethyl-9-hydroxy-5-isobutyl-3,6,10-trioxo-2,4,7,11-tetraazadodecyl)benzoate

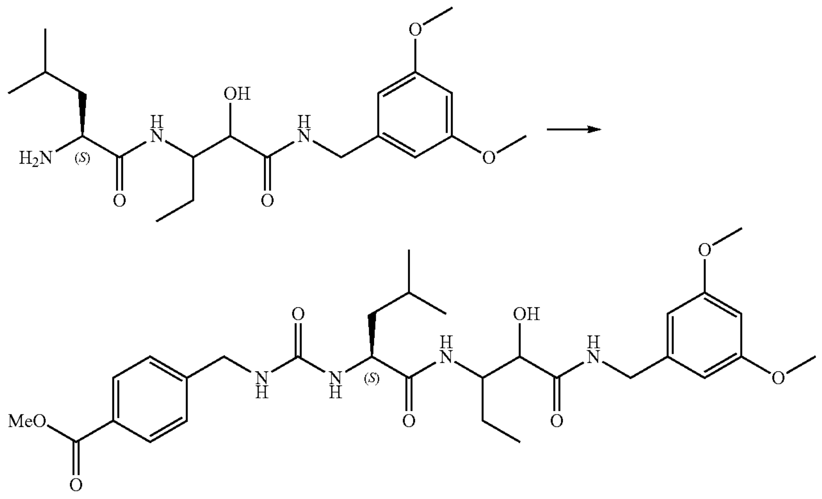

(2S)-2-amino-N-(1-((3,5-dimethoxybenzyl)amino)-2-hydroxy-1-oxopentan-3-yl)-4-methyl-pentanamide, (0.42 g, HCl salt) was dissolved in dioxane (10 mL) and $Et_3N$ (0.3 mL) and methyl 4-(isocyanatomethyl)benzoate (0.23 g) were added. The reaction mixture was stirred at room temperature for 4 h, diluted with saturated $NaHCO_3$ solution (20 mL) and extracted with ethyl acetate (2×10 mL). The organics were evaporated and crude was purified by flash column chromatography to afford methyl 4-((5S)-12-(3,5-dimethoxyphenyl)-8-ethyl-9-hydroxy-5-isobutyl-3,6,10-trioxo-2,4,7,11-tetraazadodecyl)benzoate (0.42 g, 72%).

Step 5: Preparation of 4-((5S)-12-(3,5-dimethoxyphenyl)-8-ethyl-9-hydroxy-5-isobutyl-3,6,10-trioxo-2,4,7,11-tetraazadodecyl)benzoic acid

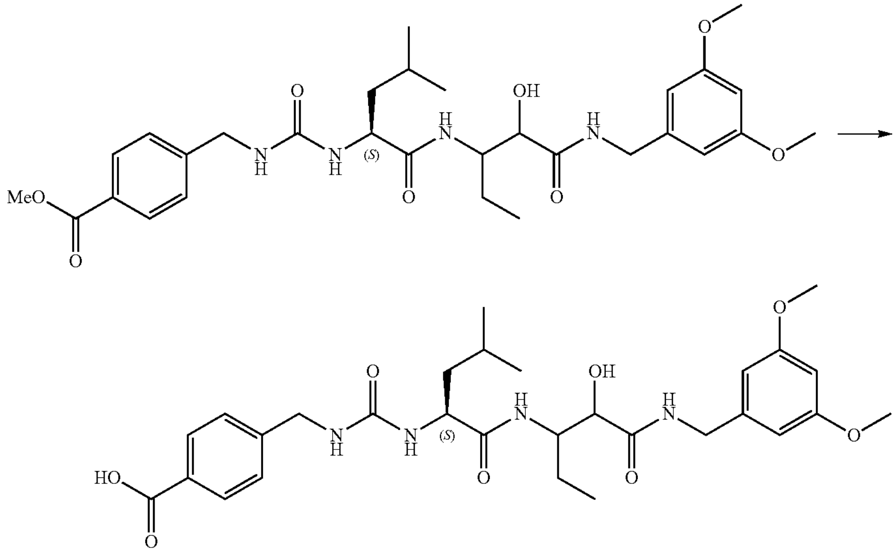

Methyl 4-((5S)-12-(3,5-dimethoxyphenyl)-8-ethyl-9-hydroxy-5-isobutyl-3,6,10-trioxo-2,4,7,11-tetraazadodecyl) benzoate (0.42 g) was dissolved in a mixture of 1M NaOH (5 mL) and THF (5 mL) and stirred overnight (LCMS control). The solution was diluted with ethyl acetate (30 mL) and 0.5M HCL (30 mL). The organic layer was separated and the aqueous phase was extracted with ethyl acetate (3×5 mL). The combined extracts were dried over sodium sulfate, filtered and evaporated to dryness to afford 4-((5S)-12-(3,5-dimethoxyphenyl)-8-ethyl-9-hydroxy-5-isobutyl-3,6,10-trioxo-2,4,7,11-tetraazadodecyl)benzoic acid (0.3 g, 75% yield).

Step 6: Preparation of 4-((5S)-12-(3,5-dimethoxyphenyl)-8-ethyl-9-hydroxy-5-isobutyl-3,6,10-trioxo-2,4,7,11-tetraazadodecyl)-N-(2-(isopropylamino) ethyl)benzamide

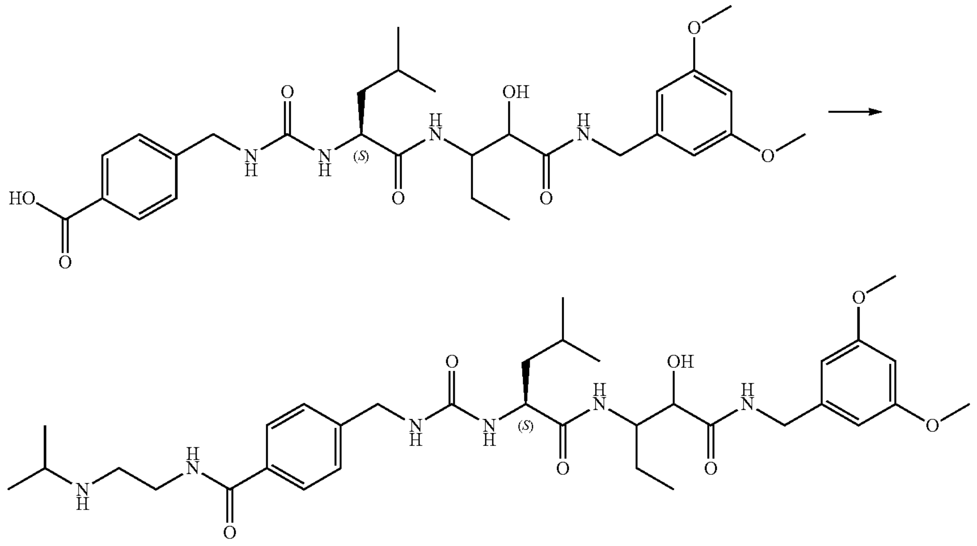

4-((5S)-12-(3,5-dimethoxyphenyl)-8-ethyl-9-hydroxy-5-isobutyl-3,6,10-trioxo-2,4,7,11-tetraaza-dodecyl)benzoic acid (100 mg, 1 equiv) was dissolved in acetonitrile (5 mL) and $N^1$-isopropylethane-1,2-diamine (1.2 equiv) was added followed by HATU (150 mg, 1.5 equiv) and DIPEA (100 µL). After 24 h the reaction was complete (LCMS). The reaction was quenched by the addition of saturated $NaHCO_3$ solution (20 ml) and extracted with ethyl acetate (3×10 ml), dried over $Na_2SO_4$ and concentrated to dryness. The crude 4-((5S)-12-(3,5-dimethoxyphenyl)-8-ethyl-9-hydroxy-5-isobutyl-3,6,10-trioxo-2,4,7,11-tetraazadodecyl)-N-(2-(isopropylamino)-ethyl)benzamide (100 mg) was used in next step without additional purification. LCMS [M+H]+=657.7.

Step 7: Preparation of 4-((5S)-12-(3,5-dimethoxyphenyl)-8-ethyl-5-isobutyl-3,6,9,10-tetraoxo-2,4,7,11-tetraazadodecyl)-N-(2-(isopropylamino) ethyl) benzamide

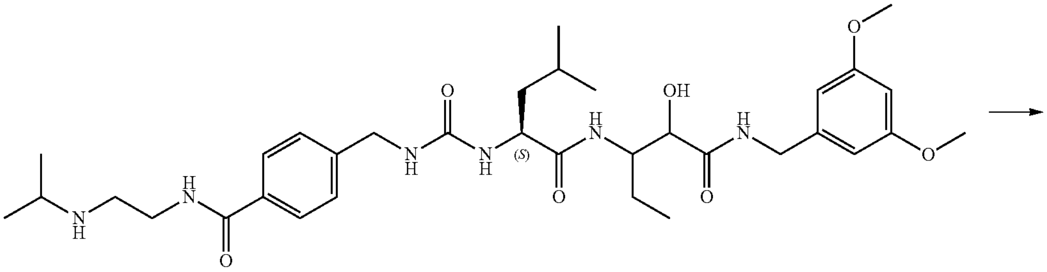

-continued

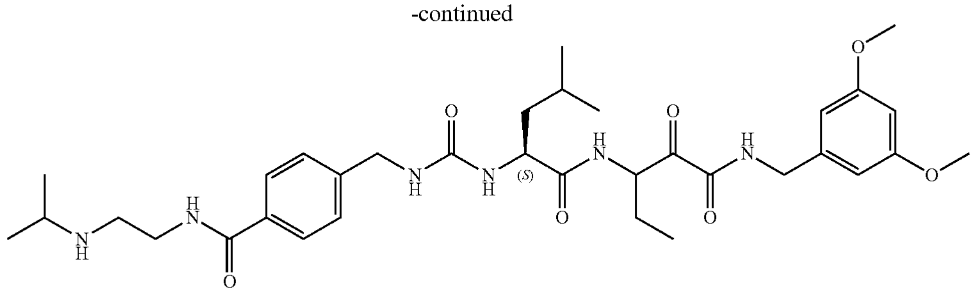

Crude 4-((5S)-12-(3,5-dimethoxy-phenyl)-8-ethyl-9-hydroxy-5-isobutyl-3,6,10-trioxo-2,4,7,11-tetraazadodecyl)-N-(2-(isopropyl-amino)ethyl)benzamide (100 mg) was dissolved in $CH_3CN$ (10 mL) and 1 drop of water, pyridine (150 μL), and DMSO (100 μL) were added. Then Dess-Martin Periodinane (150 mg) was added and the reaction was stirred at room temperature for 2 h. The mixture was quenched by the addition of saturated aqueous $NaHCO_3$ (20 ml) and extracted with ethyl acetate (3×10 ml). The organic layer was dried over $Na_2SO_4$ and concentrated. LCMS analysis showed a very messy, over oxidized reaction mixture. The desired product could not be recovered from the mixture.

Example 14-2: Alternate Order of Steps Produces Anomalous Cyclized Products

If the oxidation of the secondary alcohol is carried out earlier in the sequence, unexpected anomalous cyclized products are obtained.

Alternate Step 3: Preparation of tert-butyl ((2S)-1-((1-((3,5-dimethoxybenzyl)amino)-1,2-dioxopentan-3-yl)amino)-4-methyl-1-oxopentan-2-yl)carbamate

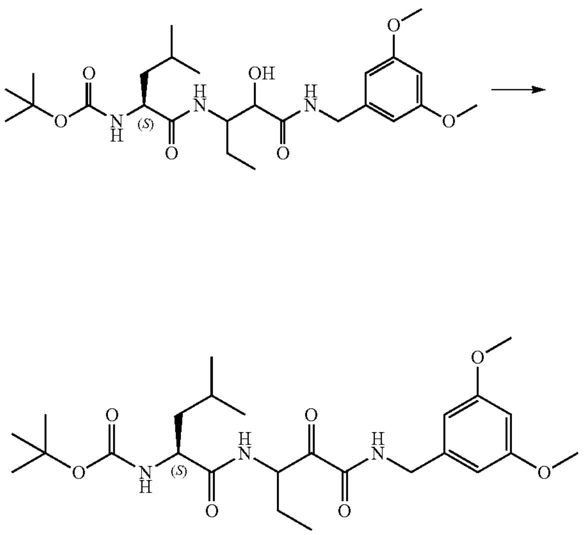

Tert-butyl ((2S)-1-((1-((3,5-di-methoxybenzyl)amino)-2-hydroxy-1-oxopentan-3-yl)amino)-4-methyl-1-oxopentan-2-yl)carbamate (1.3 g) was dissolved in $CH_3CN$ (40 mL) and 8 drops of water, pyridine (5 equiv), and DMSO (4 equiv) were added, followed by Dess-Martin Periodinane (0.95 g, 1 equiv) in 3 portions over 1 h. The reaction mixture was stirred at room temperature for 2 h, was quenched by the addition of saturated aqueous $NaHCO_3$ (100 mL) and extracted with ethyl acetate (3×50 mL). The organic layer was dried over $Na_2SO_4$ and concentrated to dryness. The crude residue was purified by silica column chromatography to give 0.96 g (78%) of pure tert-butyl ((2S)-1-((1-((3,5-dimethoxybenzyl)amino)-1,2-dioxo-pentan-3-yl)amino)-4-methyl-1-oxopentan-2-yl)carbamate. LCMC $[M+H]^+$ =494.5.

Alternate Step 4: Preparation of (2S)-2-amino-N-(1-((3,5-dimethoxybenzyl)amino)-1,2-dioxopentan-3-yl)-4-methylpentanamide and (6R)-N-(3,5-dimethoxybenzyl)-3-ethyl-6-isobutyl-5-oxo-3,4,5,6-tetrahydropyrazine-2-carboxamide

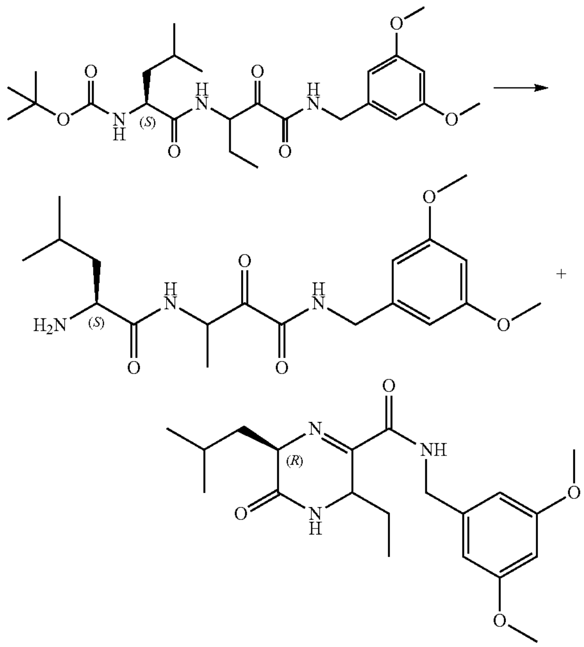

Tert-butyl ((2S)-1-((1-((3,5-dimethoxybenzyl)amino)-1,2-dioxo,pentan-3-yl)amino)-4-methyl-1-oxopentan-2-yl) carbamate (0.96 g) was dissolved in dioxane/HCl (15 mL, 4M) and stirred at room temperature for 1 h. Removal of the solvent followed by drying in vacuo afforded (0.85 g), a mixture of two compounds as determined by LCMS. The mixture was used in next step. LCMS $[M+H]^+$=376.2 and 394.5.

Alternate Step 5: Preparation of N-(3,5-dimethoxybenzyl)-3-((S)-4-isobutyl-2,5-dioxo-imidazolidin-1-yl)-2-oxopentanamide (NSN23499) and N-(3,5-dimethoxybenzyl)-3-ethyl-5-hydroxy-6-isobutylpyrazine-2-carboxamide (NSN23490)

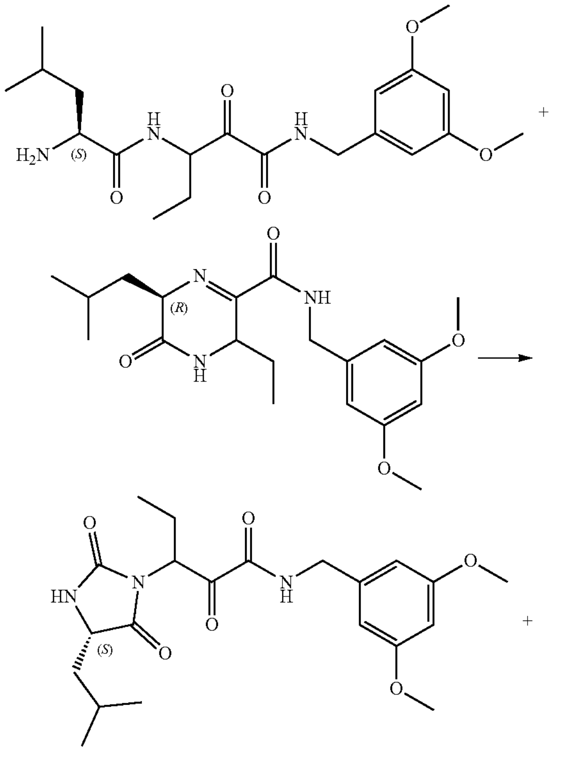

-continued

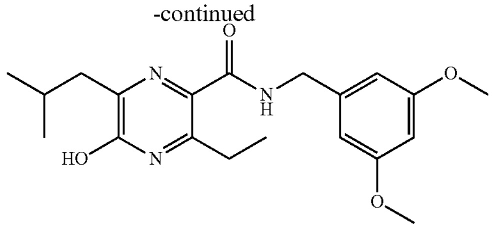

The mixture of 2 compounds from step 4 above ((2S)-2-amino-N-(1-((3,5-dimethoxybenzyl)-amino)-1,2-dioxopentan-3-yl)-4-methylpentanamide and (6R)-N-(3,5-dimethoxybenzyl)-3-ethyl-6-isobutyl-5-oxo-3,4,5,6-tetrahydropyrazine-2-carboxamide) (0.85 g) was dissolved in $CH_3CN$/dioxane 1/1, 50 mL) solution and treated with $Et_3N$ (1.5 ml) and triphosgene (0.4 g). After 0.5 h of stirring at room temperature, LC analysis showed the presence of two major products (A and B). The mixture was evaporated to dryness, dissolved in ethyl acetate (100 mL) and washed with saturated $NaHCO_3$ (20 mL) and 0.1M HCl (20 mL). The organic solution was evaporated and submitted for HPLC purification. Two products were isolated and characterized as N-(3,5-dimethoxybenzyl)-3-((S)-4-isobutyl-2,5-dioxoimidazolidin-1-yl)-2-oxopentanamide (NSN23499) and N-(3,5-dimethoxybenzyl)-3-ethyl-5-hydroxy-6-isobutylpyrazine-2-carbox-amide (NSN23491).

A –47 mg, NSN23499; LCMS [M+H]+=420.5;

B ~90 mg, NSN23491; LCMS [M+H]+=374.4

Example 14-3

Preparation of N-(2-(diethylamino)ethyl)-4-((5S)-12-(3,5-dimethoxyphenyl)-8-ethyl-9-hydroxy-5-isobutyl-3,6,10-trioxo-2,4,7,11-tetraazadodecyl)benzamide

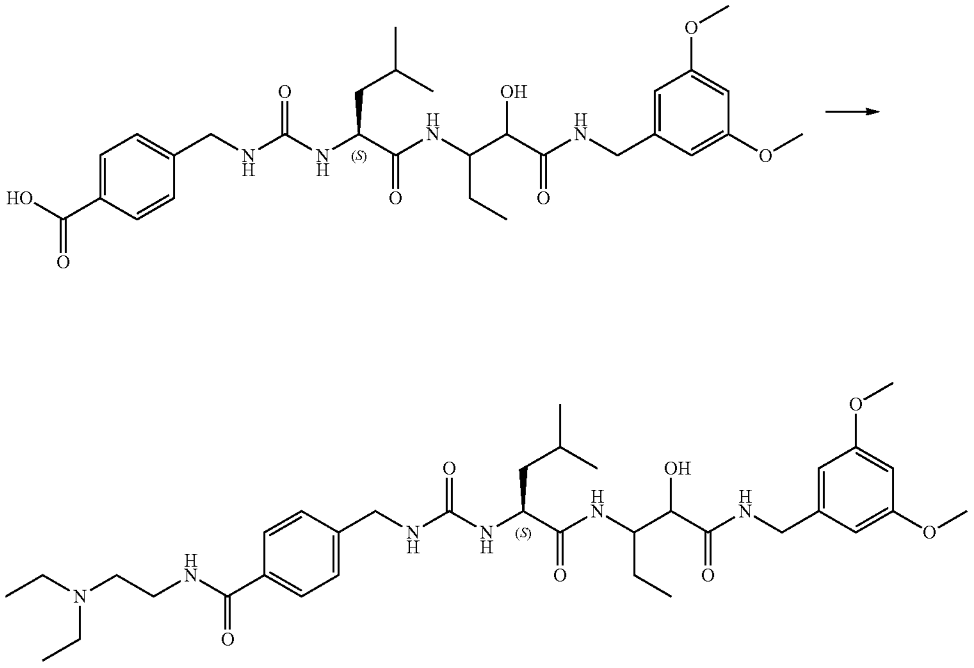

4-((5S)-12-(3,5-dimethoxyphenyl)-8-ethyl-9-hydroxy-5-isobutyl-3,6,10-trioxo-2,4,7,11-tetraaza-dodecyl)benzoic acid (100 mg, 1 equiv) was dissolved in acetonitrile (5 mL) and $N^1,N^1$-diethylethane-1,2-diamine (1.2 equiv) was added followed by HATU (150 mg, 1.5 equiv) and DIPEA (100 μL). After 24 h the reaction was complete (LCMS). The reaction was quenched by the addition of saturated $NaHCO_3$ solution (20 ml) and extracted with ethyl acetate (3×10 ml), dried over $Na_2SO_4$ and concentrated to dryness. The crude N-(2-(diethylamino)ethyl)-4-((5S)-12-(3,5-dimethoxyphenyl)-8-ethyl-9-hydroxy-5-isobutyl-3,6,10-trioxo-2,4,7,11-tetraazadodecyl)-benzamide (100 mg) was used in next step without additional purification. LCMS [M+H]+=671.6.

Preparation of N-(2-(diethylamino)ethyl)-4-((5S)-12-(3,5-dimethoxyphenyl)-8-ethyl-5-isobutyl-3,6,9,10-tetraoxo-2,4,7,11-tetraazadodecyl)benzamide

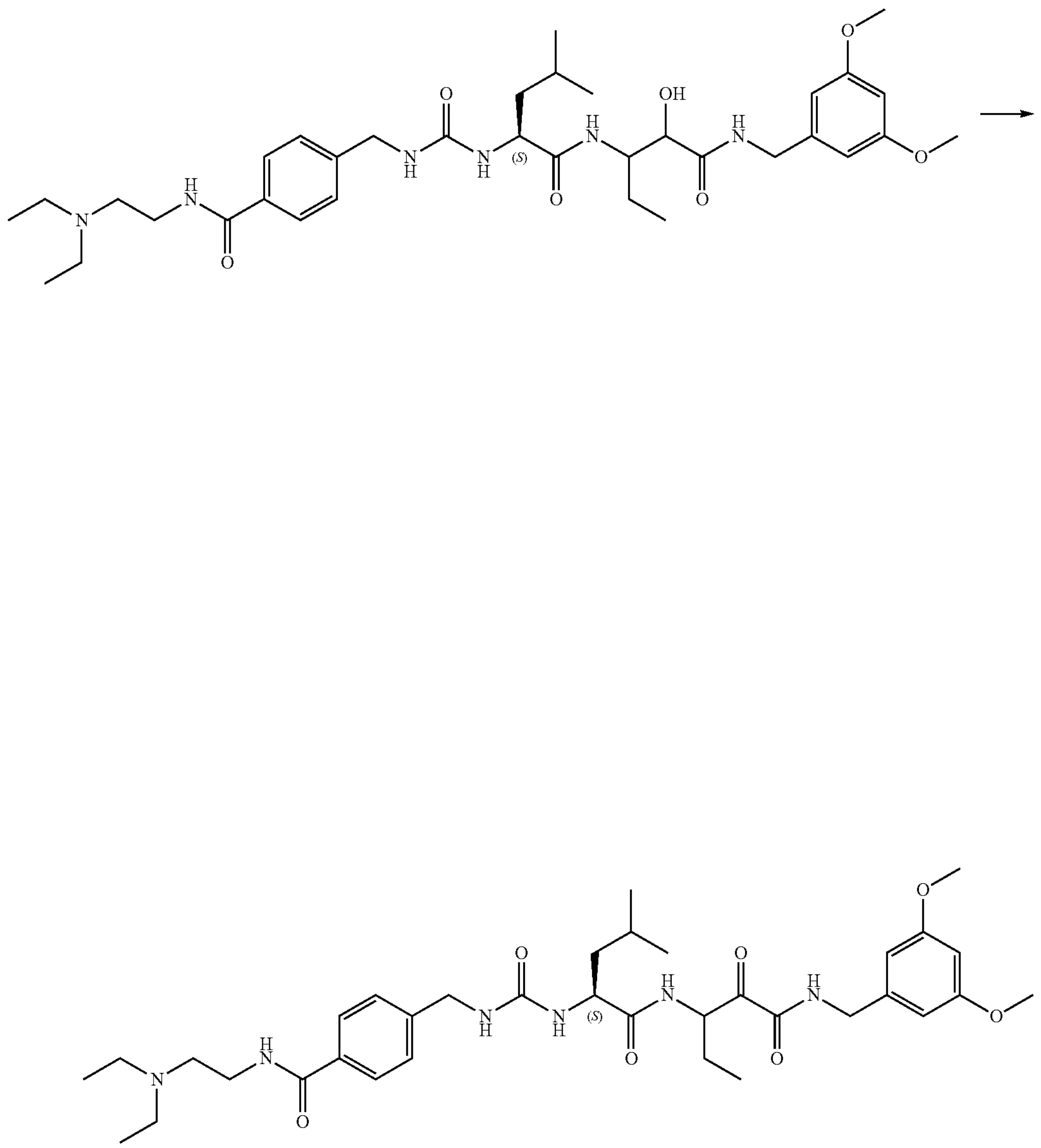

Crude N-(2-(diethylamino)ethyl)-4-((5S)-12-(3,5-dimethoxyphenyl)-8-ethyl-9-hydroxy-5-isobutyl-3,6,10-trioxo-2,4,7,11-tetraazadodecyl)benzamide (120 mg) was dissolved in $CH_3CN$ (10 mL) and 1 drop of water, pyridine (150 μL), and DMSO (100 μL) were added. Then Dess-Martin Periodinane (150 mg) was added and the reaction was stirred at room temperature for 2 h. The mixture was quenched by the addition of saturated aqueous $NaHCO_3$ (20 ml) and extracted with ethyl acetate (3×10 ml). The organic layer was dried over $Na_2SO_4$ and concentrated. The crude residue was submitted for reverse phase HPLC purification to afford pure N-(2-(diethylamino)ethyl)-4-((5S)-12-(3,5-dimethoxyphenyl)-8-ethyl-5-isobutyl-3,6,9,10-tetraoxo-2,4,7,11-tetraazadodecyl)benzamide. (2.3 mg, 3%); LCMS $[M+H]^+$=669.6.

Example 14-4: Preparation of Sulfamoylamino Analogs

Step 1: Preparation of (2S)-2-((N-benzylsulfamoyl)amino)-N-(1-((3,5-dimethoxybenzyl)-amino)-2-hydroxy-1-oxopentan-3-yl)-4-methylpentanamide

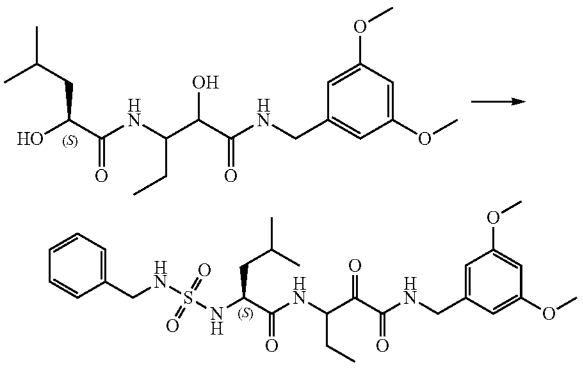

(2S)-2-amino-N-(1-((3,5-dimethoxybenzyl)amino)-2-hydroxy-1-oxopentan-3-yl)-4-methyl-pentanamide (0.09 g, HCl salt) was dissolved in acetonitrile (10 ml) and $Et_3N$ (0.2 ml) and benzylsulfamoyl chloride (60 mg) were added. The reaction mixture was stirred at room temperature for 4 h, diluted with saturated $NaHCO_3$ solution (20 ml) and extracted with ethyl acetate (2×10 ml). The organics were evaporated and the crude (2S)-2-((N-benzylsulfamoyl)-amino)-N-(1-((3,5-dimethoxybenzyl)¬amino)-2-hydroxy-1-oxopentan-3-yl)-4-methylpentan-amide was used in next step without additional purification. LCMS—565.5

Step 2: Preparation of (2S)-2-((N-benzylsulfamoyl)amino)-N-(1-((3,5-dimethoxy-benzyl)amino)-1,2-dioxopentan-3-yl)-4-methylpentanamide (NSN23501)

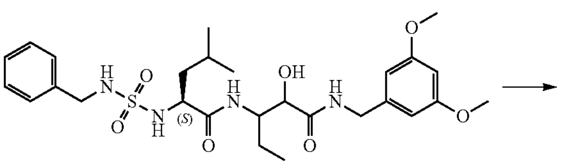

-continued

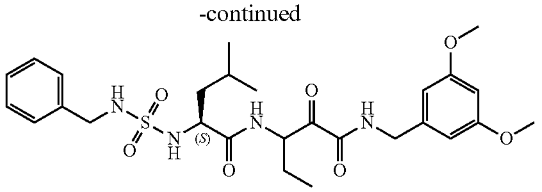

(2S)-2-((N-benzylsulfamoyl)amino)-N-(1-((3,5-dimethoxybenzyl)-amino)-2-hydroxy-1-oxopentan-3-yl)-4-methylpentanamide (150 mg) was dissolved in $CH_3CN$ (10 mL) and 1 drop of water, pyridine (150 μL), and DMSO (100 μL) were added. Then Dess-Martin Periodinane (150 mg) was added and the reaction stirred at room temperature for 2 h. The mixture was quenched by the addition of saturated aqueous $NaHCO_3$ (20 ml) and extracted with ethyl acetate (3×10 ml). The organic layer was dried over $Na_2SO_4$ and concentrated to dryness. The crude residue was submitted for reverse phase HPLC purification to afford pure (2S)-2-((N-benzylsulfamoyl)amino)-N-(1-((3,5-dimethoxy-benzyl)amino)-1,2-dioxopentan-3-yl)-4-methylpentanamide. (15 mg, 13%) NSN23501 LCMS [M+H]+=563.5.

Example 14-5: Preparation of N-(3,5-dimethoxybenzyl)amide Analogs

Example 14-5-1: Preparation of N-(3,5-dimethoxybenzyl)-3-((S)-2-(3-(4-(2-(dimethylamino)-ethoxy)benzyl)ureido)-4-methylpentanamido)-2-hydroxypentanamide Step 1: Preparation of tert-butyl (4-(2-(dimethylamino)ethoxy)benzyl)carbamate

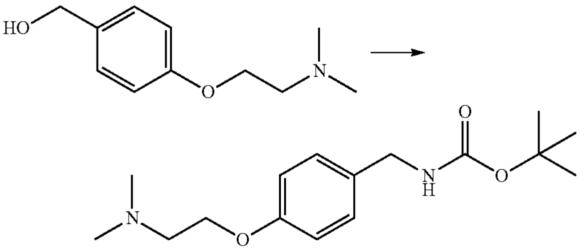

2-(4-(aminomethyl)phenoxy)-N,N-dimethylethan-1-amine (0.39 g) was dissolved in THE (5 ml) and Boc-anhydride (0.45 g) was added. The mixture was stirred at room temperature for 2 h and evaporated to dryness. The residue was purified by column silica gel chromatography to give tert-butyl (4-(2-(dimethylamino)ethoxy)benzyl)carbamate (0.49 g, 83%). The material was used without further purification.

Step 2: Preparation of N-(3,5-dimethoxybenzyl)-3-((S)-2-(3-(4-(2-(dimethylamino)-ethoxy)benzyl)ureido)-4-methylpentanamido)-2-hydroxypentanamide

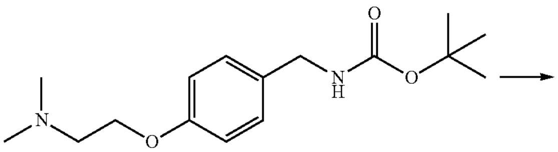

-continued

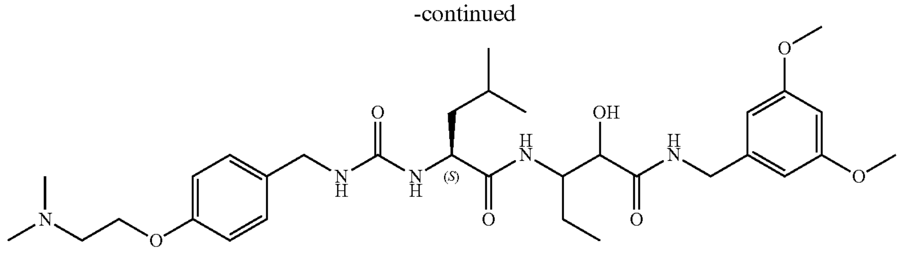

Using the procedure of Kim and Lee (Tetrahedron Letters 57 (2016) 4890-4892; see also Spyropoulos and Kokotos; J. Org. Chem. 2014, 79, 4477-4483) Boc-protected amine, tert-butyl (4-(2-(dimethylamino)ethoxy)benzyl)carbamate (1.0 mmol) and 2-chloropyridine (3.0 mmol) were dissolved in dry dichloromethane (20 ml). Triflic anhydride (1.5 mmol) was added dropwise over 5 min. After stirring for 1 h at room temperature (2S)-2-amino-N-(1-((3,5-dimethoxybenzyl)amino)-2-hydroxy-1-oxopentan-3-yl)-4-methylpentanamide hydrochloride salt (0.3 mmol) and triethylamine (3.0 mmol) were added to the resulting mixture. After additional stirring for 1 h (LC control), the mixture was diluted with water (20 ml), the layers were separated, and the aqueous was extracted with dichloromethane (3×10 mL). The combined organics were washed with brine, dried over $MgSO_4$, filtered and concentrated under reduced pressure. The crude N-(3,5-dimethoxybenzyl)-3-((S)-2-(3-(4-(2-(dimethylamino)-ethoxy)-benzyl)ureido)-4-methylpentanamido)-2-hydroxypentanamide (~150 mg) was used in next step without further purification. LCMS $[M+H]^+=616.6$ Step 3: Preparation of N-(3,5-dimethoxybenzyl)-3-((S)-2-(3-(4-(2-(dimethylamino)-ethoxy)benzyl)ureido)-4-methylpentanamido)-2-oxopentanamide (NSN23483)

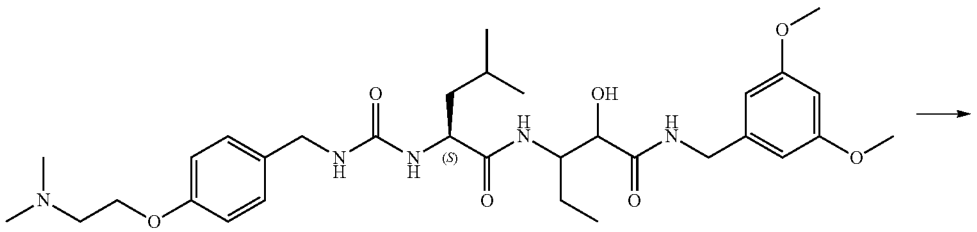

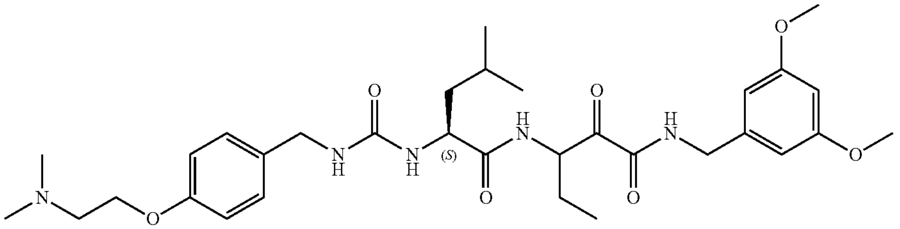

N-(3,5-dimethoxybenzyl)-3-((S)-2-(3-(4-(2-(dimethylamino)-ethoxy)benzyl)ureido)-4-methyl-pentanamido)-2-hydroxypentanamide, (150 mg) was dissolved in $CH_3CN$ (10 mL) and 1 drop of water, pyridine (150 μL), and DMSO (100 μL) were added. Then Dess-Martin Periodinane (150 mg) was added and the reaction stirred at room temperature for 2 h. The mixture was quenched by the addition of saturated aqueous $NaHCO_3$ (20 ml) and extracted with ethyl acetate (3×10 ml). The organic layer was dried over $Na_2SO_4$ and concentrated to dryness. The crude residue was submitted for reverse phase HPLC purification to afford pure N-(3,5-dimethoxybenzyl)-3-((S)-2-(3-(4-(2-(dimethylamino)ethoxy)-benzyl)ureido)-4-methylpentanamido)-2-oxopentanamide (15 mg, 12%) (NSN23483). LCMS [M+H]+=614.2.

Example 14-5-2: Preparation of N-(3,5-dimethoxybenzyl)-3-((S)-2-(3-(4-((dimethylamino)-methyl)benzyl)ureido)-4-methylpentanamido)-2-oxopentanamide

Step 1: Preparation of tert-butyl (4-((dimethylamino)methyl)benzyl)carbamate

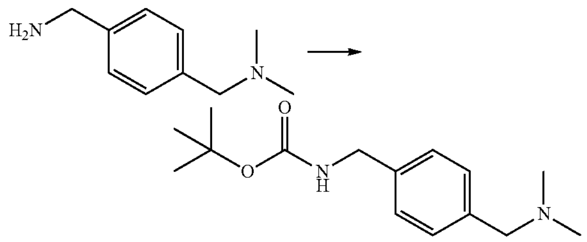

1-(4-(aminomethyl)phenyl)-N,N-dimethylmethanamine (0.33 g) was dissolved in THF (5 ml) and Boc-anhydride (0.45 g) was added. The mixture was stirred at room temperature for 2 h and evaporated to dryness. The residue was purified by column silica gel chromatography to give pure tert-butyl (4-((dimethylamino)methyl)benzyl)carbamate (0.45 g, 85%) which was used directly in the next step.

Step 2: Preparation of N-(3,5-dimethoxybenzyl)-3-((S)-2-(3-(4-((dimethylamino) methyl)benzyl) ureido)-4-methylpentanamido)-2-hydroxypentanamide

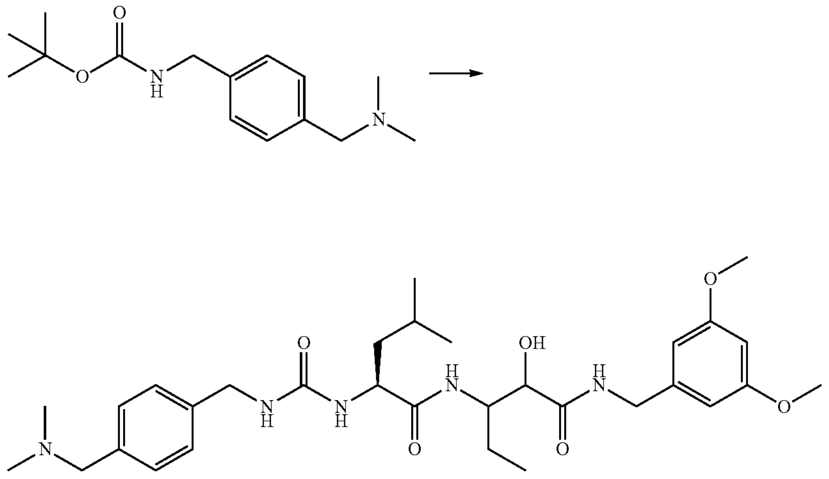

Boc-protected amine, tert-butyl (4-((dimethylamino) methyl)benzyl)carbamate (1.0 mmol) and 2-chloropyridine (3.0 mmol) were dissolved in dry dichloromethane (20 ml). Triflic anhydride (1.5 mmol) was added dropwise over 5 min. After stirring for 1 hour at room temperature (2S)-2-amino-N-(1-((3,5-dimethoxybenzyl)amino)-2-hydroxy-1-oxopentan-3-yl)-4-methylpentamide hydrochloride salt (0.3 mmol) and triethylamine (3.0 mmol) were added to the resulting mixture. After additional stirring for 1 h (LC control), the mixture was diluted with water (20 ml), the layers were separated and the aqueous phase was extracted with dichloromethane (3×10 mL). The combined organics were washed with brine, dried over $MgSO_4$, filtered and concentrated under reduced pressure. The crude N-(3,5-dimethoxybenzyl)-3-((S)-2-(3-(4-((dimethylamino)-methyl) benzyl)ureido)-4-methylpentanamido)-2-hydroxypentanamide (~150 mg) was used in next step without additional purification.

Step 3: Preparation of N-(3,5-dimethoxybenzyl)-3-((S)-2-(3-(4-((dimethylamino)methyl)-benzyl) ureido)-4-methylpentanamido)-2-oxopentanamide

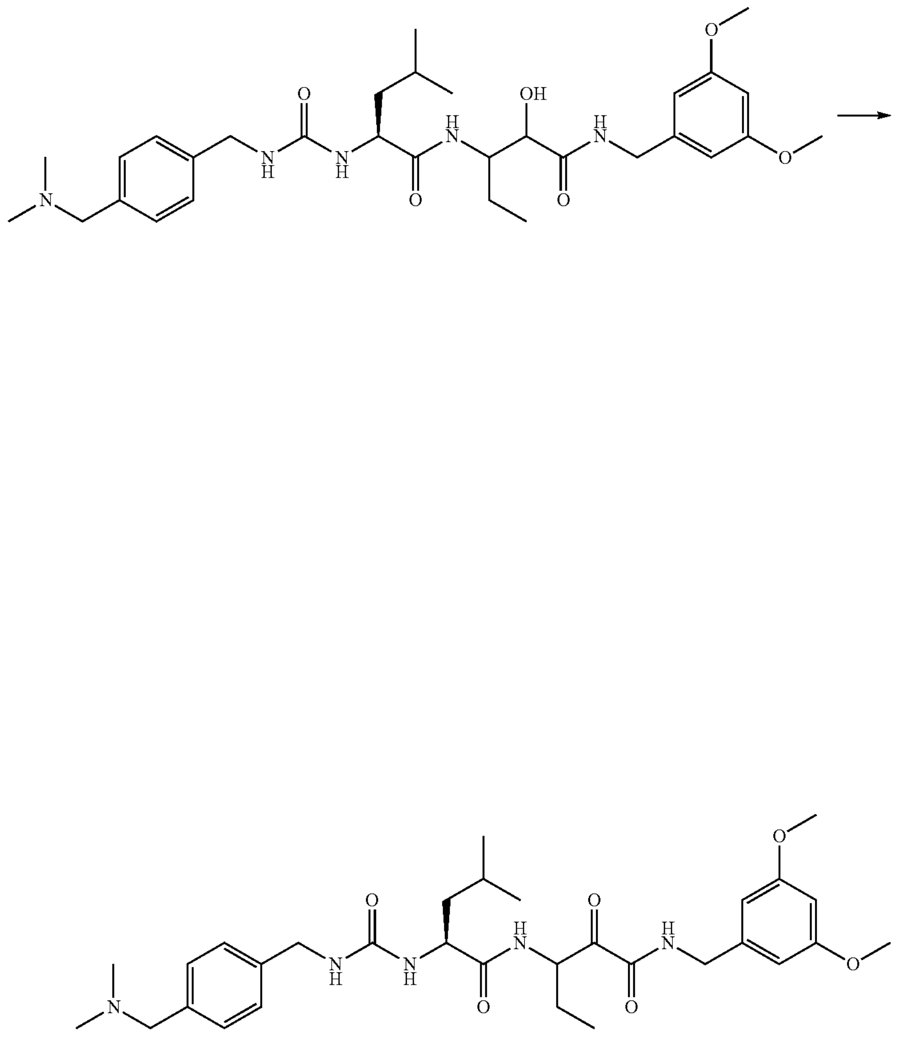

N-(3,5-dimethoxybenzyl)-3-((S)-2-(3-(4-((dimethylamino)methyl)benzyl)ureido)-4-methyl-pentanamido)-2-hydroxypentanamide, (150 mg) was dissolved in $CH_3CN$ (10 mL) and 1 drop of water, pyridine (150 μL), and DMSO (100 μL) were added. Then Dess-Martin Periodinane (150 mg) was added and the reaction was stirred at room temperature for 2 h. The mixture was quenched by the addition of saturated aqueous $NaHCO_3$ (20 ml) and extracted with ethyl acetate (3×10 ml). The organic layer was dried over $Na_2SO_4$ and concentrated. The crude residue was submitted for reverse phase HPLC purification to afford pure N-(3,5-dimethoxybenzyl)-3-((S)-2-(3-(4-((dimethylamino)methyl)benzyl)ureido)-4-methylpentanamido)-2-oxopentanamide (6 mg, 5%) LCMS [M+H]+=584.4

Example 14-6: Preparation of 4-((5S)-12-(3,5-dimethoxyphenyl)-8-ethyl-5-isobutyl-3,6,9,10-tetraoxo-2,4,7,11-tetraazadodecyl)-N-isopropylbenzamide (NSN23488)

Step 1: Preparation of tert-butyl (4-(isopropylcarbamoyl)benzyl)carbamate

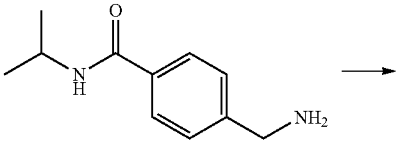

-continued

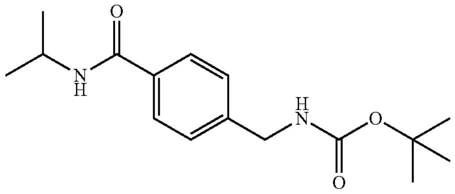

4-(aminomethyl)-N-isopropylbenzamide (0.38 g) was dissolved in THF (5 ml) and Boc-anhydride (0.45 g) was added. The mixture was stirred at room temperature for 2 h and evaporated to dryness. The residue was purified by column silica gel chromatography to give tert-butyl (4-(isopropylcarbamoyl)benzyl)carbamate (0.43 g, 74%) which was used directly in the next step.

Step 2: Preparation of 4-((5S)-12-(3,5-dimethoxyphenyl)-8-ethyl-9-hydroxy-5-isobutyl-3,6,10-trioxo-2,4,7,11-tetraazadodecyl)-N-isopropylbenzamide

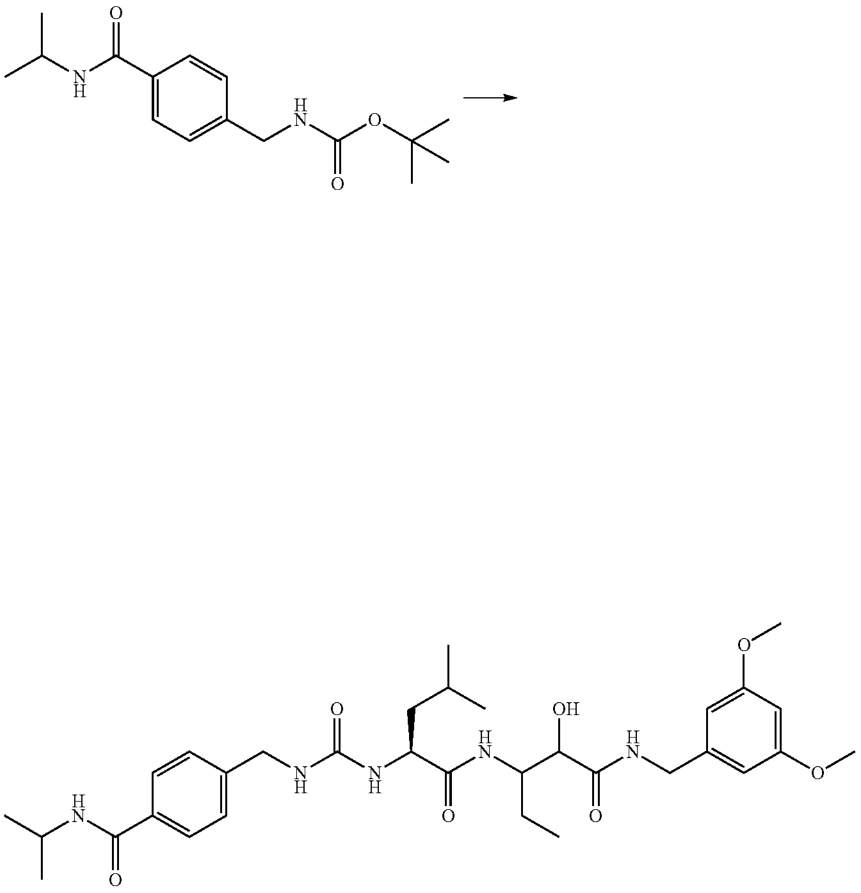

Boc-protected amine tert-butyl (4-(isopropylcarbamoyl) benzyl)carbamate (1.0 mmol) and 2-chloropyridine (3.0 mmol) were dissolved in dry dichloromethane (20 ml). Triflic anhydride (1.5 mmol) was added dropwise over 5 min. After stirring for 1 h at room temperature (2S)-2-amino-N-(1-((3,5-dimethoxybenzyl)amino)-2-hydroxy-1-oxopentan-3-yl)-4-methylpentanamide hydrochloride salt (0.3 mmol) and triethylamine (3.0 mmol) were added to the reaction mixture. After additional stirring for 1 hour (LC control), the mixture was diluted with water (20 ml), the layers were separated and the aqueous phase was extracted with dichloromethane (3×10 mL). The combined organics were washed with brine, dried over $MgSO_4$, filtered and concentrated under reduced pressure. The crude 4-((5S)-12-(3,5-dimethoxyphenyl)-8-ethyl-9-hydroxy-5-isobutyl-3,6,10-trioxo-2,4,7,11-tetraazadodecyl)-N-isopropylbenzamide (~150 mg) was used in next step without additional purification.

Step 3: Preparation of 4-((5S)-12-(3,5-dimethoxyphenyl)-8-ethyl-5-isobutyl-3,6,9,10-tetraoxo-2,4,7,11-tetraazadodecyl)-N-isopropylbenzamide (NSN23488)

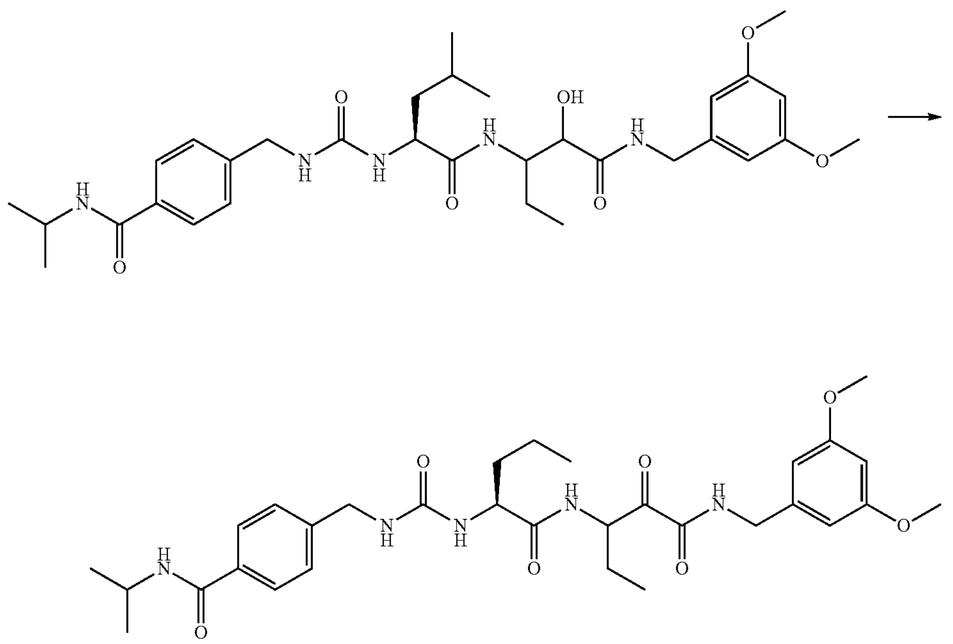

4-((5S)-12-(3,5-dimethoxyphenyl)-8-ethyl-9-hydroxy-5-isobutyl-3,6,10-trioxo-2,4,7,11-tetra-azadodecyl)-N-isopropylbenzamide, (150 mg) was dissolved in $CH_3CN$ (10 mL) and 1 drop of water, pyridine (150 μL), and DMSO (100 μL) were added. Then Dess-Martin Periodinane (150 mg) was added, and the reaction was stirred at room temperature for 2 h. The mixture was quenched by the addition of saturated aqueous $NaHCO_3$ (20 ml) and extracted with ethyl acetate (3×10 ml). The organic layer was dried over $Na_2SO_4$ and concentrated to dryness. The crude residue was submitted for reverse phase HPLC purification to afford pure 4-((5S)-12-(3,5-dimethoxyphenyl)-8-ethyl-5-isobutyl-3,6,9,10-tetraoxo-2,4,7,11-tetraazadodecyl)-N-isopropylbenzamide (18 mg, 15%); NSN23488

Example 14-7: Preparation of (2S)-2-(3-(4-cyano-2-methoxybenzyl)ureido)-N-(1-((3,5-di-methoxybenzyl)amino)-1,2-dioxopentan-3-yl)-4-methylpentanamide (NSN23489)

Step 1: Preparation of tert-butyl (4-cyano-2-methoxybenzyl)carbamate

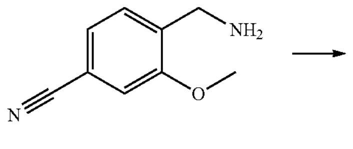

-continued

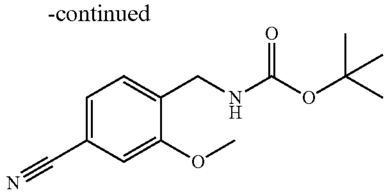

4-(aminomethyl)-3-methoxybenzonitrile (0.32 g) was dissolved in THE (5 ml) and Boc-anhydride (0.45 g) was added. The mixture was stirred at room temperature for 2 h and evaporated to dryness. The residue was purified by column silica gel chromatography to give tert-butyl (4-cyano-2-methoxybenzyl)carbamate (0.41 g, 78%) which was used directly in the next step.

Step 2: Preparation of (2S)-2-(3-(4-cyano-2-methoxybenzyl)ureido)-N-(1-((3,5-di-methoxybenzyl)amino)-2-hydroxy-1-oxopentan-3-yl)-4-methylpentanamide

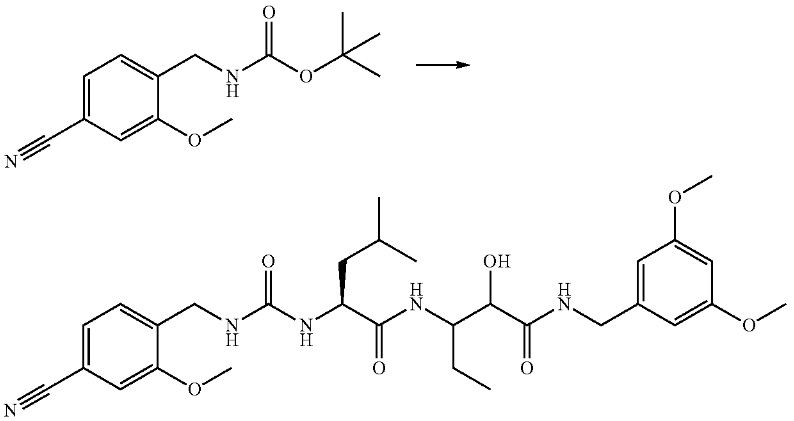

Boc-protected amine, tert-butyl (4-cyano-2-methoxybenzyl)carbamate (1.0 mmol) and 2-chloropyridine (3.0 mmol) were dissolved in dry dichloromethane (20 ml). Triflic anhydride (1.5 mmol) was added dropwise over 5 min. After stirring for 1 hour at room temperature (2S)-2-amino-N-(1-((3,5-dimethoxybenzyl)amino)-2-hydroxy-1-oxopentan-3-yl)-4-methylpentanamide hydrochloride salt (0.3 mmol) and triethylamine (3.0 mmol) were added to the reaction mixture. After additional stirring for 1 hour (LC control), the mixture was diluted with water (20 ml), the layers were separated and the aqueous phase was extracted with dichloromethane (3×10 mL). The combined organics were washed with brine, dried over $MgSO_4$, filtered and concentrated under reduced pressure to dryness. The crude (2S)-2-(3-(4-cyano-2-methoxybenzyl)ureido)-N-(1-((3,5-di-methoxybenzyl)amino)-2-hydroxy-1-oxopentan-3-yl)-4-methylpentanamide (~150 mg) was used in next step without additional purification.

Step 3: Preparation of (2S)-2-(3-(4-cyano-2-methoxybenzyl)ureido)-N-(1-((3,5-di-methoxybenzyl)amino)-1,2-dioxopentan-3-yl)-4-methylpentanamide (NSN23489)

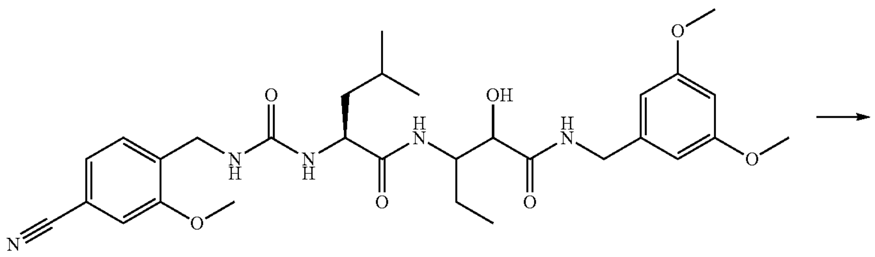

-continued

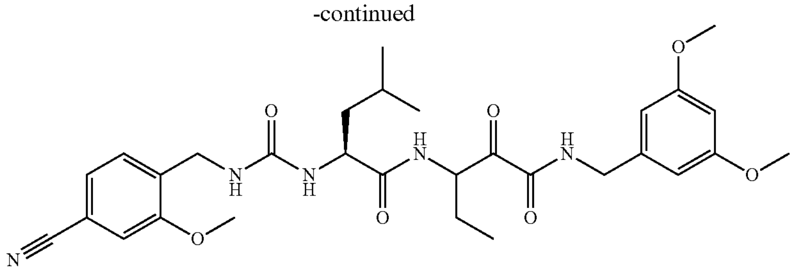

(2S)-2-(3-(4-cyano-2-methoxybenzyl)ureido)-N-(1-((3,5-di-methoxy-benzyl)amino)-2-hydroxy-1-oxopentan-3-yl)-4-methylpentanamide, (150 mg) was dissolved in $CH_3CN$ (10 mL) and 1 drop of water, pyridine (150 μL), and DMSO (100 μL) were added. Then Dess-Martin Periodinane (150 mg) was added and the reaction was stirred at room temperature for 2 h. The mixture was quenched by the addition of saturated aqueous $NaHCO_3$ (20 ml) and extracted with ethyl acetate (3×10 ml). The organic layer was dried over $Na_2SO_4$ and concentrated. The crude residue was submitted for reverse phase HPLC purification to afford pure (2S)-2-(3-(4-cyano-2-methoxybenzyl)ureido)-N-(1-((3,5-di¬methoxy-benzyl)amino)-1,2-dioxopentan-3-yl)-4-methylpentanamide (15 mg, 13%); NSN23489. LCMS $[M+H]^+$= 582.5

Example 14-8: preparation of n-(3,5-dimethoxybenzyl)-3-((s)-2-(3-(2-methoxy-4-methylbenzyl)ureido)-4-methylpentanamido)-2-oxopentanamide (NSN23490)

Step 1: Preparation of tert-butyl (2-methoxy-4-methylbenzyl)carbamate

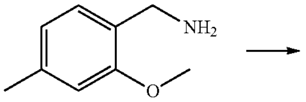

-continued

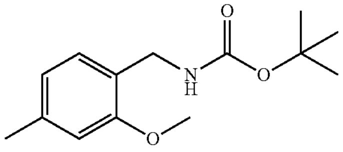

(2-methoxy-4-methylphenyl)methanamine (0.3 g) was dissolved in THE (5 ml) and Boc-anhydride (0.45 g) was added. The mixture was stirred at room temperature for 2 h and evaporated to dryness. The residue was purified by column silica gel chromatography to give tert-butyl (2-methoxy-4-methylbenzyl)carbamate (0.39 g, 78%) which was used directly in the next step.

Step 2: Preparation of N-(3,5-dimethoxybenzyl)-2-hydroxy-3-((S)-2-(3-(2-methoxy-4-methylbenzyl)ureido)-4-methylpentanamido)pentanamide

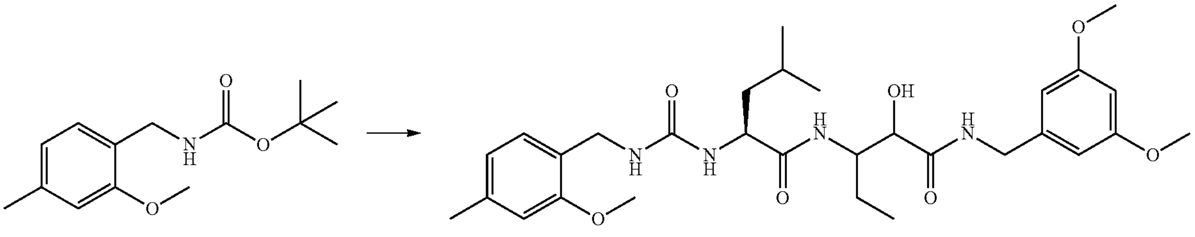

Boc-protected amine, tert-butyl (2-methoxy-4-methyl-benzyl)carbamate (1.0 mmol) and 2-chloropyridine (3.0 mmol) were dissolved in dry dichloromethane (20 ml). Triflic anhydride (1.5 mmol) was added dropwise over 5 min. After stirring for 1 hour at room temperature (2S)-2-amino-N-(1-((3,5-dimethoxybenzyl)amino)-2-hydroxy-1-oxopentan-3-yl)-4-methylpentanamide hydrochloride salt (0.3 mmol) and triethylamine (3.0 mmol) were added to the reaction mixture. After additional stirring for 1 hour (LC control), the mixture was diluted with water (20 ml), the layers were separated and the aqueous phase was extracted with dichloromethane (3×10 mL). The combined organics were washed with brine, dried over $MgSO_4$, filtered and concentrated under reduced pressure. The crude N-(3,5-dimethoxybenzyl)-2-hydroxy-3-((S)-2-(3-(2-methoxy-4-methylbenzyl)ureido)-4-methylpentanamido)pentanamide (~120 mg) was used in next step without additional purification.

Step 3: Preparation of N-(3,5-dimethoxybenzyl)-3-((S)-2-(3-(2-methoxy-4-methyl-benzyl)ureido)-4-methylpentanamido)-2-oxopentanamide (NSN23490)

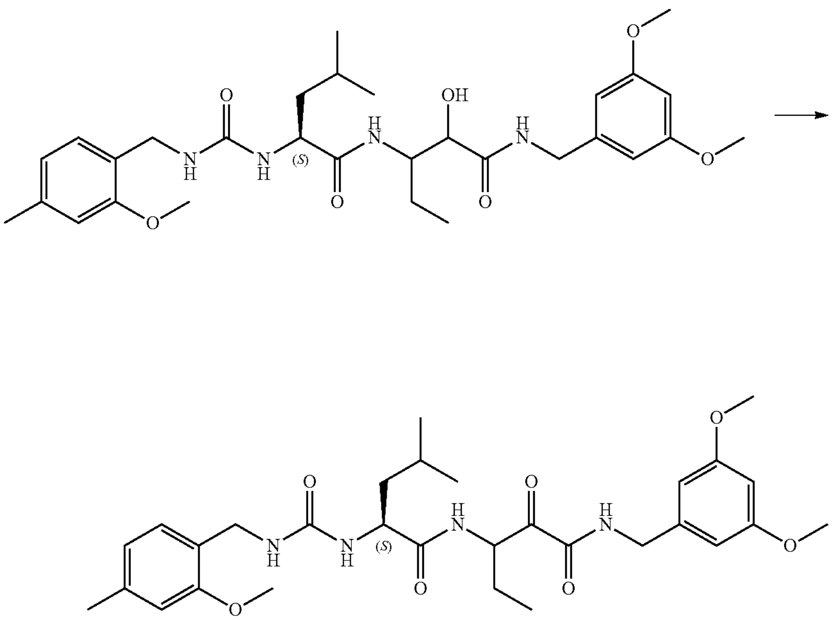

N-(3,5-dimethoxybenzyl)-2-hydroxy-3-((S)-2-(3-(2-methoxy-4-methylbenzyl)ureido)-4-methyl-pentanamido) pentanamide, (120 mg) was dissolved in $CH_3CN$ (10 mL) and 1 drop of water, pyridine (150 μL), and DMSO (100 μL) were added. Then Dess-Martin Periodinane (150 mg) was added and the reaction was stirred at room temperature for 2 h. The mixture was quenched by the addition of saturated aqueous $NaHCO_3$ (20 ml) and extracted with ethyl acetate (3×10 ml). The organic layer was dried over $Na_2SO_4$ and concentrated. The crude residue was submitted for reverse phase HPLC purification to afford pure N-(3,5-dimethoxy-benzyl)-3-((S)-2-(3-(2-methoxy-4-methyl,benzyl)-ureido)-4-methylpentanamido)-2-oxopentanamide (3 mg, 3%); NSN23490 LCMS $[M+H]^+=571.3$ Example 14-9: Preparation of (2S)-2-(3-(4-cyano-benzyl)ureido)-N-(1-((3,5-dimethoxy-benzyl)amino)-1,2-dioxopentan-3-yl)-4-methylpentanamide (NSN23492)

Step 1: Preparation of tert-butyl (4-carbamoylbenzyl)carbamate

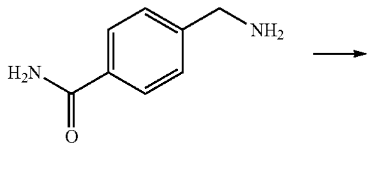

-continued

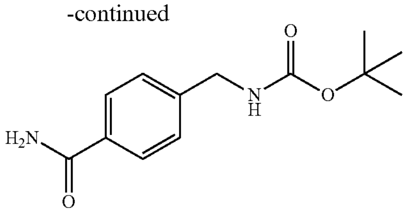

4-(aminomethyl)benzamide (0.3 g) was dissolved in THE (5 ml) and Boc-anhydride (0.45 g) was added. The mixture was stirred at room temperature for 2 h and evaporated to dryness. The residue was purified by column silica gel chromatography to give tert-butyl (4-carbamoyl-benzyl)carbamate (0.43 g, 86%) which was used directly in the next step.

Step 2: Preparation of 4-((5S)-12-(3,5-dimethoxyphenyl)-8-ethyl-9-hydroxy-5-isobutyl-3,6,10-trioxo-2,4,7,11-tetraazadodecyl)benzamide and (2S)-2-(3-(4-cyanobenzyl)ureido)-N-(1-((3,5-dimethoxybenzyl) amino)-2-hydroxy-1-oxopentan-3-yl)-4-methylpentanamide

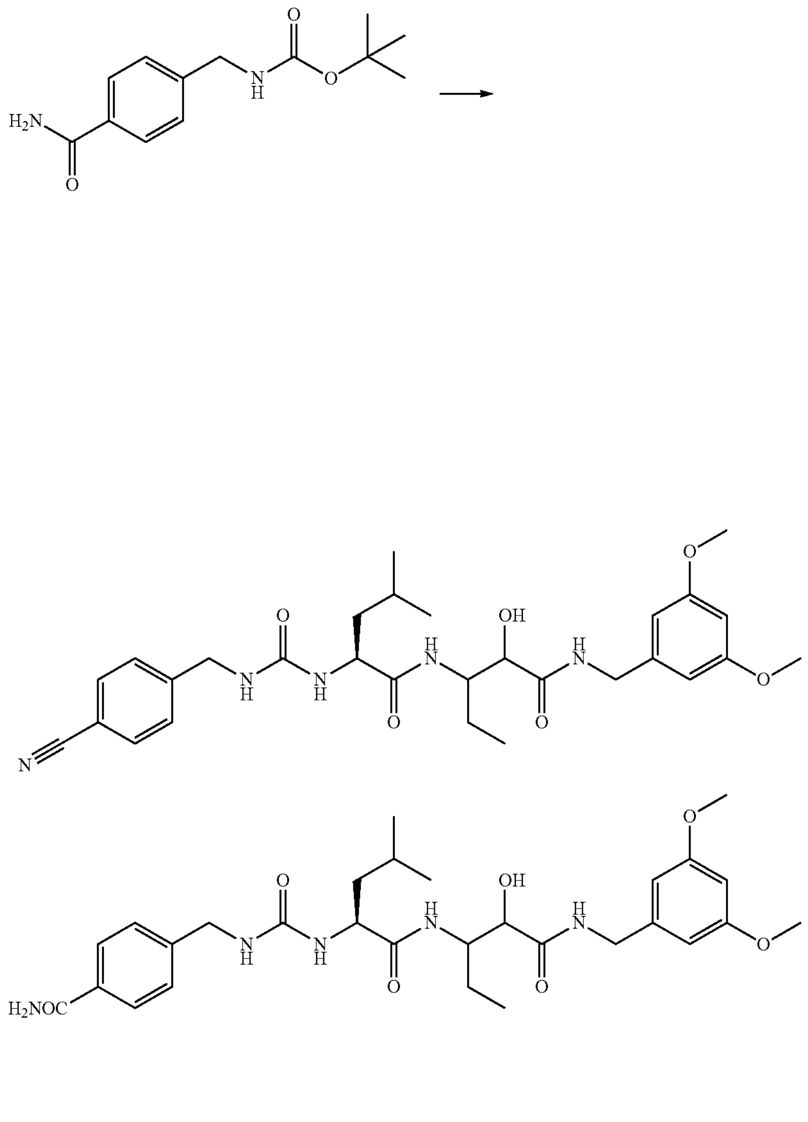

To a solution of 4-carbamidbenzylamine (300 mg) in DCM (5 mL) and THE (5 ml) was added triphosgene (300 mg) and triethylamine (0.8 mL). The mixture was stirred for 30 min at room temperature. Then (2S)-2-amino-N-(1-((3,5-dimethoxybenzyl)amino)-2-hydroxy-1-oxopentan-3-yl)-4-methylpentanamide hydrochloride (200 mg) was added and the reaction stirred for 45 min at room temperature. LC analysis of the reaction mixture shows the presence of some of the desired carboxamido product [4-((5S)-12-(3,5-dimethoxyphenyl)-8-ethyl-9-hydroxy-5-isobutyl-3,6,10-trioxo-2,4,7,11-tetraazadodecyl)benzamide](~5%), but the major compound is the corresponding cyano derivative, product of dehydration of the carboxamide [(2S)-2-(3-(4-cyanobenzyl)ureido)-N-(1-((3,5-dimethoxybenzyl)amino)-2-hydroxy-1-oxopentan-3-yl)-4-methylpentanamide](~50%). The mixture was diluted with water (20 ml), layers were separated and aqueous phase was extracted with dichloromethane (3x10 mL). The combined organics were washed with brine, dried over $MgSO_4$, filtered and concentrated under reduced pressure The crude material (~120 mg) was used in next step without additional purification.

Step 3: Preparation of (2S)-2-(3-(4-cyanobenzyl)ureido)-N-(1-((3,5-dimethoxybenzyl)-amino)-1,2-dioxopentan-3-yl)-4-methylpentanamide (NSN23492)

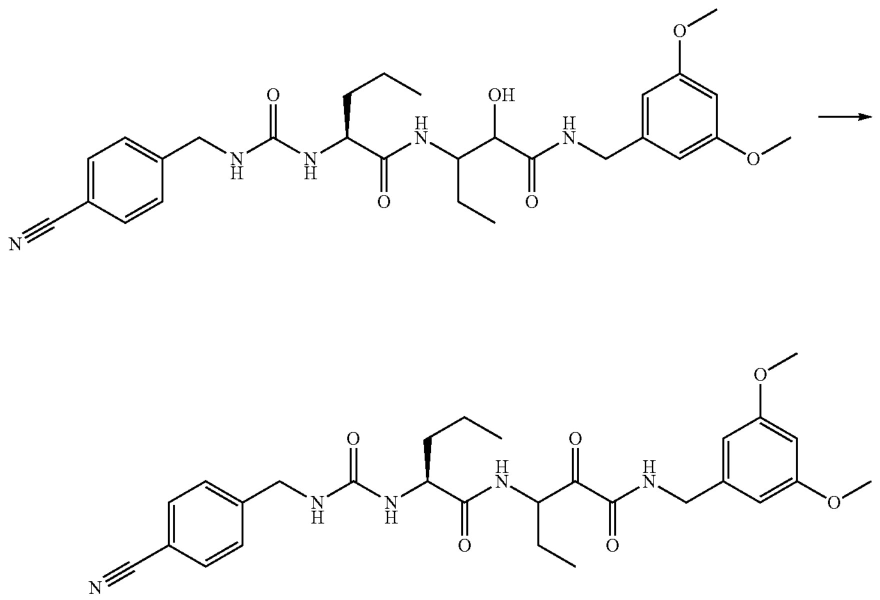

The mixture from the previous step, containing principally (2S)-2-(3-(4-cyanobenzyl)ureido)-N-(1-((3,5-dimethoxybenzyl)amino)-2-hydroxy-1-oxopentan-3-yl)-4-methylpentanamide, (120 mg) was dissolved in $CH_3CN$ (10 mL) and 1 drop of water, pyridine (150 μL), and DMSO (100 μL) were added. Then Dess-Martin Periodinane (150 mg) was added and the reaction stirred at room temperature for 2 h. The mixture was quenched by the addition of saturated aqueous $NaHCO_3$ (20 ml) and extracted with ethyl acetate (3x10 ml). The organic layer was dried over $Na_2SO_4$ and concentrated to dryness. The crude residue was submitted for reverse phase HPLC purification to afford pure (2S)-2-(3-(4-cyanobenzyl)ureido)-N-(1-((3,5-dimethoxy,benzyl)-amino)-1,2-dioxopentan-3-yl)-4-methylpentanamide (12 mg, 11%); NSN23492 LCMS $[M+H]^+$=552.4.

Example 14-10: Preparation of Preparation of N-(3,5-dimethoxybenzyl)-3-((S)-2-(3-(4-(2-hydroxyethoxy) benzyl) ureido)-4-methylpentanamido)-2-oxopentanamide Step 1: Preparation of 4-(2-((tert-butyldimethylsilyl)oxy) ethoxy) benzonitrile

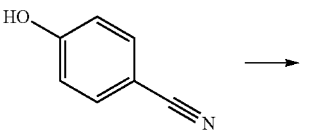

-continued

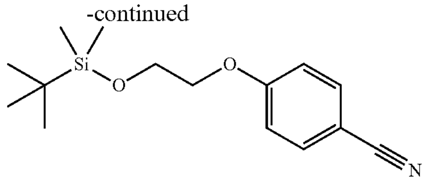

4-hydroxybenzonitrile (1.2 g) was dissolved in DMF (15 mL), and $K_2CO_3$ (2.5 g) and (2-bromo-ethoxy)-(tert-butyl) dimethylsilane (2.4 g) were added. The reaction was stirred at 50° C. for 2 h, at which time another 2.4 g of (2-bromo-ethoxy)(tert-butyl)dimethylsilane was added. Stirring at 50° C. was continued for an additional hour (LC control), and the reaction was cooled to room temperature and diluted with water. The mixture was extracted three times with EtOAc and the organic layers were washed 5 times with saturated aqueous NaCl solution, then dried over $Na_2SO_4$ and concentrated to dryness. The crude residue was dry loaded on to silica gel and purified by flash column chromatography to give 4-(2-((tert-butyldimethylsilyl)oxy) ethoxy)-benzonitrile (2.3 g, 83% yield) as colorless crystals.

Step 2: Preparation of (4-(2-((tert-butyldimethylsilyl)oxy)ethoxy)phenyl)methylamine

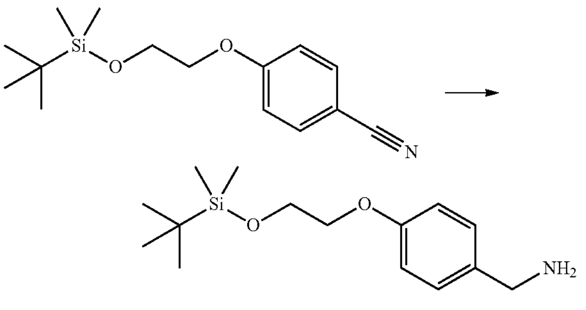

4-(2-((tert-butyldimethylsilyl)oxy)ethoxy)benzonitrile (2.3 g) was dissolved in THE and cooled to 0° C., and 15 mL of $LiAlH_4$ (15 mL, 1M in $Et_2O$) was added dropwise. The reaction was kept at 0° C. for 45 min and quenched by the slow addition of saturated aqueous sodium sulfate solution followed by $Et_2O$. The solids were filtered off and the filtrate concentrated and purified by flash chromatography to afford (4-(2-((tert-butyldimethyl-silyl)oxy)ethoxy)phenyl)-methanamine (1.5 g, 64% yield).

Step 3: Preparation of tert-butyl (4-(2-((tert-butyldimethylsilyl)oxy)ethoxy)benzyl)carbamate

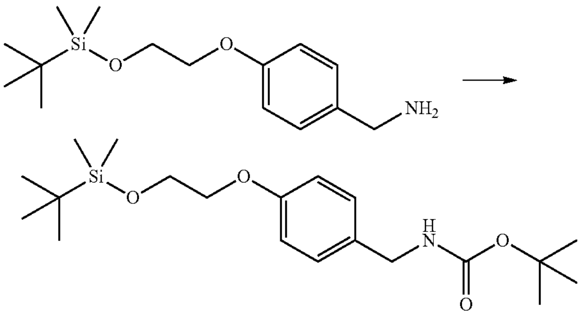

(4-(2-((tert-butyldimethyl-silyl)oxy)ethoxy)phenyl) methanamine (0.56 g) was dissolved in THE (5 ml) and Boc-anhydride (0.45 g) was added. The mixture was stirred at room temperature for 2 h and evaporated to dryness. The residue was purified by column silica gel chromatography to give tert-butyl (4-(2-((tert-butyldimethylsilyl)oxy)ethoxy) benzyl)carbamate (0.71, 93%) which was used directly in the next step.

Step 4: Preparation of (2S)-2-(3-(4-(2-((tert-butyldimethylsilyl)oxy)ethoxy)benzyl)-ureido)-N-(1-((3,5-dimethoxybenzyl)amino)-2-hydroxy-1-oxopentan-3-yl)-4-methylpentanamide

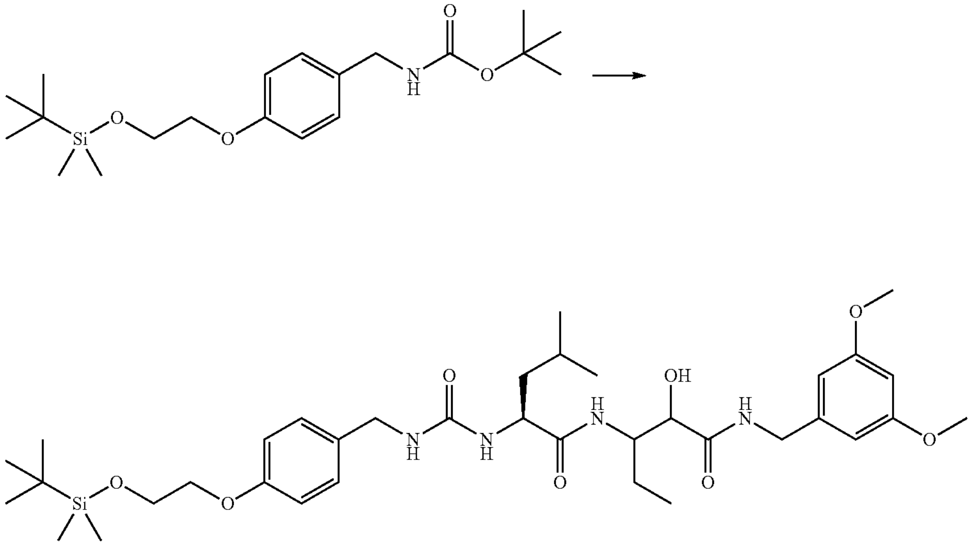 [SMILES: CC(C)(C)OC(=O)NCc1ccc(OCCO[Si](C)(C)C(C)(C)C)cc1 ; CCC(NC(=O)[C@H](CC(C)C)NC(=O)NCc1ccc(OCCO[Si](C)(C)C(C)(C)C)cc1)C(O)C(=O)NCc1cc(OC)cc(OC)c1]

Boc-protected amine, tert-butyl (4-(2-((tert-butyldimethylsilyl)oxy)ethoxy)benzyl)carbamate (1.0 mmol) and 2-chloropyridine (3.0 mmol) were dissolved in dry dichloromethane (20 ml). Triflic anhydride (1.5 mmol) was added dropwise over 5 min. After stirring for 1 hour at room temperature (2S)-2-amino-N-(1-((3,5-dimethoxybenzyl)amino)-2-hydroxy-1-oxopentan-3-yl)-4-methylpentanamide hydrochloride salt (0.3 mmol) and triethylamine (3.0 mmol) were added to the reaction mixture. After additional stirring for 1 hour (LC control), the mixture was diluted with water (20 ml), the layers were separated and the aqueous phase was extracted with dichloromethane (3×10 mL). The combined organics were washed with brine, dried over $MgSO_4$, filtered and concentrated under reduced pressure. The crude (2S)-2-(3-(4-(2-((tert-butyldimethylsilyl)oxy)ethoxy)benzyl)ureido)-N-(1-((3,5-dimethoxybenzyl)amino)-2-hydroxy-1-oxopentan-3-yl)-4-methylpentanamide (~200 mg) was used in next step without additional purification.

Step 5: Preparation of N-(3,5-dimethoxybenzyl)-3-((S)-2-(3-(4-(2-hydroxyethoxy)-benzyl) ureido)-4-methylpentanamido)-2-oxopentanamide

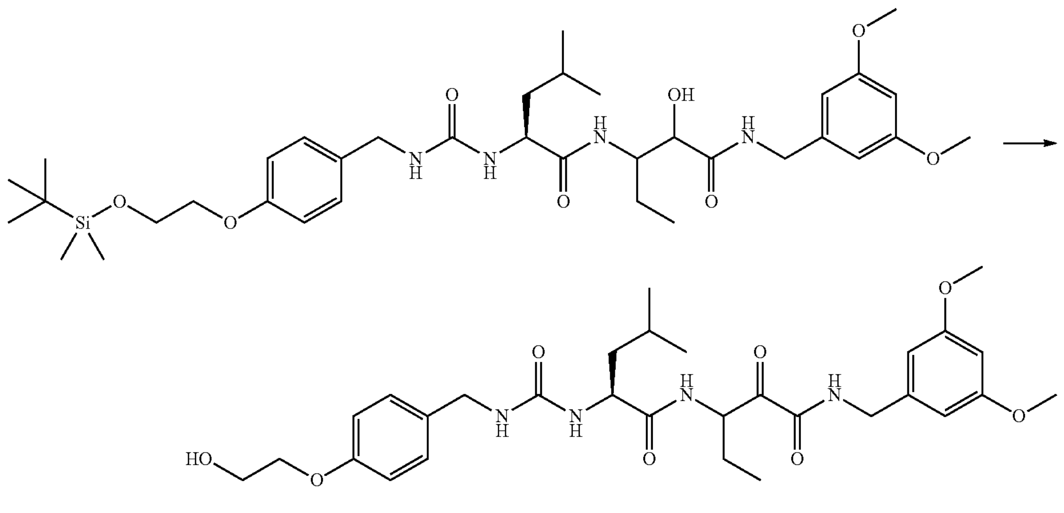

(2S)-2-(3-(4-(2-((tert-butyldimethylsilyl)oxy)ethoxy) benzyl)ureido)-N-(1-((3,5-dimethoxybenzyl)amino)-2-hydroxy-1-oxopentan-3-yl)-4-methylpentanamide, (200 mg) was dissolved in $CH_3CN$ (10 mL) and 1 drop of water, pyridine (150 μL), and DMSO (100 μL) were added. Then Dess-Martin Periodinane (150 mg) was added and the reaction was stirred at room temperature for 2 h. The mixture was quenched by the addition of saturated aqueous $NaHCO_3$ (20 ml) and extracted with ethyl acetate (3×10 ml). The organics were evaporated to dryness to afford the ketone, LCMS [M+H]+=701.7. The crude ketone was dissolved in THE (5 ml). To this solution was added TBAF (0.5 ml, 1M in THF) and the mixture was stirred overnight at room temperature (LC control of TBS deprotection). After completion of the deprotection, the mixture was diluted with water (20 ml) and extracted with ethyl acetate (3×20 ml). The organics were evaporated to dryness. The crude residue was submitted for reverse phase HPLC purification to afford pure N-(3,5-dimethoxybenzyl)-3-((S)-2-(3-(4-(2-hydroxyethoxy) benzyl)ureido)-4-methylpentanamido)-2-oxopentanamide (3 mg, 3%); NSN23498 LCMS [M+H]+=587.6

Example 14-11: Additional Analogs Prepared by Example 14

Using the strategy exemplified in the General Method #2 and examples, the following additional analogs were prepared:

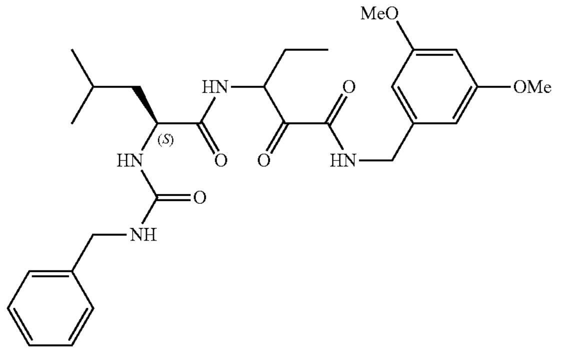

(2S)-2-(3-benzylureido)-N-(1-((3,5-dimethoxybenzyl)amino)-1,2-dioxopentan-3-yl)-4-methylpentanamide

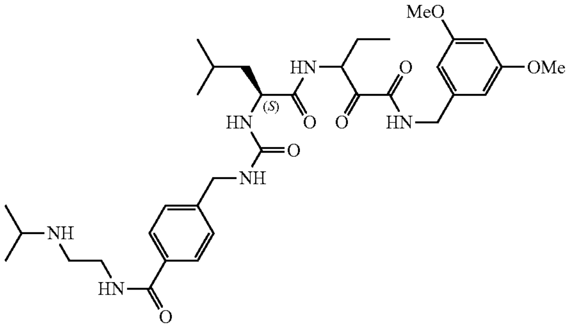

4-((5S)-12-(3,5-dimethoxyphenyl)-8-ethyl-5-isobutyl-3,6,9,10-tetraoxo-2,4,7,11-tetraazadodecyl)-N-(2-(isopropylamino)ethyl)benzamide

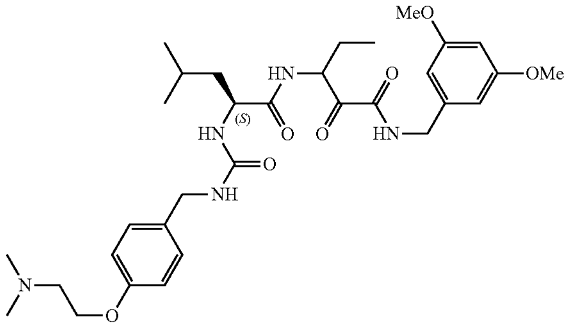

N-(3,5-dimethoxybenzyl)-3-((S)-2-(3-(4-(2-(dimethylamino)ethoxy)benzyl)ureido)-4-methylpentanamido)-2-oxopentanamide

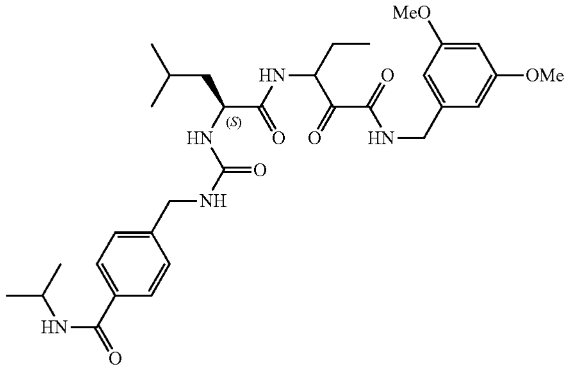

4-((5S)-12-(3,5-dimethoxyphenyl)-8-ethyl-5-isobutyl-3,6,9,10-tetraoxo-2,4,7,11-tetraazadodecyl)-N-isopropylbenzamide

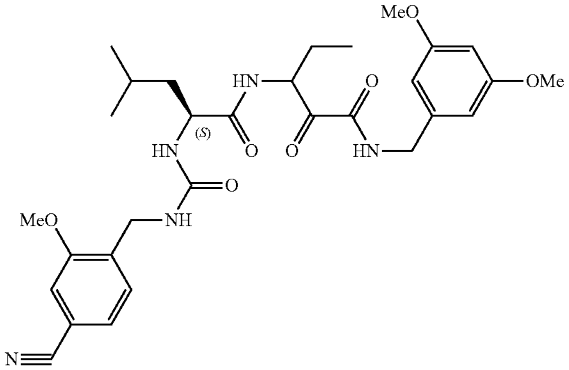

(2S)-2-(3-(4-cyano-2-methoxybenzyl)ureido)-N-(1-((3,5-dimethoxybenzyl)amino)-1,2-dioxopentan-3-yl)-4-methylpentanamide

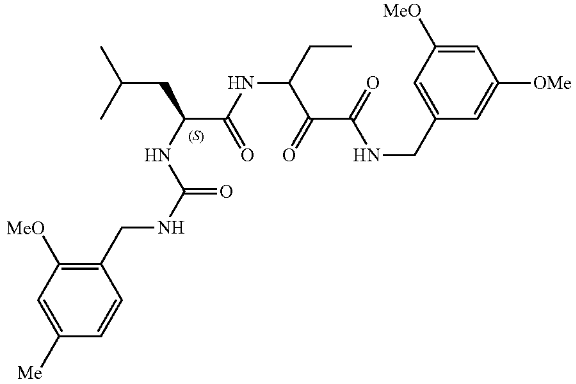

N-(3,5-dimethoxybenzyl)-3-((S)-2-(3-(2-methoxy-4-methylbenzyl)ureido)-4-methylpentanamido)-2-oxopentanamide

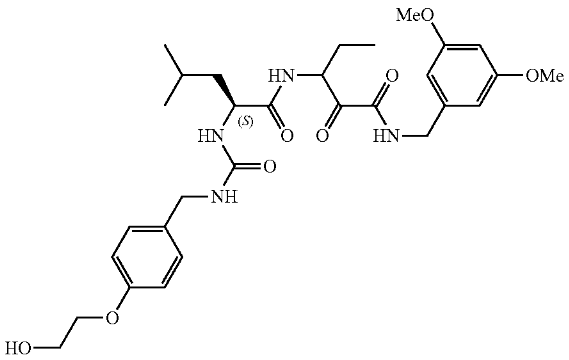

N-(3,5-dimethoxybenzyl)-3-((S)-2-(3-(4-(2-hydroxyethoxy)benzyl)ureido)-4-methylpentanamido)-2-oxopentanamide

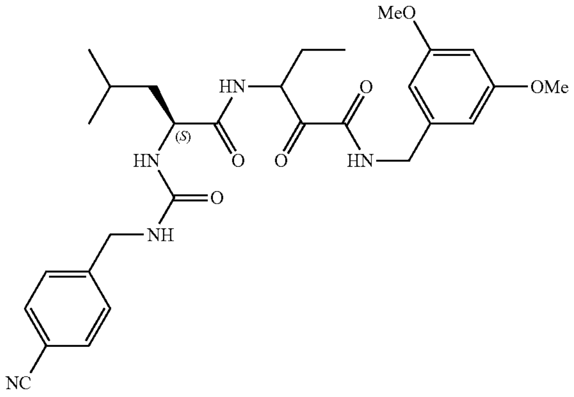

(2S)-2-(3-(4-cyanobenzyl)ureido)-N-(1-((3,5-dimethoxybenzyl)amino)-1,2-dioxopentan-3-yl)-4-methylpentanamide

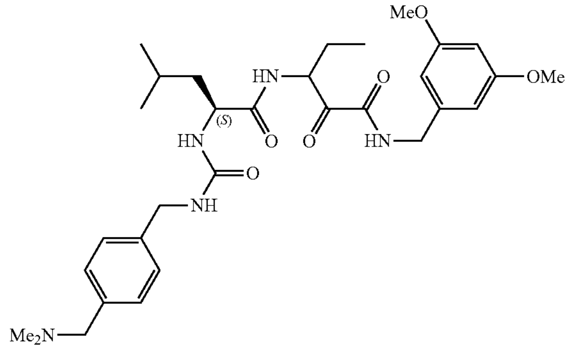

N-(3,5-dimethoxybenzyl)-3-((S)-2-(3-(4-((dimethylamino)methyl)benzyl)ureido)-4-methylpentanamido)-2-oxopentanamide

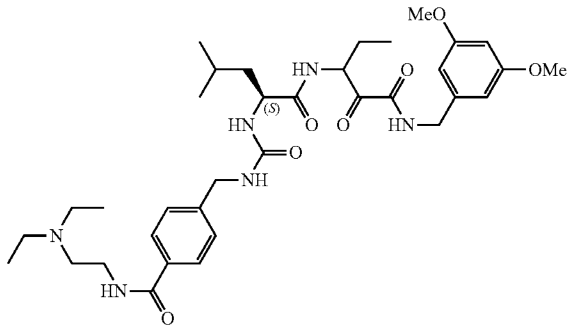

N-(2-(diethylamino)ethyl)-4-((5S)-12-(3,5-dimethoxyphenyl)-8-ethyl-5-isobutyl-3,6,9,10-tetraoxo-2,4,7,11-tetraazadodecyl)benzamide

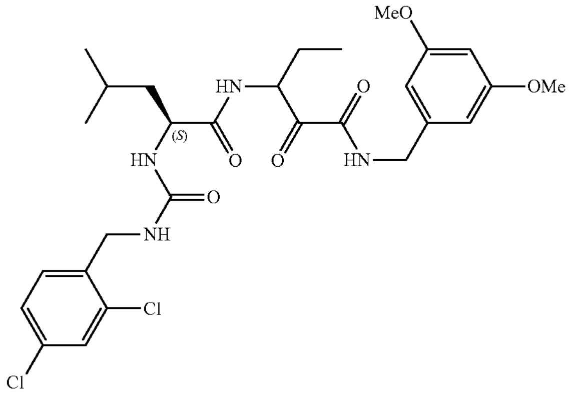

(2S)-2-(3-(2,4-dichlorobenzyl)ureido)-N-(1-((3,5-dimethoxybenzyl)amino)-1,2-dioxopentan-3-yl)-4-methylpentanamide

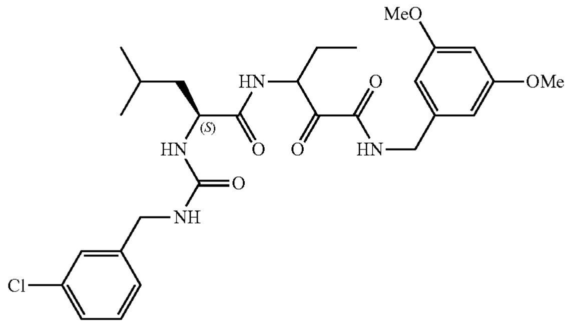

(2S)-2-(3-(3-chlorobenzyl)ureido)-N-(1-((3,5-dimethoxybenzyl)amino)-1,2-dioxopentan-3-yl)-4-methylpentanamide

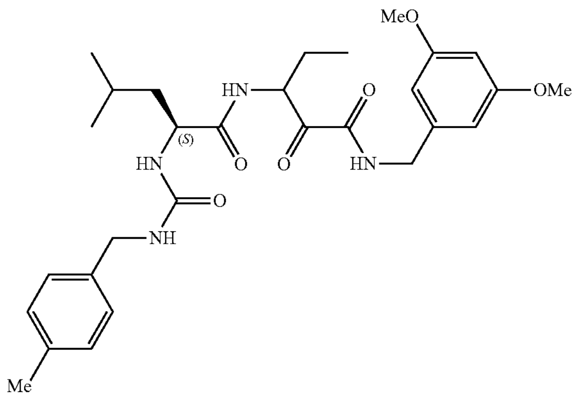

N-(3,5-dimethoxybenzyl)-3-((S)-4-methyl-2-(3-(4-methylbenzyl)ureido)pentanamido)-2-oxopentanamide

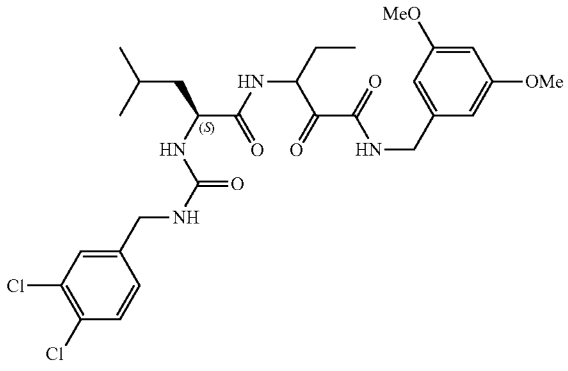

(2S)-2-(3-(3,4-dichlorobenzyl)ureido)-N-(1-((3,5-dimethoxybenzyl)amino)-1,2-dioxopentan-3-yl)-4-methylpentanamide

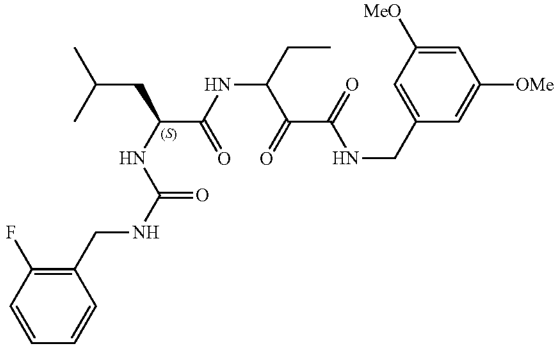

N-(3,5-dimethoxybenzyl)-3-((S)-2-(3-(2-fluorobenzyl)ureido)-4-methylpentanamido)-2-oxopentanamide

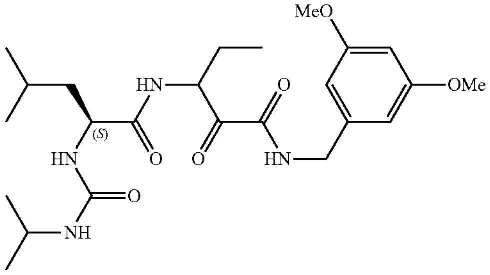

N-(3,5-dimethoxybenzyl)-3-((S)-2-(3-isopropylureido)-4-methylpentanamido)-2-oxopentanamide

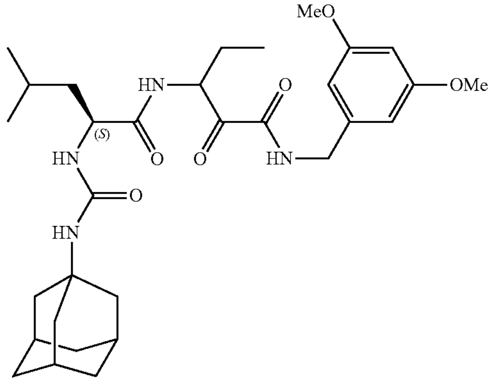

(2S)-2-(3-((3R,5R,7R)-adamantan-1-yl)ureido)-N-(1-((3,5-dimethoxybenzyl)amino)-1,2-dioxopentan-3-yl)-4-methylpentanamide

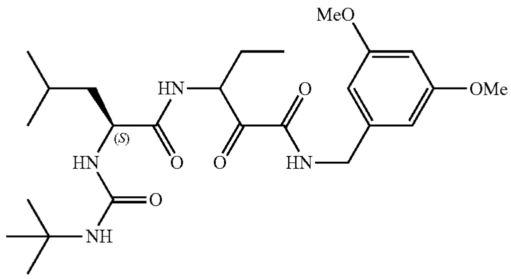

(2S)-2-(3-(tert-butyl)ureido)-N-(1-((3,5-dimethoxybenzyl)amino)-1,2-dioxopentan-3-yl)-4-methylpentanamide

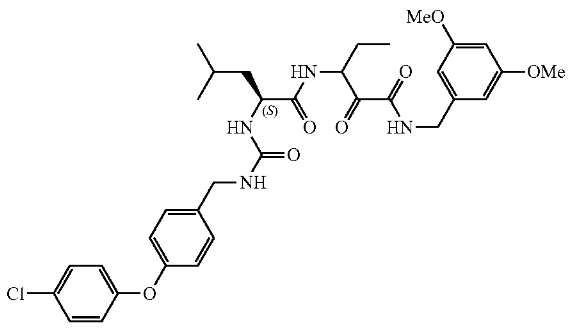

(2S)-2-(3-(4-(4-chlorophenoxy)benzyl)ureido)-N-(1-((3,5-dimethoxybenzyl)amino)-1,2-dioxopentan-3-yl)-4-methylpentanamide

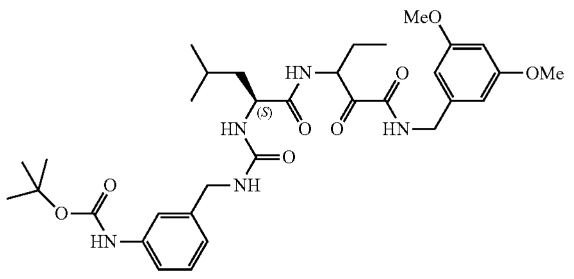

tert-butyl (3-((5S)-12-(3,5-dimethoxyphenyl)-8-ethyl-5-isobutyl-3,6,9,10-tetraoxo-2,4,7,11-tetraazadodecyl)phenyl)carbamate

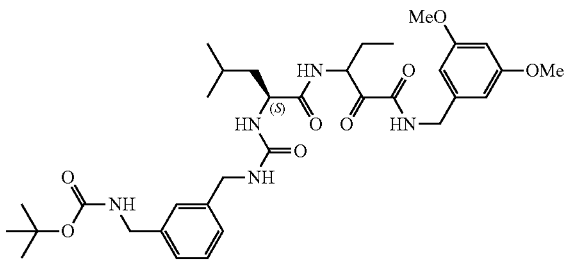

tert-butyl (3-((5S)-12-(3,5-dimethoxyphenyl)-8-ethyl-5-isobutyl-3,6,9,10-tetraoxo-2,4,7,11-tetraazadodecyl)benzyl)carbamate

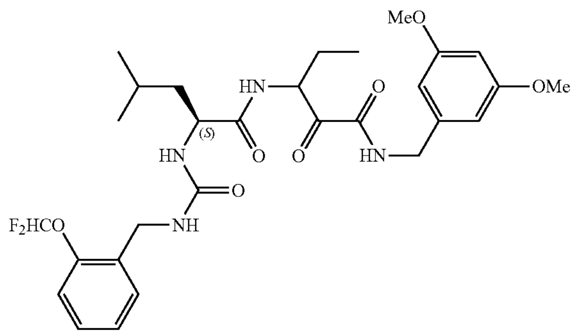

(2S)-2-(3-(2-(difluoromethoxy)benzyl)ureido)-N-(1-((3,5-dimethoxybenzyl)amino)-1,2-dioxopentan-3-yl)-4-methylpentanamide

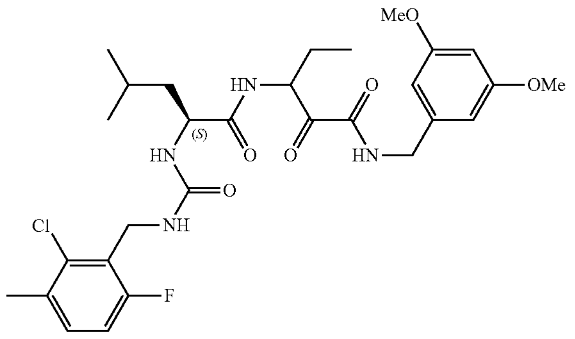

(2S)-2-(3-(2-chloro-6-fluoro-3-methylbenzyl)ureido)-N-(1-((3,5-dimethoxybenzyl)amino)-1,2-dioxopentan-3-yl)-4-methylpentanamide

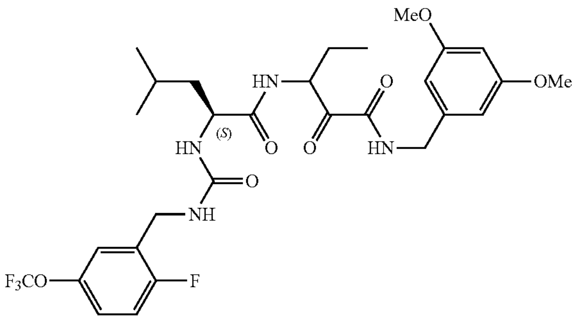

N-(3,5-dimethoxybenzyl)-3-((S)-2-(3-(2-fluoro-5-(trifluoromethoxy)benzyl)ureido)-4-methylpentanamido)-2-oxopentanamide

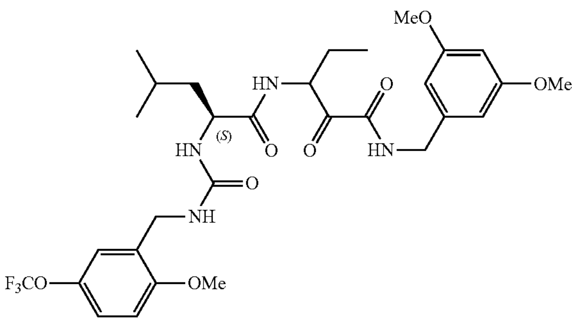

N-(3,5-dimethoxybenzyl)-3-((S)-2-(3-(2-methoxy-5-(trifluoromethoxy)benzyl)ureido)-4-methylpentanamido)-2-oxopentanamide

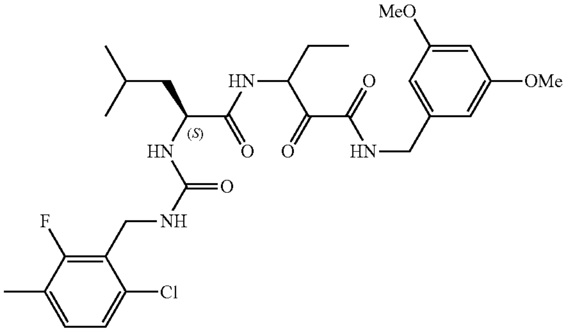

(2S)-2-(3-(6-chloro-2-fluoro-3-methylbenzyl)ureido)-N-(1-((3,5-dimethoxybenzyl)amino)-1,2-dioxopentan-3-yl)-4-methylpentanamide

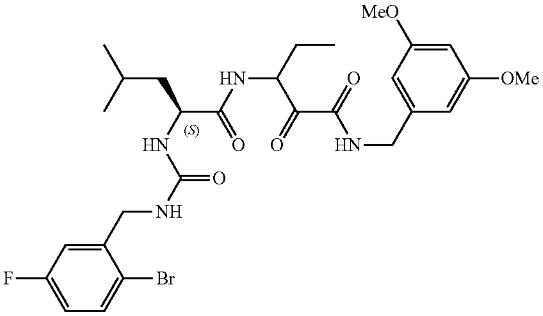

(2S)-2-(3-(2-bromo-5-fluorobenzyl)ureido)-N-(1-((3,5-dimethoxybenzyl)amino)-1,2-dioxopentan-3-yl)-4-methylpentanamide

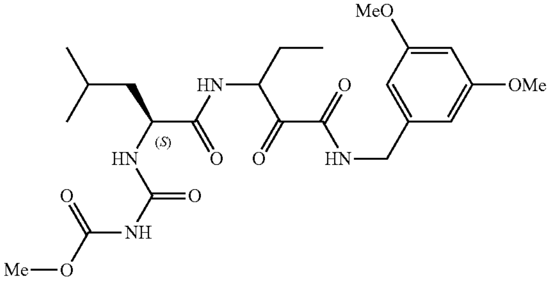

(2S)-2-(3-methoxycarbonylureido)-N-(1-((3,5-dimethoxybenzyl)amino)-1,2-dioxopentan-3-yl)-4-methylpentanamide

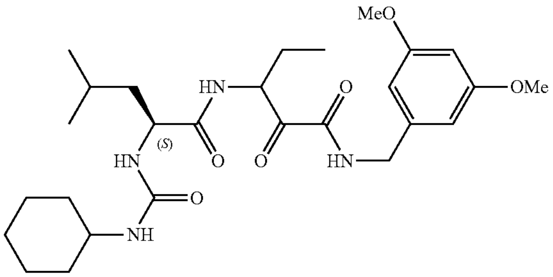

(2S)-2-(3-cyclohexylureido)-N-(1-((3,5-dimethoxybenzyl)amino)-1,2-dioxopentan-3-yl)-4-methylpentanamide

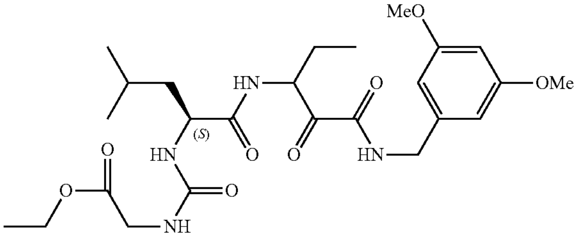

ethyl (((2S)-1-((1-((3,5-dimethoxybenzyl)amino)-1,2-dioxopentan-3-yl)amino)-4-methyl-1-oxopentan-2-yl)carbamoyl)glycinate

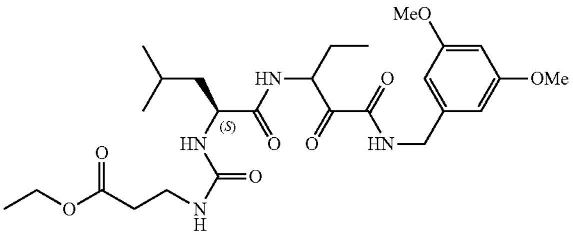

ethyl (8S)-1-(3,5-dimethoxyphenyl)-5-ethyl-8-isobutyl-3,4,7,10-tetraoxo-2,6,9,11-tetraazatetradecan-14-oate

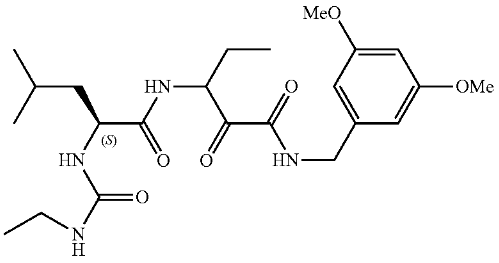

N-(3,5-dimethoxybenzyl)-3-((S)-2-(3-ethylureido)-4-methylpentanamido)-2-oxopentanamide

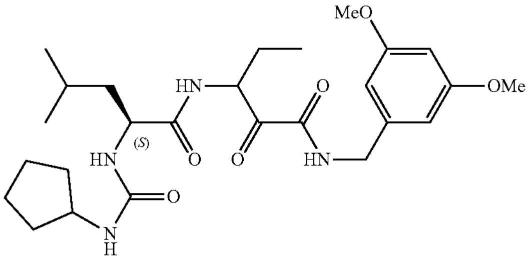

N-(3,5-dimethoxybenzyl)-3-((S)-4-methyl-2-(3-((tetrahydro-2H-pyran-4-yl)methyl)ureido)pentanamido)-2-oxopentanamide

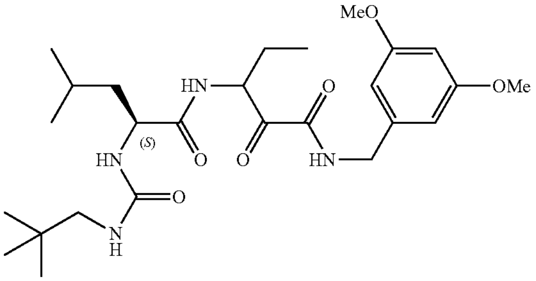

N-(3,5-dimethoxybenzyl)-3-((S)-4-methyl-2-(3-neopentylureido)pentanamido)-2-oxopentanamide

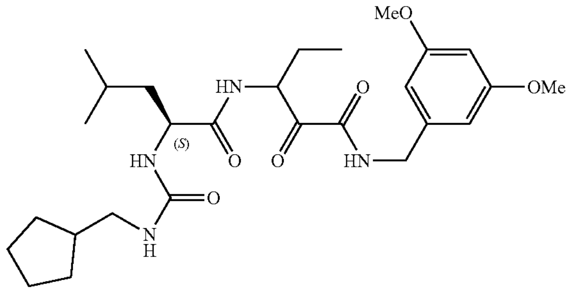

(2S)-2-(3-(cyclopentylmethyl)ureido)-N-(1-((3,5-dimethoxybenzyl)amino)-1,2-dioxopentan-3-yl)-4-methylpentanamide

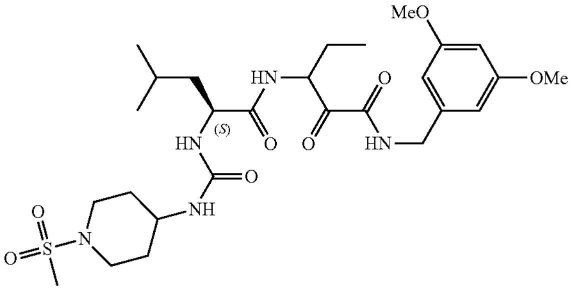

N-(3,5-dimethoxybenzyl)-3-((S)-4-methyl-2-(3-(1-(methylsulfonyl)piperidin-4-yl)ureido)pentanamido)-2-oxopentanamide

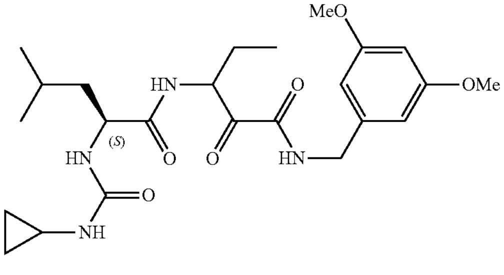

(2S)-2-(3-cyclopropylureido)-N-(1-((3,5-dimethoxybenzyl)amino)-1,2-dioxopentan-3-yl)-4-methylpentanamide

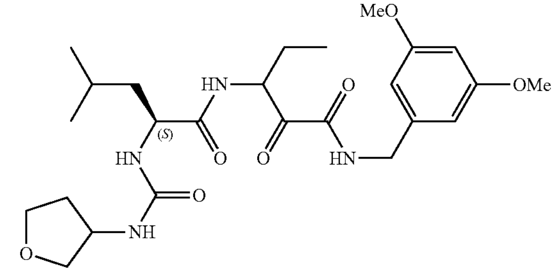

N-(3,5-dimethoxybenzyl)-3-((2S)-4-methyl-2-(3-(tetrahydrofuran-3-yl)ureido)pentanamido)-2-oxopentanamide

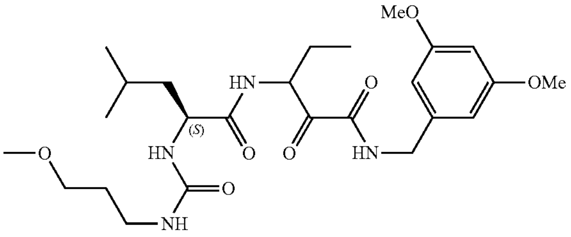

N-(3,5-dimethoxybenzyl)-3-((S)-2-(3-(3-methoxypropyl)ureido)-4-methylpentanamido)-2-oxopentanamide

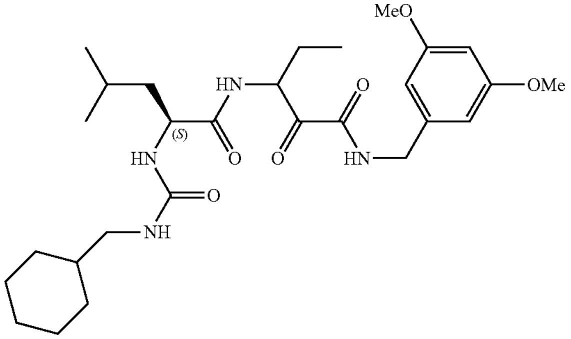

(2S)-2-(3-(cyclohexylmethyl)ureido)-N-(1-((3,5-dimethoxybenzyl)amino)-1,2-dioxopentan-3-yl)-4-methylpentanamide

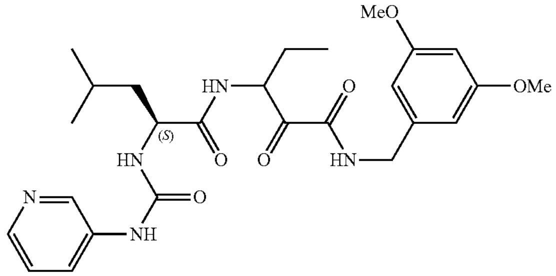

N-(3,5-dimethoxybenzyl)-3-((S)-4-methyl-2-(3-(pyridin-3-yl)ureido)pentanamido)-2-oxopentanamide

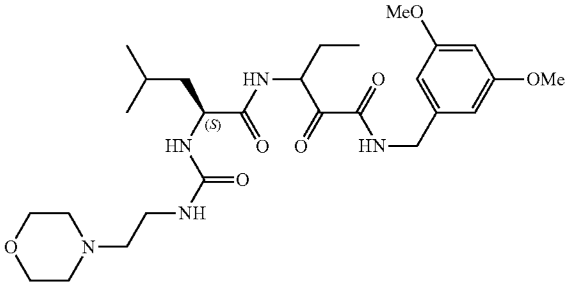

N-(3,5-dimethoxybenzyl)-3-((S)-4-methyl-2-(3-(2-morpholinoethyl)ureido)pentanamido)-2-oxopentanamide

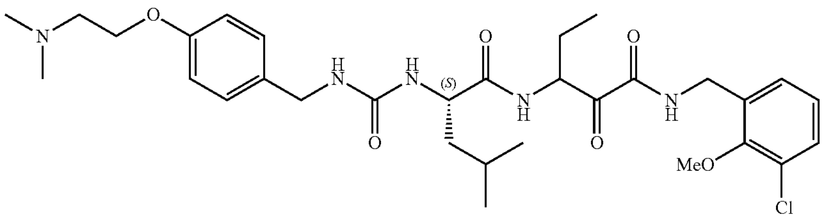

N-(3-chloro-2-methoxybenzyl)-3-((S)-2-(3-(4-(2-(dimethylamino)ethoxy)benzyl)ureido)-4-methylpentanamido)-2-oxopentanamide

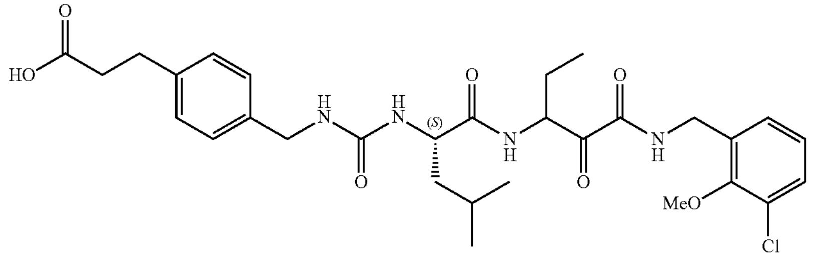

3-(4-((5S)-12-(3-chloro-2-methoxyphenyl)-8-ethyl-5-isobutyl-3,6,9,10-tetraoxo-2,4,7,11-tetraazadodecyl)phenyl) propanoic acid

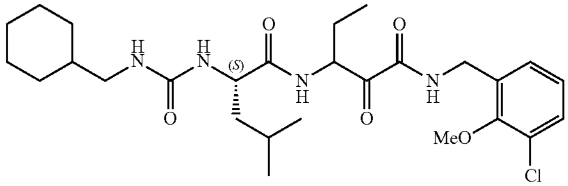

N-(3-chloro-2-methoxybenzyl)-3-((S)-2-(3-(cyclohexylmethyl) ureido)-4-methylpentanamido)-2-oxopentanamide

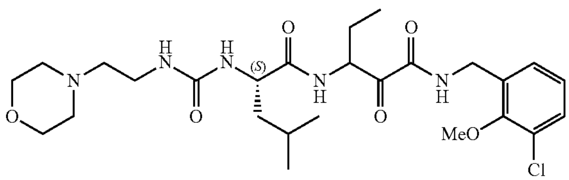

N-(3-chloro-2-methoxybenzyl)-3-((S)-4-methyl-2-(3-(2-morpholinoethyl) ureido) pentanamido)-2-oxopentanamide

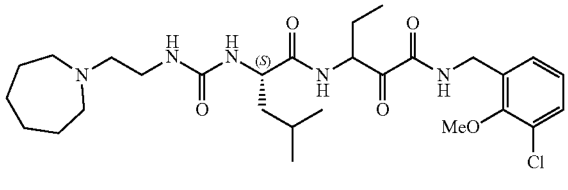

(2S)-2-(3-(2-(azepan-1-yl)ethyl) ureido)-N-(1-((3-chloro-2-methoxybenzyl)amino)-1,2-dioxopentan-3-yl)-4-methylpentanamide

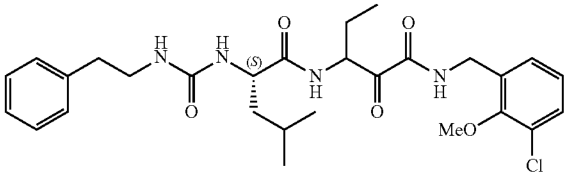

N-(3-chloro-2-methoxybenzyl)-3-((S)-4-methyl-2-(3-phenethylureido) pentanamido)-2-oxopentanamide

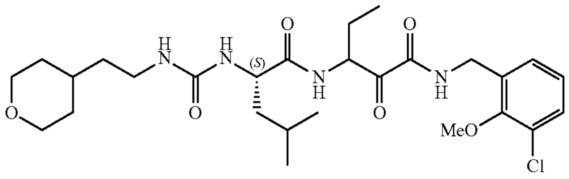

N-(3-chloro-2-methoxybenzyl)-3-((S)-4-methyl-2-(3-(2-(tetrahydro-2H-pyran-4-yl)ethyl) ureido) pentanamido)-2-oxopentanamide

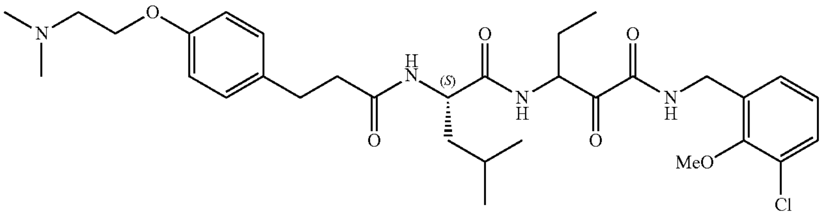

N-(3-chloro-2-methoxybenzyl)-3-((S)-2-(3-(4-(2-(dimethylamino) ethoxy)phenyl) propanamido)-4-methylpentanamido)-2-oxopentanamide

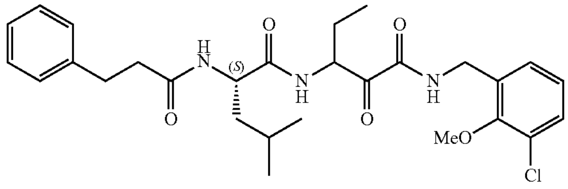

N-(3-chloro-2-methoxybenzyl)-3-((S)-4-methyl-2-(3-phenylpropanamido) pentanamido)-2-oxopentanamide

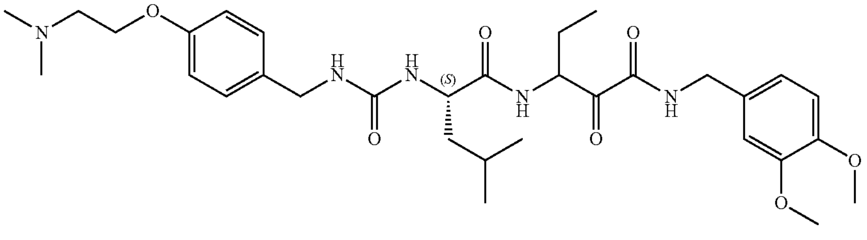

N-(3,4-dimethoxybenzyl)-3-((S)-2-(3-(4-(2-(dimethylamino) ethoxy)benzyl) ureido)-4-methylpentanamido)-2-oxopentanamide

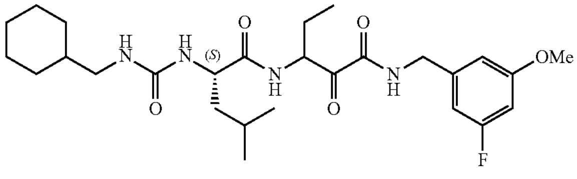

(2S)-2-(3-(cyclohexylmethyl) ureido)-N-(1-((3-fluoro-5-methoxybenzyl)amino)-1,2-dioxopentan-3-yl)-4-methylpentanamide

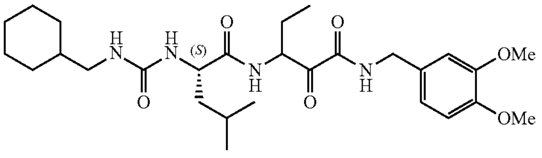

(2S)-2-(3-(cyclohexylmethyl) ureido)-N-(1-((3,4-dimethoxybenzyl)amino)-1,2-dioxopentan-3-yl)-4-methylpentanamide Non-Ureido Analogs

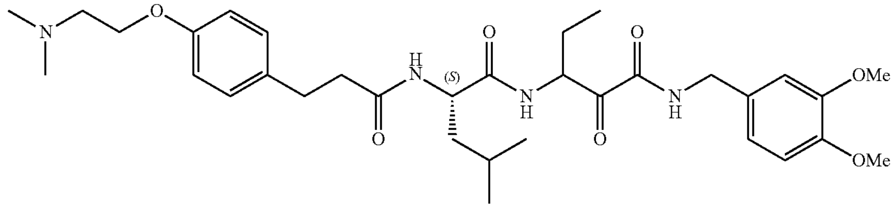

N-(3,4-dimethoxybenzyl)-3-((S)-2-(3-(4-(2-(dimethylamino) ethoxy)phenyl) propanamido)-4-methylpentanamido)-2-oxopentanamide

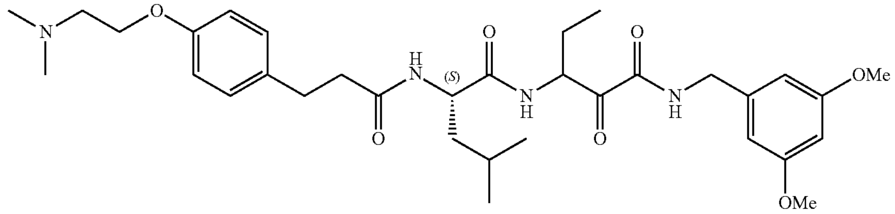

N-(3,5-dimethoxybenzyl)-3-((S)-2-(3-(4-(2-(dimethylamino) ethoxy)phenyl) propanamido)-4-methylpentanamido)-2-oxopentanamide N-(Benzylsulfamoyl)amino Analogs

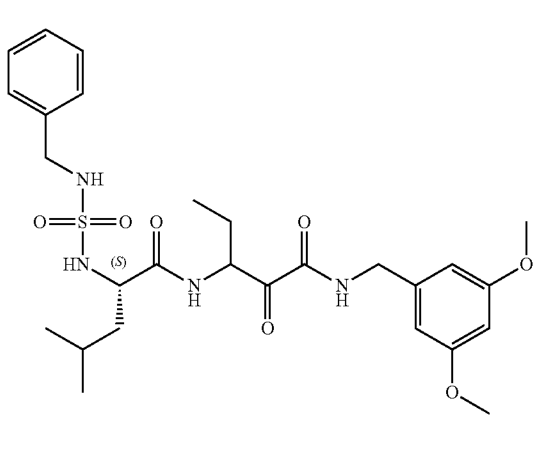

(2S)-2-((N-benzylsulfamoyl)amino)-N-(1-((3,5-dimethoxybenzyl)amino)-1,2-dioxopentan-3-yl)-4-methylpentanamide

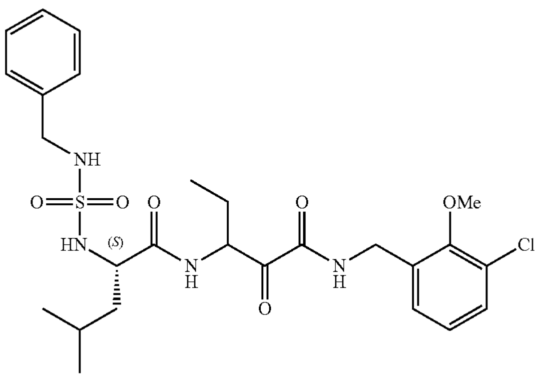

Figure 17:
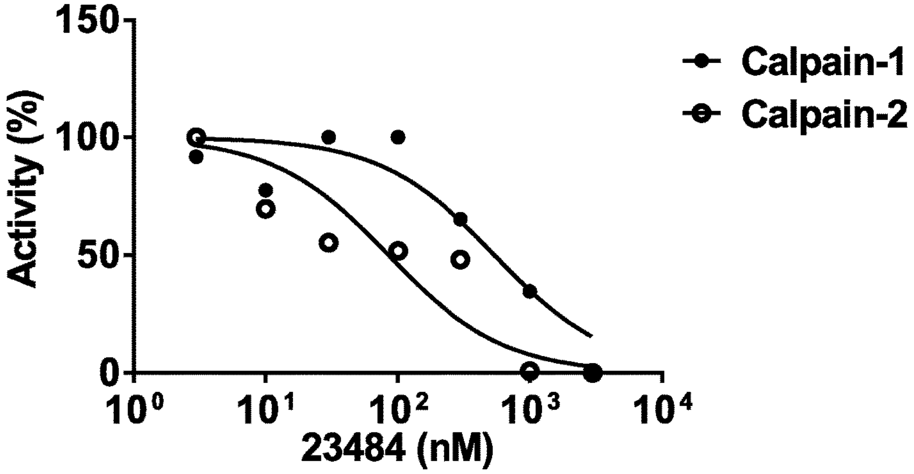
FIG. 17 shows the assay results of selectivity of NA184 for calpain-2 vs calpain-1.

(2S)-2-((N-benzylsulfamoyl)amino)-N-(1-((3-chloro-2-methoxybenzyl)amino)-1,2-dioxopentan-3-yl)-4-methylpentanamide Example 15: Calpain Assay Selectivity—In Vitro Selectivity Cerebellar homogenates from wild-type (WT) or calpain-1 Knock-out (KO) mice were incubated with 20 μM calcium to activate calpain-1 or with 2 mM calcium to activate calpain-2, respectively, and increasing concentrations of NA184. The graph in FIG. 17 shows the assay results of selectivity of 23484 for calpain-2 vs calpain-1 and the data from FIG. 17 were used to calculate the $IC_{50}$ of NA184 for calpain-1 and calpain-2 (Table 6).

TABLE 6

| 23484 | eCalpain-1 | hCalpain-2 |
|---|---|---|
| $IC_{50}$ | 543 nM | 85 nM |
| $K_i$ | 309 nM | 54 nM |

Ratio of $Ki_{calpain\text{-}1}/Ki_{calpain\text{-}2}$ = 5.7

Figure 18:
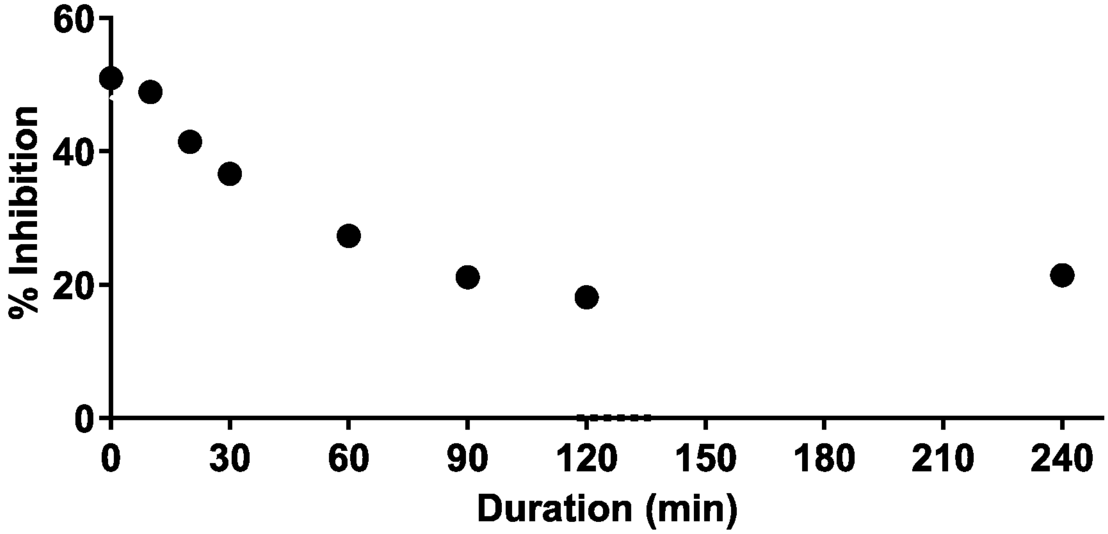
FIG. 18 shows rapid epimerization of NA184A in PBS.

Like in NA112, there are 2 chiral centers in NA184. The inhibitory activity of the compounds NA184A (S-S isomer) and NA184B (S-R stereoisomer) against erythrocyte human calpain-1 (ecalpain-1) and recombinant human calpain-2 (hcalpain-2) were determined. The NA184B compound (S-R stereoisomer) had no inhibitory activity at the highest concentration tested, 3 μM. NA184A (S-S isomer) showed the expected inhibitory activity against calpain-2 and calpain-1. NA184A (S-S stereoisomer) was incubated in PBS at 37° C. to determine whether it undergoes epimerization and therefore becomes inactive. As shown in FIG. 18, NA184A rapidly inactivated in PBS.

Example 16: Calpain Assay Selectivity—In Vivo Selectivity

WT or calpain-1 KO mouse cerebellar P2 homogenate (crude synaptosomal fraction) were used for measuring inhibitory activity of compounds against the mouse endogenous calpain-1/-2. Each reaction contains 100 ul of WT or calpain-1 KO mouse cerebellar P2 homogenate+0, 20 or 2000 uM $Ca^{2+}$+0-10,000 nM NA184.

Calpain-1 activity=calpain activity under 20 uM $Ca^{2+}$ in WT mice

Figure 19:
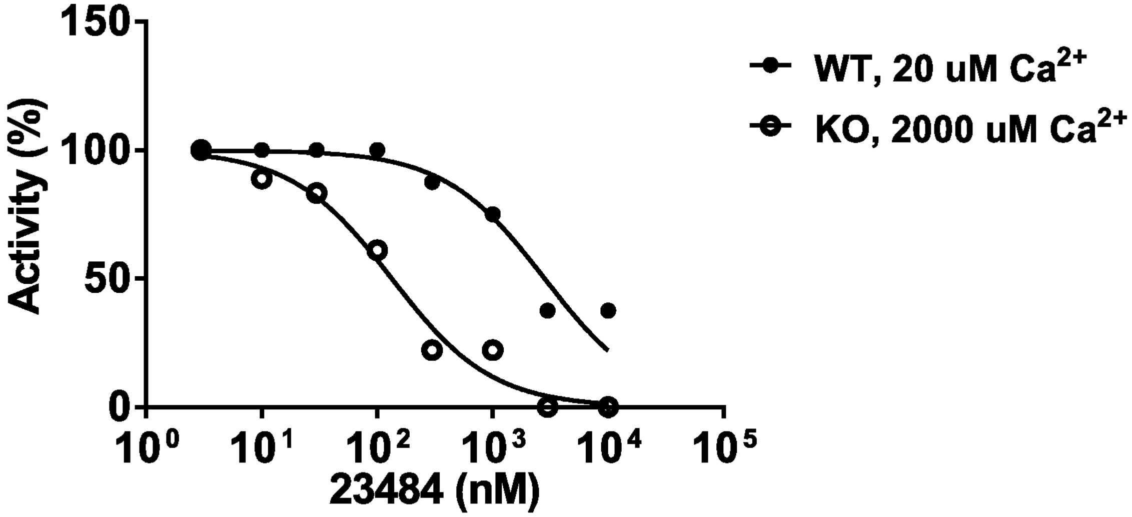
FIG. 19 shows results of NA184 $IC_{50}$ for calpain-1 activity and calpain-2 activity in WT and calpain-1 KO mice.

Calpain-2 activity=calpain activity under 2000 uM $Ca^{2+}$ in calpain-1 KO mice Results are shown in FIG. 19, and the data were used to calculate the IC50 shown in Table 7.

TABLE 7

| | WT 20 μM $Ca^{2+}$ (calpain-1) | C1KO 2000 μM $Ca^{2+}$ (calpain-2) |
|---|---|---|
| $IC_{50}$ | 2826 nM | 134 nM |
| Ratio | 21 | |

Example 17: In Vivo Efficacy (DMSO Solution)

Figure 20:
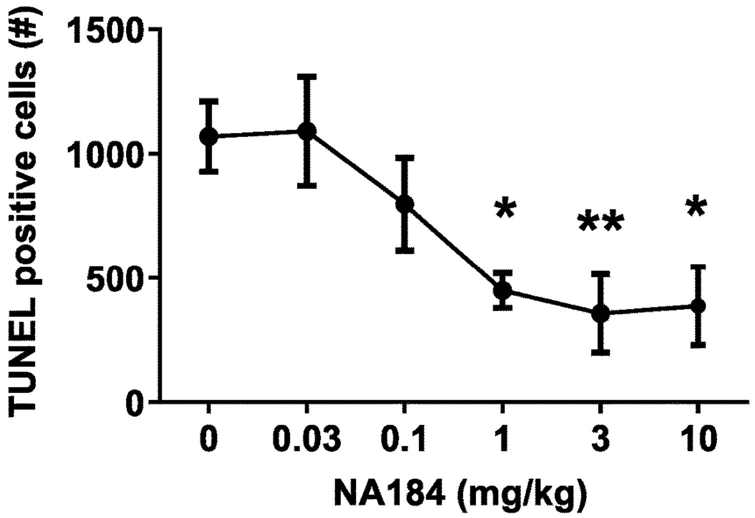
FIG. 20 shows in vivo efficacy with quantification of TUNEL staining 24 h after TBI plus i.p. injection of WT mice with NA184 at indicated doses 1 h after TBI.

Quantification of TUNEL staining 24 h after TBI plus i.p. injection of WT mice with NA184 at indicated doses 1 h after TBI. Total numbers of TUNEL-positive cells in 3 coronal sections (Bregma 0.50, −0.58, −1.58 mm) of each brain were counted and averaged. Results are means±S.E.M. of 3-6 animals. * p<0.05,  p<0.01, vs Vehicle. One-way ANOVA followed by Bonferroni test (FIG. 20**). From the curve, an ED50 was estimated to be about 0.13 mg/kg.

Example 18: In Vivo Efficacy in a Rat Model of TBI in Males and Females

Figure 21A:
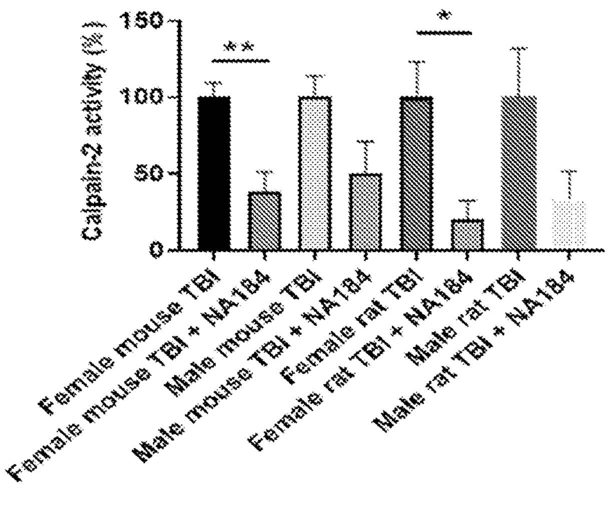
FIGS. 21A and 21B show that NA84 significantly inhibited calpain-2 under these conditions equally well in male and female mice and rats.
Figure 21B:
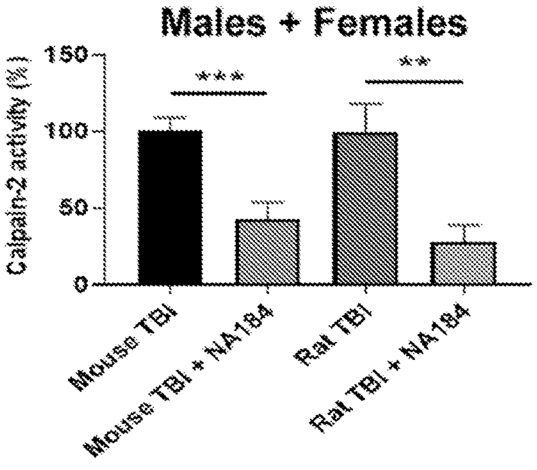
Figure 22A:
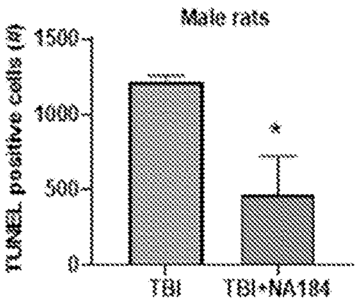
FIGS. 22A, 22B, and 22C show that NA184 significantly prevented cell death in cortex and to the same extent in male and female rats when injected twice at 1 and 8 h after TBI.
Figure 22B:
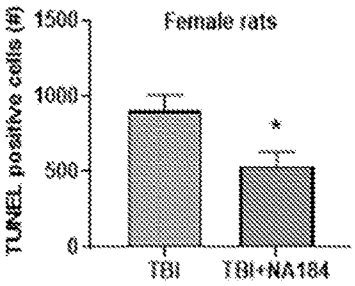
Figure 22C:
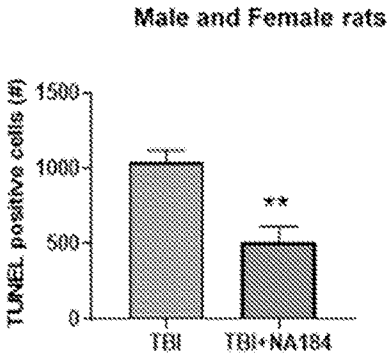
Figure 23:
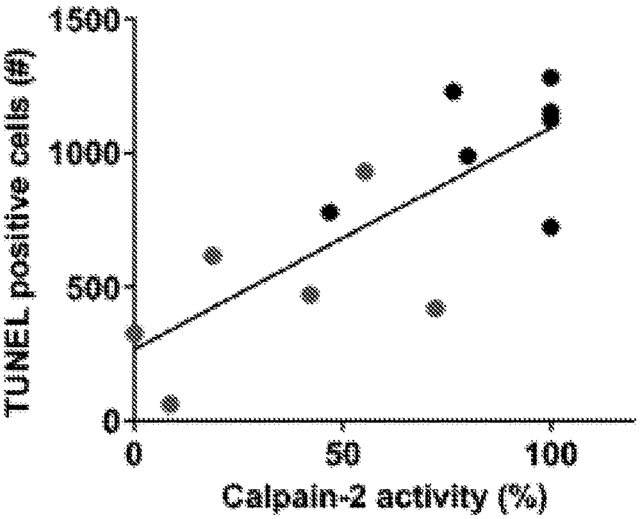
FIG. 23 shows correlation between calpain-2 activity and brain cell death in rats.

We also performed the same model of TBI in male and female mice and in male and female rats. In all cases, NA184 was injected i.p. at 1 mg/kg. For the rat experiments, NA184 was injected twice at 1 h and 8 h after TBI. Animals were sacrificed 24 h after TBI and calpain activity was assayed in brain and cell death was analyzed in cortex. Results showed that NA84 significantly inhibited calpain-2 but not calpain-1 under these conditions equally well in male and female mice and rats (FIGS. 21A and 21B). Likewise, NA184 significantly prevented cell death in cortex and to the same extent in male and female rats (FIGS. 22A, 22B, and 22C). In addition, there was a highly significant correlation between calpain-2 activity and cell death in rats (FIG. 23). $R^2$ was 0.61 and p<0.005.

What is claimed is:

1. A compound of the following Formula (I),

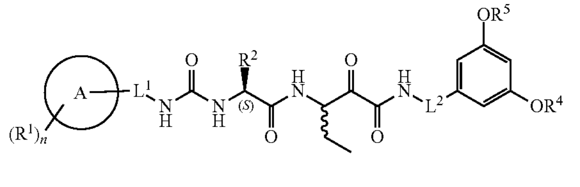

wherein A is carbocyclic aryl, or heteroaryl $R^1$ is a non-hydrogen substituent;

n is an integer of from 0 (where the ring A is unsubstituted) to the value permitted by the valence of A;

$L^1$ and $L^2$ are each the same or different optionally substituted alkylene having 1 to 6 carbons;

$R^2$ is non-hydrogen substituent, $R^4$ and $R^5$ are independently hydrogen, or unsubstituted $C_1$-$C_6$ alkyl such as methyl; and pharmaceutically acceptable salts thereof.

2. The compound of claim 1, wherein A is phenyl.

3. The compound of claim 1, wherein $L^1$ and $L^2$ each is $—CH_2—$.

4. The compound of claim 1, wherein $R^4$ and $R^5$ are methyl.

5. The compound of claim 1, wherein $R^2$ is unsubstituted $C_1$-$C_6$ alkyl.

6. The compound of claim 1 having the following structure:

(II)

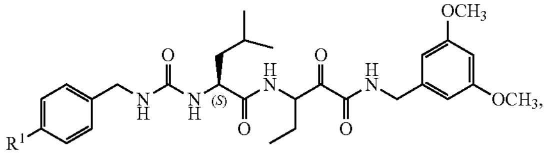

wherein $R^1$ is $C_1$-$C_6$ alkyl, halogen, cyano, nitro, $C_1$-$C_6$ alkoxy, $—CO(CH_2)_mN(R^a)(R^b)$, $—O(CH_2)_mN(R^a)(R^b)$, $—CONH(CH_2)_mN(R^a)(R^b)$, $—CONH—CH(R^c)(R^d)$, $—(CH_2)_mN(R^a)(R^b)$, or $—O(CH_2)_mOH$;

m is independently an integer from 0 to 6;

$R^a$, $R^b$, $R^c$, and $R^d$ are independently hydrogen or unsubstituted $C_1$-$C_6$ alkyl, which may be linear or branched alkyl.

7. The compound of claim 1, wherein $R^a$ and $R^b$ are independently hydrogen, methyl, ethyl, propyl or isopropyl.

8. The compound of claim 1, wherein $R^1$ is —$CONH_2$, —$OCH_2CH_2N(CH_3)_2$, —$CONHCH_2CH_2NHCH(CH_3)_2$, —$CONHCH(CH_3)_2$, —$CH_2N(CH_3)_2$, or —$CH_2N(CH_3)_2$.

9. The compound of claim 1 having the following structure:

(III)

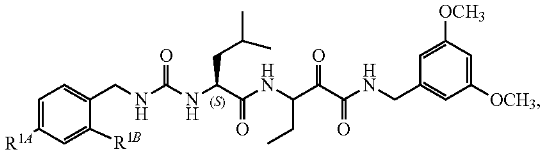

wherein $R^{1A}$ is cyano, or unsubstituted $C_1$-$C_6$ alkyl, and $R^{1B}$ is $C_1$-$C_6$ alkoxy.

10. The compound of claim 9, wherein $R^{1B}$ is —$OCH_3$.

11. The compound of claim 1, wherein the compound is

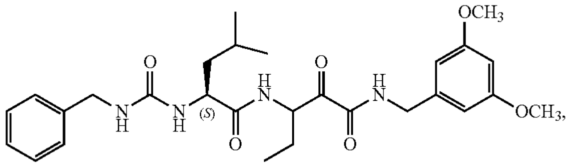

or

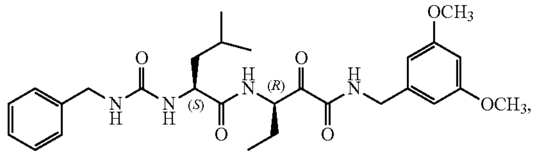

or

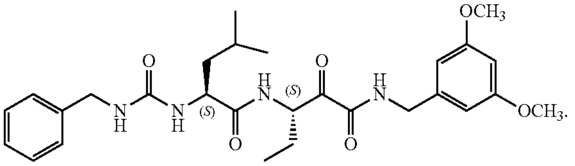

12. The compound of claim 1, wherein the compound is a racemate.

13. The compound of claim 1, wherein the compound is present as an optically enriched mixture.

14. The compound of claim 1 having the following structure:

(II)

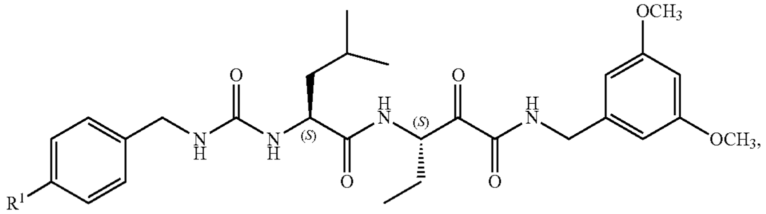

(III)

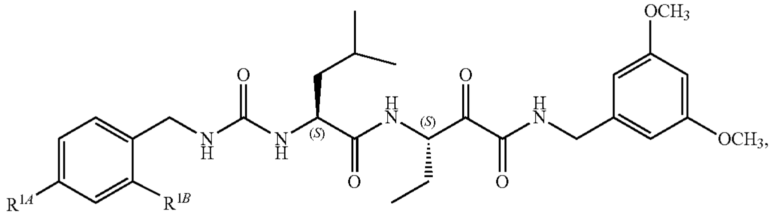

or

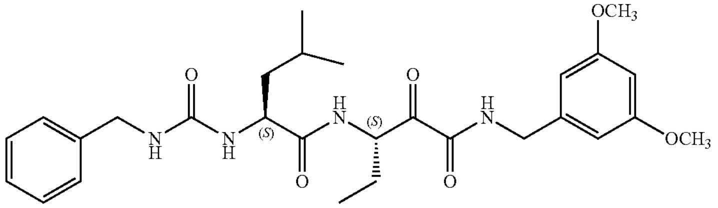

wherein $R^1$ is $C_1$-$C_6$ alkyl, halogen, cyano, nitro, $C_1$-$C_6$ alkoxy, —$CO(CH_2)_mN(R^a)(R^b)$, —$O(CH_2)_mN(R^a)(R^b)$, —$CONH(CH_2)_mN(R^a)(R^b)$, —CONHCH—$(R^c)(R^d)$, —$(CH_2)_mN(R^a)(R^b)$, or —$(CH_2)_mOH$;

m is independently an integer from 0 to 6;

$R^a$, $R^b$, $R^c$, and $R^d$ are independently hydrogen or unsubstituted $C_1$-$C_6$ alkyl, which may be linear or branched alkyl;

$R^{1A}$ is cyano, or unsubstituted $C_1$-$C_6$alkyl; and $R^{1B}$ is $C_1$-$C_6$ alkoxy.

15. A compound of the following Formula (X), (X)

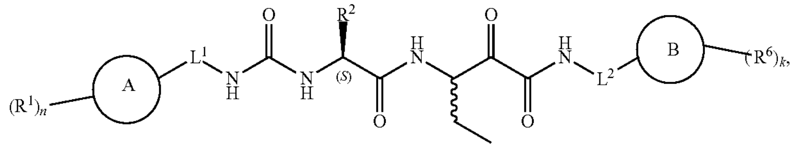

wherein:

A is $C_1$-$C_6$ alkyl, carboxyl (—C(O)O—), aryl, heteroaryl, cycloalkyl, or heterocycloalkyl;

B is carbocyclic aryl, heteroaryl, cycloalkyl, or heterocycloalkyl;

$L^1$ is a bond, or substituted or unsubstituted $C_1$-$C_6$ alkylene, $L^2$ is a bond, substituted or unsubstituted $C_1$-$C_6$ alkylene, or —$S(O)_2$—, Each $R^1$ is independently $C_1$-$C_6$ alkyl, halogen, cyano, nitro, $C_1$-$C_6$ alkoxy, aryl, heterocycloaryl, heterocycloalkyl, —$C(O)(CH_2)_mN(R^a)(R^b)$, —$O(CH_2)_mN(R^a)(R)$, —$CONH(CH_2)_mN(R^a)(R^b)$, —C(O)NH—$CH(R^c)(R^d)$, —$C(O)OCH(R)(R^d)$, —$(CH_2)_mN(R^a)(R)$, —$(CH_2)_mN(R^a)C(O)R^b$, —$(CH_2)_mN(R^a)C(O)OR^b$, —$O(CH_2)_mR^c$, —$O(CH_2)_mOH$, —$S(O)_2R^b$, or —O(Ph)X;

$R^2$ is unsubstituted $C_1$-$C_6$ alkyl;

Each $R^6$ is independently $C_1$-$C_6$ alkyl, halogen, cyano, nitro, $C_1$-$C_6$ alkoxy, aryl, heterocycloaryl, heterocycloalkyl —$C(O)(CH_2)_mN(R^a)(R^b)$, —$O(CH_2)_mN(R^a)(R)$, —$CONH(CH_2)_mN(R^a)(R^b)$, —C(O)NH—$CH(R^c)(R^d)$, —$C(O)OCH(R)(R^d)$, —$(CH_2)_mN(R^a)(R)$, —$(CH_2)_mN(R^a)C(O)R^b$, —$(CH_2)_mN(R^a)C(O)OR^b$, —$O(CH_2)_mR^c$, —$O(CH_2)_mOH$, or —O(Ph)X;

Two $R^6$ together with atoms attached thereto are optionally joined to form a cycloalkyl, or heterocycloalkyl;

$R^a$, $R^b$, $R^c$, and $R^d$ are independently hydrogen, $C_1$-$C_6$ alkyl that may be optionally substituted with halogen, —OH, amine, or unsubstituted $C_{3-6}$ cycloalkyl;

X is halogen;

n is independently an integer from 0 to 12;

m is independently an integer from 0 to 6;

k is independently an integer from 0 to 12;

and pharmaceutically acceptable salts thereof.

16. A compound has the following Formula (XIII), (XIII)

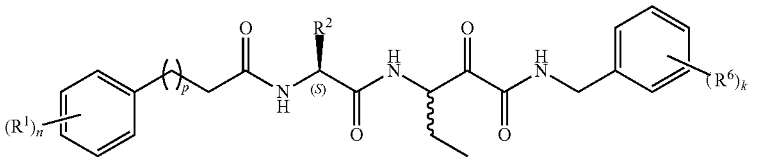

wherein:

Each $R^1$ is independently $C_1$-$C_6$ alkyl, halogen, cyano, nitro, $C_1$-$C_6$ alkoxy, aryl, heterocycloaryl, heterocycloalkyl, $—C(O)(CH_2)_mN(R^a)(R^b)$, $—O(CH_2)_mN(R^a)(R^b)$, $—CONH(CH_2)_mN(R^a)(R^b)$, $—C(O)NH—CH(R^c)(R^d)$, $—C(O)OCH(R)(R^d)$, $—(CH_2)_mN(R^a)(R)$, $—(CH_2)_mN(R^a)C(O)R^b$, $—(CH_2)_mN(R^a)C(O)OR^b$, $—O(CH_2)_mR^c$, $—O(CH_2)_mOH$, $—S(O)_2R^b$, or $—O(Ph)X$;

$R^2$ is unsubstituted $C_1$-$C_6$ alkyl;

Each $R^6$ is independently $C_1$-$C_6$ alkyl, halogen, cyano, nitro, $C_1$-$C_6$ alkoxy, aryl, heterocycloaryl, heterocycloalkyl $—C(O)(CH_2)_mN(R^a)(R^b)$, $—O(CH_2)_mN(R^a)(R)$, $—CONH(CH_2)_mN(R^a)(R^b)$, $—C(O)NH—CH(R^c)(R^d)$, $—C(O)OCH(R)(R^d)$, $—(CH_2)_mN(R^a)(R)$, $—(CH_2)_mN(R^a)C(O)R^b$, $—(CH_2)_mN(R^a)C(O)OR^b$, $—O(CH_2)_mR^c$, $—O(CH_2)_mOH$, or $—O(Ph)X$;

Two $R^6$ together with atoms attached thereto are optionally joined to form a cycloalkyl, or heterocycloalkyl;

$R^a$, $R^b$, $R^c$, and $R^d$ are independently hydrogen, $C_1$-$C_6$ alkyl that may be optionally substituted with halogen, —OH, amine, or unsubstituted $C_{3-6}$ cycloalkyl;

X is halogen;

n is independently an integer from 0 to 5;

m is independently an integer from 0 to 6;

k is independently an integer from 0 to 5;

p is independently an integer from 0 to 6;

and pharmaceutically acceptable salts thereof;

and pharmaceutically acceptable salts thereof.

17. The compound of claim 15, wherein the compound is

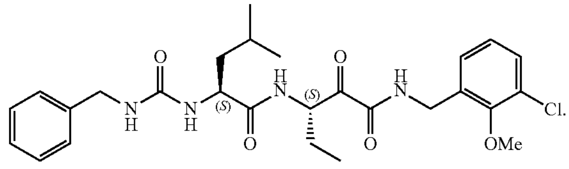

or a pharmaceutically acceptable salt thereof.

18. A pharmaceutical composition comprising the compound of claim 1, and a pharmaceutically acceptable excipient.

19. A method for treating traumatic brain injury (TBI) in a patient, said method comprising administering to a patient in need thereof an effective amount of a compound or composition of claim 1.

20. A method of treating a subject suffering from a disorder or symptom associated with neuronal cell death, comprising administering to the subject an effective amount of a compound or composition of claim 1.

21. A pharmaceutical composition comprising the compound of claim 11, and a pharmaceutically acceptable excipient.

22. A method for treating traumatic brain injury (TBI) in a patient, said method comprising administering to a patient in need thereof an effective amount of a compound or composition of claim 11.

23. A method of treating a subject suffering from a disorder or symptom associated with neuronal cell death, comprising administering to the subject an effective amount of a compound or composition of claim 11.

24. The compound of claim 15, wherein the compound is

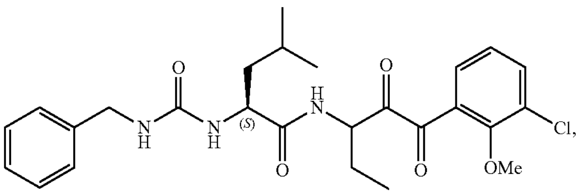

or a pharmaceutically acceptable salt thereof.

25. A pharmaceutical composition comprising the compound of claim 24, and a pharmaceutically acceptable excipient.

26. A method for treating traumatic brain injury (TBI) in a patient, said method comprising administering to a patient in need thereof an effective amount of a compound or composition of claim 24.

27. A method of treating a subject suffering from a disorder or symptom associated with neuronal cell death, comprising administering to the subject an effective amount of a compound or composition of claim 24.

28. A compound has the following Formula (XIV), (XIV)

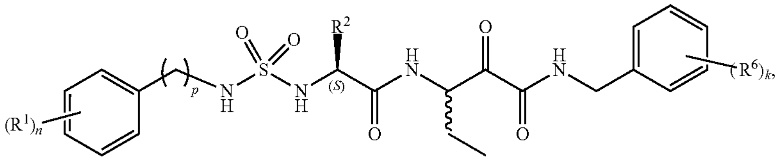

wherein:

Each $R^1$ is independently $C_1$-$C_6$ alkyl, halogen, cyano, nitro, $C_1$-$C_6$ alkoxy, aryl, heterocycloaryl, heterocycloalkyl, —$C(O)(CH_2)_mN(R^a)(R^b)$, —$O(CH_2)_mN(R^a)(R^b)$, —$CONH(CH_2)_mN(R^a)(R^b)$, —C(O)NH—$CH(R^c)(R^d)$, —$C(O)OCH(R)(R^d)$, —$(CH_2)_mN(R^a)(R^b)$, —$(CH_2)_mN(R^a)C(O)R^b$, —$(CH_2)_mN(R^a)C(O)OR^b$, —$O(CH_2)_mR^c$, —$O(CH_2)_mOH$, —$S(O)_2R^b$, or —O(Ph)X;

$R^2$ is unsubstituted $C_1$-$C_6$ alkyl;

Each $R^6$ is independently $C_1$-$C_6$ alkyl, halogen, cyano, nitro, $C_1$-$C_6$ alkoxy, aryl, heterocycloaryl, heterocycloalkyl —$C(O)(CH_2)_mN(R^a)(R^b)$, —$O(CH_2)_mN(R^a)(R^b)$, —$CONH(CH_2)_mN(R^a)(R^b)$, —C(O)NH—$CH(R^c)(R^d)$, —$C(O)OCH(R)(R^d)$, —$(CH_2)_mN(R^a)(R^b)$, —$(CH_2)_mN(R^a)C(O)R^b$, —$(CH_2)_mN(R^a)C(O)OR^b$, —$O(CH_2)_mR^c$, —$O(CH_2)_mOH$, or —O(Ph)X;

Two $R^6$ together with atoms attached thereto are optionally joined to form a cycloalkyl, or heterocycloalkyl;

$R^a$, $R^b$, $R^c$, and $R^d$ are independently hydrogen, $C_1$-$C_6$ alkyl that may be optionally substituted with halogen, —OH, amine, or unsubstituted $C_{3-6}$ cycloalkyl;

X is halogen;

n is independently an integer from 0 to 5;

m is independently an integer from 0 to 6;

k is independently an integer from 0 to 5;

p is independently an integer from 0 to 6; and pharmaceutically acceptable salts thereof.

29. A pharmaceutical composition comprising the compound of claim 28, and a pharmaceutically acceptable excipient.

30. A method for treating traumatic brain injury (TBI) in a patient, said method comprising administering to a patient in need thereof an effective amount of a compound or composition of claim 28.

31. A method of treating a subject suffering from a disorder or symptom associated with neuronal cell death, comprising administering to the subject an effective amount of a compound or composition of claim 28.

* * * * *